(12) United States Patent
Brivanlou et al.

(10) Patent No.: US 11,674,952 B2
(45) Date of Patent: Jun. 13, 2023

(54) EMBRYONIC CELL-BASED THERAPEUTIC CANDIDATE SCREENING SYSTEMS, MODELS FOR HUNTINGTON'S DISEASE AND USES THEREOF

(71) Applicant: The Rockefeller University, New York, NY (US)

(72) Inventors: Ali Brivanlou, NY, NY (US); Albert Ruzo, New York, NY (US); Alessia Deglincerti, New York, NY (US); Tomomi Haremaki, New York, NY (US); Fred Etoc, New York, NY (US)

(73) Assignee: The Rockefeller University, New York, NY (US)

( * ) Notice: Subject to any disclaimer, the term of this patent is extended or adjusted under 35 U.S.C. 154(b) by 326 days.

(21) Appl. No.: 16/079,755

(22) PCT Filed: Feb. 24, 2017

(86) PCT No.: PCT/US2017/019529
§ 371 (c)(1),
(2) Date: Aug. 24, 2018

(87) PCT Pub. No.: WO2017/147536
PCT Pub. Date: Aug. 31, 2017

(65) Prior Publication Data
US 2019/0195863 A1 Jun. 27, 2019

Related U.S. Application Data

(60) Provisional application No. 62/300,056, filed on Feb. 25, 2016, provisional application No. 62/299,544, filed on Feb. 24, 2016.

(51) Int. Cl.
| | | |
|---|---|---|
| *C12Q 1/02* | (2006.01) | |
| *G01N 33/50* | (2006.01) | |
| *C12Q 1/18* | (2006.01) | |
| *C12N 15/09* | (2006.01) | |
| *C12N 5/0735* | (2010.01) | |
| *A61K 31/506* | (2006.01) | |
| *A61K 45/06* | (2006.01) | |
| *C07K 14/47* | (2006.01) | |

(52) U.S. Cl.
CPC ....... *G01N 33/5073* (2013.01); *A61K 31/506* (2013.01); *A61K 45/06* (2013.01); *C07K 14/47* (2013.01); *C12N 5/0606* (2013.01); *C12N 15/09* (2013.01); *C12Q 1/02* (2013.01); *C12Q 1/025* (2013.01); *C12Q 1/18* (2013.01); *C12N 2503/02* (2013.01); *C12N 2510/00* (2013.01)

(58) Field of Classification Search
None
See application file for complete search history.

(56) References Cited

U.S. PATENT DOCUMENTS

| | | |
|---|---|---|
| 2003/0113813 A1 | 6/2003 | Heidaran et al. |
| 2006/0286544 A1 | 12/2006 | Mandal et al. |
| 2011/0136681 A1 | 6/2011 | Preynat-Seauve et al. |
| 2013/0045187 A1 | 2/2013 | Semechkin et al. |
| 2014/0273074 A1 | 9/2014 | Lindquist et al. |
| 2016/0108044 A1 | 4/2016 | Hertz et al. |

FOREIGN PATENT DOCUMENTS

| | | |
|---|---|---|
| WO | WO2013014164 A1 | 1/2013 |
| WO | WO2013017770 A1 | 2/2013 |
| WO | WO2014118311 A1 | 8/2014 |

OTHER PUBLICATIONS

Lu et al. A novel human embryonic stem cell-derived Huntington's disease neuronal model exhibits mutant huntingtin (mHTT) aggregates and soluble mHTT-dependent neurodegeneration. FASEB J. 27, 1820-1829 (2013) (Year: 2013).*
An et al (Version 1. PLoS Curr. Apr. 5, 2014;6) (Year: 2014).*
Warmflash et al (Nature Methods, 2014, vol. 11, No. 8, pp. 847-854). (Year: 2014).*
Warmflash et al., "A Method to Recapitulate Early Embryonic Spatial Patterning in Human Embryonic Stem Cells", Mature Methods, vol. 11, No. 8, pp. 847-856 (Aug. 2014).
Zeitlin et al., "Increased Apoptosis and Early Embryonic Lethality in Mice Nullizygous for the Huntington's Disease Gene Homologue", Nature Genetics, vol. 11, pp. 155-163 (Oct. 1995).
Hertz et al., "A Neo-Substrate that Amplifies Catalytic Activity of Parkinson's-Disease-Related Kinase PINK1", Cell 154, 737-747 (Aug. 2013).
Genetic Modifiers of Huntington's Disease (GeM-HD) Consortium—"Identification of Genetic Factors that Modify Clinical Onset of Huntington's Disease", CellPress, 162, 516-526 (Jul. 2015).
Zhang et al., "iPSC-Based Drug Screening for Huntington's Disease", ScienceDirect, Brain Research, pp. 1-15 (2015).
James et al., "Contribution of Human Embryonic Stem Cells to Mouse Blastocysts", Science Direct, Developmental Biology, 295, 90-102 (2006).

(Continued)

*Primary Examiner* — Celine X Qian
(74) *Attorney, Agent, or Firm* — Hoffmann & Baron, LLP

(57) ABSTRACT

Compositions and methods disclosed concern an isogenic population of in vitro human embryonic stem cells comprising a disease form of the Huntingtin gene (HTT) at the endogenous HTT gene locus in the genome of the cell; wherein the disease form of the HTT gene comprises a polyQ repeat of at least 40 glutamines at the N-terminus of the Huntingtin protein (HTT). The cell lines of the disclosure comprise genetically-defined alterations made in the endogenous HTT gene that recapitulate Huntington's Disease in humans. Furthermore, the cell lines have isogenic controls that share a similar genetic background. Differentiating cell lines committed to a neuronal fate and fully differentiated cell lines are also provided and they also display phenotypic abnormalities associated with the length of the polyQ repeat of the HTT gene. These cell lines are used as screening tools in drug discovery and development to identify substances that fully or partially revert these phenotype abnormalities.

17 Claims, 17 Drawing Sheets

Specification includes a Sequence Listing.

(56) References Cited

OTHER PUBLICATIONS

Khalil et al., "PINK1-Induced Mitophagy Promotes Neuroprotection in Huntington's Disease", Cell Death and Disease 6, pp. 1-12 (2015).

Lin et al., "Neurological Abnormalities in a Knock-in Mouse Model of Huntington's Disease", Human Molecular Genetics, vol. 10, No. 2, pp. 137-144 (2001).

Livet et al., "Transgenic Strategies for Combinatorial Expression of Fluorescent Proteins in the Nervous System", Nature, vol. 450, pp. 56-63 (Nov. 2007).

Loulier et al., "Multiplex Cell and Lineage Tracking with Combinatorial Labels", NeuroResource, Neuron 81, 505-520 (Feb. 2014).

Rosa et al., "The miR-430/427/302 Family Conliols Mesendodermal Fate Specification via Species-Specific Target Selection", Developmental Cell 16, 517-527 (Apr. 2009).

ThermoFisher Scientific, "Freestyle 293-F cells", User Guide, Catalog No. R790-07, Document Part No. 250457, Publication No. MAN0000255, Revision B.0 (Jan. 20, 2020).

Malik, N., et al., "A Review of the Methods for Human iPSC Derivation", Methods Mol Biol. 2013; vol. 997, pp. 23-33.

\* cited by examiner

SEQUENCE LISTING

<160> NUMBER OF SEQ ID NOS: 70

<210> SEQ ID NO 1
<211> LENGTH: 450
<212> TYPE: DNA
<213> ORGANISM: Homo sapiens

<400> SEQUENCE: 1

| cagcaacagc agcaacagca gcagcaacag cagcaacagc agcagcagca gcagcagcag | 60 |
| cagcagcagc aacaacagca gcagcagcag caacagcagc agcaacagca gcagcagcag | 120 |
| caacagcagc agcagcaaca gcagcagcag caacagcagc agcagcagca acagcagcag | 180 |
| cagcagcagc agcagcaaca gcaacagcag cagcaacagc agcagcagca gcaacagcaa | 240 |
| cagcagcagc agcagcagca gcaacaacag cagcagcagc agcagcagca acagcagcaa | 300 |
| cagcagcaac agcagcaaca gcaacagcag cagcagcagc agcagcaaca gcagcagcag | 360 |
| caacagcaac agcaacagca acagcaacag caacagcagc agcagcagca gcagcagcag | 420 |
| cagcagcagc agcaacagca gcagcaacag | 450 |

<210> SEQ ID NO 2
<211> LENGTH: 7964
<212> TYPE: DNA
<213> ORGANISM: Homo sapiens

<400> SEQUENCE: 2

| gtattaccgc ctttgagtga gctgataccg ctcgccgcag ccgaacgacc gagcgcagcg | 60 |
| agtcagtgag cgaggaagcg gaagagcgcc caatacgcaa accgcctctc cccgcgcgtt | 120 |
| ggccgattca ttaatgcagc tggcacgaca ggtttcccga ctggaaagcg ggcagtgagc | 180 |
| gcaacgcaat taatgtgagt tagctcactc attaggcacc ccaggcttta cactttatgc | 240 |
| ttccggctcg tatgttgtgt ggaattgtga gcggataaca atttcacaca ggaaacagct | 300 |
| atgaccatga ttacgccaag cgcgcaatta accctcacta aagggaacaa aagctggagg | 360 |
| ggtcacactt ggggtcctca ggtcgtgccg accacgcgca ttctctgcgc tctgcgcagg | 420 |
| agctcgccca ccctctcccc gtgcagagag ccccgcagct ggctcccgc agggctgtcc | 480 |
| gggtgagtat ggctctggcc acgggccagt gtggcgggag ggcaaacccc aaggccacct | 540 |
| cggctcagag tccacggccg gctgtcgccc cgctccaggc gtcggcgggg gatcctttcc | 600 |
| gcatgggcct gcgcccgcgc tcggcgcccc ctccacggcc ccgccccgtc catggccccg | 660 |
| tccttcatgg gcgagcccct ccatggccct gccctccgc gccccacccc tccctcgccc | 720 |
| cacctctcac cttcctgccc cgccccagc ctcccaccc ctcaccggcc agtcccctcc | 780 |
| cctatcccgc tccgcccctc agccgccccg cccctcagcc ggcctgccta atgtcccgt | 840 |
| ccccagcatc gccccgcccc gccccgtct cgccccgccc ctcaggcggc ctccctgctg | 900 |
| tgccccgccc cggcctcgcc acgcccctac ctcaccacgc ccccgcatc gccacgcccc | 960 |
| ccgcatcgcc acgcctccct taccatgcag tcccgcccg tccttcctc gtccgcctc | 1020 |
| gccgcgacac ttcacacaca gcttcgcctc accccattac agtctcacca cgccccgtcc | 1080 |
| cctctccgtt gagccccgcg ccttcgcccg ggtggggcgc tgcgctgtca gcggccttgc | 1140 |
| tgtgtgaggc agaacctgcg ggggcagggg cgggctggtt ccctggccag ccattggcag | 1200 |
| agtccgcagg ctagggctgt caatcatgct ggcggcgtg gccccgccctc cgccggcgcg | 1260 |
| gccccgcctc cgccggcgca gcgtctggga cgcaaggcgc cgtggggct gccgggacgg | 1320 |
| gtccaagatg gacggccgct caggttctgc ttttaaccct agaaagatag tctgcgtaaa | 1380 |

```
attgacgcat gcattcttga aatattgctc tctctttcta aatagcgcga atccgtcgct    1440
gtgcatttag gacatctcag tcgccgcttg gagctcccgt gaggcgtgct tgtcaatgcg    1500
gtaagtgtca ctgattttga actataacaa ccgcgtgagt caaaatgacg catgattatc    1560
ttttacgtga cttttaagat ttaactcata cgataattat attgttattt cgtgttctac    1620
ttacgtgata acttattata tatatatttt cttgttatag atatccttct cgagaagctt    1680
gatatcgaat tccacggggt tggggttgcg ccttttccaa ggcagccctg ggtttgcgca    1740
gggacgcggc tgctctgggc gtggttccgg gaaacgcagc ggcgccgacc ctgggtctcg    1800
cacattcttc acgtccgttc gcagcgtcac ccgatcttc gccgctaccc ttgtgggccc     1860
cccggcgacg cttcctgctc cgcccctaag tcgggaaggt tccttgcggt tcgcggcgtg    1920
ccggacgtga caaacggaag ccgcacgtct cactagtacc ctcgcagacg gacagcgcca    1980
gggagcaatg gcagcgcgcc gaccgcgatg ggctgtggcc aatagcggct gctcagcagg    2040
gcgcgccgag agcagcggcc gggaaggggc ggtgcgggag gcggggtgtg gggcggtagt    2100
gtgggccctg ttcctgcccg cgcggtgttc cgcattctgc aagcctccgg agcgcacgtc    2160
ggcagtcggc cccctcgttg accgaatcac cgacctctct ccccaggggg atctcgccac    2220
catggggacc gagtacaagc ccacggtgcg cctcgccacc cgcgacgacg tccccgggc     2280
cgtacgcacc ctcgccgccg cgttcgccga ctaccccgcc acgcgccaca ccgtcgaccc    2340
ggaccgccac atcgagcggg tcaccgagct gcaagaactc ttcctcacgc gcgtcgggct    2400
cgacatcggc aaggtgtggg tcgcggacga cggcgccgcg gtggcggtct ggaccacgcc    2460
ggagagcgtc gaagcggggg cggtgttcgc cgagatcggc ccgcgcatgg ccgagttgag    2520
cggttcccgg ctggccgcgc agcaacagat ggaaggcctc ctggcgccgc accgcccaa     2580
ggagcccgcg tggttcctgg ccaccgtcgg cgtctcgccc gaccaccagg gcaagggtct    2640
gggcagcgcc gtcgtgctcc ccggagtgga ggcggccgag cgcgccgggg tgcccgcctt    2700
cctggagacc tccgcgcccc gcaacctccc cttctacgag cggctcggct tcaccgtcac    2760
cgccgacgtc gaggtgcccg aaggaccgcg cacctggtgc atgacccgca agcccggtgc    2820
cggatccatg cccacgctac tgcgggttta tatagacggt cctcacggga tggggaaaac    2880
caccaccacg caactgctgg tggccctggg ttcgcgcgac gatatcgtct acgtacccga    2940
gccgatgact tactggcagg tgctgggggc ttccgagaca atcgcgaaca tctacaccac    3000
acaacaccgc ctcgaccagg gtgagatatc ggccggggac gcggcggtgg taatgacaag    3060
cgcccagata caatgggca tgccttatgc cgtgaccgac gccgttctgg ctcctcatat     3120
cggggggggag gctgggagct cacatgcccc gccccggcc ctcaccctca tcttcgaccg    3180
ccatcccatc gccgccctcc tgtgctaccc ggccgcgcga taccttatgg gcagcatgac    3240
cccccaggcc gtgctggcgt tcgtggccct catcccgccg accttgcccg gcacaaacat    3300
cgtgttgggg gccttccgg aggacagaca catcgaccgc ctggccaaac gccagcgccc    3360
cggcgagcgg cttgacctgg ctatgctggc cgcgattcgc cgcgtttacg ggctgcttgc    3420
caatacggtg cggtatctgc agggcggcgg gtcgtggcgg gaggattggg acagctttc     3480
ggggacggcc gtgccgcccc agggtgccga gcccagagc aacgcgggcc cacgacccca    3540
tatcggggac acgttattta ccctgtttcg ggccccgag ttgctggccc caacggcga     3600
cctgtacaac gtgtttgcct gggccttgga cgtcttggcc aaacgcctcc gtcccatgca    3660
cgtctttatc ctggattacg accaatcgcc cgccggctgc cgggacgccc tgctgcaact    3720
```

```
tacctccggg atggtccaga cccacgtcac caccccggc tccataccga cgatctgcga    3780
cctggcgcgc acgtttgccc gggagatggg ggaggctaac tgagcggccg cgactctaga    3840
tcataatcag ccataccaca tttgtagagg ttttacttgc tttaaaaaac ctcccacacc    3900
tccccctgaa cctgaaacat aaaatgaatg caattgttgt tgttaacttg tttattgcag    3960
cttataatgg ttacaaataa agcaatagca tcacaaattt cacaaataaa gcatttttt    4020
cactgcattc tagttgtggt ttgtccaaac tcatcaatgt atcttaagga attcgataaa    4080
agttttgtta ctttatagaa gaaattttga gttttgtttt tttttaata aataaataaa    4140
cataaataaa ttgtttgttg aatttattat tagtatgtaa gtgtaaatat aataaaactt    4200
aatatctatt caaattaata aataaacctc gatatacaga ccgataaaac acatgcgtca    4260
attttacgca tgattatctt taacgtacgt cacaatatga ttatctttct agggttaacc    4320
tgcggcccag agccccattc attgcccggg tgctgagcgg cgccgcgagt cggcccgagg    4380
cctccgggga ctgccgtgcc gggcgggaga ccgccatggc gaccctggaa aagctgatga    4440
aggccttcga gtccctcaag tccttccagc agcagcagca gcagcagcag cagcagcagc    4500
agcagcagca gcagcagcag cagcagcagc agcagcagca gcagcagcag cagcagcagc    4560
agcagcagca gcagcagcag cagcagcagc agcagcagca gcagcagcag caacagccgc    4620
caccgccgcc gccgccgccg ccgcctcctc agcttcctca gccgccgccg caggcacagc    4680
cgctgctgcc tcagccgcag ccgccccgc cgccgccccc gccgccaccc ggcccggctg    4740
tggctgagga gccgctgcac cgaccgtgag tttgggcccg ctgcagctcc ctgtcccggc    4800
gggtcccagg ctacgcggg gatggcggta accctgcagc ctgcgggccg gcgacacgaa    4860
ccccgggcc cgcagagaca gagtgaccca gcaacccaga gcccatgagg gacacccgcc    4920
ccctcctggg gcgaggcctt ccccccacttc agccccgctc cctcacttgg gtcttccctt    4980
gtcctctcgc gaggggaggc agagccttgt tggggcctgt cctgaattca ccgaggggag    5040
tcacggcctc agccctctcg cccttcgcag gatgcgaaga gttggggcga gaacttgttt    5100
cttttatt gcgagaaacc agggcggggg ttctttaac tgcgttgtga agagaacttg    5160
gaggagccga gatttgctca gtgccacttc cctcttctag tctgagaggg aagagggctg    5220
ggggcgcggg acacttcgag aggaggcggg gtttggagct ggagagatgt gggggcagtg    5280
gatgacataa tgcttttagg acgcctcggg gggagtggcg gggcagggg ggggcgggga    5340
gtgagggcgc gtccaatggg agatttcttt tcctagtggc acttaaaaca gcctgagatt    5400
tgaggctctt cctacattgt caggacattt catttagttc atgatcacgg tggtagtaac    5460
acgattttaa gcaccaccta agagatctgc tcatctaagc ctaagttggt ctgcaggcgt    5520
ttgaatgagt tgtggttgcc aagtaaagtg gtgaacttac gtggtgatta atgaaattat    5580
cttaaatatt aggaagagtt gattgaagtt ttttgcctat gtgtgttggg aataaaacca    5640
acacgttgct gatggggagg ccaattcgcc ctatagtgag tcgtattacg cgcgctcact    5700
ggccgtcgtt ttacaacgtc gtgactggga aaccctggc gttacccaac ttaatcgcct    5760
tgcagcacat cccccttttcg ccagctggcg taatagcgaa gaggcccgca ccgatcgccc    5820
ttcccaacag ttgcgcagcc tgaatggcga atggcgcctg atgcggtatt ttctccttac    5880
gcatctgtgc ggtatttcac accgcatatg gtgcactctc agtacaatct gctctgatgc    5940
cgcatagtta agccagcccc gacacccgcc aacacccgct gacgcgccct gacgggcttg    6000
tctgctcccg gcatccgctt acagacaagc tgtgaccgtc tccgggagct gcatgtgtca    6060
gaggttttca ccgtcatcac cgaaacgcgc gagacgaaag gcctcgtga tacgcctatt    6120
```

```
tttataggtt aatgtcatga taataatggt ttcttagacg tcaggtggca cttttcgggg    6180
aaatgtgcgc ggaacccta tttgtttatt tttctaaata cattcaaata tgtatccgct     6240
catgagacaa taaccctgat aaatgcttca ataatattga aaaggaaga gtatgagcca      6300 tattcaacgg gaaacgtctt gctctaggcc gcgattaaat tccaacatgg atgctgattt   6360
atatgggtat aaatgggctc gcgataatgt cgggcaatca ggtgcgacaa tctatcgatt    6420
gtatgggaag cccgatgcgc cagagttgtt tctgaaacat ggcaaggta gcgttgccaa    6480 tgatgttaca gatgagatgg tcagactaaa ctggctgacg gaatttatgc ctcttccgac   6540
catcaagcat tttatccgta ctcctgatga tgcatggtta ctcaccactg cgatccctgg    6600
gaaaacagca ttccaggtat tagaagaata tcctgattca ggtgaaaata ttgttgatgc   6660
gctggcagtg ttcctgcgcc ggttgcattc gattcctgtt tgtaattgtc cttttaacag   6720
cgatcgcgta tttcgtctcg ctcaggcgca atcacgaatg aataacggtt tggttgatgc   6780
gagtgatttt tgatgacgag cgtaatggctg gcctgttgaa caagtctgga agaaatgca    6840 taaacttttg ccattctcac cggattcagt cgtcactcat ggtgatttct cacttgataa   6900
ccttattttt gacgagggga aattaatagg ttgtattgat gttggacgag tcggaatcgc   6960
agaccgatac caggatcttg ccatcctatg gaactgcctc ggtgagtttt ctccttcatt    7020
acagaaacgg cttttttcaaa aatatggtat tgataatcct gatatgaata aattgcagtt   7080
tcatttgatg ctcgatgagt ttttctaact gtcagaccaa gtttactcat atatacttta   7140
gattgattta aaacttcatt tttaatttaa aaggatctag gtgaagatcc ttttttgataa   7200 tctcatgacc aaaatccctt aacgtgagtt ttcgttccac tgagcgtcag accccgtaga   7260
aaagatcaaa ggatcttctt gagatccttt ttttctgcgc gtaatctgct gcttgcaaac   7320
aaaaaaacca ccgctaccag cggtggtttg tttgccggat caagagctac caactctttt   7380
tccgaaggta actggcttca gcagagcgca gataccaaat actgttcttc tagtgtagcc   7440
gtagttaggc caccacttca agaactctgt agcaccgcct acatacctcg ctctgctaat   7500
cctgttacca gtggctgctg ccagtggcga taagtcgtgt cttaccgggt tggactcaag   7560
acgatagtta ccggataagg cgcagcggtc gggctgaacg gggggttcgt gcacacagcc   7620
cagcttggag cgaacgacct acaccgaact gagataccta cagcgtgagc tatgagaaag   7680
cgccacgctt cccgaaggga gaaaggcgga caggtatccg gtaagcggca gggtcggaac   7740
aggagagcgc acgagggagc ttccagggg aaacgcctgg tatctttata gtcctgtcgg    7800
gtttcgccac ctctgacttg agcgtcgatt tttgtgatgc tcgtcagggg ggcggagcct    7860
atggaaaaac gccagcaacg cggcctttt acggttcctg gccttttgct ggccttttgc    7920
tcacatgttc tttcctgcgt tatccctga ttctgtggat aacc                    7964
```

<210> SEQ ID NO 3
<211> LENGTH: 23
<212> TYPE: DNA
<213> ORGANISM: Homo sapiens

<400> SEQUENCE: 3
cgccatggcg gtctcccgcc cgg                                            23

<210> SEQ ID NO 4
<211> LENGTH: 23
<212> TYPE: DNA
<213> ORGANISM: Homo sapiens

```
<400> SEQUENCE: 4
gctgcaccga ccgtgagttt ggg                                           23

<210> SEQ ID NO 5
<211> LENGTH: 90
<212> TYPE: DNA
<213> ORGANISM: Homo sapiens

<400> SEQUENCE: 5
cctaggtgac acagcaagac gttgtctctg gggaaaaaag aaagaaacgg aaccacgcgg   60
tgtgcagcct tctgagtctg gccccttcg                                     90

<210> SEQ ID NO 6
<211> LENGTH: 20
<212> TYPE: DNA
<213> ORGANISM: Homo sapiens

<400> SEQUENCE: 6
gctgctgctg gaaggacttg                                               20

<210> SEQ ID NO 7
<211> LENGTH: 23
<212> TYPE: DNA
<213> ORGANISM: Homo sapiens

<400> SEQUENCE: 7
cgccatggcg gtctcccgcc cgg                                           23

<210> SEQ ID NO 8
<211> LENGTH: 23
<212> TYPE: DNA
<213> ORGANISM: Homo sapiens

<400> SEQUENCE: 8
gctgcaccga ccgtgagttt ggg                                           23

<210> SEQ ID NO 9
<211> LENGTH: 22
<212> TYPE: DNA
<213> ORGANISM: Homo sapiens

<400> SEQUENCE: 9
ggtaccgttc catcagtcca gc                                            22

<210> SEQ ID NO 10
<211> LENGTH: 20
<212> TYPE: DNA
<213> ORGANISM: Homo sapiens

<400> SEQUENCE: 10
gagctcgttc catcgctggt                                               20

<210> SEQ ID NO 11
<211> LENGTH: 51
<212> TYPE: DNA
<213> ORGANISM: Homo sapiens

<400> SEQUENCE: 11
ttaccagcga tggaacgagc tctgaatatg tgaataatct tttcagtcat c            51

<210> SEQ ID NO 12
<211> LENGTH: 43
```

<212> TYPE: DNA
<213> ORGANISM: Homo sapiens

<400> SEQUENCE: 12
ttcctcgcct tctgcgcctg caggtcatgg aaggtggcga cac        43

<210> SEQ ID NO 13
<211> LENGTH: 30
<212> TYPE: DNA
<213> ORGANISM: Homo sapiens

<400> SEQUENCE: 13
atgacctgca ggcgcagaag gcgaggaagc        30

<210> SEQ ID NO 14
<211> LENGTH: 72
<212> TYPE: DNA
<213> ORGANISM: Homo sapiens

<400> SEQUENCE: 14
agacgaattc ctaataactt cgtatagcat acattatacg aagttattat tacttgtaca        60
gctcgtccat gc        72

<210> SEQ ID NO 15
<211> LENGTH: 72
<212> TYPE: DNA
<213> ORGANISM: Homo sapiens

<400> SEQUENCE: 15
agctgtacaa gtaataataa cttcgtataa tgtatgctat acgaagttat taggaattcg        60
tctgaagagg ag        72

<210> SEQ ID NO 16
<211> LENGTH: 78
<212> TYPE: DNA
<213> ORGANISM: Homo sapiens

<400> SEQUENCE: 16
ccttgctgct ggcgcgccat aacttcgtat aatgtatgct atacgaagtt ataggcctct        60
agagtcagct tctgatgg        78

<210> SEQ ID NO 17
<211> LENGTH: 30
<212> TYPE: DNA
<213> ORGANISM: Homo sapiens

<400> SEQUENCE: 17
ttatggcgcg ccagcagcaa ggcccaggtc        30

<210> SEQ ID NO 18
<211> LENGTH: 56
<212> TYPE: DNA
<213> ORGANISM: Homo sapiens

<400> SEQUENCE: 18
gctggactga tggaacggta cctggctcac aaaaggaggg gcttcactaa taactg        56

<210> SEQ ID NO 19
<211> LENGTH: 20
<212> TYPE: DNA
<213> ORGANISM: Homo sapiens -continued

<400> SEQUENCE: 19
ggtacccagc ttttgttccc         20

<210> SEQ ID NO 20
<211> LENGTH: 25
<212> TYPE: DNA
<213> ORGANISM: Homo sapiens

<400> SEQUENCE: 20
aactgagctc caattcgccc tatag         25

<210> SEQ ID NO 21
<211> LENGTH: 48
<212> TYPE: DNA
<213> ORGANISM: Homo sapiens

<400> SEQUENCE: 21
gggcgaattg gagctcagtt cctgcaggtg caggaccacc ccaactac         48

<210> SEQ ID NO 22
<211> LENGTH: 45
<212> TYPE: DNA
<213> ORGANISM: Homo sapiens

<400> SEQUENCE: 22
ttcctcgcct tctgcgcctg cagggcacgt caggatagtt gcagt         45

<210> SEQ ID NO 23
<211> LENGTH: 42
<212> TYPE: DNA
<213> ORGANISM: Homo sapiens

<400> SEQUENCE: 23
aactatcctg acgtgccctg caggcgcaga aggcgaggaa gc         42

<210> SEQ ID NO 24
<211> LENGTH: 67
<212> TYPE: DNA
<213> ORGANISM: Homo sapiens

<400> SEQUENCE: 24
tcagacgaat tcctaataac ttcgtatagc atacattata cgaagttatt attacttgta         60
cagctcg         67

<210> SEQ ID NO 25
<211> LENGTH: 65
<212> TYPE: DNA
<213> ORGANISM: Homo sapiens

<400> SEQUENCE: 25
caagtaataa taacttcgta taatgtatgc tatacgaagt tattaggaat tcgtctgaag         60
aggag         65

<210> SEQ ID NO 26
<211> LENGTH: 79
<212> TYPE: DNA
<213> ORGANISM: Homo sapiens

<400> SEQUENCE: 26
ggatcaggga cctgggtacc ggcgcgccat aacttcgtat aatgtatgct atacgaagtt         60
ataggcctct agagtcagc         79

<210> SEQ ID NO 27
<211> LENGTH: 36
<212> TYPE: DNA
<213> ORGANISM: Homo sapiens

<400> SEQUENCE: 27
ttatggcgcg ccggtaccca ggtccctgat ccgccc                     36

<210> SEQ ID NO 28
<211> LENGTH: 41
<212> TYPE: DNA
<213> ORGANISM: Homo sapiens

<400> SEQUENCE: 28
agggaacaaa agctgggtac ccttgccact tcccaaggtg t               41

<210> SEQ ID NO 29
<211> LENGTH: 22
<212> TYPE: DNA
<213> ORGANISM: Homo sapiens

<400> SEQUENCE: 29
ccaattcgcc ctatagtgag tc                                    22

<210> SEQ ID NO 30
<211> LENGTH: 20
<212> TYPE: DNA
<213> ORGANISM: Homo sapiens

<400> SEQUENCE: 30
ctccagcttt tgttcccttt                                       20

<210> SEQ ID NO 31
<211> LENGTH: 42
<212> TYPE: DNA
<213> ORGANISM: Homo sapiens

<400> SEQUENCE: 31
actaaaggga acaaaagctg gatgtacaac atgatggaga cg              42

<210> SEQ ID NO 32
<211> LENGTH: 32
<212> TYPE: DNA
<213> ORGANISM: Homo sapiens

<400> SEQUENCE: 32
ctcgcccttg ctcaccatgt gtgagagggg ca                         32

<210> SEQ ID NO 33
<211> LENGTH: 27
<212> TYPE: DNA
<213> ORGANISM: Homo sapiens

<400> SEQUENCE: 33
ctctcacaca tggtgagcaa gggcgag                               27

<210> SEQ ID NO 34
<211> LENGTH: 30
<212> TYPE: DNA
<213> ORGANISM: Homo sapiens

<400> SEQUENCE: 34
ctctgccctc cttgtacagc tcgtccatgc                                              30

<210> SEQ ID NO 35
<211> LENGTH: 29
<212> TYPE: DNA
<213> ORGANISM: Homo sapiens

<400> SEQUENCE: 35
gctgtacaag gagggcagag gaagtcttc                                               29

<210> SEQ ID NO 36
<211> LENGTH: 30
<212> TYPE: DNA
<213> ORGANISM: Homo sapiens

<400> SEQUENCE: 36
tgtccggccc ttagccctcc cacacataac                                              30

<210> SEQ ID NO 37
<211> LENGTH: 28
<212> TYPE: DNA
<213> ORGANISM: Homo sapiens

<400> SEQUENCE: 37
ggagggctaa gggccggaca gcgaactg                                                28

<210> SEQ ID NO 38
<211> LENGTH: 28
<212> TYPE: DNA
<213> ORGANISM: Homo sapiens

<400> SEQUENCE: 38
ggagggctaa gggccggaca gcgaactg                                                28

<210> SEQ ID NO 39
<211> LENGTH: 23
<212> TYPE: DNA
<213> ORGANISM: Homo sapiens

<400> SEQUENCE: 39 gagggggtgtg tagtgcgcgg ggg                                                    23

<210> SEQ ID NO 40
<211> LENGTH: 23
<212> TYPE: DNA
<213> ORGANISM: Homo sapiens

<400> SEQUENCE: 40
gcagtaatat accgcggagc tgg                                                     23

<210> SEQ ID NO 41
<211> LENGTH: 23
<212> TYPE: DNA
<213> ORGANISM: Homo sapiens

<400> SEQUENCE: 41
gtgcccggca cggccattaa cgg                                                     23

<210> SEQ ID NO 42
<211> LENGTH: 25
<212> TYPE: DNA
<213> ORGANISM: Homo sapiens

<400> SEQUENCE: 42
caccgtccca agcagctgaa ctaca        25

<210> SEQ ID NO 43
<211> LENGTH: 24
<212> TYPE: DNA
<213> ORGANISM: Homo sapiens

<400> SEQUENCE: 43
caccgtcgcg tgttgcccac gcgt        24

<210> SEQ ID NO 44
<211> LENGTH: 24
<212> TYPE: DNA
<213> ORGANISM: Homo sapiens

<400> SEQUENCE: 44
caccggcatt atgaacctac ttcg        24

<210> SEQ ID NO 45
<211> LENGTH: 6721
<212> TYPE: DNA
<213> ORGANISM: Homo sapiens

<400> SEQUENCE: 45
tggtcctgca actttatccg cctccatcca gtctattaat tgttgccggg aagctagagt        60
aagtagttcg ccagttaata gtttgcgcaa cgttgttgcc attgctacag gcatcgtggt       120
gtcacgctcg tcgtttggta tggcttcatt cagctccggt tcccaacgat caaggcgagt       180
tacatgatcc cccatgttgt gcaaaaaagc ggttagctcc ttcggtcctc cgatcgttgt       240
cagaagtaag ttggccgcag tgttatcact catggttatg gcagcactgc ataattctct       300
tactgtcatg ccatccgtaa gatgcttttc tgtgactggt gagtactcaa ccaagtcatt       360
ctgagaatag tgtatgcggc gaccgagttg ctcttgcccg gcgtcaatac gggataatac       420
cgcgccacat agcagaactt taaaagtgct catcattgga aaacgttctt cggggcgaaa       480
actctcaagg atcttaccgc tgttgagatc cagttcgatg taacccactc gtgcacccaa       540
ctgatcttca gcatctttta ctttcaccag cgtttctggg tgagcaaaaa caggaaggca       600
aaatgccgca aaaagggaa taagggcgac acggaaatgt tgaatactca tactcttcct       660
tttttcaatat tattgaagca tttatcaggg ttattgtctc atgagcggat acatatttga       720
atgtatttag aaaaataaac aaatagggt tccgcgcaca tttccccgaa aagtgccacc       780
taaattgtaa gcgttaatat tttgttaaaa ttcgcgttaa attttgtta aatcagctca       840
ttttttaacc aataggccga atcggcaaa atcccttata aatcaaaaga atagaccgag       900
atagggttga gtgttgttcc agtttggaac aagagtccac tattaaagaa cgtggactcc       960
aacgtcaaag ggcgaaaaac cgtctatcag ggcgatggcc cactacgtga accatcaccc      1020
taatcaagtt ttttggggtc gaggtgccgt aaagcactaa atcggaaccc taaagggagc      1080
ccccgattta gagcttgacg gggaaagccg gcgaacgtgg cgagaaagga agggaagaaa      1140
gcgaaaggag cgggcgctag ggcgctggca agtgtagcgg tcacgctgcg cgtaaccacc      1200
acacccgccg cgcttaatgc gccgctacag ggcgcgtccc attcgccatt caggctgcgc      1260
aactgttggg aagggcgatc ggtgcgggcc tcttcgctat tacgccagct ggcgaaaggg      1320
ggatgtgctg caaggcgatt aagttgggta acgccagggt tttcccagtc acgacgttgt      1380
aaaacgacgg ccagtgaatt accagcgatg gaacgagctc tttctcacct ggcctccttc      1440

```
agcatttctg tccctcagtc cttagcaagc ccaggagctg ttgagtttgg caggtgccga      1500
gtgctgttcc tgcctgtgta gctgtggctc agtcctgtgg gggccccgct gtggcccgag      1560
tgcagtgatt cgaggcgctg agtgttccct gactccttct ccaggagctg tgttcagact      1620
ttcgcagctc ttggcttgga gctcctggag ggcttggcat tgccgaccaa tgtggaggtc      1680
gacagtgaga gaggaggaat gctagctttc ttgaccagtc cattaaataa gtgggatatt      1740
ggccaggcac ggcggctcac gccttaatcc cagcactttg ggaggctgag gcgggtggat      1800
cacgagctca ggagttcaag accagcctgg ccaacatggt gaaaccccct ctatactaaa      1860
aatacaaata ttagctgggc gtggtggcag gcgcctgtaa tcctagctac ttgggaggct      1920
gaggcaggag aacagcttga aaccggaagg tggagtttgc agtgagccaa gattgcgcca      1980
ctgcactcca acctgggcaa caagagcaaa actctatctc aaaaaaaaaa aaaaaagtag      2040
gatatctgtt tctgcttaga aaaatcagaa ttttctaaat gccaggtgtt ctgaatacgt      2100
aagtatggga gacgactcag cctgtttcat ttttatgtaa aatcttcgcg tagccatgtg      2160
gcactggacc gagatgaaag caaagacatt tctccttaac tttgtttcta ggaatgttcc      2220
ggagaatcac agcagctgcc actaggctgt tccgcagtga tggctgtggc ggcagttttct      2280 acaccctgga cagcttgaac ttgcgggctc gttccatgat caccacccac ccggccctgg      2340
tgctgctctg tgtcagata ctgctgcttg tcaaccacac cgactaccgc tggtgggcag      2400
aagtgcagca gaccccgaac ctaggtgaca cagcaagacg ttgtctctgg ggaaaaaaga      2460
aagaaacgga accacgcggt gtgcagcctt ctgagtctgg cccctttcgg taggttcata      2520
atgccccaca gcccagggcg ccagcccaga taacttcgta tagcatacat tatacgaagt      2580
tattaggaat tcgtctgaag aggagtttac gtccagccaa gcttaggatc tcgacctcga      2640
aattctaccg ggtaggggag gcgcttttcc caaggcagtc tggagcatgc gctttagcag      2700
ccccgctggg cacttggcgc tacacaagtg gcctctggcc tcgcacacat tccacatcca      2760
ccggtaggcg ccaaccggct ccgttctttg gtggccccctt cgcgccacct tctactcctc      2820
ccctagtcag gaagttcccc cccgccccgc agctcgcgtc gtgcaggacg tgacaaatgg      2880
aagtagcacg tctcactagt ctcgtgcaga tggacagcac cgctgagcaa tggaagcggg      2940
taggcctttg gggcagcggc caatagcagc tttgctcctt cgctttctgg gctcagaggc      3000
tgggaagggg tgggtccggg ggcgggctca ggggcgggct caggggcggg gcgggcgccc      3060
gaaggtcctc cggaggcccg gcattctgca cgcttcaaaa gcgcacgtct gccgcgctgt      3120
tctcctcttc ctcatctccg ggcctttcga cctgcatcca tctagatctc gagcagctga      3180
agcttagcta gcatgaccga gtacaagccc acggtgcgcc tcgccacccg cgacgacgtc      3240
ccccgggccg tacgcaccct cgccgccgcg ttcgccgact accccgccac gcgccacacc      3300
gtcgacccgg accgccacat cgagcgggtc accgagctgc aagaactctt cctcacgcgc      3360
gtcgggctcg acatcggcaa ggtgtgggtc gcggacgacg gcgccgcggt ggcggtctgg      3420
accacgccgg agagcgtcga agcggggggcg gtgttcgccg agatcggccc cgcatggcc      3480 gagttgagcg gttcccggct ggccgcgcag caacagatgg aaggcctcct ggcgccgcac      3540
cggcccaagg agcccgcgtg gttcctggcc accgtcggcg tctcgcccga ccaccagggc      3600
aagggtctgg gcagcgccgt cgtgctcccc ggagtggagg cggccgagcg cgccggggtg      3660
cccgccttcc tggagacctc cgcgcccgc aacctcccct tctacagcg gctcggcttc      3720 accgtcaccg ccgacgtcga ggtgcccgaa ggaccgcgca cctggtgcat gacccgcaag      3780
cccggtgcct gaggatcctc tgcagaaatt gatgatctat taaacaataa agatgtccac      3840
```

```
taaaatggaa gttttttcctg tcatactttg ttaagaaggg tgagaacaga gtacctacat    3900
tttgaatgga aggattggag ctacgggggt gggggtgggg tgggattaga taaatgcctg    3960
ctctttactg aaggctcttt actattgctt tatgataatg tttcatagtt ggatatcata    4020
atttaaacaa gcaaaaccaa attaagggcc agctcattcc tcccactcat gatctataga    4080
tctatagatc tctcgtggga tcattgtttt tctcttgatt cccactttgt ggttctaagt    4140
actgtggttt ccaaatgtgt cagtttcata gcctgaagaa cgagatcagc agcctctgtt    4200
ccacatacac ttcattctca gtattgtttt gccaagttct aattccatca gaagctgact    4260
ctagaggcct ataacttcgt atagcataca ttatacgaag ttatcaccct gtcctgagac    4320
tcccagtaac ctgagctttg gccaccgtta aagcattttc attttccatt ttttgtgagg    4380
gcttgtgaaa tttctgctgc atattaatat tcctttcatg gacagcatat tattgggaca    4440
aacatgcggt ccagctaaag gcattcaaaa tagcagttgc tttctaaatg cgattttctt    4500
tggcaggttc tttgacacca ttgcatcttg tgggatatgc ttgtcatgct ctgtggctcc    4560
tactaagttc tagtccttaa attggttcca tagccagaca tgttgcaatg tcttaacctc    4620
attataaagt aaatgtggtt ctggttatcc ttagataatg aagtaacagt gtagcaaatt    4680
tcaaaacctc ttggaaatgt tattttacca ttcaaaaagg cttactaagg ttctcgttat    4740
gggtggccct cttttttgcaa aaggttttca ggcttaagct ccatttctag gtgctccaac    4800
actccattat ttgtatatgt atggaaataa aagctgtgac cacccccaac cctggccccc    4860
gcccagctga atcctcagca cagtatttct ggaaggctca agatcccacg ctggggaaaa    4920
gaagttctgg agacaaaaga gggcaggtgc tgccgtgcct ctctgctcag tatggatact    4980
ggaccttgtg ctgccagggc tcccagtagg gccagttcat ggcactcagc tggaaagtcc    5040
actgttggga ggcattctta accatccact ctgtgccgta tgtagtgggg tctggtcatt    5100
ctgttggagg agacagacca gtgacgacat ttgaaatgct tggtggatgt cttaggcctg    5160
ttacgatgac tgagcactgt gggggcagga gacagaaagt cagtgtctcc tagttctgtg    5220
ctgctttaac gtgcatagaa atcagctgcg gattcagcag atcactcctt ttctgacaga    5280
tgggcctgct tactctgatg ttatttgtga gccaggtacc gttccatcag tccagcttgg    5340
cgtaatcatg gtcatagctg tttcctgtgt gaaattgtta tccgctcaca attccacaca    5400
acatacgagc cggaagcata aagtgtaaag cctggggtgc ctaatgagtg agctaactca    5460
cattaattgc gttgcgctca ctgcccgctt tccagtcggg aaacctgtcg tgccagctgc    5520
attaatgaat cggccaacgc gcggggagag gcggtttgcg tattgggcgc tcttccgctt    5580
cctcgctcac tgactcgctg cgctcggtcg ttcggctgcg gcgagcggta tcagctcact    5640
caaaggcggt aatacggtta tccacagaat caggggataa cgcaggaaag aacatgtgag    5700
caaaaggcca gcaaaaggcc aggaaccgta aaaaggccgc gttgctggcg ttttttccata    5760
ggctccgccc cctgacgag catcacaaaa atcgacgctc aagtcagagg tggcgaaacc    5820
cgacaggact ataaagatac caggcgtttc ccctggaag ctccctcgtg cgctctcctg    5880
ttccgaccct gccgcttacc ggatacctgt ccgcctttct cccttcggga agcgtggcgc    5940
tttctcatag ctcacgctgt aggtatctca gttcggtgta ggtcgttcgc tccaagctgg    6000
gctgtgtgca cgaaccccc gttcagcccg accgctgcgc cttatccggt aactatcgtc    6060
ttgagtccaa cccggtaaga cacgacttat cgccactggc agcagccact ggtaacagga    6120
ttagcagagc gaggtatgta ggcggtgcta cagagttctt gaagtggtgg cctaactacg    6180
```

```
gctacactag aaggacagta tttggtatct gcgctctgct gaagccagtt accttcggaa    6240
aaagagttgg tagctcttga tccggcaaac aaaccaccgc tggtagcggt ggttttttg     6300 tttgcaagca gcagattacg cgcagaaaaa aaggatctca agaagatcct tgatcttttt    6360
ctacggggtc tgacgctcag tggaacgaaa actcacgtta agggattttg gtcatgagat    6420
tatcaaaaag gatcttcacc tagatccttt taaattaaaa atgaagtttt aaatcaatct    6480
aaagtatata tgagtaaact tggtctgaca gttaccaatg cttaatcagt gaggcaccta    6540
tctcagcgat ctgtctattt cgttcatcca tagttgcctg actcccgtc gtgtagataa      6600 ctacgatacg ggagggctta ccatctggcc ccagtgctgc aatgataccg cgagacccac    6660
gctcaccggc tccagattta tcagcaataa accagccagc cggaagggcc gagcgcagaa    6720
g                                                                    6721
```

```
<210> SEQ ID NO 46
<211> LENGTH: 18
<212> TYPE: DNA
<213> ORGANISM: Homo sapiens

<400> SEQUENCE: 46
cgtgaattgc tgccctct                                                  18

<210> SEQ ID NO 47
<211> LENGTH: 20
<212> TYPE: DNA
<213> ORGANISM: Homo sapiens

<400> SEQUENCE: 47
cagaaacccc tagcttccaa                                                20

<210> SEQ ID NO 48
<211> LENGTH: 19
<212> TYPE: DNA
<213> ORGANISM: Homo sapiens

<400> SEQUENCE: 48
cccagagccc cattcattg                                                 19

<210> SEQ ID NO 49
<211> LENGTH: 20
<212> TYPE: DNA
<213> ORGANISM: Homo sapiens

<400> SEQUENCE: 49
aggacaaggg aagacccaag                                                20

<210> SEQ ID NO 50
<211> LENGTH: 93
<212> TYPE: DNA
<213> ORGANISM: Mus musculus

<400> SEQUENCE: 50
cagagggtgc ctggtgaaat gccttttgta ccatctgttg tcagatacaa acagtaccat    60
cattccagga agttccctct tgtccctta tca                                  93

<210> SEQ ID NO 51
<211> LENGTH: 99
<212> TYPE: DNA
<213> ORGANISM: Unknown
<220> FEATURE:
<223> OTHER INFORMATION: Description of Unknown:
```

Marmoset oligonucleotide

<400> SEQUENCE: 51
tccctggtga cagagcaaga ccttgtctct ggggaaaaaa aattaagaaa gaaatggaag    60
catgcagtgt gcagccttttt gagtctgccc tctcggtct                         99

<210> SEQ ID NO 52
<211> LENGTH: 98
<212> TYPE: DNA
<213> ORGANISM: Macaca sp.

<400> SEQUENCE: 52
accctaggtg acacagcaag accttgtctt tgggaaaaaa attaagaaag agatggaacc    60
acacagtgtg cagcctttttg agtctggccc cttgcact                          98

<210> SEQ ID NO 53
<211> LENGTH: 88
<212> TYPE: DNA
<213> ORGANISM: Pongo sp.

<400> SEQUENCE: 53
agcctgggtg acacagcaag accttgtctc tgggagaaag aaacggaacc acgcagtgtg    60
cagccttttg agtctggccc ctttcggt                                      88

<210> SEQ ID NO 54
<211> LENGTH: 94
<212> TYPE: DNA
<213> ORGANISM: Pan troglodytes

<400> SEQUENCE: 54
agcctaggtg acacagcaag acattgtctc tggggaaaaa agaaagaaac ggaaccacgc    60
agtgtgcagc cttctgagtc tggccccttt cggt                               94

<210> SEQ ID NO 55
<211> LENGTH: 94
<212> TYPE: DNA
<213> ORGANISM: Gorilla sp.

<400> SEQUENCE: 55
agcctaggtg acacagcaag acgttgtctc tggggaaaaa agaaagaaac ggaaccacgc    60
agtgtgcagc cttctgagtc tggccccttt cggt                               94

<210> SEQ ID NO 56
<211> LENGTH: 94
<212> TYPE: DNA
<213> ORGANISM: Homo sapiens

<400> SEQUENCE: 56
agcctaggtg acacagcaag acgttgtctc tggggaaaaa agaaagaaac ggaaccacgc    60
ggtgtgcagc cttctgagtc tggccccttt cggt                               94

<210> SEQ ID NO 57
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57

```
ccaagatgga cggccgctc                                                  19
```

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58

```
aggacaaggg aagacccaag                                                 20
```

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59

```
ctccagcttt tgttcccttt                                                 20
```

<210> SEQ ID NO 60
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60

```
ccaattcgcc ctatagtgag tc                                              22
```

<210> SEQ ID NO 61
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61

```
aaagggaaca aaagctggag gggtcacact tggggtcct                            39
```

<210> SEQ ID NO 62
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62

```
tctagggtta aaagcagaac ctgagcggc                                       29
```

<210> SEQ ID NO 63
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63

```
aggttctgct tttaaccctagaaagatagt ctgc                                  34
```

<210> SEQ ID NO 64
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
gggccgcagg ttaaccctag aaagataatc atattg                          36

<210> SEQ ID NO 65
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
tttctagggt taacctgcgg cccagagccc                                 30

<210> SEQ ID NO 66
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
gactcactat agggcgaatt ggcctcccca tcagcaacgt gt                   42

<210> SEQ ID NO 67
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
ggtaaaagca gaacctgagc gg                                         22

<210> SEQ ID NO 68
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
gctgcaccga ccgtgagttt ggg                                        23

<210> SEQ ID NO 69
<211> LENGTH: 8759
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 69
gtggcacttt tcggggaaat gtgcgcggaa cccctatttg tttatttttc taaatacatt    60

```
caaatatgta tccgctcatg agacaataac cctgataaat gcttcaataa tattgaaaaa    120
ggaagagtat gagtattcaa catttccgtg tcgcccttat tccctttttt gcggcatttt    180
gccttcctgt ttttgctcac ccagaaacgc tggtgaaagt aaaagatgct gaagatcagt    240
tgggtgcacg agtgggttac atcgaactgg atctcaacag cggtaagatc cttgagagtt    300
ttcgccccga agaacgtttt ccaatgatga gcacttttaa agttctgcta tgtggcgcgg    360
tattatcccg tattgacgcc gggcaagagc aactcggtcg ccgcatacac tattctcaga    420
atgacttggt tgagtactca ccagtcacag aaaagcatct tacggatggc atgacagtaa    480
gagaattatg cagtgctgcc ataaccatga gtgataacac tgcggccaac ttacttctga    540
caacgatcgg aggaccgaag gagctaaccg cttttttgca acatggggg atcatgtaa      600 ctcgccttga tcgttgggaa ccggagctga atgaagccat accaaacgac gagcgtgaca    660
ccacgatgcc tgtagcaatg gcaacaacgt tgcgcaaact attaactggc gaactactta    720
ctctagcttc ccggcaacaa ttaatagact ggatggaggc ggataaagtt gcaggaccac    780
ttctgcgctc ggcccttccg gctggctggt ttattgctga taaatctgga gccggtgagc    840
gtgggtctcg cggtatcatt gcagcactgg ggccagatgg taagccctcc cgtatcgtag    900
ttatctacac gacggggagt caggcaacta tggatgaacg aaatagacag atcgctgaga    960
taggtgcctc actgattaag cattggtaac tgtcagacca agtttactca tatatacttt   1020
agattgattt aaaacttcat ttttaattta aaaggatcta ggtgaagatc cttttgata    1080 atctcatgac caaaatccct taacgtgagt tttcgttcca ctgagcgtca gaccccgtag   1140
aaaagatcaa aggatcttct tgagatcctt ttttctgcg cgtaatctgc tgcttgcaaa    1200
caaaaaaacc accgctacca gcggtggttt gtttgccgga tcaagagcta ccaactcttt   1260
ttccgaaggt aactggcttc agcagagcgc agataccaaa tactgtcctt ctagtgtagc   1320
cgtagttagg ccaccacttc aagaactctg tagcaccgcc tacataccctc gctctgctaa   1380 tcctgttacc agtggctgct gccagtggcg ataagtcgtg tcttaccggg ttggactcaa   1440
gacgatagtt accggataag cgcagcggt cgggctgaac ggggggttcg tgcacacagc    1500
ccagcttgga gcgaacgacc tacaccgaac tgagatacct acagcgtgag ctatgagaaa   1560
gcgccacgct tcccgaaggg agaaaggcgg acaggtatcc ggtaagcggc agggtcggaa   1620
caggagagcg cacgagggag cttccagggg gaaacgcctg gtatctttat agtcctgtcg   1680
ggtttcgcca cctctgactt gagcgtcgat ttttgtgatg ctcgtcaggg gggcggagcc   1740 tatgaaaaa cgccagcaac gcggcctttt tacggttcct ggccttttgc tggccttttg    1800
ctcacatgtt ctttcctgcg ttatcccctg attctgtgga taaccgtatt accgcctttg   1860
agtgagctga taccgctcgc cgcagccgaa cgaccgagcg cagcgagtca gtgagcgagg   1920
aagcggaaga gcgcccaata cgcaaaccgc ctctccccgc gcgttggccg attcattaat   1980
gcagctggca cgacaggttt cccgactgga aagcgggcag tgagcgcaac gcaattaatg   2040
tgagttagct cactcattag gcaccccagg ctttacactt tatgcttccg gctcgtatgt   2100
tgtgtggaat tgtgagcgga taacaatttc acacaggaaa cagctatgac catgattacg   2160
ccaagcgcgc aattaaccct cactaaaggg aacaaaagct ggagctccac cgcggggcgc   2220
gccgcagcta gattaaccct agaaagatag tctgcgtaaa attgacgcat gcattcttga   2280
aatattgctc tctcttttcta aatagcgcga atccgtcgct gtgcatttag gacatctcag   2340
tcgccgcttg gagctcccgt gaggcgtgct tgtcaatgcg gtaagtgtca ctgatttga    2400 actataacaa ccgcgtgagt caaaatgacg catgattatc ttttacgtga cttttaagat   2460
```

```
ttaactcata cgataattat attgttattt cgtgttctac ttacgtgata acttattata    2520
tatatatttt cttgttatag atgggaattc agacatgata agatacattg atgagtttgg    2580
acaaaccaca actagaatgc agtgaaaaaa atgctttatt tgtgaaattt gtgatgctat    2640
tgctttattt gtaaccatta taagctgcaa taaacaagtt tcgaggtcga gtgtcagtcc    2700
tgctcctcgg ccacgaagtg cttagccctc ccacacataa ccagagggca gcaattcacg    2760
aatcccaact gccgtcggct gtccatcact gtccttcact atggctttga tcccaggatg    2820
cagatcgaga agcacctgtc ggcaccgtcc gcaggggctc aagatgcccc tgttctcatt    2880
tccgatcgcg acgatacaag tcaggttgcc agctgccgca gcagcagcag tgcccagcac    2940
cacgagttct gcacaaggtc ccccagtaaa atgatataca ttgacaccag tgaagatgcg    3000
gccgtcgcta gagagagctg cgctggcgac gctgtagtct tcagagatgg ggatgctgtt    3060
gattgtagcc gttgctcttt caatgagggt ggattcttct tgagacaaag gcttggccat    3120
ggtttagttc ctcaccttgt cgtattatac tatgccgata tactatgccg atgattaatt    3180
gtcaacacgg tccggtctaa caaaaaagcc aaaaacggcc agaatttagc ggacaattta    3240
ctagtctaac actgaaaaatt acatattgac ccaaatgatt acatttcaaa aggtgcctaa    3300
aaaacttcac aaaacacact cgccaacccc gagcgcatag ttcaaaaccg gagcttcagc    3360
tacttaagaa gataggtaca taaaaccgac aaagaaact gacgcctcac ttatccctcc    3420
cctcaccaga ggtccggcgc ctgtcgattc aggagagcct accctaggcc cgaaccctgc    3480
gtcctgcgac ggagaaaagc ctaccgcaca cctaccggca ggtggcccca ccctgcatta    3540
taagccaaca gaacgggtga cgtcacgaca cgacgagggc gcgcgctccc aaaggtacgg    3600
gtgcactgcc caacggcacc gccataactg ccgcccccgc aacagacgac aaaccgagtt    3660
ctccagtcag tgacaaactt cacgtcaggg tccccagatg gtgccccagc ccatctcacc    3720
cgaataagag cttcccgca ttagcgaagg cctcaagacc ttgggttctt gccgcccacc    3780
atgcccccca ccttgtttca cgacctcac agcccgcctc acaagcgtct tccattcaag    3840
actcgggaac agccgccatt tgctgcgct ccccccaacc cccagttcag ggcaaccttg    3900
ctcgcggacc cagactacag cccttggcgg tctctccaca cgcttccgtc ccaccgagcg    3960
gcccggcggc cacgaaagcc ccggccagcc cagcagcccg ctactcacca agtgacgatc    4020
acagcgatcc acaaacaaga accgcgaccc aaatcccggc tgcgacggaa ctagctgtgc    4080
cacacccggc gcgtccttat ataatcatcg gcgttcaccg ccccacggag atccctccgc    4140
agaatcgccg agaagggact actttcctc gcctgttccg ctctctggaa agaaaaccag    4200
tgccctagag tcacccaagt cccgtcctaa aatgtccttc tgctgatact ggggttctaa    4260
ggccgagtct tatgagcagc gggccgctgt cctgagcgtc cggcggaag gatcaggacg    4320 ctcgtgcgcc cttcgtctga cgtggcagcg ctcgccgtga ggaggggcg cccgcggggg    4380 gcgccaaaac ccggcgcgga ggccagatct cccgatctcg agcgacattg attattgact    4440
agttattaat agtaatcaat tacggggtca ttagttcata gcccatatat ggagttccgc    4500
gttacataac ttacggtaaa tggcccgcct ggctgaccgc ccaacgaccc ccgcccattg    4560
acgtcaataa tgacgtatgt tcccatagta acgccaatag ggactttcca ttgacgtcaa    4620
tgggtggagt atttacggta aactgcccac ttggcagtac atcaagtgta tcatatgcca    4680
agtacgcccc ctattgacgt caatgacggt aaatggcccg cctggcatta tgcccagtac    4740
atgaccttat gggactttcc tacttggcag tacatctacg tattagtcat cgctattacc    4800
```

```
atggtcgagg tgagccccac gttctgcttc actctcccca tctcccccc  ctccccaccc    4860
ccaattttgt atttatttat tttttaatta ttttgtgcag cgatggggc ggggggggg     4920
gggggcgcg  cgccaggcgg ggcggggcgg ggcgagggg  gggcgggc  gaggcggaga   4980
ggtgcggcgg cagccaatca gagcggcgcg ctccgaaagt ttccttttat ggcgaggcgg   5040
cggcggcggc ggccctataa aaagcgaagc gcgcggcggg cgggagtcgc tgcgcgctgc   5100
cttcgccccg tgccccgctc cgccgccgcc tcgcgccgcc cgccccggct ctgactgacc   5160
gcgttactcc cacaggtgag cgggcgggac ggcccttctc ctccgggctg taattagcgc   5220
ttggttaat  gacggcttgt ttcttttctg tggctgcgtg aaagccttga ggggctccgg   5280
gagggccctt tgtgcggggg gagcggctcg ggggtgcgt  gcgtgtgtgt gtgcgtgggg   5340
agcgccgcgt gcggctccgc gctgcccggc ggctgtgagc gctgcgggcg cggcgcgggg   5400
cttttgtgcgc tccgcagtgt gcgcgagggg agcgcggccg gggcggtgc  cccgcggtgc   5460
ggggggggct gcgaggggaa caaaggctgc gtgcggggtg tgtgcgtggg ggggtgagca   5520
gggggtgtgg gcgcgtcggt cgggctgcaa ccccccctgc accccctcc  ccgagttgct   5580
gagcacggcc cggcttcggg tgcggggctc cgtacggggc gtggcgcggg gctcgccgtg   5640
ccgggcgggg ggtggcggca ggtgggggtg ccgggcgggg cggggccgcc tcgggccggg   5700
gagggctcgg gggaggggcg cggcggcccc cggagcgccg gcggctgtcg aggcgcggcg   5760
agccgcagcc attgccttt  atggtaatcg tgcgagaggg cgcagggact tcctttgtcc   5820
caaatctgtg cggagccgaa atctgggagg cgccgccgca ccccctctag cgggcgcggg   5880
gcgaagcggt gcggcgccgg caggaaggaa atgggcgggg agggccttcg tgcgtcgccg   5940
cgccgccgtc cccttctccc tctccagcct cggggctgtc cgcgggggga cggctgcctt   6000
cggggggac  ggggcagggc ggggttcggc ttctggcgtg tgaccggcgg ctctagagcc   6060
tctgctaacc atgttcatgc cttcttcttt ttcctacagc tcctgggcaa cgtgctggtt   6120
attgtgctgt ctcatcattt tggcaaagaa ttaaattaa  ttaatctcga cggtatcggt   6180
taacgaatcc aagggcgaat tccagcacac tggcggccgt tactagtgga tccaagcttg   6240
ccaccatggc ggaaggatcc gtcgccaggc agcctgacct cttgacctgc gacgatgagc   6300
cgatccatat ccccggtgcc atccaaccgc atggactgct gctcgccctc gccgccgaca   6360
tgacgatcgt tgccggcagc gacaaccttc ccgaactcac cggactggcg atcgcgcccc   6420
tgatcggccg ctctgcggcc gatgtcttcg actcggagac gcacaaccgt ctgacgatcg   6480
ccttggccga gccggggcg  gccgtcgag  caccgatcac tgtcggcttc acgatgcgaa   6540
aggacgcagg cttcatcggc tcctggcatc gccatgatca gctcatcttc ctcgagctcg   6600
agcctcccca gcgggacgtc gccgagccgc aggcgttctt ccgccgcacc aacagcgcca   6660
tccgccgcct gcaggccgcc gaaaccttgg aaagcgcctg cgccgccgcg gcgcaagagg   6720
tgcggaagat taccggcttc gatcgggtga tgatctatcg cttcgcctcc gacttcagcg   6780
gcgaagtgat cgcagaggat cggtcgcgcc aggtcgagtc aaaactaggc ctgcactatc   6840
ctgcctcaac cgtgccggcg caggcccgtc ggctctatac catcaacccg gtacggatca   6900
ttcccgatat caattatcgg ccggtgccgg tcaccccaga cctcaatccg gtcaccgggc   6960
ggccgattga tcttagcttc gccatcctgc gcagcgtctc gcccgtccat ctggagttca   7020
tgcgcaacat aggcatgcac ggcacgatgt cgatctcgat tttgcgcggc gagcgactgt   7080
ggggattgat cgtttgccat caccgaacgc cgtactacgt cgatctcgat ggccgccaag   7140
cctgcgagct agtcgcccag gttctggcct ggcagatcgg cgtgatggaa gagggaggta   7200
```

```
gtggatcaat gccagagcca gcgaagtctg ctcccgcccc gaaaaagggc tccaagaagg    7260
cggtgactaa ggcgcagaag aaaggcggca agaagcgcaa gcgcagccgc aaggagagct    7320
attccatcta tgtgtacaag gttctgaagc aggtccaccc tgacaccggc atttcgtcca    7380
aggccatggg catcatgaat tcgtttgtga acgacatttt cgagcgcatc gcaggtgagg    7440
cttcccgcct ggcgcattac aacaagcgct cgaccatcac ctccagggag atccagacgg    7500
ccgtgcgcct gctgctgcct ggggagttgg ccaagcacgc cgtgtccgag ggtactaagg    7560
ccatcaccaa gtacaccagc gctaagtgag cggccgcgac tctagatcat aatcagccat    7620
accacatttg tagaggtttt acttgcttta aaaaacctcc cacacctccc cctgaacctg    7680
aaacataaaa tgaatgcaat tgttgttgtt aacttgttta ttgcagctta taatggttac    7740
aaataaagca atagcatcac aaatttcaca aataaagcat tttttcact gcattctagt     7800 tgtggtttgt ccaaactcat caatgtatct taaggaattc gataaaagtt ttgttacttt    7860
atagaagaaa ttttgagttt ttgttttttt ttaataaata aataaacata aataaattgt    7920
ttgttgaatt tattattagt atgtaagtgt aaatataata aaacttaata tctattcaaa    7980
ttaataaata aacctcgata tacagaccga taaaacacat gcgtcaattt tacgcatgat    8040
tatctttaac gtacgtcaca atatgattat ctttctaggg ttaatctagc tgcggcgcgc    8100
cggtacccaa ttcgccctat agtgagtcgt attacgcgcg ctcactggcc gtcgttttac    8160
aacgtcgtga ctgggaaaac cctggcgtta cccaacttaa tcgccttgca gcacatcccc    8220
ctttcgccag ctggcgtaat agcgaagagg cccgcaccga tcgcccttcc caacagttgc    8280
gcagcctgaa tggcgaatgg gacgcgccct gtagcggcgc attaagcgcg gcgggtgtgg    8340
tggttacgcg cagcgtgacc gctacacttg ccagcgccct agcgcccgct cctttcgctt    8400
tcttcccttc ctttctcgcc acgttcgccg gctttccccg tcaagctcta aatcgggggc    8460
tccctttagg gttccgattt agtgctttac ggcacctcga ccccaaaaaa cttgattagg    8520
gtgatggttc acgtagtggg ccatcgccct gatagacggt ttttcgccct tgacgttgg    8580 agtccacgtt ctttaatagt ggactcttgt tccaaactgg aacaacactc aaccctatct    8640
cggtctattc ttttgattta tagggattt tgccgatttc ggcctattgg ttaaaaaatg    8700
agctgattta acaaaaattt aacgcgaatt ttaacaaaat attaacgctt acaatttag    8759
```

<210> SEQ ID NO 70
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70 caacag                                                                6

EMBRYONIC CELL-BASED THERAPEUTIC CANDIDATE SCREENING SYSTEMS, MODELS FOR HUNTINGTON'S DISEASE AND USES THEREOF

RELATED APPLICATIONS

This international application claims priority from U.S. Provisional Application No. 62/299,544 filed Feb. 24, 2016 and No. 62/300,056 filed Feb. 25, 2016. The entire disclosure of each of the foregoing provisional applications is incorporated by reference.

GOVERNMENT RIGHTS

This application is a national stage filing under 35 USC § 371 of International PCT Application number PCT/US2017/019529, filed Feb. 24, 2017, and claims priority from U.S. Provisional Application No. 62/299,544 filed Feb. 24, 2016 and No. 62/300,056 filed Feb. 25, 2016. The entire disclosure of each of the foregoing applications is incorporated by reference in its entirety.

SEQUENCE LISTING

The instant application contains a Sequence Listing which has been submitted electronically in ASCII format and is hereby incorporated by reference in its entirety. Said ASCII copy, created on Feb. 24, 2017, is named 11012-005430-WO0_SL.TXT and is 43,621 bytes in size.

BACKGROUND OF THE INVENTION

Field of the Invention

The present invention relates generally to the field of neurodegenerative disease. More particularly, it concerns novel methods and cell lines as research and screening tools for modeling Huntington's Disease and for drug and therapeutic target discovery for Huntington's Disease. Cell lines and platforms described here are more broadly useful for elucidating disease mechanisms and for investigating other neurodegenerative diseases in addition to Huntington's and more broadly CNS disorders.

Description of Related Art

Huntington's disease (HD), a dominant autosomal neurodegenerative disease, is caused by a dominant mutation in the N-terminal region of the Huntingtin (HTT) protein. HTT is a large protein of more than 3000 amino acids (aa) in humans, encoded by a single locus made of 69 exons. In the wildtype protein, the first exon contains a stretch of 15-35 poly-glutamine (polyQ) repeats. Mutations that expand the polyQ tract to more than 40 (>40) Qs lead inevitably to the devastating neurodegenerative disease. In Huntington's disease, the size of the polyQ expansion is tightly correlated with age of onset and severity, with longer expansions leading to an earlier manifestation of the disease. While HTT protein is expressed in all cells all the time (from the fertilized egg onward), the mutation remarkably seems to cause predominantly degeneration of selective populations of neurons in the corpus striatum, in the motor, frontal, and occipital cortices as well as in the hypothalamus. This ultimately leads to severe motor disorder, psychiatric disorder, and death.

Despite the fact that HTT was among the first disease-causing genes to be identified more than 20 years ago, the molecular and cellular aspects of pathophysiology, and even the exact function(s) of HTT protein, are very poorly understood. While animal models of HD have been useful in understanding some aspects of cellular deterioration, they have not provided candidates for an effective therapy for HD. This is likely due to species-specific differences at the molecular, cellular, developmental, and cognitive level. At the molecular level, the original assumption that the HTT locus encodes a single mRNA has proven to be wrong. It was recently demonstrated that the locus encodes multiple mRNA isoforms derived from differential splicing. Notably, it has been shown that some of these isoforms are species-specific, or species-restricted, including one that is only present in higher apes and humans (Ruzo, A. et al, 2015). At the cellular level, there are striking differences between the architectural organization of the brain between mice and humans. For example, the sub-ventricular zone (SVZ) of the developing brain is largely expanded in humans, with more anatomically and functionally complex cortical layer structures (Greig et al. Nat Rev Neurosci. 2013 November; 14(11):755-69). At the cognitive level, some of the earliest manifestations of the disease affect purely human-specific traits, such as language, which cannot be modeled in the mouse. Therefore, animal models of HD, while better than none, are seriously lacking as a system to study the underlying processes that are relevant to the human disease.

Several studies have recently pioneered the use of human cells for a better understanding of HD. Those include studies performed in diseased human medium spiny neurons (MSN), diseased human cortical neurons, as well as in human embryonic stem cells (hESCs) in which the HD mutation of HTT is present and induced-pluripotent stem cells (hiPSCs) from diseased individuals. However, unlike the highly inbred mouse, the human system displays non-homogeneity in genetic backgrounds, making comparative studies difficult to interpret and to generalize from individual cases. Human iPSCs have been used to model human disease, however, while hiPSCs are a versatile model, they have major drawbacks including: incomplete reprogramming, genomic instability, and variable differentiation potential depending on the epigenetic memory of their origin. In addition, as these cells are derived from patients that have been carrying the mutation throughout their life, there may be intrinsic alterations compromising cellular homeostasis. Therefore, there is a need in the art for more effective models of Huntington's disease.

SUMMARY OF THE DISCLOSURE

The methods and cells of the current disclosure represent a significant step towards overcoming the aforementioned deficiencies in the art by applying a reverse strategy and introducing an extension of the polyQ tract in normal hESCs, thus generating genetically substantially identical isogenic cell populations or lines with one population comprising cells modified to mimic the genetic defect at the origin of HD and another population comprising isogenic cells that are wild-type and therefore do not have the genetic defect. This approach has the advantage of using human pluripotent cells that are stable and can generate all cell types including those neurons that are compromised in HD. Comparative global transcriptome and unbiased metabolome analysis of these populations or lines revealed previously undetected differences caused solely by insertion of an expanded polyQ tract in a single genomic locus. These cells exhibit a specific and quantitative signature of the human disease that can be used as a platform for drug screening as well as for therapeutic target identification and refinement. Additionally, these cell lines can be partly differentiated ("differentiating") so as to commit to a specific, here a neuronal, fate, or fully (terminally) differentiated to neurons, at which point they present further qualitative and quantitative signatures of this disease, and provide two further platforms for to serve the same goals (drug screening and target investigation).

Compositions and methods disclosed herein concern a screening platform comprising a first population of in vitro human embryonic stem cells comprising a wild-type HTT gene; and a second population of embryonic stem cells isogenic to the first except that they have been genetically modified (which term as used herein includes progeny of modified cells) to comprise at the endogenous Huntingtin gene (htt) locus a polyQ repeat of at least 35 or preferably at least 40 glutamines in the N-terminal region of the Huntingtin protein (HTT) (disease form of the polyQ repeat). In other embodiments, the cells have been partially or fully differentiated to neural progenitors or neurons.

The cell lines and screening platforms of the disclosure comprise genetically defined alterations made in the endogenous htt gene that phenotypically recapitulate Huntington's Disease in humans. Furthermore, the cell lines have isogenic controls that share substantially identical genetic backgrounds but harbor a wild type HTT gene. This allows for a more definitive study of specific genetic variances compared to the wild-type cells and removes complications introduced by comparing different cells which vary via a multitude of genetic features and/or cells which have been already damaged by consequences of a disease form of the HTT gene. Furthermore, certain embodiments relate to modified cells that do not possess any heterologous or extraneously introduced sequences other than the disease form of the HTT gene (≥36Q and preferably ≥40Q). For example, in some such minimal intervention embodiments, no heterologous sequences remain after introduction of the disease form of HTT and even the permanent incorporation into the cell genome of detectable or selectable markers has been avoided. Heterologous sequences may disrupt chromatin structure, promoter structure, and/or gene function, and may, in some instances, lead to inaccurate disease modeling.

The polyQ may comprise one or both codons for Glutamine (i.e. CAA and/or CAG) and encodes for a protein with a glutamine repeat. In some embodiments, one or both glutamine codons in the polyQ portion of HTT and the glutamine repeats in this protein are uninterrupted. In some embodiments, the polyQ repeat comprises both CAA and CAG codons. In some embodiments, the polyQ repeat comprises 40-180 (as many as 265Q have been observed in humans) glutamines at the N-terminus of the HTT gene. In some embodiments, the polyQ repeat comprises at least, at most, or exactly 20 (and up to 35Q (at as low as 36Q low-penetrance HD is sometimes observed) or up to 39Q repeats as a control) 36, 40, 42, 45, 48, 50, 55, 56, 58, 60, 65, 67, 70, 72, 74, 75, 80, 85, 90, 95, 100, 105, 110, 115, 120, 125, 130, 135, 140, 145, 150, 155, 160, 165, 170, 175, 180, 185, 190, 195, 200, 210, 220, 230, 240, 250, 265, 300, 500, or 1000 glutamines (which includes any derivable range therein having as endpoints two of the foregoing glutamine repeat numbers).

The present inventors obtained resolution between the (disease) phenotype of human embryonic stem cells harboring only a 42-polyQ repeat segment and the nondisease phenotype of cells harboring a wild type polyQ segment of the HTT gene, and thus, in principle, it is not necessary to insert into the HTT gene a large number of polyQ repeats.

In some embodiments, the polyQ repeat comprises SEQ ID NO:1 or any segment thereof having at least 36 and preferably at least 40 glutamine residues.

In other embodiments, the polyQ repeat comprises, for example 42, 45, 48, 50, 56, 58, 67, 72, or 74 glutamine residues, and only CAG codons, even more closely mimicking the human disease gene in which the glutamine repeats are all encoded by CAG. The following sequence is illustrative of a modified full length HTT gene used in the experiments described herein. The wild type version of it had only 20 or 22 glutamine repeats. The modified gene had 48 polyQ repeats but was otherwise identical. In a specific embodiment, no markers were engineered into the cell's genome. Corresponding modified cell lines were made with 42, 56, 67 and 72 glutamine repeats.

An example of a sequence of an HTT gene having 50 polyQ (48CAG followed by CAACAG (SEQ ID NO:70)) repeats in the region corresponding to the N-terminal region of the HTT protein is identified as (SEQ ID NO: 2).

In some embodiments, the modified cells are not induced pluripotent cells. In some embodiments, the modified (and isogenic control) cells are hiPSC derived from young individuals (thus reducing the chance of epigenetic signature retention) having a wild type HTT before modification. For the modified hiPSC, an HD polyQ mutation is inserted into the wildtype HTT gene in the same manner as described herein for the hESC. While such an isogenic hiPSC system would still have some of the major drawbacks of iPSCs detailed above, it would nevertheless represent an improvement over a system employing hiPSCs derived from adults with the disease form of HTT.

In some embodiments, the modified cells are human embryonic stem cells isolated from human embryonic tissues. In some embodiments, the modified cells are cells isolated from human blastocysts and then modified. In further embodiments, the modified cells are human placental or umbilical cord stem cells.

In some embodiments, the cells comprise one or more markers. In some embodiments, the markers include detectable and/or selectable markers. In some embodiments, the marker is a gene that encodes a fluorescent protein, an antibiotic resistance protein, and/or an enzyme. In some embodiments, a marker is genetically linked to the disease form of the HTT gene so that detection of the marker signals presence of an HD mutation in the HTT gene. In some embodiments, the one or more markers are markers known in the art or described herein. In some embodiments markers are entirely omitted (or excised) from the modified cells ("pristine cells"). Suitable markers are known and can be for example fluorescent proteins, antibiotic resistance markers or enzymes.

In some embodiments, the cells are cultured on a plastic substrate or on a patterned adhesive surface or on a porous or permeable surface or support which permits the cultured ESC cells to be grown in a dense culture and to be fed and stimulated with pluripotency medium from both top and bottom of the culture dish, thereby maintaining pluripotency for a longer period of time, typically more than three weeks. This results in a more stable culture which is less laborious to maintain and which is amenable to automation for the culturing and/or testing methods disclosed herein. Systems for automated cell culture are described, for example in U.S. Pat. Nos. 9,469,865; 8,815,585; 9,376,658; and 8,119,368.

Such embodiments are also suitable for platforms of partially or fully differentiated cells since these are cultured for longer periods and, unlike pluripotent cell cultures, they need not be cultured on a confined surface to exhibit a particular phenotype (germ layers) which differs between the cells having the disease form of htt and those that do not.

One type of confined surface is provided by micropatterned glass coverslips which optionally are pretreated with one or more adhesion promoting coatings to facilitate cell adhesion. Cultures on such surfaces Another such surface is provided in the form of a porous filter support, e.g., one having a pore size range of about 0.4 to 0.6 microns such as the COSTAR™ Transwell system and other commercially available comparable systems.

In some embodiments, the cells are cultured according to conditions and/or methods described in Warmflash et al., Nature Methods. 2014 August: 11(8): 847-854, which is herein incorporated by reference for all purposes. In some embodiments, the adhesive surface, e.g., the coverslips, or other culture supporting surface, are coated with coating agents, which provide a priming or base coating layer on the surface that will support the culture and a matrix to further promote adherence of the cells. Coating agents or adherence promoting substrates suitable to coat the surface of a coverslip or multi-well plate or porous support include but are not limited to poly-D-lysine, poly-L-lysine, fibronectin, collagen, laminin, laminin-511 (LN-511), laminin-521 (LN-521), poly-L-ornithine, and any combination thereof.

In some embodiments, the matrix is a basement membrane matrix such as a Matrigel, Cultrex, or Geltrex basement membrane matrix. In some embodiments, the cells are cultured with a differentiating agent. In some embodiments, the differentiating agent is one or more morphogens, such as BMP4, WINT3A, activin, and combinations of two or more thereof, inhibitors (for example SB431542, Noggin, IWP2, LDN193189) of any of the foregoing and combinations of two or more of such inhibitors.

A further aspect of the disclosure relates to a method for making human (partly or fully) differentiated cells which have been derived from embryonic or induced pluripotent stem cells modified to comprise a disease HTT gene (and not bearing a wildtype gene) therefore comprising a disease form of this gene. In some embodiments, the method comprises culturing the modified ESC cells described herein under differentiating conditions. In some embodiments, isogenic (control) human differentiated cells are also provided which have not been modified to contain a disease form of the HTT gene and therefore contain the wild-type HTT gene. In some embodiments, the method is for making a human differentiated neuronal cell comprising a disease HTT gene, and the method comprises culturing the cells under neuronal differentiating conditions. In some embodiments, the neuronal differentiating conditions comprise contacting the cells with a BMP/TGFβ signaling pathway inhibitor. In some embodiments, the BMP/TGFβ signaling pathway inhibitor comprises one or both of SB431542 and LDN193189. In some embodiments, the differentiating conditions comprise contacting the cells with one or more of the following reagents to commit them to a neuronal fate: bFGF (basic fibroblast growth factor), EGF (epidermal growth factor), RA (retinoic acid), forskolin, IBMX (3-isobutyl-1-methyl-xanthine), and combinations thereof. Differentiation protocols, media and reagents are also respectively published and commercially available, e.g., from thermofisher.com.

In some embodiments, cells differentiated to a neuronal fate are further cultured until at least a substantial fraction (for example at least 20% of the cell population) of the cultured cells detach from the culturing substrate. In some embodiments, the further culturing step continues for up to about 45 days or longer. In such embodiments, the morphology of the resulting cells, which are neurons, with respect to one or more of (i) misregulation of mitotic spindle; (ii) appearance of multipolar mitotic figures; (iii) emergence of multiple centrioles in committed neural progenitors; and (iv) impaired ciliogenesis compared to wild-type cells constitutes a marker of disease phenotype appropriate for testing the effect of a potential therapeutic compound. Additional markers in post-mitotic neurons include giant morphology, multinucleation or both. Any of these markers or any two of them or any three or any four or more of them constitute a signature for the HD phenotype.

Each of the foregoing cell population types, pluripotent germ-layer exhibiting cells, differentiated cells committed to a neuronal fate or terminally differentiated neurons bearing a disease form of the HTT gene, alone or together with their isogenic wildtype counterparts constitute platforms for screening compounds to identify as therapeutic candidates compounds that will totally or partially reverse the aberrant phenotype associated with the disease form of the HTT gene by affecting one or more or preferably three or more of the parameters identified above whether they be on pluripotent cultured cells differentiated cells or fully differentiated neurons. They also each constitute an in vitro model for HD.

In some embodiments, regarding the culturing conditions or steps for the genetically modified and isogenic wild-type stem cells and/or differentiating and differentiated cells and their uses, it is specifically contemplated that any specific combination of reagents or steps disclosed herein may be used in the methods described herein. It is also specifically contemplated that any one or any combination of disclosed reagents or steps may be excluded from the methods described herein.

In some embodiments, the method further screens for differentiating or differentiated cells. In some embodiments, screening for such cells comprises detecting neuronal markers such as PAX6 and N-Cadherin protein expression in the cells. In some embodiments, the method further comprises isolating differentiating or differentiated cells. In some embodiments, the method further comprises freezing the cells (cryopreservation). In some embodiments, the method further comprises expanding cells that were previously frozen.

In some embodiments a reporter cell or cell population is provided for use in monitoring induction of germ layers, or fate acquisition, or both, in human embryonic stem cells. The cell population comprises human embryonic stem cells, wherein each cell comprises at least one of the following: a first detectable marker inserted into the genome of the cell so as to co-express with a first germ layer specific marker; a second detectable marker inserted into the genome of the cell so as to co-express with a second germ layer specific marker; and a third detectable marker inserted into the genome of the cell so as to co-express with a third germ layer specific marker.

In some embodiments, the fate reporter cell or cell population has the first, second and third detectable marker be a fluorescent protein, provided that when more than one detectable marker is a fluorescent protein, the fluorescent proteins are different so that as to distinguish between or among the germ layer specific markers upon detection of the first, second and or third detectable marker.

In some embodiments, the reporter cell or cell population further comprises a nuclear detectable marker, said marker having been introduced into the cell so as to co-express with a histone protein; in more specific embodiments, the nuclear detectable marker is a nuclear fluorescent protein, wherein the nuclear fluorescent protein, upon its detection, is distinguishable from as many of the first second and third detectable marker as are present in said cell. The nuclear detectable marker is optionally constitutively expressed. The the nuclear detectable marker is optionally infrared fluorescent protein.

In a further embodiment, the one or more of the first, second and third fluorescent protein, is selected from the group consisting of mCitrine, mCerulian and tdTomato provided that each of said proteins associated with one germ layer is distinct from the protein or proteins associated with the other germ layers.

In yet another aspect, a cell population is provided comprising human embryonic stem cells, wherein cells of said population have been genetically modified to comprise a nucleotide segment encoding a 41b isoform of human HTT protein, such that no cells of the population express any other isoform of the HTT protein. Additionally, a cell or cell population is provided wherein one or both alleles of the HTT gene have been knocked out, for use in connection with the screening methods described herein.

Further aspects relate to a cell and a cell population prepared by a method of the disclosure. More particular aspects relate to a cell pair (one modified, one wildtype) or cell population pair (one population of modified cells, one population unmodified but otherwise isogenic cells) prepared and assembled as a testing system according to a method of the disclosure. The cell population may contain selectable or detectable markers such as reporter substances or be devoid of some or all of such features ("pristine" HTT mutant cells).

Yet further aspects relate to a method for screening for therapeutic candidates for Huntington's Disease (HD) comprising contacting a test substance (compound or biologic, for example from a library) with the cells of the disclosure. In some embodiments, the method further comprises measuring a parameter that has been shown to be altered in cells containing a disease form of the HTT gene compared to isogenic cells containing the wildtype HTT gene wherein the cells are grown to a germ layer or induced to a particular degree of differentiation, early or advanced neuronal differentiation, the latter evinced by a substantial fraction of the differentiated cells having become terminally differentiated into neurons and dropped out of the cell cycle.

In some embodiments, a method for identifying a therapeutic candidate for Huntington's disease is provided comprising:
  (a) contacting a clonal population of human embryonic stem cells that expresses a mutant Huntingtin (HTT) gene which encodes an HTT protein comprising a polyQ repeat peptide segment of least 40 glutamine residues with a test substance;
  (b) culturing said clonal population; and
  (c) detecting whether the phenotype of the clonal population partially or fully reverts to the wild-type phenotype, wherein a test substance that causes a partial or complete reversion to the wild-type phenotype is a therapeutic candidate for Huntington's disease.

In alternative embodiments, a method for identifying a therapeutic candidate for Huntington's disease is provided comprising:
  (a) inducing neural differentiation in a clonal population of human embryonic stem cells that expresses a mutant of Huntingtin (HTT) gene which encodes an HTT protein comprising a polyQ repeat peptide segment of least 40 glutamine residues;
  (b) culturing said clonal population under conditions in which neural differentiation occurs to produce a differentiating or fully differentiated clonal population;
  (c) contacting said differentiating clonal population with a test substance; and
  (d) detecting whether the phenotype of the differentiating or differentiated clonal population partially or fully reverts to the wild-type phenotype, wherein a test substance that causes a partial or complete reversion to the wild-type phenotype is a therapeutic candidate for Huntington's disease.

In some embodiments, the phenotype partially or fully reversed by the test compound is aberrant rosette formation; in other embodiments, the phenotype partially or fully reversed by the test is giant and/or polynucleated neuron formation.

A more specific method provided by the present disclosure is a method for screening for therapeutic candidates using more than one platform as described herein and assessing whether partial or total reversion of phenotype occurs. A primary screening may be performed using germlayer cultures; compounds may be tested in neuronal progenitor cultures; and compounds may be further tested in fully differentiated neuron cultures. Compounds that test negative in all three cultures will be discarded. Compounds that test positive in one, two or three screens will be ranked, assessed for potency, toxicity and pharmacokinetics and then tested further in vitro and in vivo in animals and humans.

The populations to be treated may be embryos, infants, children and/or adults afflicted with HD.

Compounds that rescue at least two phenotypes (or parameter constituents of a disease phenotype signature) may be preferred.

In some embodiments, the parameter is cell morphology and/or organization, gene expression, cytokine expression, cell number expansion or a metabolic signature (e.g., lower catalase activity, abnormal levels of TCA cycle metabolites, lower ATP/ADP ratios, lower NADH/NAD or NADHP/NADP ratios) or a combination of two or more of the foregoing. In some embodiments, the parameter is cell number or germ layer size, and/or germ layer marker expression. In some embodiments, the parameter is perturbed organization (partial loss of organization) which may be apparent prior to or after differentiation to a neuronal phenotype; in some embodiments, the parameter is rosette morphology, neuron size, neuron nuclear morphology, mitotic orientation, and/or mitotic cilial morphology and size In some embodiments, the method further comprises contacting a control isogenic cell with the potential therapeutic candidate and observing and/or quantifying whether such contact brings about one or more changes in the foregoing parameter or parameters.

In some embodiments, the method comprises comparing a parameter from the cell comprising a disease form of the HTT gene with the control cell after each has been contacted with the potential therapeutic candidate. In some embodiments, the method further comprises determining the level of expression of one or more germ layer markers in the cells. In some embodiments, the germ layer marker comprises one or more of SOX2, BRA, and CDX2. In some embodiments, the germ layer marker comprises all three of SOX2, BRA, and CDX2. In further embodiments, the germ layer marker comprises one or more of OCT4, NANOG (both pluripotency markers along with Sox2), EOMES (mesoderm marker along with BRA), SOX17, GATA6 (both endoderm markers), and CDX2 (trophoderm/mesoderm marker). In some embodiments, the level of expression is determined by immunostaining. In some embodiments, the methods further include a culturing condition and/or analysis parameter described in Warmflash et al., Nature Methods. 2014 August: 11(8): 847-854 such as a patterned culture and analysis of various cellular proteins that serve as markers for a particular cell state (e.g. germ layer markers CDX2 BRA and SOX2 or pluripotency markers NANOG, OCT4 and SOX2). In some embodiments, the cells are analyzed for expression of a protein described in Warmflash et al., Nature Methods. 2014 August: 11(8): 847-854.

Further aspects of the disclosure relate to a method for making the cells of the disclosure, comprising mutating by human intervention (e.g., by gene editing) the endogenous HTT gene on the genomic DNA of an hESC to a disease form of HTT. In some embodiments, the method comprises mutating the endogenous HTT gene by introducing into the cells a donor nucleic acid comprising HTT mutant sequences and a site-specific DNA digesting agent. In some embodiments, the DNA digesting agent is a TALEN, transposase, integrase or nuclease. In some embodiments, the DNA digesting agent is a nuclease. In some embodiments, the DNA digesting agent is a specific one described in the present disclosure. In some embodiments, the nuclease is Cas9. In some embodiments, the method further comprises contacting the cells with a guide RNA. In some embodiments, the method further comprises screening for cells with a disease form of HTT. In some embodiments, the method further comprises isolating cells or a cell with a disease form of HTT. In some embodiments, the method comprises expanding the isolated cells or cell. In some embodiments, the method further comprises freezing the cells. In some embodiments, the method further comprises expanding cells that were previously frozen.

Any of the disclosed methods may include a step employing limiting dilution of the modified cells to obtain single cell colonies. As used herein, the term "limiting dilution" refers to the process of significantly diluting a cell culture, with the goal of achieving a single cell in each culture. When such an isolated, single cell reproduces, the resulting culture will contain only clones of the original cell. For example, a multi-well plate may be used to obtain single cell cultures or colonies.

In any of the disclosed methods, a step may be employed comprising expanding a clonal isolated and selected cell to produce clonal cells with a particular genomic modification and combinations of a cell culture of cells that are genetically modified and an isogenic cell culture that is wild-type and does not possess the modification (or if it possessed an HD mutation, it has been engineered (with the polyQ region replaced or otherwise modified) to contain a wildtype number of polyQ repeats).

In disclosed methods involving the expansion of a clonal isolated cell, the expansion may be for large scale manufacturing. For example, the cells may be expanded in a volume of greater than 1 L, or the cells may be expanded in a volume of greater than 3 L. In certain aspects, the cells are expanded in a volume of greater than 1.0, 1.5, 2.0, 2.5, or 3.0 L, or any value or range of values derivable there from, such as a volume between 2 and 3 L.

With respect to any embodiment, the screening platforms described herein include those wherein the cells have been passaged less than 170 times or less than 100 times or less than 60 times.

In any of the disclosed methods, a further step may be employed comprising freezing modified and selected or screened cells. An even further step may also be employed, wherein previously frozen transfected and selected/screened cells are expanded.

In the disclosed methods, a further step may be employed comprising expanding a clonal isolated and selected or screened cell to produce clonal cells having a disease form of the Huntingtin gene (HTT). In some embodiments, a parallel further step may be employed to produce clonal cells isogenic to the foregoing but wild type, i.e., not having a disease form of HTT gene.

In yet other aspects of the disclosure, a screening tool is provided comprising a first in vitro cell population wherein the cells comprise a disease form of the HTT gene (containing more than 40 polyQ repeats) and an isogenic wild-type cell population wherein the cells comprise a wildtype HTT gene. In some embodiments, the cells are originally human embryonic stem cells. The cell populations are induced to organize into strata resembling ectoderm mesoderm and endoderm, cultured in the presence or absence of reagents for a period of time sufficient to result in one or more observable differences in phenotype (disease phenotype vs. wild-type phenotype) as between the modified cells and the wild-type cells (such differences have been exemplified above). Therapeutic candidate compounds are then screened by introducing them into the cultures. The objective is to identify tested compounds which prevent (including delay the onset, or decrease the intensity) or revert (partially or totally) the disease phenotype.

In yet another aspect, the present disclosure is directed to a method for inhibiting a disease phenotype from developing or reverting said phenotype in a human cell comprising a disease form of the HTT gene, the method comprising delivering to the cell to an effective amount of an active agent comprising minoxidil. In some embodiments, the method is practiced in vitro; in some embodiments, the method is practiced in vivo. In some embodiments of the in vivo method, the delivery of the agent is carried out by administering the active agent to a human subject the genome of which comprises a disease form of the HTT gene. In some embodiments, the subject is an adult human; in some embodiments, the subject is a human child; in some embodiments, the subject is a human embryo. In some embodiments, the delivery or administration takes place from a time prior to the appearance of morphological abnormalities in mitochondria of said cell. In some embodiments, disease phenotype is an altered cell morphology and/or organization, gene expression, cytokine expression, cell number expansion or a metabolic signature or a combination of two or more of the foregoing.

Further method aspects relate to a method for treating Huntinton's disease (HD) in a patient having HD comprising administering to the patient a composition comprising a first therapeutic agent: for example, minoxidil. In some embodiments, the composition is administered to the patient in one dose once a day for a period of time. In some embodiments, the composition ameliorates or reduces a symptom of HD. In some embodiments, the composition is administered in conjunction with an additional therapeutic agent. In some embodiments, the additional therapeutic agent is selected from tetrabenazine, antipsychotic drugs, haloperidol, risperidone, quetiapine, amantadine, levetiracetam, clonazepam, citalopram, fluoxetine, sertraline, quetiapine, risperidone, olanzapine, valproate, carbamazepine, and lamotrigine. In some embodiments, the method further comprises an additional therapeutic or treatment regimen described herein. In some embodiments, the patient is an adult or aged human.

In another aspect, a kit comprising any of one or more and optionally two or more of the foregoing screening platforms or in vitro models of HD or cell populations is provided for use in the foregoing methods. The kit optionally comprises one or more cell reporter cells or populations disclosed above.

The present disclosure is exemplified by specific embodiments below.

1. A screening platform for identifying therapeutic candidates for Huntington's disease comprising:
   (a) a first clonal population of human embryonic stem cells comprising a wild type Huntingtin (HTT) gene;
   (b) a second clonal population of human embryonic stem cells isogenic to the first population, wherein the cells in the second population have been genetically modified to comprise a nucleotide segment, wherein the nucleotide segment, upon expression, results in a polyQ repeat peptide segment comprising at least 40 glutamine residues in the N-terminal region of the HTT protein.
2. The screening platform of embodiment 1, wherein the resulting polyQ repeat comprises one or both CAA and CAG codons.
3. The screening platform of embodiment 1, wherein the resulting polyQ repeat in the genetically modified cell population comprises essentially only CAG codons.
4. The screening platform of any one of embodiments 1 to 3, wherein the resulting polyQ repeat in the genetically modified cell population comprises 40 to 180 glutamine residues.
5. The screening platform of embodiment 4, wherein the resulting polyQ repeat comprises 80-150 glutamine residues.
6. The screening platform of embodiment 4, wherein the resulting polyQ repeat comprises 40-80 glutamine residues.
7. The screening platform of embodiment 4, wherein the resulting polyQ repeat in the genetically modified cell population comprises 42 to 150 glutamine residues.
8. The screening platform of embodiment 7, wherein the resulting polyQ repeat comprises 42, 45, 48, 56, 58, 67, 74 or 150 glutamine residues.
9. The screening platform of any one of embodiments 1 to 8, wherein the poly Q repeat is at the N-terminus region of the HTT protein.
10. The screening platform of any one of embodiments 1 to 9, wherein the cells are not induced pluripotent cells.
11. The screening platform of any one of embodiments 1 to 10, wherein the cells in clonal cell populations comprise a recombinant detectable marker.
12. The screening platform of embodiment 11, wherein the detectable marker is genetically linked to the HTT gene.
13. The screening platform of embodiment 11 or embodiment 12, wherein the detectable marker is a gene that encodes a fluorescent protein or an enzyme.
14. The screening platform of any one of embodiments 1 to 13, wherein the cells in clonal cell populations comprise a recombinant selectable marker.
15. The screening platform of embodiment 14, wherein the selectable marker is genetically linked to the HTT gene.
16. The screening platform of embodiment 14 or embodiment 15, wherein the selectable marker is an antibiotic resistance gene.
17. The screening platform of any one of embodiments 1 to 11, wherein the cells in clonal cell populations are free of a recombinant detectable marker.
18. The screening platform of any one of embodiments 1 to 11 and 17, wherein the cells in clonal cell populations are free of a recombinant selectable marker.
19. The screening platform of any one of embodiments 1 to 18, wherein the clonal cell populations are obtained or obtainable by culturing on an adhesive surface.
20. The screening platform of any one of embodiments 1 to 19, wherein the cells of the clonal cell populations are on an adhesive surface.
21. The screening platform of embodiment 19 or embodiment 20, wherein the adhesive surface is a micropatterned glass coverslip or a multi-well plate.
22. The screening platform of embodiment 21, wherein the adhesive surface is a micropatterned glass coverslip.
23. The screening platform of embodiment 21, wherein the adhesive surface is a multi-well plate.
24. The screening platform of any one of embodiments 20 to 23, wherein the adhesive surface is coated with a cell adhesion promoting coating.
25. The screening platform of embodiment 24, wherein the wherein the cell adhesion promoting coating is a member of the group consisting of poly-D-lysine, poly-L-lysine, fibronectin, collagen, laminin, laminin-511 (LN-511), laminin-521 (LN-521), poly-L-ornithine, and combinations of two or more of the foregoing.
26. The screening platform of any one of embodiments 20 to 25, wherein the coverslip is coated with a matrix.
27. The screening platform of embodiment 26, wherein the matrix is matrigel, cultrex or geltrex.
28. The screening platform of any one of embodiments 1 to 27, in which the cells of the clonal cell populations have been passaged less than 170 times.
29. The screening platform of embodiment 28, in which the cells of the clonal cell populations have been passaged less than 100 times.
30. The screening platform of embodiment 29, in which the cells of the clonal cell populations have been passaged less than 60 times.
31. The screening platform of any one of embodiments 1 to 30, wherein each of the clonal cell populations is obtained or obtainable by culturing human embryonic stem cells on a confined surface so as to result in clonal cell populations organized in sections, each section containing cells expressing markers characteristic of a different germ layer.
32. The screening platform of embodiment 31, wherein each of the clonal cell population is obtained or obtainable by culturing human embryonic stem cells under conditions in which the cells form a micropatterned culture.
33. The screening platform of embodiment 31 or 32, wherein each of the clonal cell population is obtained or obtainable by culturing human embryonic stem cells under conditions in which the cells become organized into germ layers or zones, for example rings.
34. The screening platform of any one of embodiments 1 to 33, wherein each of the clonal cell populations is obtained or obtainable by culturing human embryonic stem cells in the presence of a morphogenic differentiating agent.
35. The screening platform of embodiment 34, wherein the differentiating agent is selected from the group consisting of BMP4, WINT3A, activin, and combinations of two or more of the foregoing.
36. The screening platform of any one of embodiments 1 to 35, wherein each of the clonal cell populations is obtained or obtainable by culturing human embryonic stem cells under differentiating conditions such that cells in the clonal cell population are differentiating or differentiated to a specific differentiated fate.
37. The screening platform of embodiment 36, wherein cells in the clonal cell population are in a differentiating state.
38. The screening platform of embodiment 37, in cells in the differentiating state are enriched or isolated.
39. The screening platform of embodiment 36, wherein cells in the clonal cell population are in a differentiated state.
40. The screening platform of embodiment 39, wherein cells in the clonal cell population are in a terminally differentiated state.
41. The screening platform of embodiment 39 or embodiment 40, wherein cells in the differentiated state are enriched or isolated.
42. The screening platform of any one of embodiments 36 to 41, wherein the differentiating conditions are neuronal differentiating conditions.
43. The screening platform of any one of embodiments 36 to 42, wherein the specific differentiated fate is neurons.
44. The screening platform of embodiment 42 or embodiment 43, wherein the cells have been differentiated by having been contacted with or cultured in the presence of a BMP/TGFβ signaling pathway inhibitor.
45. The screening platform of embodiment 44, wherein the BMP/TGFβ signaling pathway inhibitor is one or more dual SMAD inhibitor.
46. The screening platform of embodiment 44, wherein the BMP/TGFβ signaling pathway inhibitor comprises one or both of SB431542 and LDN193189.
47. The screening platform of any one of embodiments 36 to 46, wherein cells in the clonal cell population express one or both neuronal markers selected from the group consisting of PAX6 and N-Cadherin.
48. The screening platform of any one of embodiments 1 to 47, wherein the cells in the clonal cell population have been frozen and thawed.
49. The screening platform of any one of embodiments 1 to 47, wherein the cells in the clonal cell population are frozen.
50. A method for determining whether a test substance is a therapeutic candidate for treatment of Huntington's Disease (HD), comprising:
   (a) contacting the clonal populations of the screening platform of any one of embodiments 1 to 48 with a test substance; and
   (b) culturing the clonal populations in the presence of the test substance.
wherein a test compound that partially or completely reverses one or a plurality of phenotypes of the second clonal population is a therapeutic candidate for HD.
51. The method of embodiment 50, wherein the test compound reverses at least one phenotype of the second clonal population.
52. The method of embodiment 51, wherein said at least one phenotype is selected from morphology, organization, metabolic signature, gene expression, cytokine expression, germ layer marker expression, and cell expansion.
53. The method of embodiment 52, wherein said at least one phenotype is selected from rosette formation, rosette organization, rosette lumen, giant neuron formation, giant neuron frequency, the presence of multi- or poly-nucleation, the frequency of multi- or poly-nucleation, cell number, the expression of one or more germ layer markers, cadherin expression, nestin expression, cytokinesis defects, mitotic morphology, neuron size, and neuron polynucleation.
54. The method of embodiment 53, wherein said at least one phenotype is expression of one or more germ layer markers, optionally wherein the one or more germ layer markers comprises one or more of SOX2, BRA, and CDX2.
55. The method of embodiment 53, wherein said at least one phenotype is a neural differentiating phenotype, optionally wherein the neural differentiating phenotype is selected from rosette formation, rosette organization, or rosette lumen.
56. The method of embodiment 53, wherein said at least one phenotype is a differentiated neuron phenotype, optionally wherein the differentiated neuron phenotype is selected from giant neuron formation, giant neuron frequency, the presence of multi- or poly-nucleation, the frequency of multi- or poly-nucleation, cytokinesis defects, mitotic morphology, neuron size, and neuron polynucleation.
57. The method of embodiment 50, wherein the test compound reverses at least two or at least three phenotypes of the second clonal population.
58. The method of embodiment 57, wherein at least two or at least three phenotypes are selected from morphology, organization, metabolic signature, gene expression, cytokine expression, germ layer marker expression, and cell expansion.
59. The method of embodiment 58, wherein at least two or at least three phenotypes are selected from rosette formation, rosette organization, rosette lumen, giant neuron formation, giant neuron frequency, the presence of multi- or poly-nucleation, the frequency of multi- or poly-nucleation, cell number, the expression of one or more germ layer markers, cadherin expression, nestin expression, cytokinesis defects, mitotic morphology, neuron size, and neuron polynucleation.
60. The method of embodiment 59, wherein said at least one of said at least two or at least three phenotypes is expression of one or more germ layer markers, optionally wherein the one or more germ layer markers comprises one or more of SOX2, BRA, and CDX2.
61. The method of embodiment 59, wherein said at least one of said at least two or at least three phenotypes is a neural differentiating phenotype, optionally wherein the neural differentiating phenotype is selected from rosette formation, rosette organization, or rosette lumen.
62. The method of embodiment 59, wherein said at least one of said at least two or at least three phenotypes is a differentiated neuron phenotype, optionally wherein the differentiated neuron phenotype is selected from giant neuron formation, giant neuron frequency, the presence of multi- or poly-nucleation, the frequency of multi- or poly-nucleation, cytokinesis defects, mitotic morphology, neuron size, and neuron polynucleation.
63. The method of any one of embodiments 50 to 62, which further comprises after step (a) and/or step (b) assessing said at least one phenotype of the second clonal population.

64. The method of embodiment 63, which further comprises comparing said at least one phenotype to the corresponding phenotype in the first clonal population.
65. The method of embodiment 63, which further comprises after step (a) and/or step (b) assessing said at least two or at least three phenotypes of the second clonal population.
66. The method of embodiment 65, which further comprises comparing said at least two or at least three phenotypes to the corresponding phenotypes in the first clonal population.
67. A method for determining whether a test substance is a therapeutic candidate for treatment of Huntington's Disease (HD), comprising performing the method of any one of embodiments 50 to 66 on a plurality of screening platforms according to any one of embodiments 1 to 48, wherein each of the second clonal populations in the screening platforms carries the same number of glutamine repeats but is at a different stage of differentiation, such that the effect of the test compound is evaluated on different stages of development, and wherein a test compound that partially or completely reverses one or a plurality of phenotypes of a plurality of second clonal populations is a therapeutic candidate for HD.
68. A method for determining whether a test substance is a therapeutic candidate for treatment of Huntington's Disease (HD), comprising performing the method of any one of embodiments 50 to 66 on a plurality of screening platforms according to any one of embodiments 1 to 48, wherein each of the second clonal populations in the screening platforms carries a different length of glutamine repeats but is at the same stage of differentiation, such that the effect of the test compound is evaluated on different lengths of glutamine repeats, and wherein a test compound that partially or completely reverses one or a plurality of phenotypes of a plurality of second clonal populations is a therapeutic candidate for HD.
69. A method for determining whether a test substance is a therapeutic candidate for treatment of Huntington's Disease (HD), comprising performing the method of any one of embodiments 50 to 66 on a plurality of screening platforms according to any one of embodiments 1 to 48, wherein the second clonal populations in the screening platforms carry different lengths of glutamine repeats and/or are at different stages of differentiation, such that the effect of the test compound is evaluated on different lengths of glutamine repeats and at different stages of development, and wherein a test compound that partially or completely reverses one or a plurality of phenotypes of a plurality of second clonal populations is a therapeutic candidate for HD.
70. The method of any one of embodiments 67 to 69 which is carried out serially.
71. The method of any one of embodiments 67 to 69 which is carried out in parallel.
72. The method of any one of embodiments 67 to 69 which is partially carried out in series and partially carried out in parallel.
73. A population of human embryonic stem cells (hESC), wherein the cells originally comprised a wildtype HTT gene but have been genetically modified to comprise a nucleotide segment, wherein the nucleotide segment, upon expression, results in a polyQ repeat peptide segment comprising at least 40 glutamine residue repeats in the N-terminal region of the HTT protein, wherein a substantial fraction of the cells have been optionally differentiated in vitro into neuronal progenitors or into terminally differentiated neurons.
74. A method for treating Huntington's disease (HD) in a human patient having HD comprising administering to the patient a composition comprising an amount of minoxidil in an amount effective to alleviate or revert at least one symptom of the disease or at least one parameter selected from the group consisting of morphology, organization, number, metabolic signature, marker protein expression, cytokine production and gene expression of cells affected by the disease.
75. The method of embodiment 74, wherein the composition is administered to the patient once a day for a period of time.
76. The method of embodiment 74 or embodiment 75, wherein the composition is administered with an additional therapeutic agent.
77. The method of embodiment 76, wherein the additional therapeutic agent is selected from tetrabenazine, antipsychotic drugs, haloperidol, risperidone, quetiapine, amantadine, levetiracetam, clonazepam, citalopram, fluoxetine, sertraline, quetiapine, risperidone, olanzapine, valproate, carbamazepine, and lamotrigine.
78. An in vitro model for Huntington's Disease comprising:
    (a) a first clonal population comprising human embryonic stem cells comprising a wild-type Huntingtin gene (HTT); and
    (b) a second clonal population of human embryonic stem cells isogenic to the first population but comprising an HTT that has been genetically modified to comprise a nucleotide segment, wherein the nucleotide segment, upon expression, results in a polyQ repeat peptide segment comprising at least 40 glutamine residues in the N-terminal region of the HTT protein.
79. An in vitro model for Huntington's Disease comprising:
    (a) a first clonal population comprising human neuronal cell progenitors comprising a wild-type Huntingtin gene (HTT); and
    (b) a second clonal population of human neuronal cell progenitors isogenic to the first population but comprising an HTT that has been genetically modified to comprise a nucleotide segment, wherein the nucleotide segment, upon expression, results in a polyQ repeat peptide segment comprising at least 40 glutamine residues in the N-terminal region of the HTT protein;
    wherein the first and second population have been generated by in vitro differentiation of human embryonic stem cells.
80. An in vitro model for Huntington's Disease comprising:
    (a) a first clonal population comprising human neurons comprising a wild-type Huntingtin gene (HTT); and
    (b) a second clonal population of human neurons isogenic to the first population but comprising an HTT that has been genetically modified to comprise a nucleotide segment, wherein the nucleotide segment, upon expression, results in a polyQ repeat peptide segment comprising at least 40 glutamine residues in the N-terminal region of the HTT protein;
    wherein the first and second population have been generated by in vitro differentiation of human embryonic stem cells.

81. A fate reporter cell population for use in monitoring induction of germ layers, or fate acquisition, or both, in human embryonic stem cells, the cell population comprising human embryonic stem cells, wherein each cell comprises at least one of the following: a first detectable marker inserted into the genome of the cell so as to co-express with a first germ layer specific marker; a second detectable marker inserted into the genome of the cell so as to co-express with a second germ layer specific marker; and a third detectable marker inserted into the genome of the cell so as to co-express with a third germ layer specific marker.

82. The fate reporter cell population of embodiment 81, wherein at least one of the first, second and third detectable markers is a fluorescent protein, provided that when more than one detectable marker is a fluorescent protein, the fluorescent proteins are different so that as to distinguish between or among the germ layer specific markers upon detection of the first, second and or third detectable marker.

83. The fate reporter cell population of embodiment 82, wherein each cell further comprises a nuclear detectable marker, said marker having been introduced into the cell so as to co-express with a histone protein.

84. The fate reporter cell population of embodiment 83, wherein the nuclear detectable marker is a nuclear fluorescent protein, wherein the nuclear fluorescent protein, upon its detection, is distinguishable from as many of the first second and third detectable marker as are present in said cell.

85. The fate reporter cell population of embodiment 84, wherein the nuclear detectable marker is constitutively expressed.

86. The fate reporter cell population of embodiment 85, wherein the nuclear detectable marker is infrared fluorescent protein.

87. The fate reporter cell population of embodiment 82, wherein the one or more of the first, second and third fluorescent protein, is selected from the group consisting of mCitrine, mCerulian and tdTomato provided that each of said proteins associated with one germ layer is distinct from the protein or proteins associated with the other germ layers.

88. A cell population comprising human embryonic stem cells, wherein cells of said population have been genetically modified to comprise a nucleotide segment encoding a 41b isoform of human HTT protein, such that no cells of the population express any other isoform of the HTT protein.

89. A cell population comprising human embryonic stem cells, wherein cells of said population have been genetically modified to comprise a nucleotide segment encoding an HTT protein lacking exon 41b, such that no cells of the express a 41b isoform of the HTT protein.

90. The cell population of embodiment 89 wherein the cells have also been modified to express at least one selectable or detectable marker genetically linked to the HTT gene or are alternatively free of any such selectable or detectable markers.

91. A kit comprising any of one or more and optionally two or more of the screening platforms of any one of embodiments 1 to 48, or in vitro model cells for Huntington's Disease of any one of embodiments 78 to 80, or fate reporter cell populations of any one of embodiments 81 to 87.

92. The kit of embodiment 91, further comprising one or more of the cell populations of any one of embodiments 88 to 90.

93. A method for identifying a therapeutic candidate for Huntington's disease comprising:
   (a) contacting a clonal population of human embryonic stem cells that expresses a mutant Huntingtin (HTT) gene which encodes an HTT protein comprising a polyQ repeat peptide segment of least 40 glutamine residues with a test compound;
   (b) culturing said clonal population; and
   (c) detecting whether the phenotype of the clonal population partially or fully reverts to the wild-type phenotype, wherein a test compound that causes a partial or complete reversion to the wild-type phenotype is a therapeutic candidate for Huntington's disease.

94. The method of embodiment 93 wherein the clonal population is cultured so as to form germ layers, wherein the phenotype is the size and/or organization and/or cell number in one or more of the germ layers.

95. A method for identifying a therapeutic candidate for Huntington's disease comprising:
   (a) inducing neural differentiation in a clonal population of human embryonic stem cells that expresses a mutant Huntingtin (HTT) gene which encodes an HTT protein comprising a polyQ repeat peptide segment of least 40 glutamine residues;
   (b) culturing said clonal population under conditions in which neural differentiation occurs to produce a differentiating clonal population;
   (c) contacting said differentiating clonal population with a test compound; and
   (d) detecting whether the phenotype of the differentiating clonal population partially or fully reverts to the wild-type phenotype,
   wherein a compound that causes a partial or complete reversion to the wild-type phenotype is a therapeutic candidate for Huntington's disease.

96. The method of embodiment 95, wherein the phenotype partially or fully reversed by the test compound is aberrant rosette formation.

97. The method of embodiment 95, wherein the phenotype partially or fully reversed by the test compound is defective mitosis and/or giant and/or polynucleated neuron formation.

98. A method for identifying a therapeutic candidate for Huntington's disease comprising:
   (a) inducing neural differentiation in a first clonal population and second clonal poulation of human embryonic stem cells that each express a mutant Huntingtin (HTT) gene which encodes an HTT protein comprising a polyQ repeat peptide segment of least 40 glutamine residues;
   (b) culturing said first clonal population under conditions in which neural differentiation occurs to produce a first differentiating clonal population;
   (c) culturing said second clonal population under conditions in which neural differentiation occurs to produce a terminally differentiated clonal population;
   (d) contacting said differentiating clonal populations with a test compound; and
   (e) detecting whether the phenotypes of the differentiating and terminally differentiated clonal populations partially or fully reverts to their respective wild-type phenotype, wherein a compound that causes a partial or complete reversion of both differentiating and terminally differentiated phenotypes to the wild-type phenotype is a therapeutic candidate for Huntington's disease.

99. The method of embodiment 98, wherein the differentiating phenotype is partially or fully reversed by the test compound is aberrant rosette formation.

100. The method of embodiment 98 or embodiment 99, wherein the terminally differentiated phenotype is partially or fully reversed by the test compound is defective mitosis and/or giant and/or polynucleated neuron formation.

It is specifically contemplated that embodiments described herein may be excluded. It is further contemplated that, when a range is described, certain other ranges or segments of a range may be excluded.

Other objects, features and advantages of the present invention will become apparent from the following detailed description. It should be understood, however, that the detailed description and the specific examples, while indicating preferred or specific embodiments of the invention, are given by way of illustration only, since various changes and modifications within the spirit and scope of the invention(s) will become apparent to those skilled in the art from this disclosure.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(D) Oxidative stress in RUES2-Q150 cells is produced by the inefficiency of the main reactive oxygen species (ROS) scavenger, Catalase, which show reduced catalase activity in RUES2-Q150. Across all panels, data represents the mean of three biological replicates and error bars are S.E.M.

Figure 6:
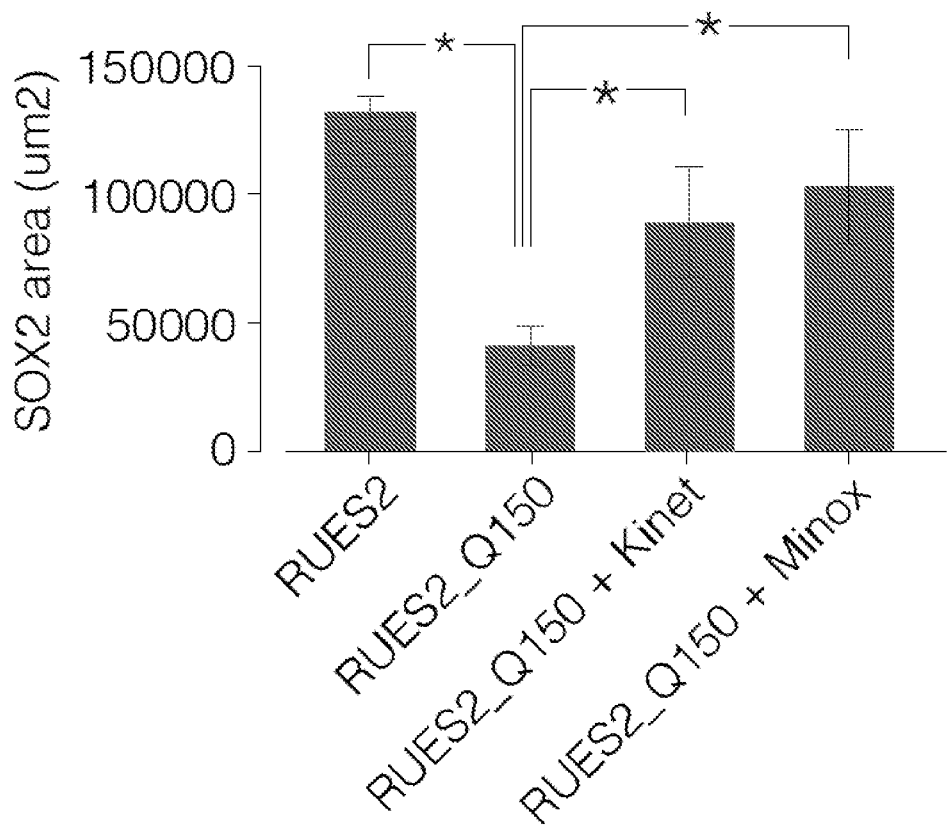

FIG. 6: Wild-type RUES2 cells, when grown as micropattern colonies and induced to differentiate by the simple addition of BMP4, self-organize to generate radially symmetrical patterns of concentric rings of fates. SOX2 is expressed in the central area of the colonies (corresponding to ectoderm), then there is a BRA+ ring (corresponding to mesoderm), followed by a SOX17+ ring (endoderm) and a CDX2+ periphery that corresponds to trophectoderm (data not shown). By contrast, when RUES2-Q150 cells are differentiated in micropatterns, they display an HD-dependent micropattern signature: i) the SOX2+ region is significantly reduced, and therefore the BRA/CDX2 territories are expanded, and ii) there is an overall reduction in cell number (data shown below). Shown is a quantification of the SOX2+ area, demonstrating that treatment of RUES2-Q150 (HD) cells with minoxidil (wherein cells were treated with minoxidil prior to differentiation with BMP4), showed that minoxidil partially but significantly rescues the HD micropattern phenotype, making it closer to the wildtype phenotype. These data (partial but significant rescue of phenotype) were confirmed by adding kinetin to the HD cells instead of minoxidil.

Figure 7:
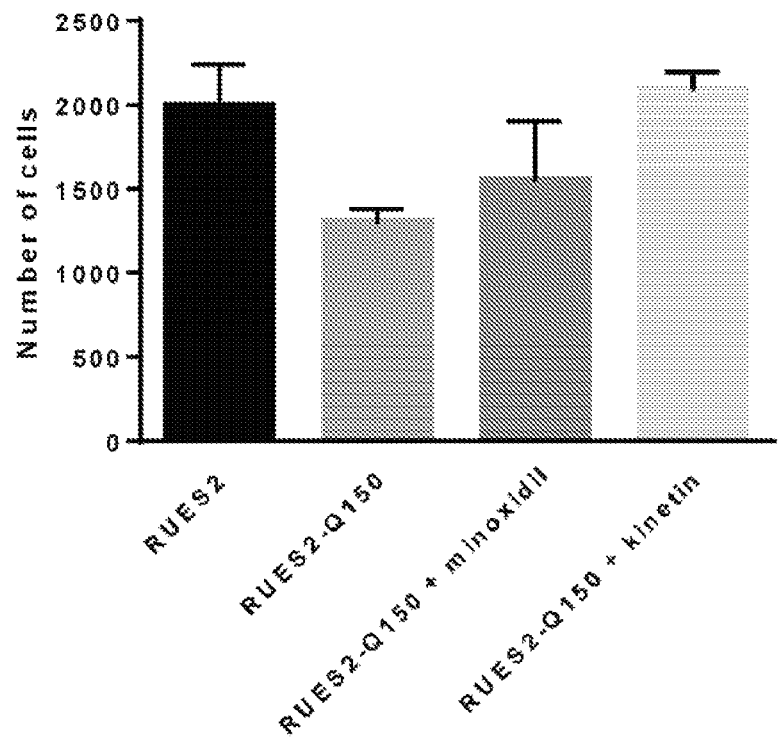

FIG. 7 is a bar graph showing that kinetin also rescues the cell number phenotype. Cells were treated with kinetin prior to differentiation with BMP4. Micropatterns were analyzed and total number of cells counted.

FIG. 8A-B shows a successful generation of the triple-tagged hESC line containing SOX2, BRA, and SOX17 reporters. (A) Schematic of the CRISPR-mediated targeting of the three germ layer-specific marker genes. (B) Triple-tagged hESC cells displayed self-organized radially symmetrical germ layer markers when induced to differentiate with presentation of BMP4 in micropatterns, that can be used to track germ layer formation dynamically using time-lapse fluorescent imaging (data not shown). Scale bar is 100 μm.

FIG. 9A-D shows of a novel HTT isoform 41b (A) RNAseq analysis showing the clear incorporation of a non-reported exon. (B) Alignment of the genomic sequences of exon 41b of mouse and primates (SEQ ID NO:50-56), demonstrating the very recent acquisition of this exon along human evolution. Only hominidae family members (in bold) have both splice donor and acceptor and maintain the frame. (C) RT-PCR with primers specific for HTT-41b isoform detects expression of HTT-41b in hES cells, without amplifying the canonical HTT isoform. (D) Quantification of HTT-41b isoform expression through qRT-PCR at different time points upon neural differentiation of hES cells. Results are shown as mean+SEM of 3-6 independent replicates.

FIG. 10A-B shows that addition of exon 41b modifies serine/threonine phosphorylation predictions. Phosphorylation prediction of the region surrounding exon 41b in the major canonical HTT isoform (A) and with the incorporation of the novel exon 41b (B). Black Asterisks indicate differences in phosphorylation site predictions.

Figure 11:
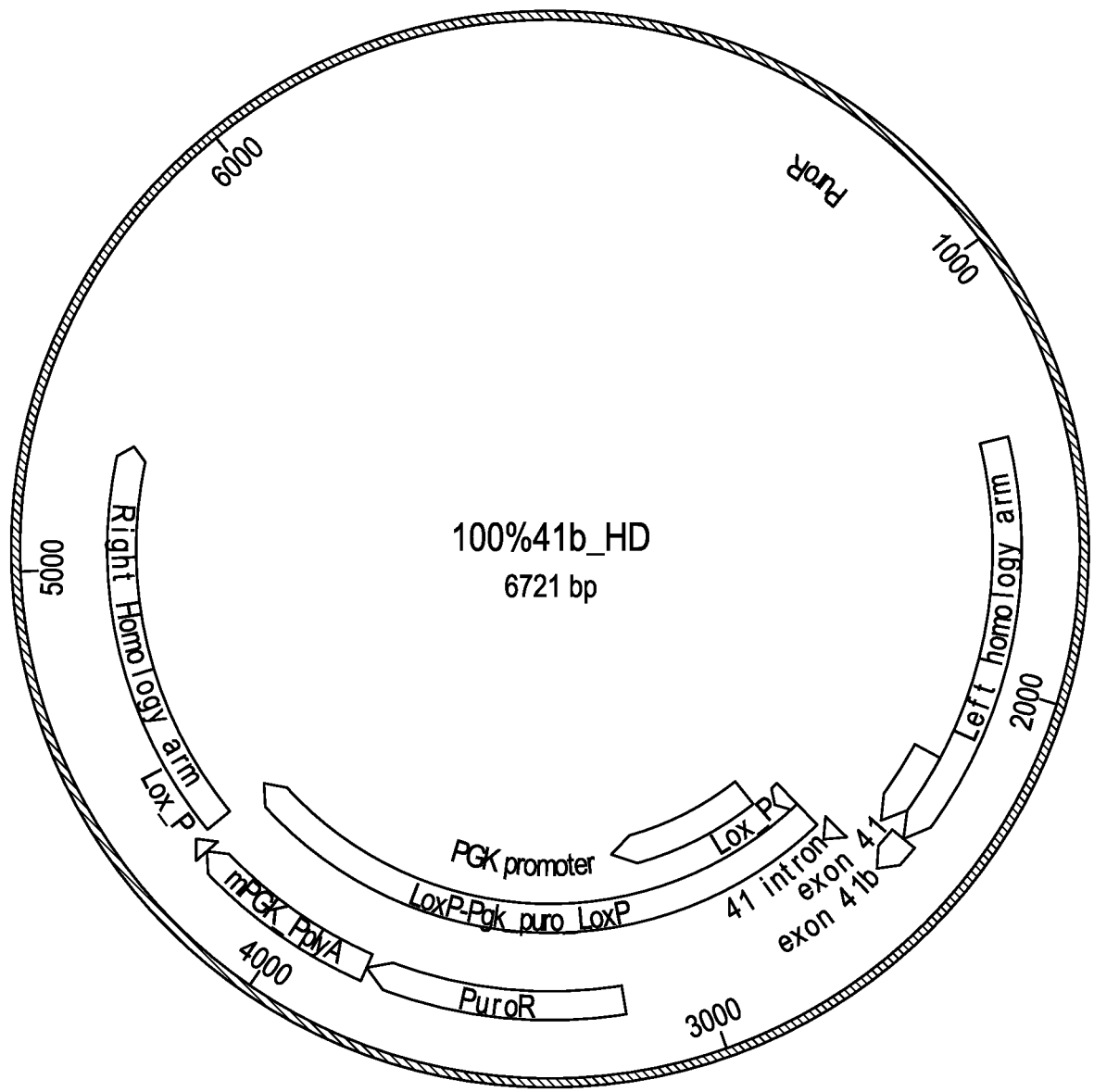

FIG. 11 shows the design of the 100%41b_HD plasmid.

Figure 12:
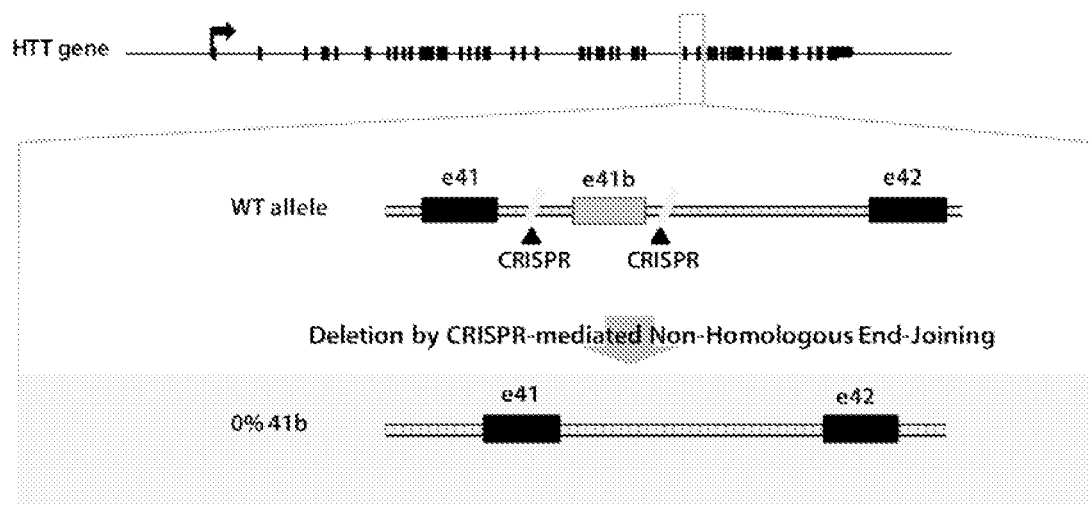
Figure 12:
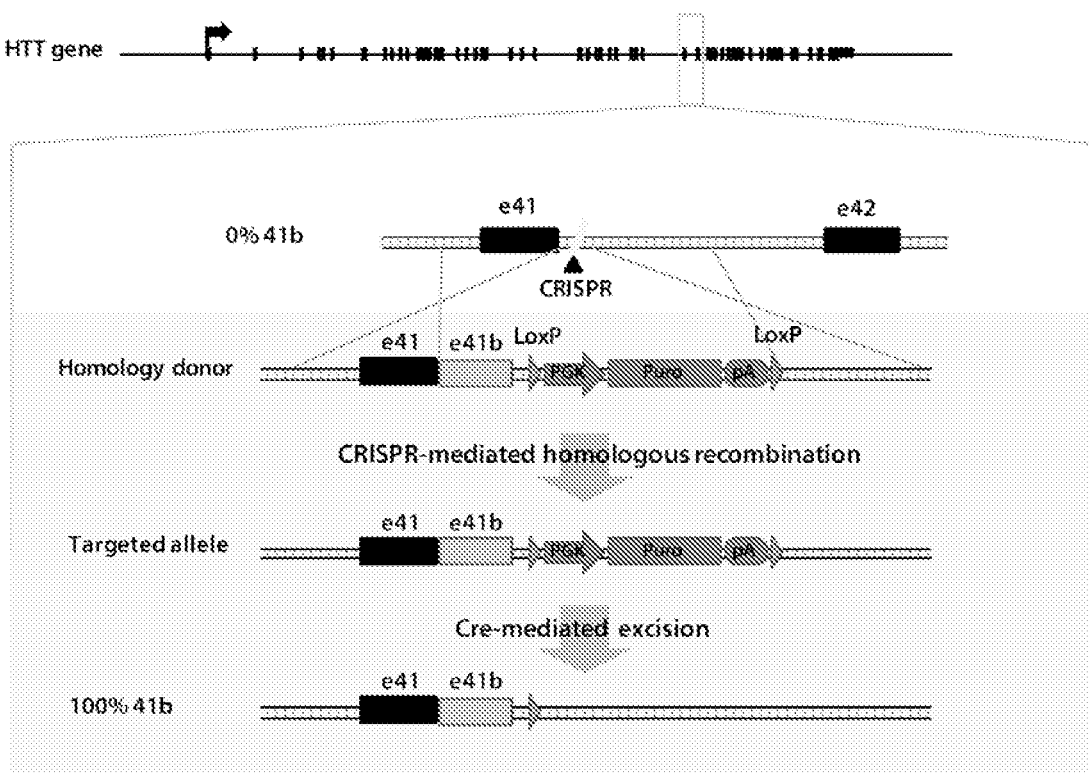

FIG. 12 schematically shows the construct for a cell line containing 100% exon 41b. (A) CRISPR/Cas9 technology was used first to delete the region of HTT exon 41b to create RUES2-HTT-0%41b. (B) Using this line as parental, another round of CRISPR/Cas9-based homologous recombination was used to fuse exon 41b sequence immediately downstream of the 41 exon, thereby forcing the incorporation of the 41b exon in all transcripts, creating RUES2-HTT-100%41b.

Figure 13:
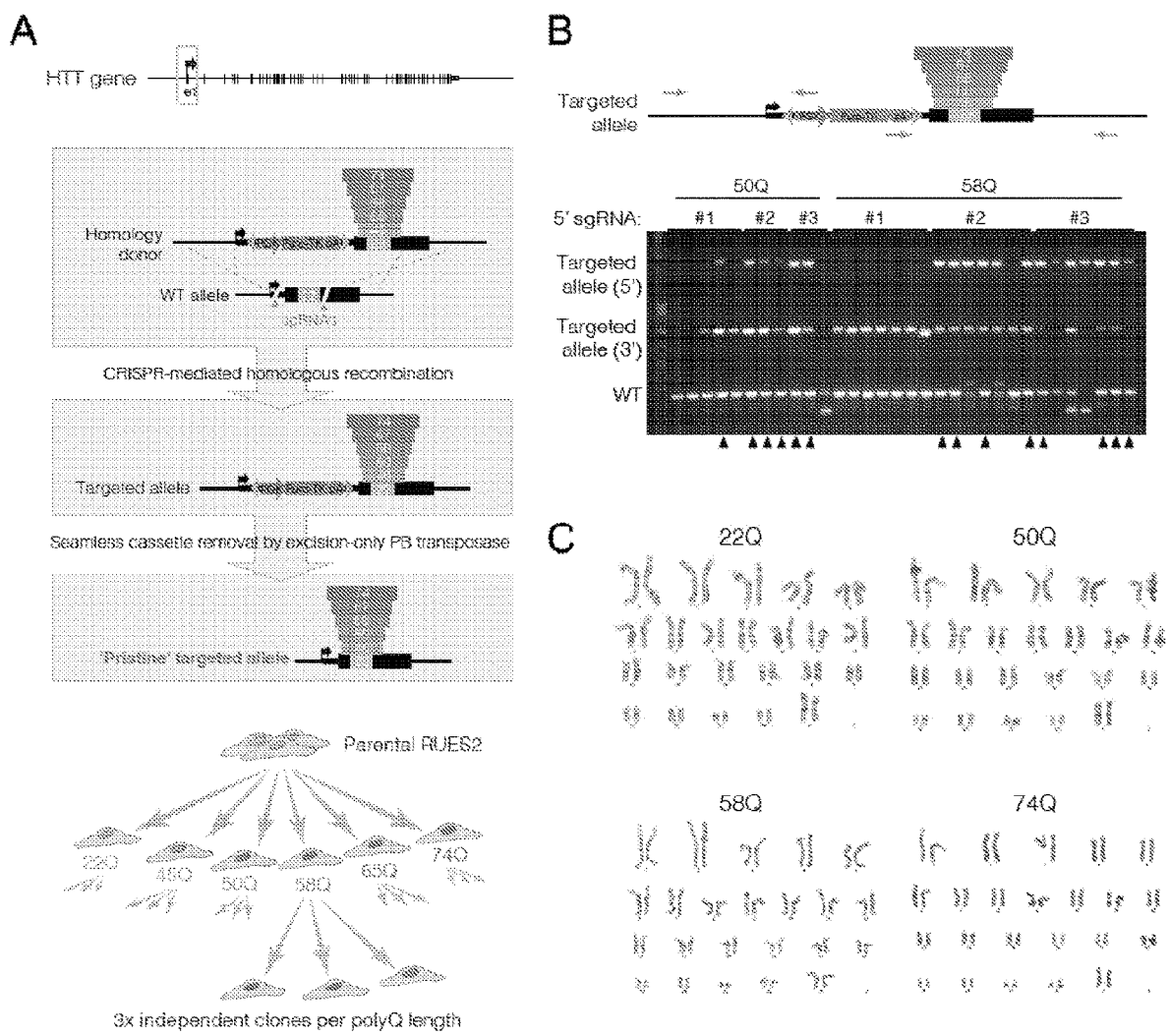

FIG. 13A-C Shows the generation scheme and karyotype of isogenic 'pristine' HD-RUES2 line sets. (A) Strategy for the generation of the isogenic 'pristine' HD-RUES2 line set: CRISPR/Cas9 was used to generate HD-RUES2 isogenic lines with increasing CAG repeat lengths and a selection cassette flanked by ePiggyBac (ePB) terminal repeats. In a second step, the ePB selection cassette was removed by transfecting an excision-only transposase. All the lines contained they right sequence (B and data not shown), were able to maintain pluripotency (data not shown), were karyotypically normal (C), and failed to show any unwanted mutations of the CRISPR editing by Whole Genome Sequencing analysis (data not shown).

FIG. 14A-B are graphs showing germ layer differentiation in micropatterns using the isogenic 'pristine' HD-RUES2 line set. The ectodermal SOX2+ domain decreased in size proportionally to the CAG length. (A) Radial profile of SOX2 intensities demonstrates a decrease in the SOX2 region with longer CAG lengths. (B) The observed phenotypes are highly reproducible as demonstrated by graphing the SOX2 areas of individual colonies. The same reduction in SOX2 area was observed when iPSCs generated from HD patients were differentiated in micropatterns (data not shown). We thus validated and expanded the conclusions based on our original observation with RUES2-Q150, to conclusively identify human HD-specific phenotypic signatures that distinguishes the different mutations find in HD patients.

FIG. 15A-D are graphs and images of isogenic Huntington's disease model hESC lines that reveal defective mitoses in neural plate stage rosettes. (A) Expanded CAG clones exhibited a randomization of angle of mitotic plane compared to orthogonal mitoses in control lines. Immunostaining for DNA (DAPI, white), centrosomes (PERICENTRIN, green), scale bar 10 μm. (B) Quantification of the angles of mitotic planes related to the center of rosette lumen. (C,D) Expanded CAG clones exhibited defects in mitosis, including (C) multipolar mitoses and (D) supernumerary centrosomes. Immunostaining for DNA (DAPI, white), centrosomes (PERICENTRIN, green), and acetylated TUBULIN (red), scale bar 5 μm.

FIG. 16A-C are images and graphs illustrating impairment of inter-rosettes self-organization in expanded polyQ lines. The distribution of the nearest-neighbor distances between nuclear rosette lumens is significantly different to a random distribution in wild-type cultures, but it is not as organized in expanded CAG lines. (A) Representative immunostainings of NCAD foci, and their corresponding locations after image processing. (B) Cumulative distributions of the nearest neighbor distances of individual lines compared to the one expected from a random arrangement of rosettes (black dashed line). (C) Expanded polyQ clones displayed less degree of inter-rosette self-organization, as their distribution of nearest-neighbor distances were closer to randomness than their wild-type counterparts.

FIG. 17A-H are graphs and images of HD hESC lines showing CAG length-proportional phenotypes in progenitor cells and defects in cytokinesis in early neurogenesis phase. (A) At day 45, cultures are composed of post-mitotic neurons expressing cortical neuronal marker CTIP2, and progenitor cells expressing SOX2, with no difference in abundance between genotypes. Mean % of DAPI+/−SEM. (B) IF for NESTIN, MAP2, and DNA (DAPI) identifies two mutant cellular phenotypes in expanded CAG clones: large progenitor cells (arrow) with large soma, multiple nuclei, disorganized filaments and vacuoles, as well as neurons with multiple nuclei (arrowheads). Scale bar 40 μm. (C) Higher resolution image of aberrant progenitor cell, scale bar 20 um. (D) Mean NESTIN+ cell soma area was significantly increased compared to 22Q control, in proportion to Q-length. *p<0.05. (E) Population histograms show an increase in larger NESTIN+ cells. (F) High resolution image of mutant neuronal phenotype: increased cell body size with multiple nuclei connected by DNA stalks in rosette shape (arrow), scale bar 10 um. (G) Quantification of the frequency of abnormal cells. (H) Representative frames (20 min intervals) from continuous timelapse imaging of NLS-marked nuclei (green), day 36-38, show supernumerary nuclei are generated by nuclear replication and failed cytokinesis.

DETAILED DESCRIPTION OF ILLUSTRATIVE EMBODIMENTS

Definitions

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate "approximately" the meaning of which depends on the context. In the context of a value, "about" include the inherent variation of error for the device, or the method being employed to determine the value, or the variation that exists among the study subjects. In the context of illustrating the flexibility of a limit provided for a particular quantity or range, depending on the context may mean the quantity±10% or +20% of the quantity or range. For example, "about 20 nuleotides" will encompass from 18 to 22 nucleotides or from 16 to 24 nucleotides.

The term "isogenic" refers to cells having the same or closely similar genotypes. For example, in the case of the modified ESC of the present disclosure, the HTT gene is modified to the disease form or the HTT gene is knocked out in one or both alleles but not in the controls. Other variations may include the incorporation of one, two three or more markers. The resulting cell will still be isogenic to the control ESC compared to which it was modified. In some of the methods described herein, an "isogenic control cell" or an isogenic "wild-type cell" is used. Cell line pairs that are isogenic i.e., they share the same genetic background except for one or a small number (such as 2, 3, 4, 5 or 10) of defined variances (for example variances that are introduced by genetically modifying the cell), allow for the definitive study of specific genetic variances compared to the wild-type cells and alleviate complications introduced by comparing different patient cells which vary by a multitude of genetic features (especially but not exclusively genetic features that are not known). In some embodiments, substantial genetic identity may extend to the DNA level: inserted polyQ repeats may be all CAG (with the exception of the penultimate one which is CAA, just as it occurs in nature) or may be all CAA or a combination of CAG or CAA. All variants fit the present definition of "isogenic" and the definition of "substantially identical" below.

The term "Huntingtin gene," also called the HTT or HD (Huntington's disease) gene, is the IT15 ("interesting transcript 15") gene, which codes for a protein called the huntingtin protein in this context, ("gene can refer to the entire gene including regulatory elements or merely to the encoding section, including or excluding introns). The human HTT is represented by GenBank Accession No.: NM_002111.7 and NC 000004.12 (mRNA and genomic DNA respctively) and NP_002102.4 (protein). The sequences associated with these GenBank Accession Nos. are incorporated by reference. Genomic coordinates of the HTT gene using GRCh37/hg19 human genome assembly are the following: chr4:3,076,408-3,245,676.

The term "polyQ" refers to repeated stretches of glutamine residues, preferably uninterrupted. The length of the polyQ repeat is critical to pathogenesis, however other protein factors, including the location, type and number of flanking domains of the HTT protein are thought to modulate pathogenesis. Accordingly, therapeutic targets may be identified, inter alia, among such modulating factors.

The term "induced pluripotent stem cells" (also known as iPS cells or iPSCs) are a type of pluripotent stem cell that are generated directly from young or adult or even aged somatic cells by reprogramming them to a plutipotent state.

"A polynucleotide or polynucleotide region (or a polypeptide or polypeptide region) that has a certain percentage" (for example, at least or at most 60%, 65%, 70%, 75%, 80%, 85%, 90%, 95%, 98% or 99%, or any range derivable from the recitation of the foregoing percentages) of "sequence identity" or "homology" to another sequence means that, when aligned, that percentage of bases (or amino acids) are the same in comparing the two sequences. This alignment and the percent homology or sequence identity can be determined using software programs known in the art, for example those described in Ausubel et al. eds. (2007) Current Protocols in Molecular Biology.

The term "complementary" as used herein refers to Watson-Crick base pairing between nucleotides and specifically refers to nucleotides hydrogen bonded to one another with thymine or uracil residues linked to adenine residues by two hydrogen bonds and cytosine and guanine residues linked by three hydrogen bonds. In general, a nucleic acid includes a nucleotide sequence described as having a "percent complementarity" to a specified second nucleotide sequence. For example, a nucleotide sequence may have 80%, 90%, or 100% complementarity to a specified second nucleotide sequence, indicating that 8 of 10, 9 of 10 or 10 of 10 nucleotides of a sequence are complementary to the specified second nucleotide sequence. For instance, the nucleotide sequence 3'-TCGA-5' is 100% complementary to the nucleotide sequence 5'-AGCT-3'. Further, the nucleotide sequence 3'-TCGA- is 100% complementary to a region of the nucleotide sequence 5'-TTAGCTGG-3'. It will be recognized by one of skill in the art that two complementary nucleotide sequences include a sense strand and an antisense strand.

The term "wildtype" or "wild type" when used in conjunction with a gene or nucleic acid shall refer to the allele most commonly encountered in the population and therefore not to a disease form thereof. It shall also refer to a gene or nucleic acid that has not been modified or mutated but it shall encompass instances where a nucleic acid or gene has been modified to insert a wildtype segment, for example a number of glutamine residues smaller than 40 in the HTT gene, as is done in some experiments herein.

The term "metabolic signature" refers to a set of at least 2, 3, 4 or more metabolites of a cell, in some embodiments in the same metabolic pathway, the quantities of which are substantially altered (for example misregulated, showing a decrease or increase in value) in response to a change made to the cell or to the cell's environment, which set of values can be used to characterize the change.

The term "substantially identical" in the context of genetic similarity between two cells described herein as isogenic allows for at least one and up to a small number (for example no greater than about 10) of specific and known differences between the genomes of such cells. Cells that are genetically substantially identical are termed isogenic in the present disclosure.

The term "in conjunction" in the context of administering two therapeutically active agents refers to the relative timing of such administrations. Thus the two agents may be administered together or separately, simultaneously or sequentially in any order, including the first therapeutic agent being administered first and the additional therapeutic agent administered after a certain time interval or vice versa. The time interval can be within the same day, after a lapse of 24 hours, 48 hours, a week, or two weeks.

The term "population" with specific reference to cells means a group of at least 3 and preferably at least 10, 100, 1000 or at least 10,000 cells.

Stem Cells

The term "somatic cell" refers to any cell of an organism, which is a constituent unit of a tissue, skin, bone, blood, or organ, other than a gamete, germ cell, gametocyte, or undifferentiated (stem) cell (defined below). Somatic cells include both progenitor cells (defined below) and terminally differentiated cells. Somatic cells include, but are not limited to, neurons (including without limitation midbrain dopamine neurons, motoneurons, and cortical neurons), fibroblast cells, cardiomyocyte cells, epithelial cells, neuroendocrine cells, pancreatic cells, astrocytes, and hematopoietic cells.

The term "stem cell" refers to an undifferentiated cell (not committed to a specific differentiation lineage) that has the ability to self-renew and is capable of differentiating into one or more different cell types, including self-renewing progenitors, non-renewing progenitors, and terminally differentiated cells of different types. Stem cells, depending on their level of differentiation, are also characterized by their ability to differentiate into functional cells of various cell lineages from multiple germ layers (endoderm, mesoderm and ectoderm), as well as to give rise to tissues of multiple germ layers following transplantation and to contribute substantially to most, if not all, tissues following injection into blastocysts. Stem cells display morphological characteristics that distinguish them from differentiated cells of embryo or adult origin. Undifferentiated embryonic stem (ES) cells are easily recognized by those skilled in the art, and typically appear in the two dimensions of a microscopic view in colonies of cells with high nuclear/cytoplasmic ratios and prominent nucleoli. They also express proteins that serve as markers of "stemness" such as described below and can be selected on this basis.

Stem cells may be embryonic stem cells or stem cells isolated from organs, for example, mesenchymal or skin stem cells or induced pluripotent stem cells. As used herein, the term "embryonic stem cell" refers to an undifferentiated cell isolated from an embryo. As used herein, the term "induced pluripotent stem cell" or "iPSC" refers to a type of pluripotent stem cell that is created when somatic (e.g., adult) cells are reprogrammed to enter an embryonic stem cell-like state by being forced to express factors important for maintaining the "stemness" of embryonic stem cells (ESCs), i.e., their ability to be led to commit to different differentiation pathways. As used herein, the term "progenitor" in reference to a cell refers to an intermediate cell stage wherein said cell is no longer a pluripotent stem cell and is also not yet a fully committed cell. Progenitor cells in this disclosure are included within somatic cells.

Stem cells are classified by their developmental potential as: (1) totipotent, able to give rise to all embryonic cell types (and therefore able to differentiate into any type of cell in a differentiated organism) and extraembryonic cell types; (2) pluripotent, able to give rise to all embryonic cell types. i.e., endoderm, mesoderm, and ectoderm and in turn to any differentiated cell type; (3) multipotent, able to give rise to a subset of cell lineages (and differentiate into at least two cell types), but all within a particular tissue, organ, or physiological system (for example, hematopoietic stem cells (HSC) can produce progeny that include HSC (self-renewal), blood cell restricted oligopotent progenitors and the cell types and elements (e.g., platelets) that are normal components of the blood); (4) oligopotent, which is able to give rise to a more restricted subset of cell lineages than multipotent stem cells; and (5) unipotent, which is able to give rise to a single cell lineage (e.g., spermatogenic stem cells).

Stem cells useful in the compositions and methods of the current disclosure include embryonic cells of various types, exemplified by human embryonic stem (hES) cells, described for example by U.S. Pat. Nos. 7,615,374; 7,611,852; 7,582,479; 7,514,260; 7,439,064, 7,390,657; 7,220,584; 7,217,569; 7,148,062; 7,029,913; 6,887,706; 6,613,568; 6,602,711; 6,280,718; 6,200,806; and 5,843,780, each of which is herein incorporated in their entirety by reference; and human embryonic germ (hEG) cells (Shambloft et al., Proc. Natl. Acad. Sci. USA 95:13726, 1998).

Adult stem cells are generally limited to differentiating into different cell types of their tissue of origin. However, if the starting stem cells are derived from the inner cell mass of the embryo, they can give rise to all cell types of the body derived from the three embryonic germ layers: endoderm, mesoderm and ectoderm. Stem cells with this property are said to be pluripotent. Embryonic stem cells are one kind of pluripotent stem cell.

In some embodiments, the cells of the disclosure may be derived from an isolated cell. Most conventional methods to isolate a particular cell of interest involve positive and negative selection using markers of interest. Agents can be used to recognize stem cell markers, for instance labeled antibodies that recognize and bind to cell-surface markers or antigens on desired stem cells. Antibodies or similar agents specific for a given marker, or set of markers, can be used to separate and isolate the desired stem cells using fluorescent activated cell sorting (FACS), panning methods, magnetic particle selection, particle sorter selection and other methods known to persons skilled in the art, including density separation and separation based on other physical properties. Alternatively, genetic selection methods can be used, where a stem cell can be genetically engineered to express a reporter protein operatively linked to a tissue-specific promoter and/or a specific gene promoter; therefore, the expression of the reporter can be used for positive selection methods to isolate and enrich the desired stem cell. For example, a fluorescent reporter protein can be expressed in the desired stem cell by genetic engineering methods to operatively link the marker protein to a promoter active in a desired stem cell. Other means of positive selection include drug selection involving enrichment of desired cells by density gradient centrifugation. Negative selection can be performed, selecting and removing cells with undesired markers or characteristics, for example fibroblast markers, epithelial cell markers etc.

Undifferentiated ES cells express genes that can be used as markers to detect the presence of undifferentiated cells. The polypeptide products of such genes can be used as markers for negative selection. Human ES cell lines express cell surface markers that characterize undifferentiated non-human primate ES and human ES cells, including stage-specific embryonic antigen (SSEA)-3, SSEA-4, TRA-1-60, TRA-1-81, and alkaline phosphatase. The globo-series glycolipid GL7, which carries the SSEA-4 epitope, is formed by the addition of sialic acid to the globo-series glycolipid Gb5, which carries the SSEA-3 epitope. Thus, GL7 reacts with antibodies to both SSEA-3 and SSEA-4. Undifferentiated human ES (hES) cell lines do not stain for SSEA-1, but differentiated cells stain strongly for SSEA-1. Methods for proliferating hES cells in the undifferentiated form are described in WO 99/20741, WO 01/51616, and WO 03/020920, which are herein incorporated by reference in their entirety.

In one embodiment, the methods provide for enrichment and isolation of stem cells. The stem cells are selected for a characteristic of interest. In some embodiments, a wide range of markers may be used for selection. One of skill in the art will be able to select markers appropriate for the desired cell type. The characteristics of interest include expression of particular markers of interest, for example specific subpopulations of stem cells and stem cell progenitors each express specific markers. In some embodiments, stem cells of the current disclosure are selected using one or more pluripotency markers, which include, but are not limited to OCT4, NANOG, and SOX2. In further embodiments, stem cells of the current disclosure are selected using one or more differentiation markers, which include, but are not limited to BRA, SOX17, EOMES, GATA3, GATA6, and SNAIL.

In one embodiment, the stem cells are expanded. The cells are optionally collected, separated, and further expanded, generating larger populations of stem cells for use in making cells of a particular cell type or cells having an enhanced efficiency of homologous recombination.

In some embodiments, cells are isolated from a sample of tissue by a method comprising enzymatic digestion, mechanical separation, filtration, centrifugation and combinations thereof. The number and quality of the isolated stem cells can vary depending, e.g., on the quality of the tissue used, the compositions of perfusion buffer solutions, and the type and concentration of enzyme. Frequently used enzymes include, but are not limited to, collagenase, pronase, trypsin, dispase, hyaluronidase, thermolysin and pancreatin, and combinations thereof. Collagenase is most commonly used, often prepared from bacteria (e.g. from Clostridium histolyticum), and may often consist of a poorly purified blend of enzymes, which may have inconsistent enzymatic action. Some of the enzymes exhibit protease activity, which may cause unwanted reactions affecting the quality and quantity of viable/healthy cells. It is understood by those of skill in the art to use enzymes of sufficient purity and quality to obtain viable stem cell populations.

The methods of the disclosure comprise culturing the cells. In one embodiment, the populations of stem cells are plated onto a substrate. In the present disclosure, cells (e.g., stem cells) are plated onto a substrate which allows for adherence of cells thereto, i.e., a surface which is not generally repulsive to cell adhesion or attachment. This may be carried out, e.g., by plating the cells in a culture system (e.g., a culture vessel or a multi-well plate) which displays one or more substrate surfaces compatible with cell adhesion. When the said one or more substrate surfaces contact the suspension of cells (e.g., suspension in a medium) introduced into the culture system, cell adhesion between the cells and the substrate surfaces may ensue. Accordingly, the term "plating onto a substrate which allows adherence of cells thereto" refers to introducing cells into a culture system which features at least one substrate surface that is generally compatible with adherence of cells thereto, such that the plated cells can contact the said substrate surface and adhere thereto. General principles of maintaining adherent cell cultures are well-known in the art.

In some embodiments, the substrate constitutes a confined surface past the limits of which the cells cannot spread out. A coverslip or a cell culture plate or a six-well microplate are nonlimiting examples of a confined surface.

Typically, after plating of the stem cells of the current disclosure, the cell suspension is left in contact with the adherent surface to allow for adherence of cells from the cell population to the said substrate. In contacting the stem cells with adherent substrate, the cells may be advantageously suspended in an environment comprising at least a medium, in the methods of the disclosure typically a liquid medium, which supports the survival and/or growth of the cells. The medium may be added to the system before, together with or after the introduction of the cells thereto. The medium may be fresh, i.e., not previously used for culturing of cells, or may comprise at least a portion which has been conditioned by prior culturing of cells therein, e.g., culturing of the cells which are being plated or antecedents thereof, or culturing of cells more distantly related to or unrelated to the cells being plated.

The medium may be a suitable culture medium as described elsewhere in this specification. Preferably, the composition of the medium may have the same features, may be the same or substantially the same as the composition of medium used in the ensuing steps of culturing the attached cells. Alternatively, the medium may be different.

The cells of the disclosure are cultured in the presence of a liquid culture medium. Typically, the medium will comprise a basal medium formulation as known in the art. Many basal media formulations can be used to culture the stem cells herein, including but not limited to Eagle's Minimum Essential Medium (MEM), Dulbecco's Modified Eagle's Medium (DMEM), alpha modified Minimum Essential Medium (alpha-MEM), Basal Medium Essential (BME), Iscove's Modified Dulbecco's Medium (IMDM), BGJb medium, F-12 Nutrient Mixture (Ham), Liebovitz L-15, DMEM/F-12, Essential Modified Eagle's Medium (EMEM), RPMI-1640, and modifications and/or combinations thereof. Compositions of the above basal media are generally known in the art and it is within the skill of one in the art to modify or modulate concentrations of media and/or media supplements such as growth factors, e.g., bFGF, as necessary for the cells cultured. In some embodiments, a culture medium formulation may be explants medium (CEM) which is composed of IMDM supplemented with 10% fetal bovine serum (FBS, Lonza), 100 U/ml penicillin G, 100 µg/ml streptomycin and 2 mmol/L L-glutamine (Sigma-Aldrich). Other embodiments may employ further basal media formulations, such as chosen from the ones above.

The cells of the disclosure may be at a certain passage level. The passage number refers to the number of times the cells in the culture have been subcultured, often without consideration of the inoculation densities or recoveries involved. The population doubling level (PDL) refers to the total number of times the cells in the population have doubled since their primary isolation in vitro. This is usually an estimate rounded off to the nearest whole number. A formula to use for the calculation of population doublings is as follows: n=3.32 (log UCY−log 1)+X, where n=the final PDL number at end of a given subculture, UCY=the cell yield at that point, 1=the cell number used as inoculum to begin that subculture, and X=the doubling level of the inoculum used to initiate the subculture being quantitated. In some embodiments, the passage number and/or population doubling level may be at least, at most, or exactly 1, 2, 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, or 170 times, or any range delineated between any two of the foregoing doubling levels.

The cells of the present disclosure can be maintained in culture for as long as they exhibit karyotypic stability. In one embodiment, cells of the present disclosure are grown for up to 100 passages. The Applicants have determined cell stability after 50 passages and concluded that normal karyotype was maintained.

For use in culture, media can be supplied with one or more further components. For example, additional supplements can be used to supply the cells with the necessary trace elements and substances for optimal growth and expansion. Such supplements include by way of nonlimiting example insulin, transferrin, selenium salts, and combinations thereof. These components can be included in a salt solution such as, but not limited to, Hanks' Balanced Salt Solution (HBSS), Earle's Salt Solution. Further antioxidant supplements may be added, e.g., β-mercaptoethanol. While many media already contain amino acids, some amino acids may be supplemented later, e.g., L-glutamine, which is known to be less stable when in solution. A medium may be further supplied with antibiotic and/or antimycotic compounds, such as, typically, mixtures of penicillin and streptomycin, and/or other compounds, exemplified but not limited to, amphotericin, ampicillin, gentamicin, bleomycin, hygromycin, kanamycin, mitomycin, mycophenolic acid, nalidixic acid, neomycin, nystatin, paromomycin, polymyxin, puromycin, rifampicin, spectinomycin, tetracycline, tylosin, and zeocin.

Also contemplated is supplementation of cell culture medium with mammalian plasma or sera. Plasma or sera often contain cellular factors and components that are necessary for viability and expansion. The optional use of suitable serum replacements is also contemplated (e.g., FBS) as is provision within the culture of nonreplicating (e.g., irradiated) feeder cells to supply various secreted factors and other proteins if needed. Feeder cell free media such as mTeSR can also be used.

In some embodiments, stem cells of the current disclosure are identified and characterized by their expression of specific marker proteins, such as cell-surface markers. Detection and isolation of these cells can be achieved, e.g., through flow cytometry, ELISA, and/or magnetic beads. Reverse-transcription polymerase chain reaction (RT-PCR) can also be used to monitor changes in gene expression in response to differentiation. In certain embodiments, the marker proteins used to identify and characterize the stem cells are selected from the list of pluripotency markers, which include, but are not limited to OCT4, NANOG, and SOX2. In other embodiments, the marker proteins used to identify and characterize the stem cells are selected from the list of differentiation markers, which include, but are not limited to BRA, SOX17, EOMES, GATA3, GATA6, and SNAIL.

DNA Digesting Agent for Mutating HTT

The current disclosure provides for cells modified to harbor disease forms of the HTT gene at the endogenous site and, in some embodiments, isogenic wild-type cells that do not harbor a disease form of the HTT gene. Also described are methods for producing these cells from stem cells. In some embodiments, the cells do not contain heterologous sequences outside of the HTT gene; in some embodiments, the cells contain an introduced marker or label. The term "heterologous sequences" refers to DNA segments introduced into a cell that does not normally have those sequences, whether the provenance of such segments is from the same species or not. In some embodiments, the cells, whether with a modified HTT gene or not, do not have any heterologous sequences besides a marker. Methods for modification of genomic DNA are known in the art. For example, methods may use a DNA digesting agent to modify the DNA by either the non-homologous end joining DNA repair pathway (NHEJ) or the homology directed repair (HDR) pathway. The term "DNA digesting agent" refers to an agent that is capable of cleaving bonds (i.e. phosphodiester bonds) between the nucleotide subunits of nucleic acids.

In one embodiment, the DNA digesting agent is a transposase. For example, a synthetic DNA transposon (e.g. "Sleeping Beauty" transposon system) designed to introduce precisely defined DNA sequences into the chromosome of vertebrate animals can be used. The Sleeping Beauty transposon system is composed of a Sleeping Beauty (SB) transposase and a transposon that was designed to insert specific sequences of DNA into genomes of vertebrate animals. DNA transposons translocate from one DNA site to another in a simple, cut-and-paste manner. Transposition is a precise process in which a defined DNA segment is excised from one DNA molecule and moved to another site in the same or different DNA molecule or genome.

As do all other Tc1/mariner-type transposases, SB transposase inserts a transposon into a TA dinucleotide base pair in a recipient DNA sequence. The insertion site can be elsewhere in the same DNA molecule, or in another DNA molecule (or chromosome). In mammalian genomes, including humans, there are approximately 200 million TA sites. The TA insertion site is duplicated in the process of transposon integration. This duplication of the TA sequence is a hallmark of transposition and used to ascertain its mechanism in some experiments. The transposase can be encoded either within the transposon or the transposase can be supplied by another source, in which case the transposon becomes a non-autonomous element. Non-autonomous transposons are most useful as genetic tools because after insertion they cannot independently continue to excise and re-insert. All of the DNA transposons identified in the human genome and other mammalian genomes are non-autonomous because even though they contain transposase genes, the genes are non-functional and unable to generate a transposase that can mobilize the transposon.

In a further embodiment, the DNA digesting agent is an integrase. For example, The phiC31 integrase is a sequence-specific recombinase encoded within the genome of the bacteriophage phiC31. The phiC31 integrase mediates recombination between two 34 base pair sequences termed attachment sites (att), one found in the phage and the other in the bacterial host. This serine integrase has been show to function efficiently in many different cell types including mammalian cells. In the presence of phiC31 integrase, an attB-containing donor plasmid can be unidirectional integrated into a target genome through recombination at sites with sequence similarity to the native attP site (termed pseudo-attP sites). phiC31 integrase can integrate a plasmid of any size, as a single copy, and requires no cofactors. The integrated transgenes are stably expressed and heritable.

In specific embodiments, the DNA digesting agent is a nuclease. Nucleases are enzymes that hydrolyze nucleic acids. Nucleases may be classified as endonucleases or exonucleases. An endonuclease is any of a group of enzymes that catalyze the hydrolysis of bonds between nucleic acids in the interior of a DNA or RNA molecule. An exonuclease is any of a group of enzymes that catalyze the hydrolysis of single nucleotides from the end of a DNA or RNA chain. Nucleases may also be classified based on whether they specifically digest DNA or RNA. A nuclease that specifically catalyzes the hydrolysis of DNA may be referred to as a deoxyribonuclease or DNase, whereas a nuclease that specifically catalyses the hydrolysis of RNA may be referred to as a ribonuclease or an RNase. Some nucleases are specific to either single-stranded or double-stranded nucleic acid sequences. Some enzymes have both exonuclease and endonuclease properties. In addition, some enzymes are able to digest both DNA and RNA sequences. The term "nuclease" is used herein to generally refer to any enzyme that hydrolyzes nucleic acid sequences.

Optimal reaction conditions vary among the different nucleases. The factors that should be considered include temperature, pH, enzyme cofactors, salt composition, ionic strength, and stabilizers. Suppliers of commercially available nucleases (e.g., Promega Corp.; New England Biolabs, Inc.) provide information as to the optimal conditions for each enzyme. Most nucleases are used between pH 7.2 and pH 8.5 as measured at the temperature of incubation. In addition, most nucleases show maximum activity at 37° C.; however, a few enzymes require higher or lower temperatures for optimal activity (e.g., Taq I, 65° C.; Sma I, 25° C.). DNA concentration can also be a factor as a high DNA concentration can reduce enzyme activity, and DNA concentrations that are too dilute can fall below the Km of the enzyme and also affect enzyme activity.

Non-limiting examples of nucleases include, DNase I, Benzonase, Exonuclease I, Exonuclease III, Mung Bean Nuclease, Nuclease BAL 31, RNase I, S1 Nuclease, Lambda Exonuclease, RecJ, and T7 exonuclease. DNase I is an endonuclease that nonspecifically cleaves DNA to release di-, tri- and oligonucleotide products with 5'-phosphorylated and 3'-hydroxylated ends. DNase I acts on single- and double-stranded DNA, chromatin, and RNA:DNA hybrids. Exonuclease I catalyzes the removal of nucleotides from single-stranded DNA in the 3' to 5' direction. Exonuclease III catalyzes the stepwise removal of mononucleotides from 3'-hydroxyl termini of duplex DNA. Exonuclease III also acts at nicks in duplex DNA to produce single-strand gaps. Single-stranded DNA is resistant to Exonuclease III. Mung Bean Nuclease degrades single-stranded extensions from the ends of DNA. Mung Bean Nuclease is also an RNA endonuclease. Nuclease BAL 31 degrades both 3' and 5' termini of duplex DNA. Nuclease BAL 31 is also a highly specific single-stranded endonuclease that cleaves at nicks, gaps, and single-stranded regions of duplex DNA and RNA. RNase I is a single strand specific RNA endonuclease that will cleave at all RNA dinucleotide. S1 Nuclease degrades single-stranded DNA and RNA endonucleolytically to yield 5'-phosphoryl-terminated products. Double-stranded nucleic acids (DNA:DNA, DNA:RNA or RNA:RNA) are resistant to S1 nuclease degradation except with extremely high concentrations of enzyme. Lambda Exonuclease catalyzes the removal of 5' mononucleotides from duplex DNA. Its preferred substrate is 5'-phosphorylated double stranded DNA, although Lambda Exonuclease will also degrade single-stranded and non-phosphorylated substrates at a greatly reduced rate. Lambda Exonuclease is unable to initiate DNA digestion at nicks or gaps, RecJ is a single-stranded DNA specific exonuclease that catalyzes the removal of deoxy-nucleotide monophosphates from DNA in the 5' to 3' direction. T7 exonuclease catalyzes the removal of 5' mononucleotides from duplex DNA. T7 Exonuclease catalyzes nucleotide removal from the 5' termini or at gaps and nicks of double-stranded DNA.

Restriction endonucleases are another example of nucleases that may be used in connection with the methods described herein. Restriction endonucleases include, for example, AatII, Acc65 I, Acc I, Aci I, Acl I, Afe I, Afl II, Afl III, Age I, Ahd I, Alu I, Alw I, AlwN I, Apa I, ApaL I, Apo I, Asc I, Ase I, Ava I, Ava II, Avr II, Bae I, BamH I, Ban I, Ban II, Bbs I, Bbv I, BbvC I, Bcg I, BciV I, Bcl I, Bfa I, Bgl I, Bgl II, Blp I, Bmr I, Bpm I, BsaA I, BsaB I, BsaH I, Bsa I, BsaJ I, BsaW I, BseR I, Bsg I, BsiE I, BsiHKA I, BsiW I, Bsl I, BsmA I, BsmB I, BsmF I, Bsm I, BsoB I, Bsp1286 I, BspD I, BspE I, BspH I, BspM I, BsrB I, BsrD I, BsrF I, BsrG I, Bsr I, BssH II, BssK I, Bst4C I, BssS I, BstAP I, BstB I, BstE II, BstF5 I, BstN I, BstU I, BstX I, BstY I, BstZ17 I, Bsu36 I, Btg I, Btr I, Cac8 I, Cla I, Dde I, Dpn I, Dpn II, Dra I, Dra III, Drd I, Eae I, Eag I, Ear I, Eci I, EcoN I, EcoO109 I, EcoR I, EcoR V, Fau I, Fnu4H I, Fok I, Fse I, Fsp I, Hae II, Hae III, Hga I, Hha I, Hinc II, Hind III, Hinf I, HinP1 I, Hpa I, Hpa II, Hph I, Kas I, Kpn I, Mbo I, Mbo II, Mfe I, Mlu I, Mly I, Mnl I, Msc I, Mse I, Msl I, MspA1 I, Msp I, Mwo I, Nae I, Nar I, Nci I, Nco I, Nde I, NgoMI V, Nhe I, Nla III, Nla IV, Not I, Nru I, Nsi I, Nsp I, Pac I, PaeR7 I, Pci I, PflF I, PflM I, PleI, Pme I, Pml I, PpuM I, PshA I, Psi I, PspG I, PspOM I, Pst I, Pvu I, Pvu II, Rsa I, Rsr II, Sac I, Sac II, Sal I, Sap I, Sau3A I, Sau96 I, Sbf I, Sca I, ScrF I, SexA I, SfaN I, Sfc I, Sfi I, Sfo I, SgrA I, Sma I, Sml I, SnaB I, Spe I, Sph I, Ssp I, Stu I, Sty I, Swa I, Taq I, Tfi I, Tli I, Tse I, Tsp45 I, Tsp509 I, TspR I, Tth111 I, Xba I, Xcm I, Xho I Xma I, and Xmn I.

Those of ordinary skill in the art will be able to select an appropriate nuclease depending on the characteristics of the target genomic sequence and method of genomic alteration. In one embodiment, the nuclease is a site-specific nuclease. In a related embodiment, the nuclease has a recognition sequence of at least 8, at least 10, at least 12, at least 14, at least 16, at least 18, at least 20, or at least 25 base pairs.

In some embodiments, the DNA digesting agent is a site-specific nuclease. In some embodiments, the site-specific nuclease is a Cas nuclease. In more specific related embodiments, the Cas nuclease is Cas9. In further embodiments, the nuclease is cas9 and the DNA digesting agent is a combination or composition that further comprises a guide RNA.

Another example of a sequence-specific nuclease system that can be used with the methods and compositions described herein includes the Cas9/CRISPR system (Wiedenheft, B. et al. Nature 482, 331-338 (2012); Jinek, M. et al. Science 337, 816-821 (2012); Mali, P. et al. Science 339, 823-826 (2013); Cong, L. et al. Science 339, 819-823 (2013)). The Cas9/CRISPR (Clustered Regularly interspaced Short Palindromic Repeats) system exploits RNA-guided DNA-binding and sequence-specific cleavage of target DNA. The guide RNA/Cas9 combination confers site specificity to the nuclease. A guide RNA (gRNA) contains about 20 nucleotides that are complementary to a target genomic DNA sequence upstream of a genomic PAM (protospacer adjacent motifs) site (NNG) and a constant RNA scaffold region. The Cas (CRISPR-associated)9 protein binds to the gRNA and the target DNA to which the gRNA binds and introduces a double-strand break in a defined location upstream of the PAM site. Cas9 harbors two independent nuclease domains homologous to HNH and RuvC endonucleases, and by mutating either of the two domains, the Cas9 protein can be converted to a nickase that introduces single-strand breaks (Cong, L. et al. Science 339, 819-823 (2013)). It is specifically contemplated that the methods and compositions of the present disclosure can be used with the single- or double-strand-inducing version of Cas9, as well as with other RNA-guided DNA nucleases, such as other bacterial Cas9-like systems. The sequence-specific nuclease of the present methods and compositions described herein can be engineered, chimeric, or isolated from an organism. The sequence-specific nuclease can be introduced into the cell in form of an RNA encoding the sequence-specific nuclease, such as an mRNA.

In one embodiment, the DNA digesting agent is a zinc finger nuclease. Zinc finger nucleases generally comprise a DNA binding domain (i.e., zinc finger) and a cutting domain (i.e., nuclease). Zinc finger binding domains may be engineered to recognize and bind to any nucleic acid sequence of choice. See, for example, Beerli et al. (2002) Nat. Biotechnol. 20:135-141; Pabo et al. (2001) Ann. Rev. Biochem. 70:313-340; Isalan et al. (2001) Nat. Biotechnol. 19:656-660; Segal et al. (2001) Curr. Opin. Biotechnol. 12:632-637; Choo et al. (2000) Curr. Opin. Struct. Biol. 10:41 1-416; Zhang et al. (2000) J. Biol. Chem. 275(43):33850-33860; Doyon et al. (2008) Nat. Biotechnol. 26:702-708; and Santiago et al. (2008) Proc. Natl. Acad. Sci. USA 105:5809-5814. An engineered zinc finger binding domain may have a novel binding specificity compared to a naturally-occurring zinc finger protein. Engineering methods include, but are not limited to, rational design and various types of selection. Rational design includes, for example, using databases comprising doublet, triplet, and/or quadruplet nucleotide sequences and individual zinc finger amino acid sequences, in which each doublet, triplet or quadruplet nucleotide sequence is associated with one or more amino acid sequences of zinc fingers which bind the particular triplet or quadruplet sequence. See, for example, U.S. Pat. Nos. 6,453,242 and 6,534,261, the disclosures of which are incorporated by reference herein in their entireties. As an example, the algorithm of described in U.S. Pat. No. 6,453,242 may be used to design a zinc finger binding domain to target a preselected sequence.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok1 catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) Proc. Natl. Acad. Sci. USA 89:4275-4279; Li et al. (1993) Proc. Natl. Acad. Sci. USA 90:2764-2768; Kim et al. (1994a) Proc. Natl. Acad. Sci. USA 91:883-887; Kim et al. (1994b) J. Biol. Chem. 269:31, 978-31, 982. Thus, a zinc finger nuclease may comprise the cleavage domain from at least one Type IIS restriction enzyme and one or more zinc finger binding domains, which may or may not be engineered. Exemplary Type IIS restriction enzymes are described for example in International Publication WO 07/014,275, the disclosure of which is incorporated by reference herein in its entirety. Additional restriction enzymes also contain separable binding and cleavage domains, and these also are contemplated by the present disclosure. See, for example, Roberts et al. (2003) Nucleic Acids Res. 31:418-420.

In other embodiments, the DNA digesting agent is a meganuclease. Meganucleases are endodeoxyribonucleases characterized by a large recognition site, i.e., the recognition site generally ranges from about 12 base pairs to about 40 base pairs. As a consequence of this requirement, the recognition site generally occurs only once in any given genome. Naturally-occurring meganucleases recognize 15-40 base-pair cleavage sites and are commonly grouped into four families: the LAGLIDADG family, the GIY-YIG family, the His-Cyst box family and the HNH family. Meganucleases can be targeted to specific chromosomal sequence by modifying their recognition sequence using techniques well known to those skilled in the art.

In a further embodiment, the DNA digesting agent is a transcription activator-like effector (TALE) nuclease. TALEs are transcription factors from the plant pathogen Xanthomonas that can be readily engineered to bind new DNA targets. TALEs or truncated versions thereof may be linked to the catalytic domain of endonucleases such as Fok1 to create targeting endonuclease called TALE nucleases or TALENs.

In some embodiments, the DNA digesting agent is a site-specific nuclease. In particular, the site-specific nuclease may be a "rare-cutter' endonuclease whose recognition sequence occurs rarely in a genome. Preferably, the recognition sequence of the site-specific nuclease occurs only once in a genome. Rare cutter enzymes tend to have longer recognition sequences (at least 7 or 8 nucleotides) than more common restriction enzymes.

In yet another embodiment, the DNA digesting agent may be an artificial targeted DNA double strand break inducing agent (also called an artificial restriction DNA cutter). For example, the artificial targeted DNA double strand break inducing agent may comprise a metal/chelator complex that cleaves DNA and at least one oligonucleotide that is complementary to the targeted cleavage site. The artificial targeted DNA double strand break inducing agent, therefore, does not contain any protein, The metal of the metal/chelator complex may be cerium, cadmium, cobalt, chromium, copper, iron, magnesium, manganese, zinc, and the like. The chelator of the metal/chelator complex may be EDTA, EGTA, BAPTA, and so forth. In a preferred embodiment, the metal/chelator complex may be Ce(IV)/EGTA. In another preferred embodiment, the artificial targeted DNA double strand break inducing agent may comprise a complex of Ce(IV)/EGTA and two strands of pseudo-complementary peptide nucleic acids (PNAs) (Katada et al., Current Gene Therapy, 201 1, 1 1 (1):38-45).

In a further embodiment, the nuclease may be a homing nuclease. Homing endonucleases include 1-5'ce1, 1-Ceu1, 1-Psp1, V1-Sce, 1-SceTV, I-Csm1, 1-Pan1, 1-Sce11, 1-Ppo1, 1-Sce111, 1-Cre1, 1-Tev1, 1-Tev and I-7evIII. Their recognition sequences are known. See also U.S. Pat. Nos. 5,420,032; 6,833,252; Belfort et al. (1997) Nucleic Acids Res. 25:3379-3388; Ou on et al. (1989) Gene 82: 115-118; Perler et al. (1994) Nucleic Acids Res. 22, 1 125-1 127; Jasin (1996) Trends Genet. 12:224-228; Gimble et al. (1996) J.

Mol. Biol. 263: 163-180; Argast et al. (1998) J Mol. Biol. 280:345-353 and the New England Biolabs catalogue.

In certain embodiments, the nuclease comprises an engineered (non-naturally occurring) homing endonuclease (meganuclease). The recognition sequences of homing endonucieases and meganucleases such as 1-Sce1, 1-Ceu1, VI-Psp1, V1-Sce, 1-Sce1N, 1-Csm1, 1-Pan1, 1-Sce11, 1-Ppo1, 1-Sce111, 1-Cre1, 1-Tev1, 1-Tev11 and I-7evIII are known. See also U.S. Pat. Nos. 5,420,032; 6,833,252; Belfort et al. (1997) Nucleic Acids Res. 25:3379-3388; Dujon et al. (1989) Gene 82: 115-118; Perler et al. (1994) Nucleic Acids Res. 22, 1125-1127; Jasin (1996) Trends Genet. 12:224-228; Gimble et al. (1996) J. Mol. Biol. 263: 163-180; Argast et al. (1998) J. Mol. Biol. 280:345-353 and the New England Biolabs catalogue. In addition, the DNA-binding specificity of homing endonucleases and meganucleases can be engineered to bind non-natural target sites. See, for example, Chevalier et al. (2002) Molec. Cell 10:895-905; Epinat et al. (2003) Nucleic Acids Res. 31:2952-2962; Ashworth et al. (2006) Nature 441:656-659; Paques et al. (2007) Current Gene Therapy 7:49-66; U.S. Patent Publication No. 20070117128. The DNA-binding domains of the homing endonucleases and meganucleases may be altered in the context of the nuclease as a whole (i.e., such that the nuclease includes the cognate cleavage domain) or may be fused to a heterologous cleavage domain.

In some embodiments, the DNA digesting agent is a site-specific nuclease of the group or selected from the group consisting of omega, zinc finger, TALE, and CRISPR/Cas9.

Markers

In certain embodiments, a disease HTT gene hasbeen incorporated (or an existing HTT gene has been modified to the disease form) in the genome of stem cells. These cells may be identified in vitro or in vivo by including a marker (such as a detectable or selectable marker) genetically linked to the disease HTT gene. Such markers would confer an identifiable change to the cell permitting easy identification of cells that have the disease form of HTT. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker or an antibiotic resistance gene/marker.

Usually the inclusion of a drug selection marker aids in the cloning and identification of transformants, for example, genes that confer resistance to neomycin, puromycin, hygromycin, DHFR, GPT, zeocin, G418, phleomycin, blasticidin, and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. Further examples of selectable and screenable markers are well known to one of skill in the art. In certain embodiments, the marker is a fluorescent marker, an enzymatic marker, a luminescent marker, a photoactivatable marker, a photoconvertible marker, or a colorimetric marker. Flouorescent markers include, for example, GFP and variants such as YFP, RFP etc., and other fluorescent proteins such as DsRed, mPlum, mCherry, YPet, Emerald, CyPet, T-Sapphire, and Venus. Photoactivatable markers include, for example, KFP, PA-mRFP, and Dronpa. Photoconvertible markers include, for example, mEosFP, KikGR, and PS-CFP2. Luminescent proteins include, for example, Neptune, FP595, and phialidin.

In certain embodiments, the nucleic acid segments, regardless of the length of the coding sequence itself, may be combined with other nucleic acid sequences, such as promoters, polyadenylation signals, additional restriction enzyme sites, multiple cloning sites, other coding segments, and the like, such that their overall length may vary considerably.

Disease Modeling and Drug Discovery Applications

Generation of the Isogenic hESC Lines to Model Human HD

In the experiments described in Examples 1A, 2, 3 and 4 below, CRISPR/Cas9 gene editing technology was used to introduce the HD mutation into the endogenous HTT locus, thus modifying the RUES2 line to generate RUES2-Q150: the first isogenic hESC line to model human HD. Comparative RNA-seq analysis and unbiased metabolomics of RUES2 and RUES2-Q150 cells provide transcriptional and metabolic signatures of HD in pluripotent stem cells. The conclusions drawn from this work have applicability past the specific reagents and embryonic cell line used: For example, transcriptional and metabolic signatures associated with the extension of polyQ tract (Examples 2, 3, and 4) can be used in drug discovery process, where a "hit" drug candidate has the ability to at least partially restore the transcriptional and/or metabolic signature of wild type cells.

The work described in these Examples allows, for the first time, a comparison with what has been previously reported both in isogenic mouse embryonic stem cells (mESCs) (R56) as well as in isogenic human iPSC lines of HD origin (R7). In the prior reports, the HTT polyQ tract in isogenic mESC lines was expanded from 7 to 140Qs, while human iPSCs reprogrammed from patients with 74 Qs (hiPSC-Q74) were nucleofected with a targeting construct and a vector which replaced the disease gene with a wildtype HTT gene having the normal length of 23 (R70). The present system on the other hand provides a unique opportunity to uncover both species-specific differences (as between human and mouse ESC systems), as well as differences between isogenic hESCs and iPSCs for HD when cultured under pluripotency conditions.

As RNA-seq data in isogenic HD-mESCs has not been reported, as of yet, the present RNA-seq data set cannot be directly compared with the mouse literature. However, it is noted that most of the genes that are identified in the present experiments have never been observed to be changed in mouse models. A recent study analyzing iPSCs from HD mouse iPSCs highlighted changes in genes involved in the cholesterol biosynthesis pathway as well as lysosomal genes. However, no differences between RUES2 and RUES2-Q150 were found in any of these genes in the present study, suggestingspecies-specific differences between mouse and human and correspondingly detracting further from the value of the mouse mESC model of HD.

Comparison of the RNA-seq data from the hESC-isogenic lines with microarray analysis performed in hiPSCs-isogenic lines reveals striking differences. 88 genes were found to be differentially regulated between the isogenic lines, while comparative microarray analysis between HD-iPSCs isogenic lines demonstrated a much larger variation of 323 genes. This difference can be due to the fact that hiPSCs were derived from adult tissue of HD patients and therefore have a longer cellular history, potentially retaining some of their epigenetic and genetic memory. In addition, these cells had to adapt to the diseased state during a long period of time and have therefore likely accumulated compensatory changes and perhaps also suffered expansion of the disease phenotype manifest as misregulation of additional genes. Nevertheless 3 of the 43 genes up-regulated in RUES2-Q150: H19, CAT, and CSRP1 (respectively the 22nd, 3rd and 13th most upregulated gene in Table 1) were also increased in hiPSC-Q747. H19 and CSRP1, which are both evolutionarily conserved genes, showed 5- and 16-fold increases in RUES2-Q150 respectively (Table 1). Not much is known about either H19 or CSRP1 function in pluripotent cells. H19 is a non-coding RNA that is maternally expressed in human and has been shown to function as a tumor suppressor. CSRP1 belongs to the Cysteine-rich protein family and has been shown to be required for morphogenetic gastrulation movements underlying convergent-extension is zebrafish. CAT, an evolutionarily conserved ROS scavenger protein, was among the most up-regulated genes (600 fold). CAT-knockout in the mouse surprisingly does not perturb normal NAD-linked electron transfer activity and energy coupling capacities in brain mitochondria are decreased. The connection of CAT to the metabolomics results is discussed below.

In contrast to the relatively limited similarities among the modified mouse ESC, human iPSC and human ESC discussed above, comparison of the RNA-seq dataset with microarray studies of postmortem human HD caudate brain reveals surprising overlap. The commercially available human microarray used in those studies had only 77 of the set of 88 differentially regulated genes printed on the array (but the microarray did include the 12 most upregulated and the 12 most downregulated genes of Example 2). 24 transcripts, out of these 77, showed the same differential expression pattern, with 10 transcripts upregulated and 14 downregulated. 4 out of the 10 upregulated transcripts were also in the top 12 upregulated list in Example 2. These are: ZNF558, CAT, ZNF680, and CTSF. 3 out of 14 downregulated transcripts were also in the top 12 most downregulated collection in Example 2. These are: C8orf55, LY6E, and QPCT. These results indicate that some of the changes seen in the brains of HD patients actually occur very early during human embryonic development. This establishes that despite the different character of the cells (hESCs versus mature neurons) some of the molecular changes are conserved thus validating the present system as robust and relevant to model HD. Interestingly, QPCT has been recently identified as a druggable target to counter HD pathology (Jimenez-Sanchez, 2015) providing further validation for the present screening/research tool. Lower QPCT protein levels increase the amounts of chaperones in charge of reducing protein aggregation, and thus novel QPCT inhibitors are being developed to reduce HTT aggregates. Since RUES2-Q150 cells have 7-fold lower QPCT mRNA expression, this suggests that HD hESCs might have compensatory mechanisms in place to limit HTT aggregation. The present work therefore identifies parameters that include the set of misregulated genes with no known function, as priority for diagnostic and therapeutic targeting of HD.

The RNA-seq analysis also revealed the presence of a shorter HTT splicing isoform encoding a putative N-terminus truncated protein of 217 amino acids. This CAG-expansion dependent isoform was only detected in RUES2-Q150 cells. While this transcript has been previously detected in neural tissue of HD patients and HD mouse models, it has not been described in mESCs, hESCs, or hiPSCs. This finding reaffirms that aberrant splicing might be involved in the production of the toxic short HTT fragment and provides a system in which to study its contribution to the human molecular and cellular alterations observed in HD. It also provides yet another aspect in which the present screening and research tool for HD is closer to the human situation than prior mESC or HD iPSC based models.

In addition to changes at the transcriptome level, comparison of the isogenic hESC lines allowed for the identification of differences in intracellular metabolites, with 76 metabolites significantly changed in RUES2-Q150. Since Applicants have previously performed untargeted metabolomics analysis of isogenic mESCs56, the new dataset offers the opportunity to compare and contrast metabolic differences caused by the HD mutation across species between hESCs and mESCs, as well as in human isogenic lines. In the cross-species comparison it was found that the human HD metabolic signature is significantly different from that of the mouse Q7/140 that was previously described. Among the 76, only 8 metabolites were similarly changed in both human and mouse datasets. Four of these: acetyl-CoA, lactate, α-ketogluterate, and succinate, are all intermediate of the TCA cycle, suggesting that the HD mutation leads to a state of energy deficiency. Similar results have also been described in neural stem cells derived from HD-iPSCs and HD cybrids and rat models. In addition, GDP, phosphocholine, NADH, and deoxyribose were also consistently different between isogenic hESCs and mESCs. However, the majority (68 out of 76, or 89%) of changed metabolites did not overlap between the two species. The dramatic difference in the metabolic consequences of expanded HTT in human and mouse cells raises the intriguing possibility that underlying species-specific differences significantly modify the cellular response to the mutation.

Through comparison between the 2 human lines, alterations in a novel pathway that has not been previously linked to HD has been identified: the lysine pathway. Lysine is an essential amino acid in humans. There are two degradation pathways, the saccharopine pathway which predominates in extracerebral tissues and in the fetal brain and the pipecolate pathway which is the predominant pathway in the adult brain. The altered metabolites observed in RUES2-Q150 cells are downstream of the intersection between these two pathways, suggesting that the effect of the polyQ expansion may influence both branches of the pathway. Therefore, in addition to species-specific differences, major CAG-dependent metabolite differences in hESCs were also noted.

Taken together, the RNA-seq results as well as the comparative metabolomics described in Example 3 led to the discovery of novel genes and metabolites specifically changed as a consequence of the HD mutation. These players provide a new platform for the next generation biomarkers and/or therapeutic targets for HD. As the isogenic lines have a different transcriptome and metabolome signature, the RUES2-Q150 can be used to screen for compounds that would convert its signature back to the normal RUES2. Perhaps more importantly, this study highlights the advantages of using a human system to model a human disease.

Additionally, cells and cell lines produced by the methods used herein may be used for drug development and/or reverse genetic studies (to provide insights into the development of Huntington's disease and identify therapeutic targets for this disease). Such cells may reveal phenotypes associated with a particular mutation or with the sequence modification of mutant expression products, and may be used to screen drugs that will interact either specifically with the mutation(s) or mutant proteins in question, or that are otherwise useful for treatment of the disease in an afflicted subject by restoring the function of cell parameters altered in the disease compared to cells that harbor the wild-type gene. These cell lines can also provide tools to investigate the effects of specific mutations since a wild-type cell line and its corresponding "modified" cell line represent an "isogenic" cell line system and thus provide a powerful tool for targeting disease-specific mutations, drug screening and drug discovery, and disease mechanism research which is anticipated to reveal additional therapeutic targets. It is believed that this approach will provide insights into Huntington's disease, its mechanism and methods of treating it, that are not available using methods and HD models of the prior art.

Applications of Micropattern Technology in Huntington Disease

Cells in situ are embedded into a highly structured microenvironment. The cell microenvironment imposes specific boundary conditions that influence not only cell architecture and mechanics, but also cell polarity and function. The size of the microenvironment also limits the cell volume and cell spreading. Its structure, i.e. the positioning of adjacent cells governs the spatial distributions of cell adhesion. The biochemical composition of the microenvironment specifies the factors that can engage in cell adhesion, and thereby affect intracellular signaling pathways where these pathways further dictate the assembly and dynamics of cytoskeleton networks. Just like other cell types, stem cells reside in complex and heterogeneous compartments throughout the body, and interactions with one another and with surrounding cells can modulate their fate decisions. Therefore, the specific balance of cell types within the niche is a regulator of stem cell behavior.

Given that the important properties of the cell microenvironment are abolished under classic cell culture conditions, using surfaces with micropatterned cell adhesive features, such as those described in the present disclosure allows the reconstitution of in vivo-like conditions for in vitro cell culture.

Thus, in one embodiment, the cells of the present disclosure are grown according to methods described in Example 5, leading to generation of spatially ordered germ layers. For example, differentiation of cells with BMP4 ligand or with another morphogen represents an early step in the embryonic signaling cascade that initiates gastrulation. The Applicants have previously shown that cells confined to circular micropatterns and differentiated with BMP4 produce an ordered array of germ layers along the radial axis of the colony. Thus, embryonic cells can be grown using growth factors, such as BMP4, to differentiate colonies into an outer trophectoderm-like ring, an inner ectodermal circle and a ring of mesendoderm expressing primitive-streak markers in between (Warmflash et al). Instead of using BMP4, cells of the present disclosure can be differentiated into different germ layers using factors other than BMP4, including but not limited to other morphogen molecules such as Wnt3a and activin. The thus created ordered arrays can be visualized for example by detecting markers characteristic of each germ layer and quantitated. This can be done in both the modified and the control cells. Information for example on cell morphology and number can thus be gleaned and differences attributed to the >40polyQ on these early stage cells. The ability of putative drugs can be assessed in reducing or eliminating these phenotypic differences between the modified and the wildtype cells. Additional differences can be explored by further differentiating the cells into for example progenitor cells committed to a neuronal fate or even fully differentiated neurons.

Thus, in the present disclosure, the applicants have used the intrinsic tendency of stem cells to form patterns to generate a quantitative, single cell resolution screening platform for HD (See for example Example 5). This provides an early human HD phenotypic signature. It was further discovered that the signature is different depending on the length of the polyQ repeat. Thus ESC lines having 43, 48, 56, 65 and 72 ras well as the originally described Q150 repeats, on stimulation with BMP4, showed progressively more aberrant human gastrular phenotypic signatures. Such signatures are described in Example 9 and are characterized by reduction of the ectodermal (centrally located) cell, and expansion but increasing irregularity of the other two layers.

The present inventors confirmed these results using hiPSC reprorammed from human fibroblasts having different polyQ lengths collected from young HD patients. When stimulated with BMP4, these revealed patterns qualitatively similar to those observed with ESC modified with pathologic levels polyQ as described herein and similarly stimulated. This indicates that the present findings are of clinical relevance. See for example, Example 10 including methods described for this example.

In more detail, by comparing the micropatterns of isogenic normal (RUES2) and HD (RUES-Q150) line (Example 5) or HD (RUES-Q43 etc.), Applicants have identified an HD-dependent micropattern signature (FIGS. 6 and 7). Features of HD-dependent micropattern signature include, but are not limited to, change in germ layer marker expression. More specifically, the Applicants have identified reduced SOX2 germ layer marker expression and expanded germ layer markers Bra/Cdx2 territories. Moreover, as shown in Example 5, the expression of SOX2, Bra, and Cdx2 is complementary in terms of overall radius, wherein reduction in SOX2 expression is accompanied by increase in Bra/CDx2 territories and vice versa. Additionally, HD-dependent micropattern signature exhibited an overall reduction in cell number, as well as reduction in cell number of each germ layer (see for Example FIG. 12). A reduction (or increase) in cell number of 1% or a higher percentage is considered significant. Thus, in some embodiments, the HD-dependent micropattern signature of RUES-Q150 cells comprises changes in germ layer marker expression when compared to the micropattern signature of isogenic normal cells (RUES2). In additional embodiments, the germ layer marker comprises one or more of SOX2, BRA, and CDX2. In some embodiments, the germ layer marker comprises all three of SOX2, BRA, and CDX2. In further embodiments, the germ layer marker comprises one or more of OCT4, NANOG (both pluripotency markers along with Sox2), EOMES (mesoderm marker along with BRA), SOX17, GATA6 (both endoderm markers), and CDX2 (trophoderm/mesoderm marker). In yet another embodiment, HD-dependent micropattern signature comprises a reduced total number of cells in a micropattern and/or reduced number of cells of one or more specific germ layers. In further embodiments, an HD-dependent micropattern signature comprises a reduced number of cells and changes in germ layer marker expression.

In some embodiments, an HD-dependent micropattern signature comprises a change in three-dimensional cellular geometry when compared to the micropattern signature of wildtype cells. In more specific embodiments an HD-dependent micropattern signature comprises an increase in three-dimensional cellular geometry when compared to the micropattern signature of wildtype cells (the >40Q cells have an increased height and a more confined "rounder" volume as revealed by microscopic imaging at different heights followed by 3D reconstruction). In yet other embodiments, an HD-dependent micropattern signature comprises an increase in three-dimensional cellular geometry of SOX2 positive cells when compared to the micropattern signature of wildtype cells.

More generally, parameters that can be assessed and compared in a micropattern signature include without limitation, cell morphology, cell organization, cell expansion number, cell reduction number, gene expression, cytokine expression, a cell metabolic signature or a combination of two or more of the foregoing.

The present disclosure provides for a comparison of distinct micropattern signatures displayed by the isogenic wildtype and modified cell lines described herein (whether these are modified by extending the polyQ segment repeats or by knocking down one or both alleles of HTT). Any of the cell lines described in the present disclosure can be grown using micropattern technology at least at the stem cell, germ layer formation, pluripotency and progenitor stages. In addition to the germ layer micropattern cultures, differentiating cells committed to a neuronal pathway also display characteristic phenotypes, providing an additional screening platform. Fully differentiated neurons take longer and require a more spacious culture container Such terminally differentiated neurons in the mitotic or post-mitotic state have also been shown to display phenotypic differences depending on whether they have a wildtype or a >40Q HTT gene. Again, the aberrant phenotype depended on the number of Q repeats. See for example Example 10 wherein neuronal mitotic and post-mitotic phenotype was shown to be aberrant culminating in giant neurons and or in polynucleated neurons. This provides yet another platform for screening therapeutic candidates. These platforms can be used in combination of two or more with one another as well as with other tools described herein, such as the HTT+/− or the HTT−/− cells or the exon 41b. each of the last three tools is useful in target identification.

All screening platforms provided herein, whether the cells are in early stages of organization, in early stages of differentiation, or whether they are fully differentiated neurons, whether they are hiPSC or hESC and whether they have slightly or considerably higher than normal poly Q repeats are amenable to quantification.

Differences in micropattern signatures between the cells of the present disclosure, more specifically between isogenic wildtype and modified cell lines comprising an extended polyQ tract, alone or in conjunction with HTT+/−, and HTT−/− cells can be exploited for drug discovery purposes in pursuit of treatments for Huntington's disease. Since cells described herein comprise human embryonic stem cells, the present disclosure provides a drug screening platform for compounds that inhibit the development of, or revert early aberrant patterns associated with, HD. The isogenic modified and wildtype cells can be differentiated all the way to neurons and further screenings or target identification can be performed. Within this context, compounds that partly or fully inhibit the development of, or partly or fully revert (i.e. partly or fully restore) the wildtype state of the micropatterns associated with HD would be considered "hits" or potential drug candidates for the treatment of Huntington's disease.

In some embodiments, the present disclosure provides a drug screening platform for testing a combination of two or more drug candidates for the treatment of Huntington's disease In further embodiment, the present disclosure provides a drug screening platform for testing a combination of two or more drug candidates for the treatment of Huntington's disease, where one or more of the drug candidates is already used or has been reported to be active as a therapeutic agent in the treatment of Huntington's disease.

The drug candidates for the treatment of Huntington's disease can be screened using cells of the present disclosure, where for example, isogenic wildtype and HD cells comprising one or more of an extended polyQ tract, HTT+/−, and/or HTT−/− human embryonic stem cells and differentiated cells derived therefrom, is contacted with a test compound (e.g., a Huntington disease potential therapeutic candidate). Following incubation of the cells with a test compound, the method further comprises detecting changes in one or more features of the micropattern signature compared to that of cells that were not treated with the test compound.

In one embodiment, a "hit" is a test compound that alone or in combination with one or more other drug candidates inhibits the development of or reverts one or more features of a disease form t micropattern signature. In another embodiment, a "hit" is one that alone or in combination with one or more other drug candidates inhibits the development of or reverts spatial expression of Sox2, Bra, and Cdx2 of HD-dependent micropattern signature to reduce the assessed difference with the corresponding control (for example the wildtype HTT cells). In further embodiments, a "hit" is a test compound alone or in combination with one or more other drug candidates inhibits the development of or reverts a reduction in total and/or specific germ layer cell number associated with HD-dependent micropattern signature. In yet another embodiment, a "hit" is one that alone or in combination with one or more other drug candidates inhibits the development of or reverts a change in three-dimensional cellular geometry associated with HD-dependent micropattern signature.

Advantages of a micropattern drug screening platform using cells of the present disclosure include, but are not limited to: 1) rapid (48-72 hours) screen of HD-related phenotypes directly in the human system; 2) no need to collect and grow neurons from diseased individuals; 3) provision for the use of a fast visualization technique that can be automated and scaled up; and 4) ability to use as a platform for drug toxicity studies. Thus, human HD micropattern signature described herein can be used as a tool for in vitro "clinical trials" for human neurodegenerative diseases such as HD. It is anticipated that assays and methods of the present disclosure can be automated, which can significantly facilitate the drug discovery process. In some embodiments, it is anticipated that assays and methods of the present disclosure can be adapted for the use in high-throughput screening.

Using >40Q lines of the present disclosure, Applicants have carried out a screen for compounds that have the potential to revert the HD signature back to that of the normal isogenic cells. This screen led to identification of two compounds, minoxidil and kinetin, that reduced or reverted HD-dependent micropattern signature, specifically Sox2 and Bra/Cdx2 expression to that of isogenic wild-type cells (Example 5). Additionally, kinetin also restored the cell density of a >40Q cell line to that of wild-type cells (Example 5).

Thus, in some embodiments, the present disclosure provides for the use of minoxidil to inhibit the development of or to fully or partially revert one or more subclinical characteristic or clinical symptom of Huntington's disease.

Similarly, other therapeutic candidates can be thus identified by screening compound libraries with one or more screening platforms disclosed herein.

Indeed, as the inventors have demonstrated in the present disclosure, the present methods are readily adaptable to high throughput screening, confirming yet again that a micropatterned culture is not necessary for performance of the screening assays of the present disclosure.

Discovery and Exploration as a Target of Hominid-Specific Exon of HTT

Figure 14:
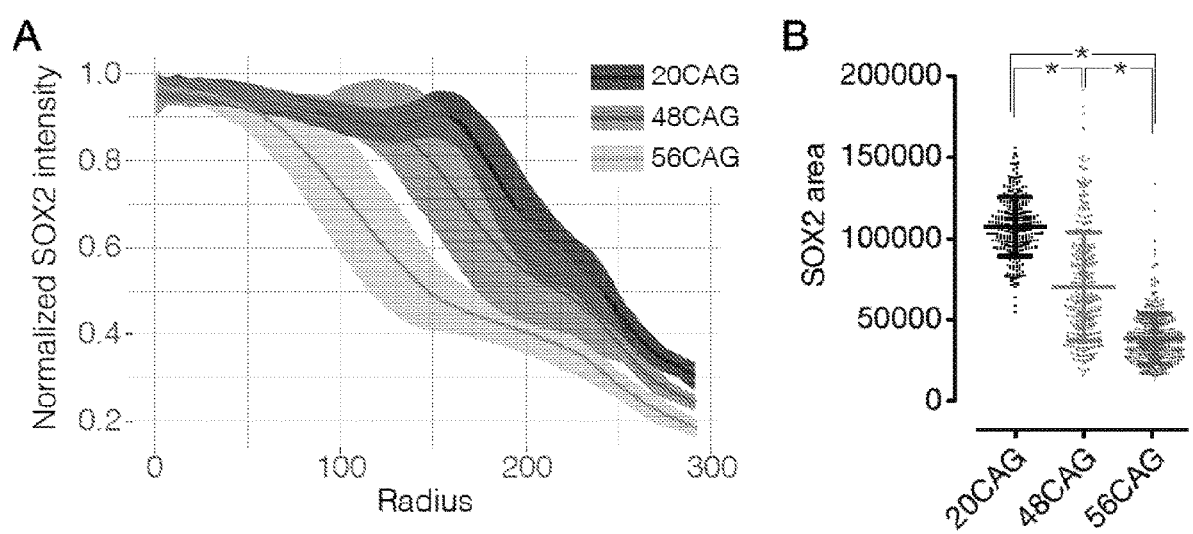

In the present disclosure, Applicants have identified a novel isoform of HTT, which incorporates a previously unreported additional exon, named 41b, and which adds 30 new amino acids to the full HTT protein (Example 8, FIG. 14). The applicants have postulated that addition of these extra amino acids may change posttranslational modifications, which in turn can result in change of protein conformation, for example making HTT protein more prone to aggregation. Additionally, computational analysis revealed that the additional amino acids of 41b lead to introduction of a new predicted phosphorylation site within HTT protein and removal of one phosphorylation site found within canonical HTT (asterisks in FIG. 14 specify differences in phosphorylation site predictions). Such changes in posttranslational modifications and/or conformation can impact the activity of HTT protein and consequently downstream signaling of HTT.

This splice isoform, due to its conservation only in great apes and humans, is potentially a significant factor in HD pathogenesis as HD is a human disease. Indeed, the nucleotide sequence of the exon region suggests that it was acquired through the insertion of a new Alu element during evolution of the hominidae family. This novel human-specific HTT isoform (41b) is important to a better understanding of the HD mechanism. In addition, 41b provides a new potential therapeutic target for HD.

One approach to assessing a role of 41b in human pathology can include, but not be limited to, evaluating the expression levels or status of posttranslational modifications of 41b in Huntington's Disease patients and comparing it to that of healthy individuals. Furthermore, studies including deletion of 41b in hESC cells by adapting methods described herein for deletion of the entire HTT gene and then culturing such cells as described and exemplified herein can be used. Assessment of various parameters including, but not limited to parameters such as cell morphology, cell organization, cell expansion number, gene expression, cytokine expression, a cell metabolic signature or a combination of two or more of the foregoing can serve as a functional readout of the phenotypic characteristics associated with deletion of 41b from hESC. Comparison of such parameters to corresponding parameters in wild type hESC can lead to a delineation of 41b function in the context of Huntington's Disease. If such function is indeed confirmed, drug screening experiments can be designed to search for compounds that target 41b. Potential drug candidates could include those that are capable of interfering with function of 41b by for example modulating phosphorylation status or by altering conformation of 41b.

Methods of Treatment for Huntington's Disease

Pharmaceutical Compositions

The current disclosure includes methods for treating Huntington's disease in a patient diagnosed with Huntington's disease. Administration of the compositions according to the disclosure will typically be via any common route. This includes, but is not limited to parenteral, intrathecal orthotopic, intradermal, subcutaneous, intramuscular, intraperitoneal, intranasal, intracranial or intravenous injection. Additional formulations which are suitable for other modes of administration include oral formulations. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain about 10% to about 95% of active ingredient, preferably about 25% to about 70%.

Compositions of the disclosure are administered in a manner compatible with the dosage formulation, and in such amount as will be therapeutically effective.

The manner of administration may be varied widely. Any of the conventional methods for administration are applicable. These are believed to include oral application on a solid physiologically acceptable base or in a physiologically acceptable dispersion, parenterally, by injection and the like.

The phrases "pharmaceutically acceptable" or "pharmacologically acceptable" refer to molecular entities and compositions that do not produce an adverse, toxic, allergic, inflammatory, or other untoward reaction when administered to an animal, or human. As used herein, "pharmaceutically acceptable carrier" includes any and all solvents, dispersion media, coatings, antibacterial and antifungal agents, isotonic and absorption delaying agents, and the like that are pharmaceutically acceptable as the term is used herein and preferably inert. The use of such media and agents for pharmaceutical active substances is well known in the art. Except insofar as any conventional media or agent is incompatible with the active ingredients, its use in therapeutic compositions is contemplated.

To prepare pharmaceutical or sterile compositions of the compositions of the present disclosure, the compounds or cells, or similar compositions may be admixed with a pharmaceutically acceptable carrier or excipient. See, e.g., Remington's Pharmaceutical Sciences and U.S. Pharmacopeia: National Formulary, Mack Publishing Company, Easton, Pa. (1984).

Formulations of therapeutic and diagnostic agents may be prepared by mixing with acceptable carriers, excipients, or stabilizers in the form of, e.g., lyophilized powders, slurries, aqueous solutions or suspensions (see, e.g., Hardman, et al. (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N.Y.; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, NY; Weiner and Kotkoskie (2000) Excipient Toxicity and Safety, Marcel Dekker, Inc., New York, N.Y.).

The compositions of the disclosure can be formulated for parenteral administration, e.g., formulated for injection via the intravenous, intramuscular, sub-cutaneous, intracranial, intrathecal or intraperitoneal routes. The preparation of an aqueous composition that contain compounds and active ingredients described herein will be known to those of skill in the art in light of the present disclosure. Typically, such compositions can be prepared as injectables, either as liquid solutions or suspensions; solid forms suitable for use to prepare solutions or suspensions upon the addition of a liquid prior to injection can also be prepared; and, the preparations can also be emulsified.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and preferably preserved against the contaminating action of microorganisms, such as bacteria and fungi.

The compositions may be formulated into a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases (base addition salts) such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active ingredients in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder comprising the active ingredient, plus any additional desired ingredient from a previously sterile-filtered solution thereof.

An effective amount of therapeutic or prophylactic composition is determined based on the intended goal. The term "unit dose" or "dosage" refers to physically discrete units suitable for use in a subject, each unit containing a predetermined quantity of the composition calculated to produce the desired responses discussed above in association with its administration, i.e., the appropriate route and regimen. The dosage of the pharmaceutical composition and the frequency of its administration will depend on a variety of factors, such as the disease to be treated, the result and/or protection desired, the potency of the active ingredient, the duration of its activity once administered, the route of administration, the size, age, sex and physical condition of the subject, the risk of adverse reactions and the judgment of the medical practitioner.

Upon formulation, solutions will be administered in a manner compatible with the dosage formulation and in such amount as is therapeutically or prophylactically effective.

The formulations are easily administered in a variety of dosage forms, such as the type of injectable solutions described above.

The therapeutically effective amount will be initially determined based on the concentration or concentrations found to confer a benefit to cells in culture. Effective amounts can be extrapolated from data within the cell culture and can be adjusted up or down based on factors such as detailed above. An exemplary range of effective amounts for kinetin is between about $10^{-6}$ M and $5 \times 10^{-4}$ M in the blood and for minoxidil an orally is 5 to 40 mg per patient per day, preferably 5-10 mg per patient per day when orally administered or for from 0.25 to 1.0 mg/kg/day with a maximum dose of 50 mg. Alternatively, effective amount can be expressed as a concentration in the blood betweem $10^{-6}$M and $10^{-3}$ M.

Dosage and manner of application of effective amounts of pharmaceutical compositions of the present disclosure can also vary depending on the timing of treatment. For example, treatment of the subject carrying an HTT mutation can be initiated in utero (during pregnancy). In some embodiments, treatment of a subject carrying an HTT mutation is initiated at birth. In further embodiments, treatment of a subject carrying an HTT mutation can be initiated at the time of onset of symptoms associated with HD. In other embodiments, treatment of a subject carrying an HTT mutation is initiated at any time during the progression of HD.

Combination Therapy

The compositions and related methods of the disclosure may also be used in combination with the administration of traditional therapies. For example, these include medications for movement disorders. Drugs to treat movement disorders include the following: Tetrabenazine (Xenazine) is specifically approved by the Food and Drug Administration to suppress the involuntary jerking and writhing movements (chorea) associated with Huntington's disease. Antipsychotic drugs, such as haloperidol, risperidone, and quetiapine may also be used. Other medications that may help suppress chorea include amantadine, levetiracetam and clonazepam.

Medications for psychiatric disorders may also be used. Medications to treat psychiatric disorders will vary depending on the disorders and symptoms. Possible treatments include the following: antidepressants include such drugs as citalopram, fluoxetine, and sertraline. These drugs may also have some effect on treating obsessive-compulsive disorder. Antipsychotic drugs such as quetiapine, risperidone, and olanzapine may suppress violent outbursts, agitation, and other symptoms of mood disorders or psychosis. Mood-stabilizing drugs that can help prevent the highs and lows associated with bipolar disorder include anticonvulsants, such as valproate, carbamazepine, and lamotrigine.

Other conventional therapies such as psychotherapy, speech therapy, physical therapy, and occupational therapy may be used in combination with the methods described herein.

Administration of an active ingredient described herein (such as minoxidil or kinetin) may precede or follow the other treatment by intervals ranging from minutes to weeks. In embodiments where the other agents are administered separately, one would generally ensure that a significant period of time did not expire between the time of each delivery, such that the agent and antibody would still be able to exert an advantageously combined effect on the subject. In such instances, it is contemplated that one may administer both modalities substantially simultaneously or within about 12-24 h of each other and, more preferably, within about 6-12 h of each other. In some situations, it may be desirable to extend the time period for administration significantly, however, where several days (2, 3, 4, 5, 6 or 7) to several weeks (1, 2, 3, 4, 5, 6, 7 or 8) lapse between the respective administrations.

Administration of compositions described in the disclosure to a patient/subject will follow general protocols for the administration of such compounds, taking into account the compound toxicity, if any. It is expected that the treatment cycles would be repeated as necessary and that therapy may be continued for months or years or indefinitely as long as benefits persist. It also is contemplated that various standard therapies, such as hydration therapy, may be applied in combination with the described therapy.

Treatment of Huntington's Disease

"Treating" as used herein may include the amelioration of a symptom of the disease such as amelioriation or lessening or reduction in chorea, dystonia, slow or abnormal eye movements, impaired gait, posture, and balance, and difficulty with the physical production of speech or swallowing. Treating may also include the improvement of a cognitive disorder associated with HD such as difficulty organizing, prioritizing or focusing on tasks, lack of flexibility or a tendency to get stuck on a thought, behavior or action (perseveration), lack of impulse control that can result in outbursts, acting without thinking and sexual promiscuity, lack of awareness of one's own behaviors and abilities, slowness in processing thoughts or "finding" words, or difficulty in learning new information. Treating may also include an amelioration or lessening of a psychiatric disorder in a patient having Huntington's disease. Psychiatric disorders include feelings of irritability, sadness or apathy, social withdrawal, insomnia, fatigue and loss of energy, frequent thoughts of death, dying or suicide, obsessive-compulsive disorder, mania, and bipolar disorder.

In some embodiments, the method is for treating juvenile Huntington's disease. In some embodiments, the treatment reverses (partially or completely) molecular phenotypes such as structural changes in particular sites in the brain affected by HD. In some embodiments, the treatments reduce or increase striatal and cortical atrophy, hypometabolism in the cerebral cortex, presynaptic and postsynaptic dopamine, and connectivity between the basal ganglia and cortical areas.

Kits

The present invention also provides kits comprising the components of the combinations of the disclosure in kit form. A kit may include one or more components including, but not limited to, any of the HD screening or model HD cell lines, as discussed herein, optionally in association with one or more additional components including, a therapeutic agent, as discussed herein. The compositions and/or the therapeutic agent/s can be formulated as a pure composition or in combination with a pharmaceutically acceptable carrier, in a pharmaceutical composition.

In one embodiment, a kit may include any of the HD screening or model cells lines of the disclosure, with each in a separate container (e.g., in a sterile glass or plastic vial). A preferred option includes in one container: a first clonal population of human embryonic stem cells comprising a normal Huntingtin gene (HTT); and in a second container: a second clonal population of human embryonic stem cells isogenic to the first population but comprising an HTT that has been genetically modified to comprise a nucleotide segment, wherein the nucleotide segment upon expression, results in a polyQ repeat peptide segment comprising at least 40 glutamine residues in the N-terminal region of the HTT protein. In certain embodiments, the kit may include in addition to the reference strain (comprising the normal HTT gene), 1, 2, 3, 4, 5, or up to 15 different HD disease cell lines representing differing numbers of polyQ repeats. The kit can include a package insert including information concerning cell growth and maintenance, as well as buffers and/or growth factors in the kit.

EXAMPLES

The following examples are included to demonstrate certain embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the claims that follow.

Example 1

Generation of Human Embryonic Stem Cell Lines as Screening and Research Tools

As stated in the Background section, Huntington's disease (HD) is a dominant autosomal neurodegenerative disease that is caused by a mutation that leads to the expansion of a polyQ repeat at the N-terminus of the Huntingtin protein (HTT). Despite years of scrutiny, current animal models fail to accurately recapitulate the pathophysiology of human HD, possibly due to species-specific differences. This has hindered progress toward finding effective candidate therapies for the disease. In order to provide a human platform as a drug screening and research tool to study the function and malfunction of HTT in healthy and >40Q cells, this example describes the use of CRISPR/Cas9 genome editing technology to generate the first isogenic human embryonic stem cell lines of HD (and an isogenic wild-type control).

Described in this example is the application of a reverse editing strategy utilizing CRISPR-Cas9 to introduce a large expansion of the polyQ tract in normal hESCs, thus generating HD lines that are genetically identical to wild-type counterparts (except for the polyQ expansion in the HTT gene) and therefore can be termed isogenic. This approach has the advantage of using human pluripotent cells that are stable and can generate all cell types including those that are compromised in HD. Comparative global transcriptome and unbiased metabolome analysis of these lines revealed previously undetected differences caused solely by insertion of an expanded polyQ tract in a single genomic locus.

1A. Generation of Isogenic Human Embryonic Stem Cell Lines

Figure 1:
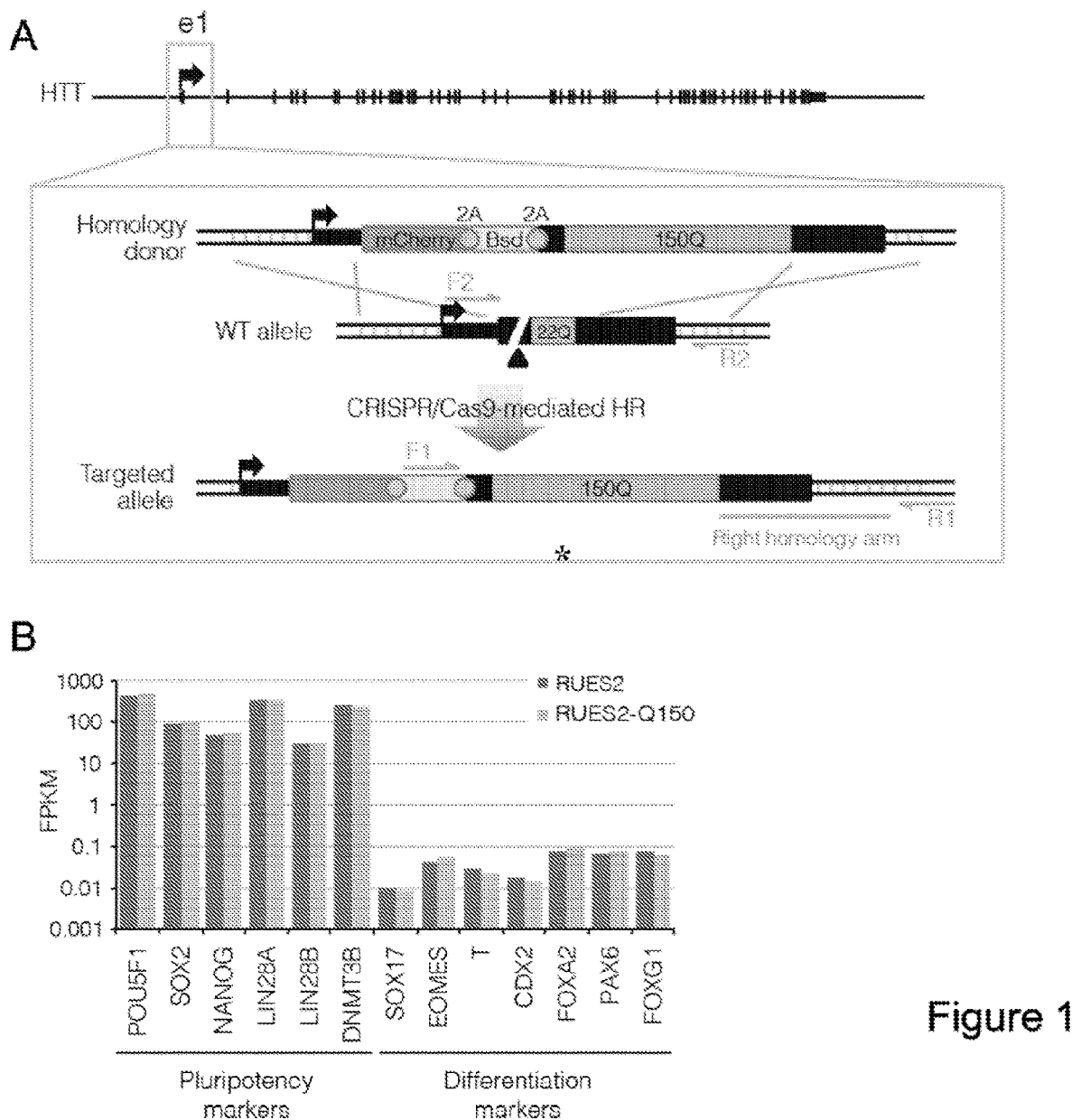
FIG. 1A-B: Creation of an isogenic hESC model of Huntington's disease using CRISPR/CAS9 mediated gene editing. (A) The 22CAG (=24Q) allele of HTT in the RUES2 hESC line was modified to include a mCherry-blastadicine (Bsd) cassette and increase the length of the polyQ tract in exon 1 to 150Q using CRISPR/Cas9 technology. 2A=peptide 2A. Integration of the donor vector was confirmed by PCR using primers shown in (A) (data not shown) and protein expression from the expanded HTT allele was confirmed using western blot (data not shown).(B) RUES2-Q150 cells maintain pluripotency as shown by high expression of pluripotency markers (left, light bars) and low expression of differentiation markers (right, light bars) at levels similar to those observed in RUES2 (dark bars). The expression data were extrapolated from RNA-seq results (see FIG. 2). RUES-Q150 colonies show normal morphology when cultured in pluripotency conditions and express mCherry fluorescent protein, which can be used to track these cells in cell mixing experiments (data not shown). RUES2-Q150 cells show similar rates of cell replication (measured by EdU incorporation) and similar apoptosis levels (measured by active Caspase3 staining). RUES2-Q150 cells are also perfectly able to differentiate towards neurons normally, as demonstrated by their ability to form neuronal rosette structures that stain positive for the neuronal markers PAX6 and N-Cadherin, and which resemble WT-RUES2-derived neuronal rosettes (data not shown).

Briefly, CRISPR-Cas9 technology was used to genetically engineer the RUES2 hESC line that was previously derived. The parent cell line, RUES2 is registered with the NIH (NIHhESC-09-0013) and available from the Rockefeller University and WiCell (lot number WB33127); it is a female (XX) line that has a wild type HTT locus (chromosome 4p16.3) that encodes 22Qs on one allele and 24Qs on the second. The 22Q allele was modified by adding 128Qs, thus generating a 150Q line (RUES2-Q150; FIG. 1A). The relatively large number of resulting polyQs was selected in order to speed up the appearance of disease phenotypes but a smaller number may be used as long as it is 40Q or more as described herein.

A lineage trace marker mCherry and blastidicine cassette were also incorporated into RUES2 hESC.

Other embryonic cell lines having a wild-type HTT gene could have been used instead and genetically modified as described herein to create modified hESC cell lines and isogenic controls. In addition, three unmodified isogenic cell lines were generated with a normal allele 20 CAG codons) as a control.

The insert length (to create a 150Q HTT gene) was chosen to model the early-onset juvenile form of HD, which represents the worst case of the disease, in order to maximize the chances to discover possible differences. (As it turned out, this high number of polyQ was not necessary although it served the purpose.) For lineage tracing and selection purposes, a mCherry-blastidicine cassette flanked by self-cleaving peptide 2A sites upstream of the start codon was inserted (FIG. 1A). Successful modification of the locus was confirmed by PCR. The resulting RUES2-Q150 cells were karyotypically normal and expressed both HTT alleles, as evidenced by Western blotting of cell lysates for HTT. It is anticipated that expression of one HTT allele would have been sufficient to display the HD phenotype. Expression of mCherry was confirmed using fluorescent imaging.

To show that the genome editing strategy did not affect the basic properties of hESCs, it was confirmed that, when grown under pluripotency conditions (which can be checked by testing for expression of one or more pluripotency markers such as POU5F1 (a/k/a OCT4), SOX2, NANOG, LIN28A, LIN28B, and DNMT3, all of which were tested here). RUES2-Q150 cells maintained normal hESC morphology, and expressed pluripotency markers for example at levels similar to wild type RUES2 cells (FIG. 1B). In addition, the rate of cell proliferation by EdU incorporation was examined, as well as the rate of apoptosis by activated Caspase-3 immunostaining, and no differences were found between the two lines.

Finally, to determine the differentiation potential of these cells toward a lineage that is relevant to HD, dual-SMAD inhibition comprising SB431542 and LDN 193189 was used to induce neuronal fate by default. Alternatively, a combination of SB (SB431542) and Noggin could have been used instead to induce neuronal fate. RUES2-Q150 cells formed rosettes of typical morphology expressing the neuronal-specific markers PAX6 and N-Cadherin. Other differentiation markers were also expressed, such as SOX17, EOMES, T (BRA), CDX2, FOXA2 and FOXG1. Any one of these markers would have been enough to show differentiation. However, if all are revealed, the various germ layers can be visualized and differentiation in each layer can be assessed. Taken together, these results demonstrate that the genome editing did not change the basic properties of isogenic hESCs.

1B. Generation of ESCs Spanning a Various Range of polyCAG Lengths Found in HD Patients Without Detectable and Selectable Markers In addition to HD ESC lines spanning various polyQ lengths of HTT gene and comprising detectable marker (expression marker) mCherry and blastidicine cassette, the Applicants also generated cells that comprise various polyQ lengths, but lack the detectable marker and selectable marker cassettes.

The present inventors generated a set of >40Q ESC lines spanning the typical range of polyCAG lengths found in HD patients 42, 48, 56, 67, and 150 CAGs (FIG. 13A). RUES2 hESC line was again used as the parental line. All of the codons were CAG except for the penultimate one which was CAA, as it occurs in nature. However, a mixture of CAG and CAA codons could have been used as was done for the 150Q modified cells. Briefly, cells were generated using CRISPR technology as described in Materials and Methods below. In order to generate cells in which polyQ tract is the same as the one found in HD patients (comprising essentially only CAG repeat), the inventors used a PCR to amplify a mutant Huntington's gene locus directly from patient samples using the following cells: ND38548 from the Coriell Institute, GENEA020 from GENEA Biocells, and QS-001 and QS-004 fibroblasts from the Tabrizi laboratory (United Kingdom). These cells were used as starting material for PCR to make the donor plasmid. Fibroblasts are available from many public and commercial sources and these could have been used instaed. The same is true for the remaining cells: they are available from alternative sources. The polyQ tract comprising only CAG trinucleotide can also be synthesized in the lab.

Additionally, the Applicants used a selectable marker that contained an ePiggybac transposable element, which allowed marker removal once the selected cells were identified. The excision-only trasnposase was purchased from Transposagen (Lexington, Ky. 40508). Thus, ultimately, these cells do not comprise a selectable marker, and differ from isogenic wildtype control cells only in the length of the polyQ tract. Importantly, all of these modified cell lines exhibited the disease phenotype.

Given that these cells have fewer differences when compared to isogenic normal control cells than the cells comprising expression marker and selectable marker cassette, they provide another set of embodiments for modeling Huntington Disease, which is essentially devoid of inserted sequences except for the introduced polyQ tract.

Example 2

The HTT Extension Leads to Changes in the Transcriptome of Isogenic hESCs

Because the HD ESC lines are the first generation of isogenic hESCs modeling aspects of HD, Applicants sought to perform comparative analysis on lines grown under the exact same conditions, and processed in parallel for transcriptome RNA-seq analysys.

As RUES2 and RUES2-Q150 have the same genetic background, Applicants had an opportunity to ask if the simple addition of polyQs can generate transcriptional differences between the two lines. To address this, Applicants performed comparative RNA-seq analysis in duplicates. The presence of HTT splice isoforms was first examined, and the question was asked whether the polyQ tract expansion affected HTT mRNA isoform expression. Consistent with previous observations in both mouse and human, a highly enriched HTT isoform of about 2 kb was detected, arising from the read-through of exon-1 into intron-1 only in RUES2-Q150, which encodes and enriches the expression N-terminal fragment of HTT protein (FIG. 2A). The expression of other isoforms previously reported was also confirmed, including the human-specific HTT isoform, 41b, in RUES2-Q150 at similar levels as the wildtype (Ruzo et al. *PLoS One.* 2015 May 26; 10(5)).

Figure 2:
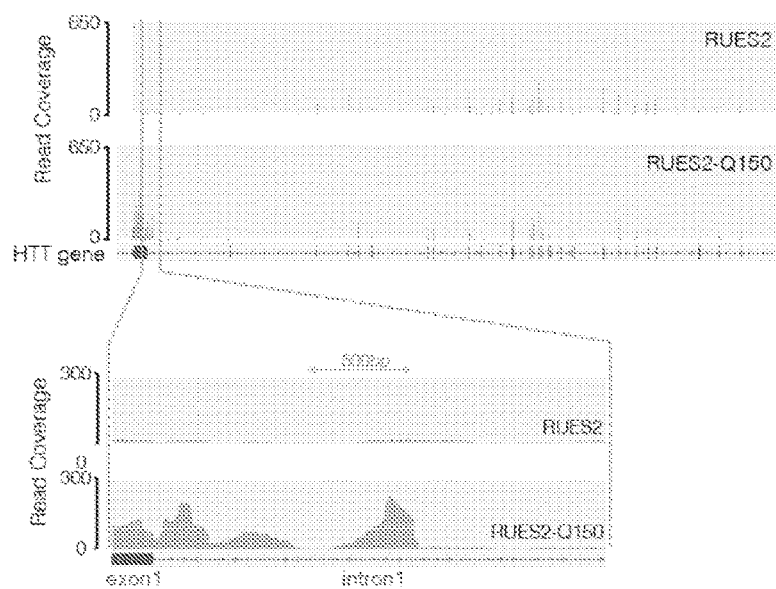
FIG. 2A-C: RNA-seq analysis of pluripotent RUES2 and RUES2-Q150 cells uncovers transcriptional differences. (A) RNAseq analysis uncovers the presence of a short HTT transcript generated by read-through from exon 1 into intron 1. This isoform is present only in RUES2-Q150. A comparison of FPKM values from RUES2 and RUES2-Q150 indicates that both lines have an overall similar expression profile, with only few dozen genes showing differential expression (q-value<0.05 and a fold change>2, see Table 1). (B) The expression levels of the 12 most upregulated and most downregulated genes were confirmed using qPCR analysis. Error bars are S.E.M. Immunostaining of RUES2 and RUES2-Q150 using an HTT antibody showed no nuclear localization of HTT protein and therefore transcriptional changes are unlikely to be caused by a direct trantscriptional regulation function of HTT, but may be caused by a secondary mechanism (data not shown). (C) Gene ontology classification of genes that were significantly upregulated in RUES2-Q150 compared to RUES2 performed using the DAVID online suite of bioinformatics tools.
Figure 2:
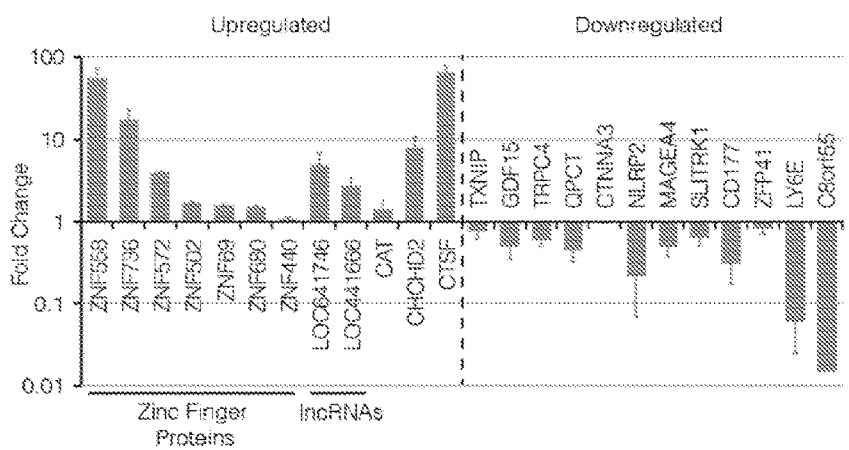
Figure 2:
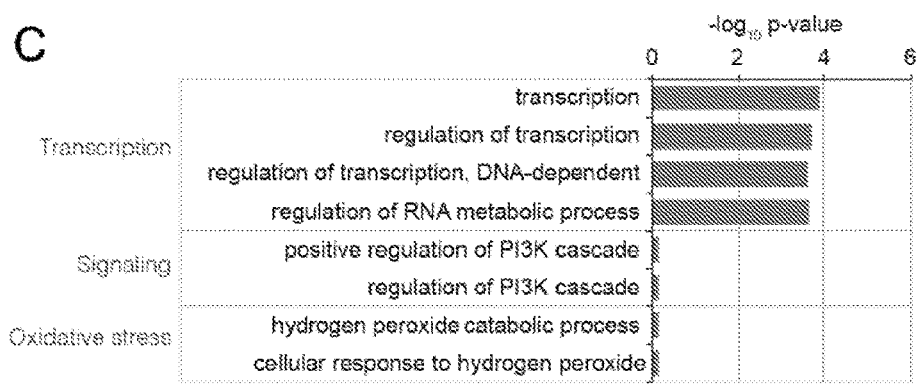

Global examination of the RNA-seq data revealed that the expression level of 88 genes was significantly (q-value<0.05) altered between the isogenic lines (FIGS. 2-B-C). The list of the 43 up (Table 1A) and the 45 down-regulated genes (Table 1B) are shown below. Gene Ontology (GO) analysis of these 88 genes identified 3 classes of highly regulated transcripts: those involved in regulation of transcription, mostly belonging to the Zinc-Finger family of proteins; those involved in PI3 Kinase signaling pathway; and finally those involved in the regulation of oxidative stress in metabolic pathways (FIG. 2C).

To provide quality control for the RNA-seq results the top 24 misregulated genes (12 upregulated and 12 downregulated) were selected, and results were validated by qPCR (FIG. 2B). Each group was subdivided into three categories: genes with unknown function(s); genes with known function but not previously linked to HD; and genes that have been previously associated with HD.

Tables 1A-B: Comparative RNA-seq analysis identified transcripts that are upregulated (A) and downregulated (B) in RUES2-Q150 cells. The boxes highlight the transcripts that were used for qRT-PCR confirmation.

TABLE 1A

| | Gene Symbol | Gene Name | Genomic Location | FPKM RUES2 | FPKM RUESE-Q150 | Fold Change | q-value |
|---|---|---|---|---|---|---|---|
| Upregulated | ZNF558 | zinc finger protein 558 | chr19: 8920381-89335R5 | 0.00 | 0.86 | Inf | 0.0005 |
| | LOC641746 | similar to glycine cleavage system protein H (aminomethyl carrier) | chr7: 64042987-64044129 | 0.00 | 1.41 | Inf | 0.0061 |
| | CAT | catalase | chr11: 34460471-34493807 | 0.01 | 3.52 | 594.03 | 0.0034 |
| | ZNF572 | zinc finger protein 572 | chr8: 125985538-125991630 | 0.02 | 1.14 | 72.67 | 0.0000 |
| | CHCHD2 | coiled-coil-helix-coiled-coil-helix domain containing 2 | chr7: 56169265-56174187 | 0.48 | 30.96 | 64.91 | 0.0000 |
| | LOC441666 | zinc finger protein 91 pseudogene | chr10: 42827313-42863493 | 0.09 | 4.68 | 52.12 | 0.0000 |
| | ZNF736 | zinc finger protein 736 | chr7: 63773185-63810017 | 0.05 | 1.64 | 32.78 | 0.0000 |
| | ZNF680 | zinc finger protein 680 | chr7: 63980254-64023505 | 0.54 | 14.02 | 25.80 | 0.0000 |
| | ZNF502 | zinc finger protein 502 | chr3: 44754134-44765323 | 0.06 | 1.26 | 21.81 | 0.0000 |
| | ZNF440 | zinc finger protein 440 | chr19: 11925106-11946016 | 0.07 | 1.16 | 17.38 | 0.0000 |
| | CTSF | cathepsin F | chr11: 66330934-66336047 | 0.20 | 3.43 | 16.78 | 0.0000 |
| | ZNF69 | zinc finger protein 69 | chr19: 11998669-12025365 | 0.18 | 3.05 | 16.60 | 0.0000 |
| | CSRP1 | cysteine and glycine-rich protein 1 | chr1: 201452657-201476387 | 0.29 | 4.74 | 16.51 | 0.0000 |
| | ZNF732 | zinc finger protein 732 | chr4: 264463-289944 | 0.88 | 14.10 | 16.00 | 0.0000 |
| | SLC2A14 | solute carrier family 2 (facilitated glucose transporter), member 14 | chr12: 7966398-8025495 | 0.26 | 4.11 | 15.95 | 0.0000 |
| | DNAJA4 | DnaJ Hsp40) homolog, subfamily A, member 4 | chr15: 78556486-78574538 | 0.11 | 1.49 | 13.07 | 0.0000 |
| | ZNF506 | zinc finger protein 506 | chr19: 19903519-19932560 | 0.43 | 5.30 | 12.39 | 0.0000 |
| | PXDNL | peroxidasin homolog (Drosophila)-like | chr8: 52232136-52722005 | 0.05 | 0.50 | 10.34 | 0.0005 |
| | ZNF248 | zinc finger protein 248 | chr10: 38117898-38146486 | 0.03 | 0.33 | 9.71 | 0.0018 |
| | SEC14L4 | SEC14-like 4 (S. cerevisiae) | chr22: 30884897-30901698 | 0.07 | 0.65 | 8.92 | 0.0066 |
| | ZNF350 | zinc finger protein 350 | chr19: 52467592-52490079 | 0.23 | 1.97 | 8.62 | 0.0000 |
| | H19 | Imprinted Maternally Expressed Transcript (Non-Protein Coding) | chr11: 2016405-2019065 | 0.16 | 0.85 | 5.18 | 0.0201 |
| | ZNF717 | zinc finger protein 717 | chr3: 75786028-75834255 | 0.84 | 4.21 | 4.99 | 0.0000 |
| | ANKLE1 | ankyrin repeat and LEM domain containing 1 | chr19: 17392453-17398454 | 0.62 | 2.75 | 4.47 | 0.0000 |
| | LHX4 | LIM homeobox 4 | chr1: 180199432-180244188 | 0.93 | 4.06 | 4.35 | 0.0010 |
| | ZNF829 | zinc finger protein 829 | chr19: 37288451-37407193 | 0.47 | 1.74 | 3.70 | 0.0391 |
| | ZNF37A | zinc finger protein 37A | chr10: 38883263-38412278 | 0.73 | 2.53 | 3.45 | 0.0007 |
| | MB21D1 | Mab-21 Domain Containing 1 | chr6: 74134855-74162043 | 1.41 | 4.36 | 3.09 | 0.0098 |
| | ZNF354C | zinc finger protein 354C | chr5: 178487606-178507691 | 0.89 | 2.65 | 2.99 | 0.0191 |
| | PCDHB5 | protocadherin beta 5 | chr5: 140514799-140517704 | 2.72 | 8.10 | 2.99 | 0.0002 |
| | ZNF528 | zinc finger protein 534: zinc finger protein 528 | chr19: 52901120-52921657 | 0.46 | 1.37 | 2.98 | 0.0313 |
| | C17orf51 | chromosome 17 open reading frame 51 | chr17: 21431570-21454941 | 0.60 | 1.58 | 2.65 | 0.0119 |
| | ZNF252 | zinc finger protein 252 | chr8: 146198974-146231432 | 1.48 | 3.62 | 2.44 | 0.0143 |
| | SYT11 | synaptotagmin XI | chrl: 155829259-155854990 | 0.89 | 2.17 | 2.43 | 0.0370 |
| | ZNF300 | zinc finger protein 300 | chr5: 150273953-150284545 | 1.97 | 4.77 | 2.43 | 0.0469 |
| | PUS7L | pseudouridylate synthase 7 homolog (S. cerevisiae)-like | chr12: 44122411-44152596 | 3.50 | 7.78 | 2.22 | 0.0321 |
| | PPP2R2B | protein phosphatase 2 (formerly 2A), regulatory subunit B, beta | chr5: 145969067-146461033 | 5.40 | 11.82 | 2.19 | 0.0409 |
| | HIST1H3E | histone cluster 1, H3e | chr6: 26225382-26225844 | 91.90 | 189.45 | 2.06 | 0.0095 |
| | ERBB2 | v-erb-b2 erythroblastic leukemia viral oncogene homolog 2 | chr17: 37844392-37884915 | 31.31 | 63.90 | 2.04 | 0.0062 |
| | ACOT9 | acyl-CoA thioesterase 9 | chrX: 23721776-23761407 | 9.88 | 20.13 | 2.04 | 0.0301 |
| | CDKL5 | cyclin-dependent kinase-like 5 | chrX: 18443724-18690223 | 4.13 | 8.24 | 2.00 | 0.0434 |
| | HIST1H3A | historie cluster 1, H3a | chr6: 26020717-26021186 | 68.45 | 134.63 | 1.97 | 0.0406 |
| | GNAI3 | G protein, alpha inhibiting activity polypeptide 3 | chr1: 110091185-110138452 | 6.26 | 12.24 | 1.96 | 0.0251 |

TABLE 1B

| | Gene Symbol | Gene Name | Genomic Location | FPKM RUES2 | FPKM RUES2-Q150 | Fold Change | q-value |
|---|---|---|---|---|---|---|---|
| Downregulated | MDM4 | Mdm4 p53 binding protein homolog (mouse) | chr1: 204485506-204527248 | 13.15 | 7.21 | 0.55 | 0.0321 |
| | ATP6AP2 | ATPase, H + transporting, lysosomal accessory protein 2 | chrX: 40440215-40465888 | 46.45 | 25.13 | 0.54 | 0.0365 |
| | PHLDA1 | Plekstrin homology-like domain, family A, member 1 | chr12: 76419226-76425556 | 15.13 | 8.13 | 0.54 | 0.0358 |
| | COL1A1 | collagen, type I, alpha 1 | chr17: 48261456-48279000 | 19.55 | 10.29 | 0.53 | 0.0201 |
| | ZIC3 | Zic family member 3 (odd-paired homolog, *Drosophila*) | chrX: 136648345-136654259 | 18.73 | 9.86 | 0.53 | 0.0313 |
| | ARMCX2 | armadillo repeat containing, X-linked 2 | chrX: 100910267-100914863 | 45.03 | 23.70 | 0.53 | 0.0144 |
| | ATP11C | ATPase, class VI, type 11C | chrX: 138808504-138914447 | 28.49 | 14.61 | 0.51 | 0.0093 |
| | RAI14 | retinoic acid induced 14 | chr5: 34656432-34832717 | 51.80 | 26.13 | 0.50 | 0.0058 |
| | DMXL2 | Dmx-like 2 | chr15: 51739920-51914967 | 8.32 | 4.09 | 0.49 | 0.0069 |
| | TSPAN6 | Tetraspanin 6 | chrX: 99883794-99891794 | 30.36 | 14.77 | 0.49 | 0.0094 |
| | CLDN4 | claudin 4 | chr7: 73245192-73247015 | 17.78 | 8.56 | 0.48 | 0.0391 |
| | STAG2 | stromal antigen 2 | chrX: 123094474-123236505 | 42.96 | 20.55 | 0.48 | 0.0058 |
| | EIF1AX | eukaryotic translation initiation factor 1A, X-linked | chrX: 20142635-20159966 | 54.09 | 25.83 | 0.48 | 0.0057 |
| | SLC9A6 | Solute carrier family 9 (sodium/hydrogen exchanger), member 6 | chrX: 135067582-135129428 | 8.55 | 3.99 | 0.47 | 0.0098 |
| | BBS9 | Bardet-Biedl syndrome 9 | chr7: 33169151-33645680 | 12.00 | 5.59 | 0.47 | 0.0177 |
| | IL13RA1 | interleukin 13 receptor, alpha 1 | chrX: 117861558-117928496 | 7.23 | 3.22 | 0.44 | 0.0114 |
| | RPS6KA3 | ribosomal protein S6 kinase, 90 kDa, polypeptide 3 | chrX: 20168028-20284750 | 4.73 | 2.10 | 0.44 | 0.0060 |
| | LCP1 | lymphocyte cytosolic protein 1 (L-plastin) | chr13: 46700057-46756459 | 4.48 | 1.98 | 0.44 | 0.0378 |
| | DOCK11 | dedicator of cytokinesis 11 | chrX: 117629871-117820123 | 7.18 | 3.14 | 0.44 | 0.0014 |
| | XIAP | X-linked inhibitor of apoptosis | chrX: 122993661-123047829 | 14.46 | 6.30 | 0.44 | 0.0003 |
| | MMGT1 | membrane magnesium transporter 1 | chrX: 35044230-135056134 | 19.91 | 8.56 | 0.43 | 0.0006 |
| | ARHGEF6 | Rac/Cdc42 guanine nucleotide exchange factor (GEF) 6 | chrX: 135747711-135863503 | 2.96 | 1.26 | 0.42 | 0.0321 |
| | NEAT1 | non-protein coding RNA 84 | chr11: 65190268-65194003 | 4.03 | 1.64 | 0.41 | 0.0312 |
| | CXorf38 | chromosome X open reading frame 38 | chrX: 40486172-40506819 | 5.98 | 2.19 | 0.37 | 0.0008 |
| | CDKN1A | cyclin-dependent kinase inhibitor 1A (p21, Cip1) | Chr6: 36644236-36655116 | 9.21 | 3.30 | 0.36 | 0.0097 |
| | LINC00086 | Long intergenic Non-Protein Coding RNA 86 | chrX: 134555867-134560225 | 3.91 | 1.32 | 0.34 | 0.0031 |
| | RASAL3 | RAS protein activator like 3 | chr19: 15562437-15575382 | 1.29 | 0.39 | 0.30 | 0.0336 |
| | NAP1L6 | nucleosome assembly protein 1-like 6 | chrX: 72345875-72347919 | 1.87 | 0.57 | 0.30 | 0.0313 |
| | TNFSF9 | tumor necrosis factor (ligand) superfamily, member 9 | chr19: 6531009-6535939 | 2.58 | 0.78 | 0.30 | 0.0378 |
| | ONECUT1 | one cut homeobox 1 | chr15: 53049352-53082209 | 5.88 | 1.75 | 0.30 | 0.0013 |
| | CR1L | complement component (3b/4b) receptor 1-like | chr1: 207818457-207897036 | 2.28 | 0.66 | 0.29 | 0.0243 |
| | C20orf54 | chromosome 20 open reading frame 54 | chr20: 740723-749228 | 3.25 | 0.89 | 0.27 | 0.0017 |
| | RWDD2B | RWD domain containing 2B | chr21-30378079-30391685 | 2.54 | 0.65 | 0.26 | 0.0069 |
| | TXNIP | thioredoxin interacting protein | chr1: 145438461-145442628 | 10.29 | 2.52 | 0.24 | 0.0000 |
| | GDF15 | growth differentiation factor 15 | chr19: 18496967-18499986 | 9.45 | 1.82 | 0.19 | 0.0000 |
| | TAPC4 | Transient receptor potential cation channel, subfamily C, member 4 | chr13: 38210772-38443939 | 4.01 | 0.72 | 0.18 | 0.0000 |
| | QPCT | glutaminyl-peptide cyclotransferase | chr2: 37571752-37600465 | 11.54 | 1.17 | 0.13 | 0.0000 |
| | CTNNA3 | catenin (cadherin-associated protein), alpha 3 | chr10: 67679724-69455949 | 1.20 | 0.14 | 0.12 | 0.0005 |
| | NLRP2 | NLR family, pyrin domain containing 2 | chr19: 55476651-55512510 | 22.09 | 2.45 | 0.11 | 0.0000 |
| | MAGEA4 | melanoma antigen family A, 4 | chrX: 151081360-151093642 | 3.51 | 0.39 | 0.11 | 0.0012 |
| | SLITRK1 | SLIT and NTRK-like family, member 1 | chr13: 84451342-84456528 | 0.95 | 0.10 | 0.11 | 0.0000 |
| | CD177 | CD177 molecule | chr19: 43857824-43867480 | 0.79 | 0.07 | 0.08 | 0.0005 |
| | ZFP41 | zinc finger protein 41 homolog (mouse) | chr8: 144329108-144344875 | 1.23 | 0.00 | 0.00 | 0.0085 |
| | LY6E | lymphocyte antigen 6 complex, locus E | chr8: 144099901-144103827 | 30.04 | 0.03 | 0.00 | 0.0093 |
| | C8orf55 | chromosome 8 open reading frame 55 | chr8: 143808620-143818350 | 1.48 | 0.00 | 0.00 | 0.0005 |

Among the 12 genes that displayed higher expression in RUES2-Q150, 8 belong to the first category, 1 to the second, and 3 to the third category. Surprisingly, a clustering of 7 Zinc Finger proteins (ZNFs: 558, 736, 572, 502, 69, 680, and 440) was found. Also intriguingly there were 2 genes for which only the genomic locus (LOC) is known with no other available information (LOC641746 and LOC441666). Both of these LOCs represent non-coding RNAs and one, LOC441666, is actually a transcribed pseudogene of yet another Zinc Finger protein (ZNF91). The 3 genes that have been previously linked to HD are: Catalase (CAT), which is involved in protecting cells from oxidative damage by reactive oxygen species; the coiled-coil-helix-coiled-coil-helix-domaincontaining protein 2 (CHCHD2), involved in mitochondrial function and required for cytochrome C oxidase activity; and Cathepsin-F (CTSF), involved in lysosomal functions. This finding both confirms similarity of this in vitro tool to the human disease and opens up possibilities for exploring novel therapeutic targets among the genes of altered expression found, starting with the 24 most dysregulated genes identified above.

Among the downregulated genes, 3 genes with unknown function were also found. These include Thioesterase Superfamily Member 6 (THEM6, also known as C8orf55);

another Zinc Finger protein (ZFP41); and the melanoma antigen family MAGEA4. 8 genes belong to the second category. They include: (i) Lymphocyte Antigen 6 Complex, locus E (LY6E), which is involved in T cell-differentiation; (ii) the tumor suppressor gene, Catenin (Cadherin-associated protein), alpha 3 (CTNNA3); (iii) the TGFβ ligand, Growth and Differentiation Factor 15, (GDF15) involved in cell fate determination and maintenance; (iv) the Transient-Receptor-Potential-Channel 4 (TRPC4) a nonselective Ca++ permeable cation channel; (v-vi) two genes that are involved in inflammation pathways and inflammasome: NACHT, LRR and PYD domains containing protein 2 (NLRP2), and Thioredoxin Interacting Protein (TXNIP). NLRP2 is involved in the activation of caspase-1. TXNIP is a thioredoxin interacting protein that controls the levels of cellular reactive oxygen. (vii) Cluster of Differentiation (CD177), a gene associated with human myeloproliferative disorders. (viii) SLIT, and NTRK-Like family member 1 (SLITRK1), which is a developmentally regulated stimulator of neurite outgrowth. Finally, one gene in the third category: Glutaminyl-Peptide-Cyclotransferase (QPCT), which is a glutaminyl cyclase. QPCT was recently identified by siRNA screens in human cultured cells as having one of the strongest modifier effects on mutant HTT-induced toxicity and aggregation in cells. QPCT inhibitors were shown to rescue HD-related phenotypes in cells, Drosophila, and zebrafish HD models. It thus appears that the isogenic HD tools of the present disclosure can be used to identify both genes, transcripts, and their expression products that are involved in HD pathogenesis and therefore present potential targets for therapeutic intervention.

Regulation of transcript levels by HTT can occur directly at the transcriptional level in the nucleus, or indirectly in the cytoplasm. Consistent with a direct role, nuclear localization of HTT protein has been detected in mouse MSNs, however, this has not been established in either mouse or human pluripotent stem cells. Therefore, the subcellular localization of HTT was examined in both of the isogenic lines. Because the exon-1/intron-1 HTT isoform was detected, an N-terminus specific antibody (LS-Bio EPR5526, commercially available) was used to detect all HTT proteins in cells. It was found that neither wildtype nor expanded HTT localize to the nucleus of pluripotent hESCs. HTT expression is instead confined to the cytoplasm. This evidence eliminates the possibility of HTT acting directly at the transcriptional level, and instead points to an indirect effect in the cytoplasm by modulation of RNA stability or sequestration of one or more transcriptional regulators.

Example 3

The HTT Expansion Leads to Changes in the Metabolite Signature of Isogenic hESCs In parallel with the RNA-seq and on samples grown under the same exact pluripotency conditions, comparative untargeted liquid chromatography/mass spectrometry (LC/MS) metabolite profiling of RUES2 and RUES2-Q150 cells was performed. Profiling data were acquired using aqueous normal phase LC and both negative-ion and positive-ion MS detection for broad coverage of potential changes in hydrophilic metabolite levels that contribute to intermediary metabolism. Three independent cultures of RUES2 and RUES2-Q150 were analyzed each as five technical replicates. Together, this metabolomic analysis surveyed 2693 molecular features of 50-1000 Da/e mass/charge (m/z) ratio. Of these species, 1196 were quantified as negative ions (FIGS. 3A and 3C) and 1497 were detected as positive ions (FIGS. 3B and 3D).

Figure 3:
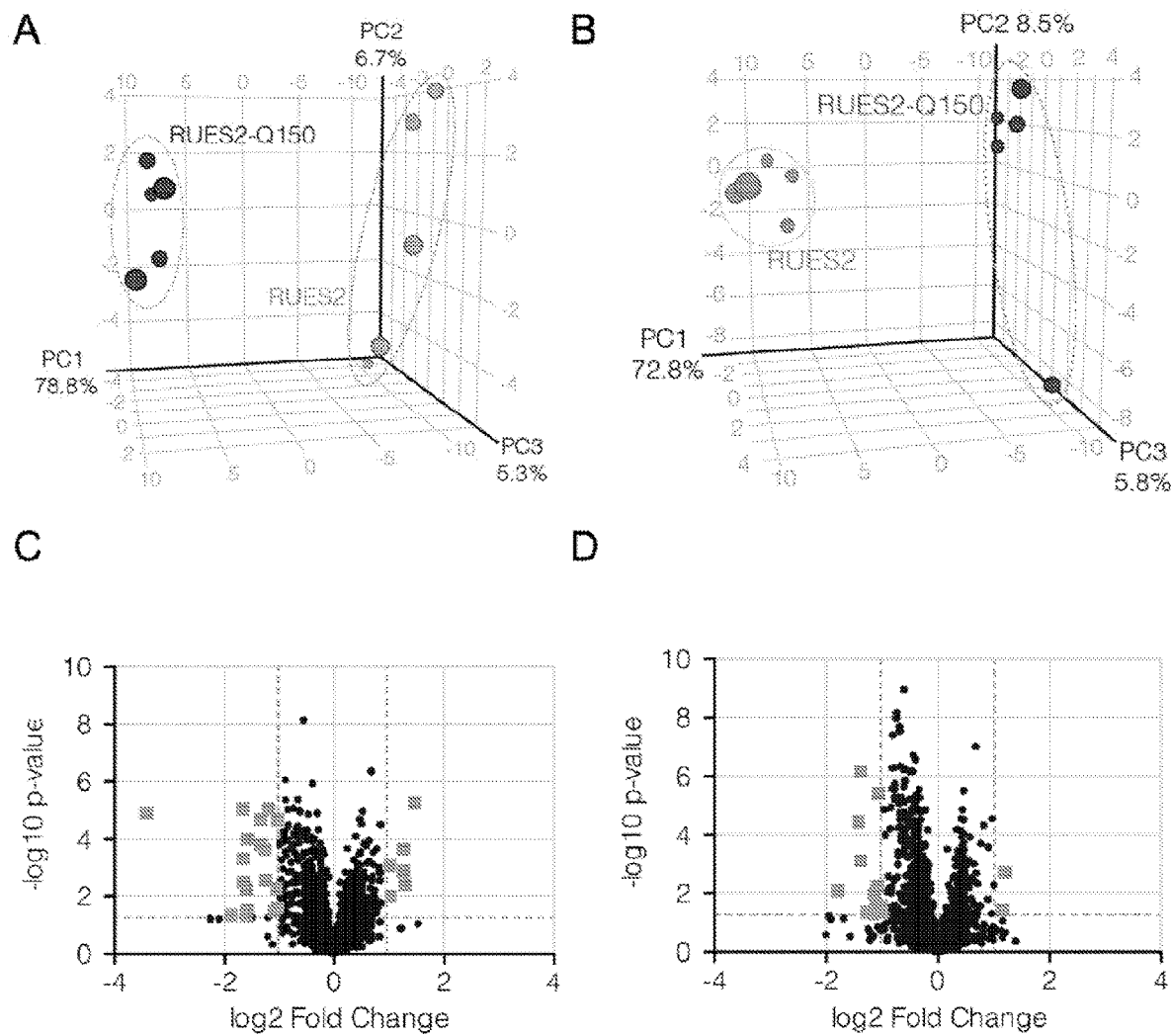
FIG. 3A-D: Untargeted LC/MS-based metabolic profiling identifies differentially expressed metabolites between pluripotent RUES2 and RUES2-Q150 cells. Negative ion mass spectrometry findings and positive ion mass spectrometry findings, depicting the results of 5 technical replicates from RUES2 and RUES2-Q150. Data is representative of the three biological replicates performed. Considering mass and chromatographic retention times, untargeted molecular feature extraction quantified relative levels of 1196 negative and 1497 positive ion features. (A, C) PCA score plot showeds a clustering and separation of samples from both cell lines with respect to relative metabolite levels (data not shown). Unsupervised hierarchical clustering showed clustering and branching of samples from RUES2 and RUES2-Q150 (data not shown). (B, D) Metabolites with a p-value<0.05, considered significant, and a fold-change>1.5, considered substantial, are shown as gray squares.

Principal component analysis (PCA) and unsupervised hierarchical cluster analysis (HCA) revealed within-group clustering and between-group separation of metabolites in the two cell lines (FIGS. 3A-B). Levels of 76 metabolites were significantly altered in RUES2-Q150 cells when compared to RUES2 cells, with 11 increased and 65 decreased (Table 2, FIG. 3C-D). These findings provide for the first time a unique metabolic signature of human HD in pluripotent hESCs.

TABLE 2

Unbiased metabolomics analysis revealed increased and decreased metabolites identified in RUES2-Q150 cells.

| Pathway | Compound Name | Average Fold Change | Min p-value |
| --- | --- | --- | --- |
| Citrate cycle (TCA cycle) | Acetyl-CoA | 2.507 | 5.17E−03 |
| Lysine degradation | -Aminoadipic Acid | 1.948 | 5.61E−08 |
| Methane metabolism | N-Methylglutamic Acid | 1.848 | 6.42E−08 |
| Food component | Trimyristin | 1.545 | 2.68E−02 |
| Folate metabolism | Folic acid | 1.439 | 3.18E−02 |
| Beta-alaninemetabolism; Propanoate metabolism | Propiolic Acid | 1.278 | 3.03E−02 |
| Alanine, Aspartate, and Glutamate metabolism | Aspartic Acid | 1.217 | 1.46E−04 |
| Fatty acid biosynthesis; Beta oxidation of fatty acids | Caprylic Acid | 1.200 | 1.57E−03 |
| Citrate cycle (TCA cycle) | Succinate | 1.191 | 3.52E−03 |
| Plant metabolite; No pathway info | Nonanoic Acid | 1.180 | 1.27E−02 |
| Glycerophospholipid metabolism | PC(36:2) | 0.936 | 4.38E−02 |
| Glycolysis/Gluconeogenesis | Pyruvate | 0.902 | 1.86E−02 |
| Amino acid modification | N-Acetylglycine | 0.892 | 1.35E−02 |
| Glyoxylate and dicarboxylate metabolism | Glycolic acid | 0.882 | 3.03E−04 |
| Glycerophospholipid metabolism | PC(35:2) | 0.878 | 1.42E−03 |
| Nicotinate and nicotinamide metabolism | Maleic acid | 0.861 | 3.04E−02 |
| Arginine and Proline metabolism | Proline | 0.858 | 1.94E−02 |
| Neuroactive ligand-receptor interaction | Octopamine | 0.851 | 1.14E−02 |
| Tyrosine metabolism; Neurotransmitter | Dopamine | 0.851 | 1.14E−02 |
| Bacterial metabolite: Phenylalanine, Tyrosine and Tryptophan | m-Salycylic Acid | 0.849 | 1.48E−02 |
| Pyrimidine metabolism | Orotidine | 0.848 | 4.36E−02 |
| Nicotinate and nicotinamide metabolism; Oxidative phosphorylation | NAD | 0.837 | 8.55E−05 |
| Amino sugar and nucleotide sugar metabolism | GDP-Glucose | 0.828 | 8.56E−03 |

TABLE 2-continued

Unbiased metabolomics analysis revealed increased
and decreased metabolites identified in RUES2-Q150 cells.

| Pathway | Compound Name | Average Fold Change | Min p-value |
|---|---|---|---|
| Pantothenate and CoA biosynthesis | Coenzyme A (CoA) | 0.825 | 3.96E−02 |
| Nonprotein amino acid | 2-Aminoisobutyric acid | 0.823 | 1.75E−03 |
| Pantothenate and CoA biosynthesis | Pantothenic Acid | 0.822 | 4.69E−04 |
| Amino sugar and nucleotide sugar metabolism | GDP-Mannose | 0.819 | 2.08E−03 |
| Amino sugar and nucleotide sugar metabolism | ADP-Glucose | 0.818 | 1.67E−04 |
| Linked to glutaryl coenzyme A dehydrogenase deficiency | 3-Hydroxyglutaric Acid | 0.817 | 6.83E−06 |
| Tryptophan metabolism?; Used in synthesis of dyes | 2-Aminophenol | 0.810 | 3.22E−03 |
| Valine, Leucine and Isoleucine degradation | Ketoleucine | 0.806 | 4.29E−02 |
| Synthesis and degradation of ketone bodies | 3-Hydroxybutyric acid | 0.802 | 4.68E−02 |
| Pyrimidine metabolism | UTP | 0.798 | 5.34E−06 |
| Amino sugar and nucleotide sugar metabolism | dTDP-Glucose | 0.796 | 1.05E−04 |
| Lysine biosynthesis | Homocitric acid | 0.795 | 8.55E−06 |
| Alanine, Aspartate and Glutamate metabolism; Neurotransmitter | 4-Aminobutanoic Acid (GABA) | 0.792 | 3.17E−04 |
| Glycolysis/Gluconeogenesis | Lactic Acid | 0.790 | 5.44E−03 |
| No pathway information found | Uracil 5-Carboxylic Acid | 0.784 | 7.77E−04 |
| Amino sugar and nucleotide sugar metabolism | UDP-N-Acetylgalactosamine | 0.781 | 5.51E−05 |
| Amino sugar and nucleotide sugar metabolism | UDP-N-Acetylglucosamine | 0.779 | 5.19E−05 |
| No pathway information found | 2-Pyridylacetic acid | 0.775 | 3.97E−04 |
| Plant metabolite; No pathway info | Methyl Vanillic Acid | 0.774 | 1.73E−07 |
| Phenylalanine metabolism (phenylketonuria) | Phenylacetic Acid | 0.773 | 3.94E−02 |
| Tyrosine metabolism | 4-Hydroxyphenyllactic Acid | 0.770 | 2.37E−07 |
| Arginine and Proline metabolism | N-Acetylglutamic Acid | 0.769 | 1.71E−04 |
| Glycolysis/Gluconeogenesis | a-D-Glucose 1-phosphate | 0.763 | 2.33E−03 |
| Glycerophospholipid metabolism | 3-Phosphoglyceroinositol | 0.753 | 2.87E−04 |
| Phosphatidylinositol phosphate metabolism; Second messenger | myo-Inositol | 0.752 | 1.22E−07 |
| Galactose metabolism | Galactitol | 0.750 | 2.14E−02 |
| Amino acid acetylation | N-Acetylserine | 0.743 | 2.25E−03 |
| No pathway information found | 2,4-Dihydroxypteridine (Lumazine) | 0.743 | 2.30E−03 |
| Fructose and mannose metabolism | D-Sorbitol | 0.740 | 1.01E−03 |
| Diagnostic and research tool | Mannitol | 0.739 | 8.67E−04 |
| Pentose phosphate pathway | Erythrose 4-phosphate | 0.735 | 2.81E−04 |
| Riboflavin metabolism | Flavin adenine dinucleotide (FAD) | 0.719 | 4.21E−02 |
| Arginine and proline metabolism | 4-Acetamidobutanoic Acid | 0.719 | 4.37E−03 |
| Purine metabolism | GTP | 0.713 | 2.13E−04 |
| Amino sugar and nucleotide sugar metabolism | N-Acetylneuraminic Acid | 0.713 | 1.36E−04 |
| Glycolysis/Gluconeogenesis | D-Fructose 6-phosphate | 0.709 | 6.09E−05 |
| Glycine, serine, and threonine metabolism; Arginine and Proline | Creatine | 0.705 | 1.55E−02 |
| No pathway information found | Citramalic Acid | 0.691 | 2.19E−06 |
| Purine metabolism | ADP-Ribose | 0.686 | 7.68E−03 |
| Cysteine and methionine metabolism | 5-Methylthioadenosine | 0.684 | 6.34E−03 |
| Purine metabolism | CTP | 0.666 | 3.28E−04 |
| Arginine and Proline metabolism | cis-4-Hydroxyproline | 0.664 | 4.19E−04 |
| Citrate cycle (TCA cycle) | 2-Oxoglutaric Acid | 0.660 | 9.30E−04 |
| Plant metabolite; Pentose phosphate pathway | Gluconic Acid | 0.645 | 4.51E−04 |
| Purine metabolism | GDP | 0.614 | 4.34E−05 |
| Glycerophospholipid metabolism | Phosphocholine | 0.608 | 1.77E−02 |
| Oxidative phosphorylation | NADH | 0.586 | 1.45E−05 |
| Pentose phosphate pathway | Deoxyribose | 0.450 | 2.11E−04 |
| Purine metabolism | Adenosine | 0.439 | 5.16E−03 |
| Pyrimidine metabolism | Dihydroorotic Acid | 0.421 | 1.18E−03 |
| Plant metabolite; Food component | Erythritol | 0.416 | 3.51E−02 |
| Nicotinate and nicotinamide metabolism | Nicotinamide | 0.380 | 2.11E−02 |

Several classes of metabolites were consistently, and in a statistically significant manner, altered in the RUES2-Q150 (Table 2). These include Glycolysis and Gluconeogenesis, the tricarboxylic acid (TCA) cycle, nucleotide triphosphates, pyridine nucleotides, and the Lysine metabolism pathway.

In the Glycolysis and Gluconeogenesis pathway, which is the main source of energy production in pluripotent cells, it was found that lactic acid, α-glucose-1-phosphate, and fructose-6-phosphate were consistently decreased in RUES2-Q150 cells (Table 2). This decrease suggests that RUES2-Q150 cells have an energy deficit compared to the RUES2 line.

Figure 4:
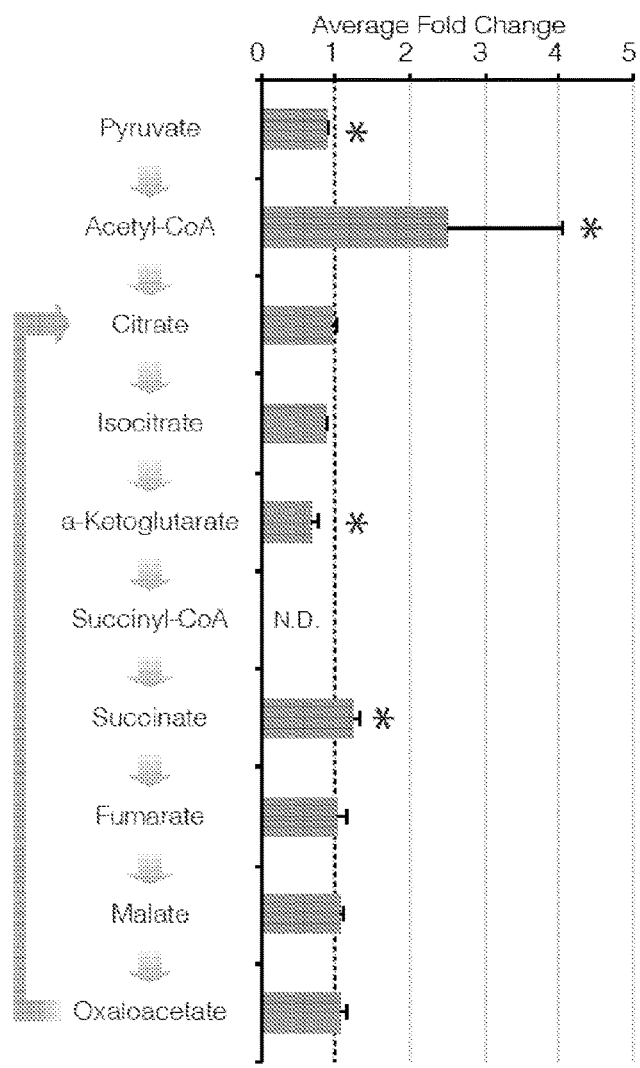
FIG. 4A-E: Pluripotent RUES2-Q150 hESCs have a unique metabolic signature compared to RUES2. (A) Several metabolites in the TCA cycle were significantly misregulated in at least one biological replicate. (B) Nucleotide triphosphates levels were reduced in RUES2-Q150 compared to RUES2. (C) Levels of GDP were significantly reduced in one biological replicate but other nucleotide diphosphates were not significantly changed. (D) Levels of nucleotide monophosphates were not changed across all three biological replicates. N.D.: no data. (E) Ratios of NADH:NAD and NADPH:NADP from all three biological replicates were significantly reduced in RUES2-Q150 cells compared to RUES2. For all figure panels, data represent the mean of 3 replicates, and error bars are S.E.M., * p-value<0.05.
Figure 4:
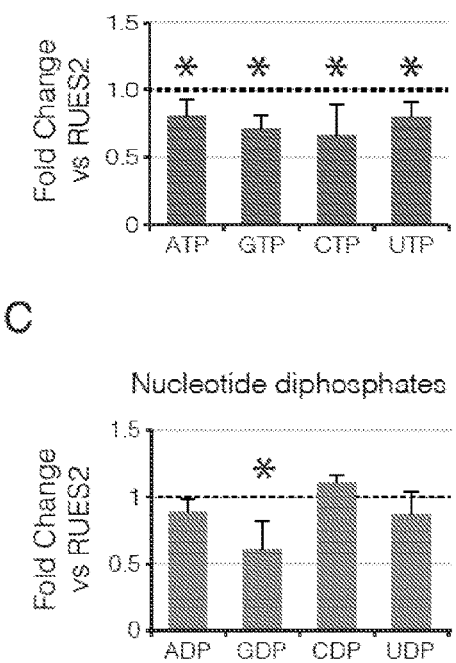
Figure 4:
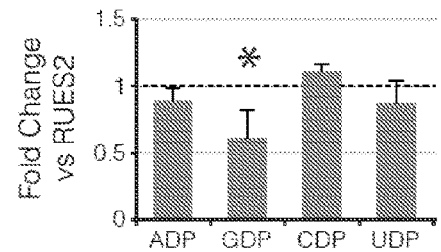
Figure 4:
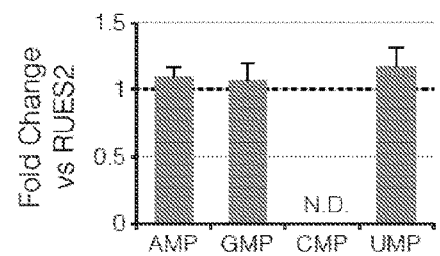
Figure 4:
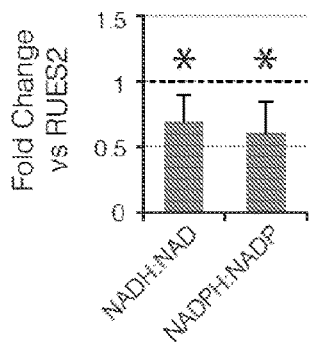

In the TCA cycle (also known as citric acid cycle), several key intermediates were misregulated, including increased acetyl-CoA and succinate, and decreased pyruvate and α-ketogluterate (FIG. 4A). However, as the TCA cycle is not used as the main energy source in pluripotent hESCs, the changes observed could be due to other metabolic pathways that influence availability of TCA cycle intermediates such as those involved in lipid and amino acid biosynthesis.

Nucleotide triphosphates: ATP, CTP, GTP, and UTP, the building blocks of RNA biosynthesis, and energy carriers, were significantly decreased in RUES2-Q150 cells (FIG. 4B). This reduction was specifically affecting nucleotide triphosphates, as levels of either nucleotide diphosphates (ADP, CDP, UDP, and TDP), or monophosphates (AMP, CMP, GMP, UMP and TMP) were not changed (FIGS. 4C-D). This is consistent with the observation on the glycolytic pathway, and points again to energy deficiency in the RUES2-Q150 line.

Pyridine nucleotides, specifically NAD+/NADH and NADP+/NADPH are essential coenzymes necessary for redox reactions. These coenzymes act as electron carriers by being either oxidized (NAD and NADP) or reduced (NADH and NADPH). Ratios of both NADH:NAD and NADP:NADP were found to be diminished across all three biological replicates (FIG. 4E), revealing a higher oxidative stress in RUES2-Q150 cells.

Taken together, these results surprisingly indicate that there are major changes in cellular metabolism resulting from a simple expansion of polyQ in the HTT protein in RUES2-Q150 and support the utility of this tool as a model for studying HD. Furthermore, the differences in the metabolic signature due to the expansion of polyQ in the HTT protein can be exploited as a drug screening tool, wherein drug candidates capable of partly or fully inhibiting the development of or restoring, the HD-associated metabolic signature can be used or further explored as therapeutics in the treatment of Huntington's disease.

In addition, and unexpectedly, it was found that the Lysine degradation pathway, which ultimately uses the essential amino acid Lysine as a substrate to produce Acetyl-CoA and α-ketogluterate via α-aminoadipic-acid is severely misregulated. The levels of the intermediate α-aminoadipic-acid and the product Acetyl-CoA were increased, while the level of the product, α-ketogluterate, was decreased. This suggests that the metabolic flux along the Lysine pathway is increased. Although the physiological consequences of this misregulation are currently unclear, this represents the first evidence linking the Lysine pathway to HD.

Example 4

Integration of RNA-Seq and Metabolomics Studies in RUES2-Q150

Figure 5:
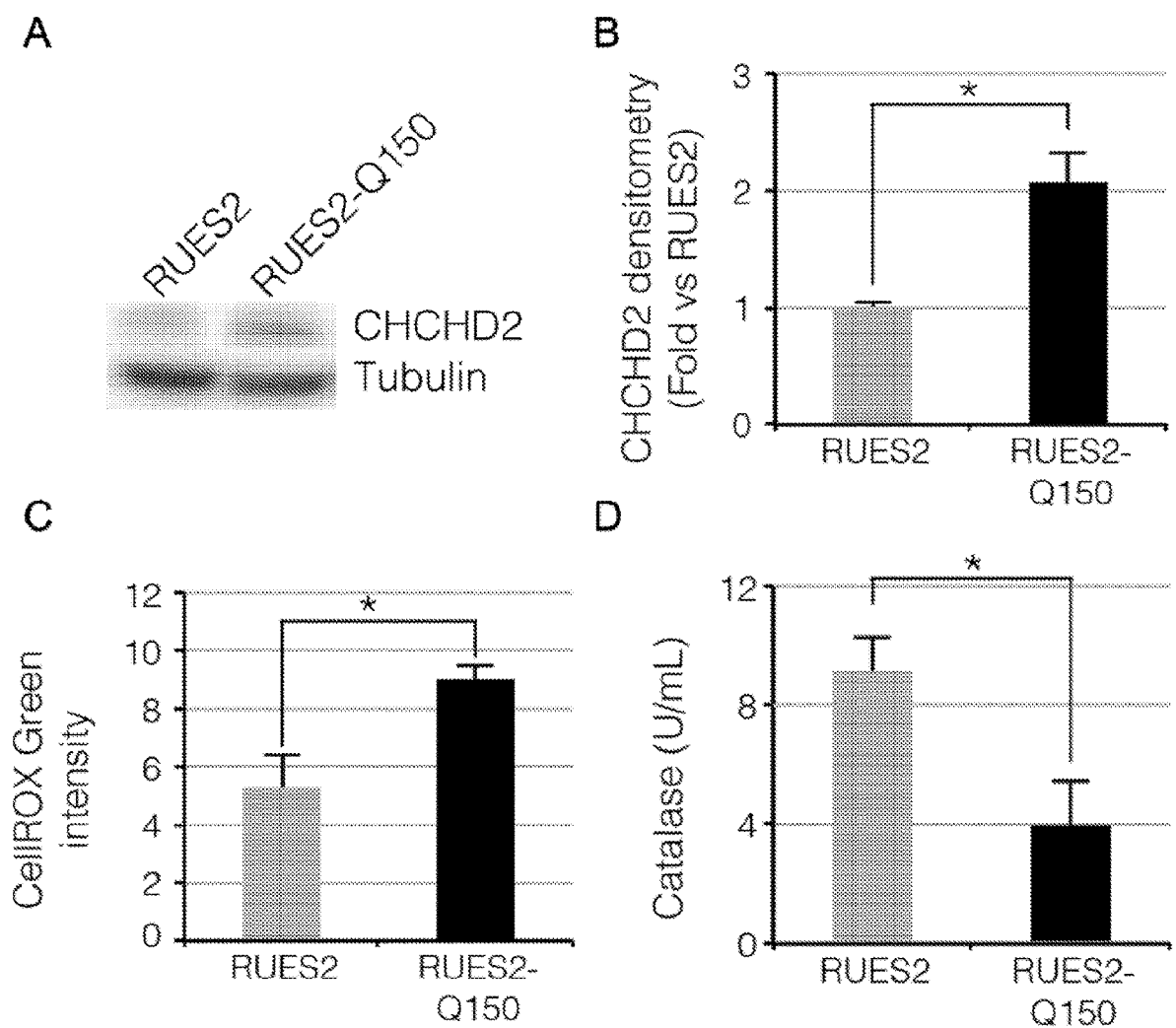
FIG. 5A-D: Pluripotent RUES2-Q150 cells are under oxidative stress and exhibit reduced catalase activity. (A) RUES2-Q150 cells express higher levels of CHCHD2 protein as detected by Western blot. (B) Quantification of results in (A) using densitometric analysis. * p<0.05. (C) Quantification of cellROX staining results (normalized to DAPI) revealed that RUES2-Q150 cells suffer higher oxidative stress. No changes in the number or morphology of mitochondria were observed in RUES2-Q150 compared to RUES2 (data not shown). Similarly, RUES2-Q150 cells did not display changes in mitochondrial polarization, as determined by using the polarization-sensitive dye Rhodamine123 (data not shown). Western blot analysis of whole cell lysates from RUES2 and RUES2-Q150 showed that the two cell lines express the same levels of the mitochondrial proteins Cytochrome c, Rieske iron sulfur proteins (RISP) and voltagedependent anion channel 1 (VDAC1) (data not shown), and therefore the observed oxidative stress is not due to a decrease number or viability of their mitochondria.

When comparing the RNA-seq with the metabolomics data, several interesting correlations were noted. Among these, were components involved in regulation of the intracellular redox state. For example, RNA-seq analysis demonstrated an increase in the expression of CHCHD2 transcript, which was confirmed independently by qPCR (FIG. 2B), and that led to an increase in the levels of the CHCHD2 protein as demonstrated by western blot (FIGS. 5A-B). CHCHD2 activity is essential for proper function of mitochondrial complex I and IV, and thus oxidative phosphorylation, a central metabolic pathway that produces reactive oxygen species (ROS). To measure intracellular ROS levels, a cell permeable dye, CellROX, which increases in fluorescence intensity upon oxidation by ROS was used. While RUES2 cells displayed minimal fluorescence consistent with low levels of ROS, RUES2-Q150 cells showed a robust increase in fluorescent signal (FIG. 5C). This provides a molecular mechanism for the observed increased in oxidative stress in RUES2-Q150. This metabolomics study also supports the findings above with RNA seq.

Because oxidative stress is frequently associated with mitochondrial dysfunction the number, functionality, polarization state, and structural integrity of mitochondria in RUES2 and RUES2-Q150 cells was determined. The number of mitochondria was determined by using MitoTracker dye in live cells. No changes were detected in the two isogenic lines. Polarization state of the mitochondria inner membrane was measured using the dye Rhodamine123. Again, no differences were observed between the two lines. Structural integrity of mitochondria was measured by examination of the expression levels of key mitochondrial proteins. Whole cell lysate from both cell lines was used to examine the amount of the voltage-dependent anion channel 1 (VDAC1), Rieske iron-sulfur protein (RISP, also known as cytochrome b-c1 subunit 5), and Cytochrome c. No changes were detected in mitochondrial proteins. Taken all together these results demonstrate that the increased oxidative stress observed in RUES2-Q150 is not a consequence of mitochondrial dysfunction, but rather points to cytosolic pathways, such as glycolysis.

Another player in the regulation of ROS levels is the enzyme Catalase, which is a scavenger of $H_2O_2$, one of the most abundant ROS in cells. RNA-seq results showed an increase of CAT transcripts in RUES2-Q150 (FIG. 2B). This is very surprising because high Catalase expression should reduce ROS levels. Therefore, the activity of Catalase in RUES2 and RUES2-Q150 cells was measured. This was done by using a colorimetric activity assay that directly and specifically measures the rate of decomposition of H2O2 by Catalase. It was found that RUES2-Q150 cells had lower Catalase activity than RUES2 cells (FIG. 5D). This is also consistent with the metabolomic observation that NADPH levels are reduced, as NADPH is a critical reducing agent and is required to maintain Catalase in an active conformation. RUES2-Q150 cells compensate for the lower activity of their Catalase (documented in HD) by increasing its expression.

This study demonstrates that there is consistency between the RNA-Seq and metabolomics datasets, and highlights the advantage of performing these comparative experiments in CRISPR-Cas9 edited isogenic hESCs to model HD.

Example 5

Micropattern Screen for Potential HD Therapeutics

Micropattern cultures were established according to methods described in Warmflash et al., Nature Methods. 2014 August: 11(8):847-854. This procedure is briefly described in Materials and Methods.

Cells confined to circular micropatterns and differentiated with BMP4 produce an ordered array of germ layers along the radial axis of the colony. This order results from self-organized signaling which confines response to the BMP4 to the colony border while inducing a broader gradient of Activin/Nodal signaling to pattern mesendodermal fates. Control of fates is established from the border of the colony so that as colony size is reduced the central fates are lost. Thus, given minimal geometric and signaling cues, hESCs will self-organize to generate embryonic patterns such as those of the human gastrula.

The Applicants next applied micropattern technology to the isogenic hESC lines for Huntington's Disease. Treatment of micropatterned hESC colonies with 50 ng/ml BMP4 led to morphological differentiation within 24 hours of treatment with a dense ring of cells forming at a reproducible radius within the colony with larger, more spread cells radially to the inside and outside. Differences in micropattern formation between RUES2 and RUES2-Q150 cells allowed the Applicants to identify an HD-dependent micropattern signature.

The spatial expression of germ markers Sox2, Bra, and Cdx2 was compared between RUES2 and RUES2-Q150 cells (FIG. 6). The HD-dependent micropattern signature consisted of reduced Sox2 and expanded Bra/Cdx2 territories, and an overall reduction of approximately 20-25% in cell number. Furthermore, several additional features were observed in the micropattern of RUES2-Q150: reduction in total cell number and reduction in cell number of individual germ layers (same percentage per layer as overall cell number reduction) and increase in the tri dimensional geometry of SOX2 positive core and reduction in footprint of SOX2 positive area. The increase in height (reflective of tri dimensional geometry) was in the range of 20-50%. Tri dimensional geometry was evaluated by first generating images of cells at different focal planes known as "Z-stacks". Such obtained Z-stacks were then processed using software to obtain a 3D reconstruction profile. Any publically or commercially available software can be used for this purpose, such as ImageJ from National Institutes of Health. Finally, 3D profiles of wild type (RUES2) and RUES2-Q150 cells were compared.

The Applicants used the micropattern platform to screen for drug candidates that have the ability to revert the HD-dependent micropattern signature back to that of wild-type isogenic cells. The screen resulted in identification of two compounds, kinetin and minoxidil, which had the ability to restore the HD-dependent micropattern signature, leading to an increase in expansion of Sox2 positive cells, and a reduction in Cdx2/Bra territories (FIG. 6). Moreover, treatment of RUES-Q150 cells with kinetin also restored the cell number phenotype (FIG. 7). In these experiments, cells were treated with minoxidil (10 μM) or kinetin (1 μM) for a duration of 2-24 hours prior to BMP4 addition. Alternatively, cells can be treated with minoxidil or kinetin following BMP4 addition. These results serve as proof of concept that treatment of HD tissues with an effective amount of minoxidil (or, as confirmation, kinetin) may restore the cells to a near wildtype state and serve as an effective treatment for HD.

As exemplified by this example, cells of the present disclosure can be used as a screening platform for identification of drug candidates that may be used in the treatment of Huntington's Disease.

This experiment can be repeated with marker-free ("pristine") versions of the foregoing micropattern screen harboring a lower number of polyQs (e.g., the aforementioned 40-CAG, 46 CAG, 54 CAG and 65 CAG which correspond to 42Q, 48Q, 56Q and 67Q constructs) but still within the pathogenic range. Based on preliminary observations of these cultures in which they exhibit HD phenotype, the results are anticipated to be qualitatively the same as with cultures bearing the 150Q HTT construct.

Indeed such pristine cell lines have been constructed as described in Example 9 having 22Q, 44Q, 50Q, 69Q and 75Q.

Example 6

Generation of HTT Knockout (HTT$^{-/-}$) and Heterozygous (HTT$^{+/-}$) Cells

In order to generate additional tools that can improve the study of Huntington's disease, as well as drug discovery applications, the Applicants used CRISPR technology to generate isogenic hESC lines in which the HTT gene has been knocked out. For optimal experimental settings, 3 independent homozygous HTT knockout (HTT$^{-/-}$) and 3 heterozygous (HTT$^{+/-}$) cell lines were generated. RUES2 hESC line was used as a parental line. To create HTT$^{-/-}$ and HTT$^{+/-}$ lines, CRISPR/Cas9 technology was used to delete the first exon of HTT, ensuring that no protein fragment would be produced in the targeted ("null") allele. An optimized strategy that combined two single guide RNAs (sgRNAs) that flanked the first exon was efficient in generating the desired deletion:

| sgRNA | Protospacer + PAM sequence |
|---|---|
| hHTT_sgRNA22 | CGCCATGGCGGTCTCCCGCC CGG (SEQ ID NO: 3) |
| hHTT_sgRNA14 | GCTGCACCGACCGTGAGTTT GGG (SEQ ID NO: 4) |

HTT expression levels were validated by Western Blot, which confirmed that HTT expression is absent in HTT$^{-/-}$ cells and reduced in HTT$^{+/-}$ lines. The pluripotency status and absence of differentiation of the clones were validated through qRT-PCRs and immunofluorescence staining. All lines were karyotyped to confirm the stability of their genomic integrity. Moreover, HTT$^{-/-}$ cells and HTT$^{+/-}$ lines were tested for their ability to differentiate into neurons, and the Applicants observed successful generation of neural progenitors and of neurons, despite the lack of HTT.

Together with the parental RUES2 line and lines containing various lengths of polyQ tract of HTT (described in Example 1), HTT$^{-/-}$ and HTT$^{+/-}$ lines can be used to study the effects of different HTT gene dosage on cellular functions. The dosage studies can be done both at the embryonic stage in order to assess the effects of HTT gene dosage in human gastrulation, as well as at the mature stage using differentiated HTT$^{-/-}$ and HTT$^{+/-}$ lines, to study the effects of gene dosage in cell populations of interest (i.e. neurons).

While the Applicants observed phenotypic changes in RUES2 cells due to polyQ extension, it is not known whether extension of polyQ tract leads to a gain-of-function mutation or a dominant negative mutation. A dominant negative mutation comprises a mutation whose gene product adversely affects the normal, wild-type gene product within the same cell. A gain-of-function mutation comprises a mutation that confers new or enhanced activity on a protein. Thus, a comparison of phenotypic differences between HTT$^{-/-}$ and HTT$^{+/-}$ lines with RUES2 cells comprising an extended polyQ tract can be used to distinguish between the two types of mutations. For example, if extension of polyQ tract leads to a dominant negative mutation, it would result in a phenotype that is similar to that seen in HTT null cells. A gain-of-function mutation can be distinguished from a dominant negative mutation because it will cause a novel phenotype that would not be observed in the HTT null cells.

Additionally, HTT$^{-/-}$ and HTT$^{+/-}$ cells can be used in combination with RUES2 cells comprising an extended polyQ tract to study extrinsic versus intrinsic phenotypes. Cells heterozygote for HTT (HTT$^{-/+}$) can be used to evaluate haploinsufficiency of HTT. Taken together, the HTT$^{-/-}$ and HTT$^{+/-}$ isogenic cells can be used in conjunction with the >40QHTT cells to gain more insight on the pathogenesis attending the polyQ extension of HTT.

Example 7

Generation of Fate-Reporter RUES2 Lines

During gastrulation, the cells of the embryo are allocated into three germ layers (endoderm, mesoderm and ectoderm) in an ordered spatial sequence. To understand the spatio-temporal dynamics of self-organization of human cells, the Applicants have generated fate-reporter RUES2 lines that allow following and monitoring of fate acquisition and induction of germ layers in real time. In this Example, CRISPR-Cas9 technology was used to knock-in different fluorescent proteins into either 1, 2 or 3 loci that encode germ-layer-specific markers in an otherwise unmodified single RUES2 hESC line.

Figure 8:
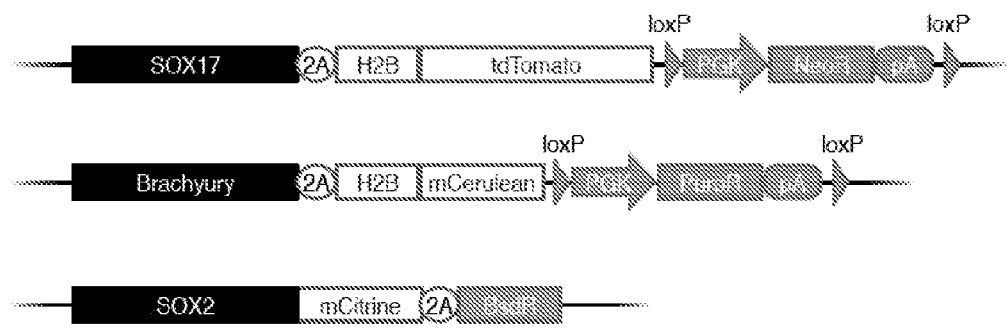
Figure 8:
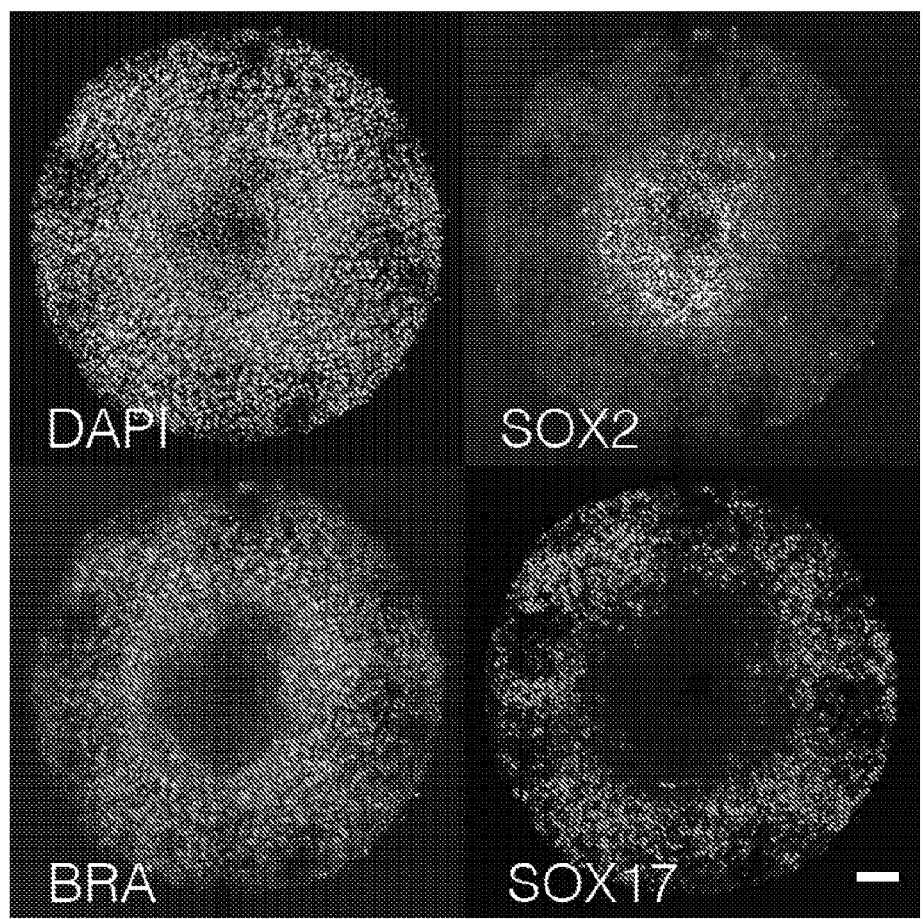

To generate individual reporter RUES2 lines that allow following of fate acquisition and induction of germ layers in real time. CRISPR-Cas9 technology was used to knock-in different fluorescent proteins into one of 3 loci that encode germ-layer-specific markers (FIG. 8). For example, in some cells, the pluripotency and ectodermal marker Sox2 was fused to mCitrine (mCit-Sox2), the mesodermal marker BRA was tagged with mCerulean (mCer-BRA), and in yet other cells, the endodermal marker Sox17 with tdTomato (Tom-Sox17), the last two using the peptide 2A self-cleaving system. Use of peptide 2A is not required. Any other strategy for co-expressing genes could have been used instead (see, Wong et al. *Gene Ther.* 2002 March; 9(5):337-44) Accuracy of the reporters was independently confirmed by immunofluorescence for each of the lineage-specific markers.

These three new hESC lines allow for a novel dynamic quantification of each fate acquisition in human embryonic cells. It also provides a platform to study in depth the molecular mechanisms involved in differentiation in each one of the 3 germ layers.

To generate double reporter RUES2 lines that allow following and monitoring of the acquisition of two different embryonic fates together in real-time (mesoderm and endoderm), the Applicants used CRISPR-Cas9 technology to knock-in 2 different fluorescent proteins into 2 loci that encode endoderm- and mesoderm-specific markers. The mesodermal marker BRA was tagged with mCerulean (mCer-BRA), and the endodermal marker Sox17 with tdTomato (Tom-Sox17), both using the peptide 2A self-cleaving system. Accuracy of the reporters was independently confirmed by immunofluorescence (IF) for each of the lineage-specific markers. In fact, a cell modified and confirmed to be a single reporter cell can be re-engineered to knock in a second fluorescent protein so that it co-expresses with a second germ layer marker.

This new hESC line allows for dynamic quantification of the transition from pluripotency into endo- and mesoderm fates during human gastrulation. Furthermore, these cells also provide a platform to study the molecular mechanisms necessary for differentiation into these 2 embryonic germ layers.

The Applicants next generated cells that can be used to follow and monitor acquisition of all three germ layers in real time.

Briefly, CRISPR-Cas9 technology was used to knock-in different fluorescent proteins into 3 loci that encode germ-layer-specific markers in a single RUES2 hESC line. The pluripotency and ectodermal marker Sox2 was fused to mCitrine (mCit-Sox2), the mesodermal marker BRA was tagged with mCerulean (mCer-BRA), and the endodermal marker Sox17 with tdTomato (Tom-Sox17; FIG. 13A8A), both using the peptide 2A self-cleaving system. A fusion approach for Sox2, rather than peptide 2A was chosen in each of the lines (single reporter, dual reporter, and triple reporter line) to enable the dynamic measurement of the transition between pluripotency and ectodermal specification, as well as the graded Sox2 disappearance upon differentiation to mesendodermal lineages.

The triple reporter line exhibited normal karyotype, and upon presentation of BMP4, the emergence and self-organization of the 3 human embryonic germ layers was observed (FIG. 13B8B). Accuracy of the reporters was independently confirmed by IF for each of the lineage-specific markers. In addition to providing dynamic quantification of fate acquisition in human embryonic cells, these cells can be used as a platform to study the molecular mechanisms important for differentiation into each one of the 3 embryonic germ layers.

Single, double and triple reporter cell lines described in this example can be grown in micropattern cultures and be used to perform screens to identify genes that are involved in germ layer formation and further development or small molecules or more broadly agents that would improve the efficiency of directed differentiation of stem cells to a cell type of interest for therapeutic purposes (i.e. neurons/glia for neurodegenerative diseases or brain injuries, beta cells for Type I diabetes, RPE cells for macular degeneration, etc). Furthermore, these cell lines can additionally be used as a screening tool to assess the real-time behavior of the cells that do not exhibit a disease phenotype while treated with drug candidates. Thus, the cell lines described in this example can be used to evaluate the real-time response of cells to drug candidates and to determine toxicity, potential teratogenicity, and other secondary effects potentially caused by the drug candidates. Such effects could be evaluated by determining cellular features that include but are not limited to the formation of germ layers, total number of cells in a micropattern, number of cells in each germ layer, timing of emergence of specific germ layer marker, and specific geometry of germ layer emergence.

Additionally, the Applicants have further modified the triple reporter line (RUES2-mCitrine-SOX2/mCerulean-BRA/tdTomatoSOX17) and added a nuclear fluorescent protein in order to allow for live cell tracking capabilities. Briefly, a cassette expressing the fluorescent protein iRFP fused to the histone H2B was introduced in the genome through ePiggyBac technology. This line had a normal karyotype, and upon presentation of BMP4, the applicants could observe the emergence and self-organization of the 3 human embryonic germ layers. The addition of the nuclear marker allows for optimal single-cell tracking in time-lapse experiments of fate acquisition in human embryonic cells. It also provides a platform to study in depth the molecular mechanisms required/necessary for differentiation into each one of the 3 embryonic germ layers.

Example 8

Discovery of New Hominid-Specific Exon of HTT: HTT-41b

In order to decipher the function of HTT in humans, the Applicants investigated the presence and diversity of HTT transcripts in pluripotent human embryonic stem cells (hESCs). The canonical HTT isoform is expressed in both pluripotent mESCs and hESCs (Dragatsis et al. *Development*. 1998 April; 125(8):1529-39; Feyeux et al. *Hum Mol Genet*. 2012 Sep. 1; 21(17):3883-95). In this Example, high-throughput RNA sequencing (RNA-seq) was used to scan the transcriptome of hESCs, both wild-type and HD mutants, in order to assess the presence of differentially spliced HTT mRNA transcripts. RNA-seq was performed in 3 independent hESCs lines cultured under pluripotency conditions. The lines included RUES2, (NIHhESC-09-0013), and two hESC lines derived from sibling female (XX) embryos, one wild-type and one containing mutant HTT (Genea019 and Genea020, respectively (*Stem Cells Dev.* 2011 March; 20(3):495-502)). Five novel isoforms of HTT were discovered: HTT-Δ10, HTT-Δ12, HTT-Δ13 and HTT-Δ46, and HTT-41b, where each can give rise to HTT protein variants lacking specific domains. Exon-specific PCR analysis confirmed the presence of 5 HTT transcripts detected by RNA-seq. All novel isoforms were detected in both normal and HD hESC lines and expressed with no significant differences in expression levels between cell lines when assessed by qPCR.

Importantly, the Applicants identified a hominid-specific isoform of HTT (HTT-41b), with the following 41b exon sequence, SEQ ID NO 5:

```
CCTAGGTGACACAGCAAGACGTTGTCTCTGGGGAAAAAAGAAAGAA
ACGGAACCACGCGGTGTGCAGCCTTCTGAGTCTGGCCCCTTTCG.
```

Figure 9:
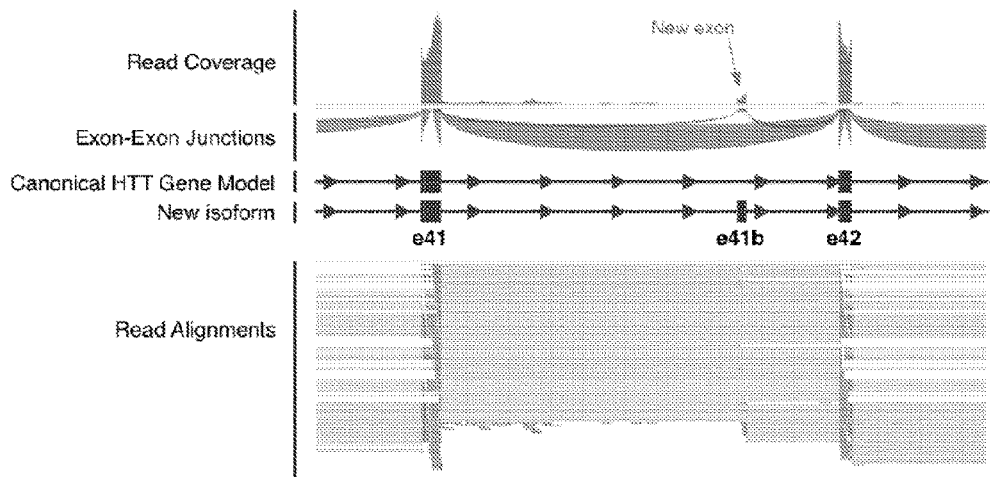
Figure 9:
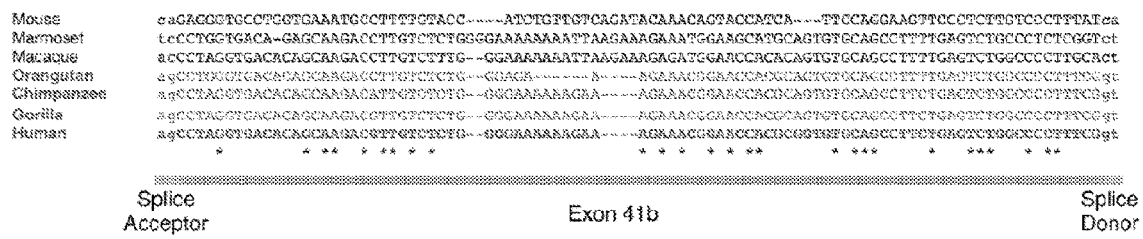
Figure 9:
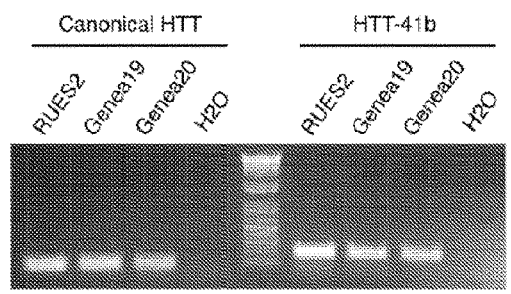
Figure 9:
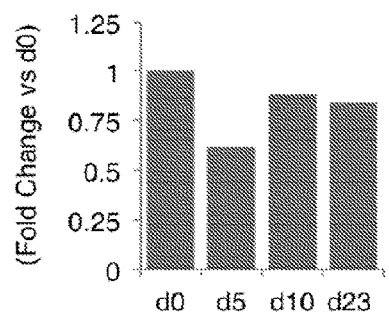

The 41b isoform incorporates a previously unreported exon located between exons 41 and 42 (hence named 41b), which potentially adds 30 new amino acids to the canonical HTT protein (FIG. 9A). Strikingly, both the coding frame and the splice acceptor-donor sites are exclusively present in Great Apes (orangutan, gorilla, chimpanzee) and humans, reflecting a very recent acquisition in the human evolutionary scale (FIG. 9B). Thus, this discovery could explain at least some of the phenotypic differences observed between HD patients and mouse models. This HTT-41b isoform was validated by PCR in hESCs and its expression was stably maintained upon neural differentiation as determined by qPCR (FIGS. 9C and 9D). Importantly, the HTT-41b isoform was the only isoform clearly detected in RNA-seq samples of human adult brain cortex (data analyzed from GEO accession number GSE59612) (Gill et al. Proc Natl Acad Sci USA 111: 12550-12555)), and its expression level was similar to what was detected in hESCs, ranging from 7.5-14% compared to the major HTT isoform. In fact, the HTT-41b isoform was clearly identified in all human adult tissues analyzed in the Illumina's BodyMap 2.0 project suggesting that this isoform is ubiquitously expressed.

Figure 10:
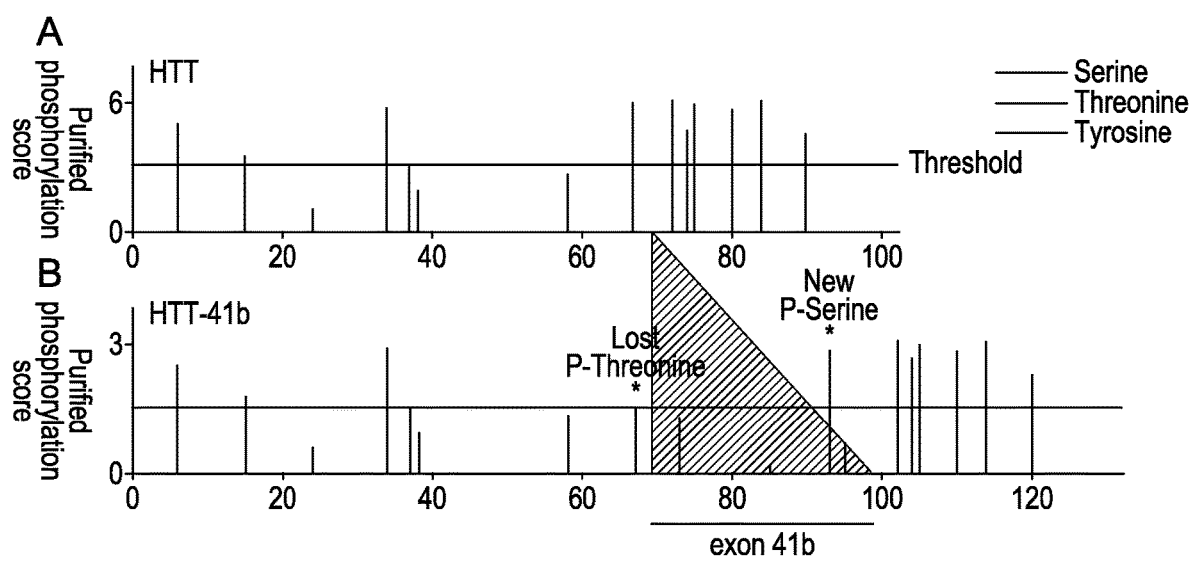

No structural domain of HTT has been detected within the additional 30 amino acids of 41b, but the addition of these extra amino acids leads to addition of a new phosphorylation site, while it removes a phosphorylation site found in canonical HTT (FIG. 10). Furthermore, additional 30 amino acids could generate conformational changes that may affect or modify its function. Such a hominid-specific isoform may help explain phenotypic differences between human patients and current mouse models of HD.

Normal and HD hESCs have ~15% of HTT transcripts containing 41b. To understand the functions of 41b, the inventors used CRISPR/Cas9 to generate hESC lines lacking 41b (called 0%41b) and hESC lines with forced expression of 41b in all HTT transcripts (called 100% 41b). These lines were generated both in unmodified RUES2 cells as well as in the triple reporter cell line described in Example 7. These new hESC lines (0%41b and 100% 41b, the construction of the latter schematically shown in FIG. 12) will provide insights into the functions of human specific exon 41b. Comparison of 0%41b, wild type, and 100% 41b will be used to delineate not only the function of 41b, but also its mechanism of function, including its downstream targets. In turn, newly discovered downstream targets of human specific 41b could then be used in drug candidate screens in search for novel Huntington's disease therapy. Thus, in addition to 41b being a potential target itself, the newly generated cell lines will be used to look for targets of 41b alone or in combination with the screening tools and HTT+/− and HTT−/− cell lines.

Since the inventors also generated 0%41b and 100% 41b in the context of triple (SOX2, BRA, and SOX17) reporter cell line (Example 7), these cells were grown on a micropattern cover slip, which allowed the inventors to monitor the role that 41b plays in differentiation into each one of the 3 embryonic germ layers. While 0%41b cells exhibited larger SOX-2 core compared to wild type cells, 100% 41b cells displayed smaller SOX-2 core compared to wild type cells.

Example 9

Specific HD-Phenotypic Signature in HD-hESC Line

In order to generate a hESC HD-phenotypic signature, we combined CRISPR-Cas9 genome editing with micropattern culture technology developed in our laboratory. The cell hESC line RUES2 was utilized for these studies (as described above; and derived from NIH0013; James et al., 2006; Rosa et al., 2009). RUES2 is a female (XX) line with a wild type HTT locus (chromosome 4p16.3) that encodes a normal stretch of 22Qs on one allele and 24Qs on the second. We modified the 22Q allele by adding 128Qs, thus generating a 150Q line (RUES2-Q150; FIG. 1A). The rationale for starting with a large polyQ insertion, which represents the extreme early-onset juvenile form of HD, was to maximize our chances of seeing a HD-specific phenotypic signature. To facilitate screening, we inserted a mCherry-blastidicine cassette upstream of the HTT coding region. This cassette is flanked by self-cleaving peptide 2A sites upstream of HTT start codon (FIG. 13A). Successful modification of the locus by CRISPR-Cas9 was confirmed by PCR. The resulting RUES2-Q150 cells were karyotypically normal, and no off target CRISPR-Cas9 modification was detected by RT-PCR. RUES2-Q150 expressed both HTT alleles, as evidenced by Western blotting of cell lysates for HTT. Insertion of the polyQs did change the stability of the mutant HTT as demonstrated by comparative western blots for the isogenic lines over time.

We then tested whether the genome editing strategy affected the basic properties of hESCs, maintenance of pluripotency, their rate of proliferation, and differentiation to discrete fates. When grown under pluripotency conditions, RUES2-Q150 cells maintained normal hESC morphology and expressed pluripotency markers, OCT4, NANOG, and SOX2 at levels similar to RUES2 cells. Additionally, the rate of cell proliferation was evaluated by EdU incorporation, and apoptosis by activated Caspase-3 expression as detected by immunostaining. We found no difference between RUES2 and RUES2-Q150 lines. This demonstrates that the insertion of polyQ did not affect their pluripotency or their rate of growth. Finally, to compare the differentiation potential of our two isogenic lines we used our micropattern culture technology comparatively between the two lines.

We have previously shown that when hESCs are grown in geometrically confined colonies on standardized micropatterned substrates, display a surprising self-organization, and induce all three embryonic germ layers in radially symmetrical patterns, when stimulated with BMP4. Wildtype RUES2 colonies generated radially symmetrical patterns of embryonic germ layers, with ectoderm (SOX2+) in the center, extra-embryonic tissue (CDX2+) at the edge, and mesoderm (BRA+) in between (FIG. 13B, top panel). This provides a phenotypic signature of wildtype hESCs in response to BMP4, which can be quantified with subcellular resolution. However, no mutant model cell lines had previously been tested to evaluate their phenotype for any particular signature or pattern. Under the exact same conditions, RUES2-

Q150 were tested and shown to induce the three embryonic germ layers, demonstrating that their ability to differentiate is maintained.

Surprisingly, however, while the germ layers were all induced, and displayed concentric rings, their radii and the number of cells contributing to each germ layer was changed. In the mutant cells, the ectoderm (SOX2+) region is reduced, while the mesoderm (BRA+) and endoderm (SOX17+) regions are expanded while the total cell number is reduced compared to the wildtype cells. This change of phenotype in response to a single insertion of polyQ in the RUES2 genome unveiled for the first time, a human HD-Phenotype in hESC cells.

Generation of additional pristine isogenic HD-hESC lines with different polyQ length The HD-specific human phenotypic signature provided a novel potential platform to screen for drugs and compounds that can rescue the HD-phenotype back to normal. However, it can be argued that the RUES2-Q150 is not really an HD-isogenic line because in addition to the polyQ expansion, it also harbors a selection blasticidine cassette, peptide 2A, and the mCherry lineage tracer. These can be argued to influence the phenotype in a non-specific manner. Therefore before embarking on the screen, a collection of "pristine HD-isogenic lines" was generated harboring only the polyQ insertions and nothing else. CRISPR/Cas9 was used in combination with the transposable element ePiggyBac to create additional HD isogenic lines with polyQ-expansions that are in the range of what is observed in the majority of HD patients namely Q44, Q50, Q58, Q69, and Q75. To make sure that the editing technology itself does not impact any readout, CRISPR/Cas9 was used to regenerate the RUES2 wildtype line carrying Q22 as an additional control, by cutting and reinserting the normal 22 Q repeat (FIG. 13A).

For each line, three independent clones were picked and validated by most stringent criteria: whole genome sequencing of a total of 21 genomes. No off-target event, or major modification of the genome was detected in any of these lower polyQ lines. Additionally, all isogenic lines were tested for the maintenance of basic hESCs properties. Thus, self-renewal, pluripotency, and their ability to differentiate to the embryonic germ layers were tested and proven to be indistinguishable among the different lines.

Because these lines have identical genetic background, any differences observed can be ascribed to the polyQ expansion and not to genetic modifiers or other confounding factors. Thus, in addition to the RUES2-Q150 line, an additional 6 HD-isogenic lines was generated: Wildtype RUES2-Q22 (un-manipulated), RUES2-Q22 (CRISPR control), RUES2-Q44, RUES2-Q50, RUES2-Q69, and RUES2-Q75. This collection of isogenic lines represents a unique tool that allows comparison of molecular and cellular differences specifically due to the HD mutation, with no background variability, directly in hESCs.

Phenotypic Signature of Isogenic HD-hESC Lines

In order to test if the RUES2-Q150 phenotype is specifically due to the polyQ-expansion, the ability of the 6 HD-isogenic lines harboring different polyQ repeats was analyzed in the micropattern culture platform. Cells of each line were cultured in triplicate samples on micropatterned colonies of different radii, induced with BMP4 to self organize, and quantified the phenotype under the exact same conditions as for RUES2-Q150. Astonishingly, each one of three HD-isogenic lines displayed a specific phenotype manifested by the reduction in size of the concentric germ layers rings, specifically the SOX2+ region area was inversely proportional to the length of the CAG repeats (FIG. 14). Even more surprising, each of the HD-isogenic lines displayed a different, and specific phenotypic signature that can be distinguished from others. This was revealed by our subcellular resolution quantification tool which allows the detection and accurate measurement of very small differences (FIG. 14B). The ectodermal SOX2+ domain decreased in size proportionally to the polyQ length. These results validated and expended the conclusions based on the original data with RUES2-Q150, to conclusively identify human HD-specific phenotypic signatures that distinguish the different mutations found in HD patients. These results also highlight the connection between the polyQ-expanded HTT mutants and TGFβ signaling with changes qualitatively similar to those seen with polyQ150 and described above.

Materials and Methods

Cell Culture and Generation of RUES2-Q150, $HTT^{-/-}$, and $HTT^{+/-}$ Cell Lines:

All reagents are from Life Technologies except where otherwise indicated. All experiments were performed using the RUES2 hESC line (NIH0013). However, any other human ESC lines may have been used for example those registered with the NIH and available from providers listed in the registry. hESC cells were maintained under pluripotency conditions in mTeSR-1 medium (Stemcell Technologies) on geltrex-coated cell culture dishes per manufacturer's instructions.

Generation of RUES2-Q150 Cells

A CRISPR-guide RNA (sgRNA) was designed to target the first exon of HTT using the online design software Benchling (which can be further described on the worldwide web at benchling.com), and cloned into a Cas9n-expressing plasmid (pX335). The resulting construct was named pX335-HTT-sgRNA1. The sgRNA sequence was GCTGCTGCTGGAAGGACTTG (SEQ ID NO: 6). The HTT-Q150 homology donor was constructed through Gibson assembly of multiple fragments: i) a 1-kb right homology arm containing the 5'UTR and part of the promoter, ii) an mCherry-T2A-Bsd-P2A fragment, iii) a synthesized fragment (IDT) coding for the first exon with an expansion of 150 glutamines, iv) a right homology arm containing 900 bp of the first intron.

hESCs were passaged as single cells using accutase and co-transfected with the pX335-HTT-sgRNA1 and HTT-Q150 homology donor plasmids (FIG. 1A) using the Amaxa Cell Line Nucleofector Kit L (Lonza) and program B-016 on the Amaxa Nucleofector II system. Cells were plated on geltrex-coated plates in the presence of Rock Inhibitor Y27632 (10 μM) and selection was performed using 10 ug/mL blasticidin starting 4 days after nucleofection. Single colonies were picked, and expanded as above. Karyotype analysis was performed by cytogenetic analysis on 20 G-banded metaphase cells (Cell Line Genetics). HTT protein localization was analyzed by immunofluorescence using an anti-N-terminal HTT antibody (LSBio #LS-B8023; 1:500), and a donkey anti-rabbit secondary antibody (#A21206).

Neuronal differentiation was induced by blocking both branches of the BMP/TGFβ signaling pathway. hESCs were grown to confluency and then treated with SB431542 (10 μM) and LDN193189 (100 μM) for 10 days in 3N medium (equal amounts of DMEM/F12 and Neurobasal/1× B27 supplement/1× N2 supplement/1 mM GlutaMAX/1× non-essential amino acids/0.5 mM Sodium Pyruvate/2.5 μg Insulin). Cells were then passaged and re-plated at high density and treated with SB431542 (10 μM) and LDN193189 (100 μM) for an additional 5 days. At day 15, the medium was changed to 3N medium without any inhibitor and rosettes formed between days 16-20. Rosettes were stained for PAX6 (BD biosciences #561462; 1:200) and N-Cadherin (BioLegend #350802; 1:50) confirming neuronal fate. The differences in phenotype can be quantified by measuring the ratio of the inner ring over the size of the colony measured to its outer edge. Lumen sizes are if=dentified from cadherin stains using for example Ilastik. Sommer C, Straehle C, Kothe U, Hamprecht F A: Ilastik: Interactive learning and segmentation toolkitIEEE, 2011, pp 230-233.

Generation of HTT$^{+/-}$ and HTT$^{-/-}$ hESC Lines

RUES2 hESC line (NIHhESC-09-0013) was used as the parental line. To generate HTT$^{-/-}$ and HTT$^{+/-}$ lines, CRISPR/Cas9 technology was used to delete the first exon of HTT, ensuring that no protein fragment would be produced in the targeted ("null") allele. An optimized strategy that combined two sgRNAs that flanked the first exon was used to generate the desired deletion:

| sgRNA | Protospacer + PAM sequence |
| --- | --- |
| hHTT_sgRNA22 | CGCCATGGCGGTCTCCCGCC CGG (SEQ ID NO: 3) |
| hHTT_sgRNA14 | GCTGCACCGACCGTGAGTTT GGG (SEQ ID NO: 4) |

The two sgRNAs were cloned into a Cas9 expression vector (pX330 from the Zhang lab at MIT, commercially available from Addgene, Cambridge, Mass.), modified to coexpress a puromycin-2A-EGFP cassette to facilitate selection of transfected cells, thus maximizing the percentage of targeted colonies. Both CRISPR plasmids were nucleofected into RUES2 cells using a Nucleofector II instrument and Cell Line Nucleofector Kit L (Lonza). Puromycin was added to the cultures 24 h after nucleofection, and kept in for additional 24 hours in order to select for transfected cells. Colonies derived from puromycin-resistant cells were picked and expanded for screening.

PCR amplification and Sanger-sequencing identified correctly targeted clones, with the desired exon1 deletion. Three heterozygous (HTT$^{+/-}$) and three homozygous (HTT$^{-/-}$) clones were identified and selected for further validations.

Generation of 0%41b and 100% 41b Cells

RUES2 and triple reporter cells generated in Example 7 were used as parental cells. The inventors used CRISPR/Cas9 to generate hESC lines lacking 41b (called 0%41b) and hESC lines with forced expression of 41b in all HTT transcripts (called 100% 41b—see FIG. 16 for donor plasmid sequence). 100% 41b cells were derived from 0%41b. The following sequences were usedfor the generation of %41b and 100% 41b cells:

```
gRNA sequence for 0%41b
1) hHTT_0%41b_5_1s:
                                (SEQ ID NO: 42)
caccgTCCCAAGCAGCTGAACTACA 2) hHTT_0%41b_3_1s:
                                (SEQ ID NO: 43)
caccGTCGCGTGTTGCCCACGCGT gRNA sequence and HD sequence for 100%41b
1) gRNA: hHTT_100%41b_1s:
                                (SEQ ID NO: 44)
caccGGCATTATGAACCTACTTCG 2) 100%41b_HD_puro.
                                (SEQ ID NO: 45)
```

Generation of Human Embryonic Stem Cell Line for Fate Mapping Analysis

All three homology donors were constructed using Gibson assembly. The BRA-mCerulean homology donor consisted of a 550 bp left homology arm, a P2A-H2B-mCerulean cassette, a floxed PGK-Puro-pA cassette, and a 700 bp right homology arm. All fragments were amplified with Q5 polymerase (NEB), using the following primers and templates:

| Fragment | Fw primer sequence | Rv primer sequence | Template |
| --- | --- | --- | --- |
| bb | GGTACCGTTCC ATCAGTCCAGC (SEQ ID NO: 9) | GAGCTCGTTCCATCGCTGG T (SEQ ID NO: 10) | pUC57-Amp plasmid |
| Left homology arm | TTACCAGCGAT GGAACGAGCTCTGAAT ATGTGAATAATCTTTTC AGTCATC (SEQ ID NO: 11) | TTCCTCGCCTTCTGCGCCT GCAGGTCATGGAAGGTGG CGACAC (SEQ ID NO: 12) | gDNA from RUES2 (WT) |
| 2A-H2B-mCer | ATGACCTGCAGGCGCA GAAGGCGAGGAAGC (SEQ ID NO: 13) | AGACGAATTCCTAATAAC TTCGTATAGCATACATTAT ACGAAGTTATTATTACTTG TACAGCTCGTCCATGC (SEQ ID NO: 14) | Synthesized fragment |
| Floxed Puro | AGCTGTACAAGTAATA ATAACTTCGTATAATGT ATGCTATACGAAGTTAT TAGGAATTCGTCTGAA GAGGAG (SEQ ID NO: 15) | CCTTGCTGCTGGCGCGCCA TAACTTCGTATAATGTATG CTATACGAAGTTATAGGC CTCTAGAGTCAGCTTCTGA TGG (SEQ ID NO: 16) | PGK-Puro-pA plasmid |
| Right homology arm | TTATGGCGCGCCAGCA GCAAGGCCCAGGTC (SEQ ID NO: 17) | GCTGGACTGATGGAACGG TACCTGGCTCACAAAAGG AGGGGCTTCACTAATAAC TG (SEQ ID NO: 18) | gDNA from RUES2 (WT) |

The SOX17-tdTomato homology donor contained a 850 bp left homology arm, a P2A-H2B-tdTomato cassette, a floxed PGK-Neo-pA cassette, and a 830 bp right homology arm. All fragments were amplified with Q5 polymerase (NEB), using the following primers and templates:

| Fragment | Fw primer sequence | Rv primer sequence | Template |
|---|---|---|---|
| bb | GGTACCCAGCTTTTGTT CCC (SEQ ID NO: 19) | AACTGAGCTCCAATT CGCCCTATAG (SEQ ID NO: 20) | pUC57-Amp plasmid |
| Left homology arm | GGGCGAATTGGAGCTC AGTTCCTGCAGGTGCA GGACCACCCCAACTAC (SEQ ID NO: 21) | TTCCTCGCCTTCTGC GCCTGCAGGGCACG TCAGGATAGTTGCA GT (SEQ ID NO: 22) | gDNA from RUES2 (WT) |
| P2A-H2B-tdTomato | AACTATCCTGACGTGCC CTGCAGGCGCAGAAGG CGAGGAAGC (SEQ ID NO: 23) | TCAGACGAATTCCTA ATAACTTCGTATAGC ATACATTATACGAA GTTATTATTACTTGT ACAGCTCG (SEQ ID NO: 24) | Synthesized fragment |
| Floxed Neo | CAAGTAATAATAACTT CGTATAATGTATGCTAT ACGAAGTTATTAGGAA TTCGTCTGAAGAGGAG (SEQ ID NO 25) | GGATCAGGGACCTG GGTACCGGCGCGCC ATAACTTCGTATAAT GTATGCTATACGAA GTTATAGGCCTCTAG AGTCAGC (SEQ ID NO: 26) | PGK-Neo-pA plasmid |
| Light homology arm | TTATggcgcgccGGTACCca ggtccctgatccgccc (SEQ ID NO: 27) | AGGGAACAAAAGCT GGGTACCCTTGCCAC TTCCCAAGGTGT (SEQ ID NO: 28) | gDNA from RUES2 (WT) |

The SOX2-mCitrine homology donor contained a 950 bp left homology arm, a mCitrine-T2A-Bsd cassette, and a 1 kb right homology arm. All fragments were amplified with Q5 polymerase (NEB), using the following primers and templates:

| Fragment | Fw primer sequence | Rv primer sequence | Template |
|---|---|---|---|
| bb | CCAATTCGCCCTATAGT GAGTC (SEQ ID NO: 29) | CTCCAGCTTTTGTTCCCTTT (SEQ ID NO: 30) | pUC57-Amp plasmid |
| Left homology arm | ACTAAAGGGAACAAAA GCTGGATGTACAACAT GATGGAGACG (SEQ ID NO: 31) | CTCGCCCTTGCTCACCATG TGTGAGAGGGGCA (SEQ ID NO: 32) | gDNA from RUES2 (WT) |
| mCitrine | CTCTCACACATGGTGA GCAAGGGCGAG (SEQ ID NO: 33) | CTCTGCCCTCCTTGTACAG CTCGTCCATGC (SEQ ID NO: 34) | mCitrine-2A-SOX2 plasmid |
| T2A-Bsd | GCTGTACAAGGAGGGC AGAGGAAGTCTTC (SEQ ID NO: 35) | TGTCCGGCCCTTAGCCCTC CCACACATAAC (SEQ ID NO: 36) | Synthesized fragment |
| Right homology arm | GGAGGGCTAAGGGCCG GACAGCGAACTG (SEQ ID NO: 37) | CGACTCACTATAGGGCGA ATTGGGTACCGGGCAGAC TGATTCAA (SEQ ID NO: 38) | gDNA from RUES2 (WT) |

For the CRISPR/Cas9-mediated targeting, multiple sgR-NAs were designed to recognize sequences near the STOP codons of each targeted gene. After preliminary testing, we used the most efficient sgRNA for each targeted gene:

| sgRNA | Protospacer + PAM sequence |
|---|---|
| hT_sgRNA1 | GAGGGGTGTGTAGTGCGCGG GGG (SEQ ID NO: 39) |
| hSOX17_sgRNA1 | GCAGTAATATACCGCGGAGC TGG (SEQ ID NO: 40) |
| hSOX2_sgRNA1 | GTGCCCGGCACGGCCATTAA CGG (SEQ ID NO: 41) |

These three sgRNAs were cloned into a Cas9-nickase expression vector individually, 2 at the same time, or all 3 at the same time) (pX335 from the Zhang lab (MIT)). The Applicants chose to target each gene sequentially, ensuring correct gene targeting at every step, before targeting the following gene. First, the Applicants targeted Brachyury, by nucleofecting both the Bra-mCer homology donor and the pX335-hT_sgRNA1 plasmids into RUES2 cells using a Nucleofector II instrument and Cell Line Nucleofector Kit L (Lonza). Puromycin was added to the cultures 5 days after nucleofection, and kept in for 5 more days, to ensure selection of correctly targeted clones. Colonies derived from single puromycin-resistant cells were picked and expanded for screening. PCR amplification and Sanger-sequencing identified correctly targeted clones, with no mutations in the CRISPR/Cas9 target sites. All positive clones were heterozygously targeted, which is a common finding in long genetic insertions via CRISPR/Cas9-mediated HR. Then the same process was used for targeting the SOX17 gene in one of the positive Bra-mCer clones, using a neomycin resistance cassette for selection. Finally, SOX2 was targeted in a double Bra-mCer+SOX17-tdTom clone, using the same approach and selecting with blastadicin. At all steps of the process, positive lines were karyotyped to assess genomic integrity. The pluripotency status and absence of differentiation of the clones were validated through qRT-PCRs and immunofluorescence staining. Finally, targeted clones were screened for their ability to generate all three embryonic layers. Accuracy of the reporters was independently confirmed by immunofluorescence for each of the lineage-specific markers.

Generation of RUES2-mCitrine-SOX2/mCerulean-BRA/tdTomatoSOX17) expressing the fluorescent protein iRFP fused to the histone H2B To maximize the utility of this line, the inventors decided to add a constitutively expressed nuclear marker for tracking of single cells in live imaging experiments. To achieve this, the inventors first cloned an infra-red fluorescent protein fused to H2B (iRFP-H2B) into a constitutive expression cassette flanked by ePiggyBac terminal repeats (seesequence below). The resulting plasmid (ePB-B-iRFP-H2B) was nucleofected, together with a ePiggyBac transposase-expressing plasmid, into the Triple Reporter line, using a Nucleofector II instrument and Cell Line Nucleofector Kit L (Lonza). Colonies expressing the highest amounts of iRFP were identified using an epifluorescence microscopy, handpicked and expanded. Karyotype and pluripotency were assessed to validate the line.

Sequence of infra-red fluorescent protein fused to H2B (iRFP-H2B) and cloned into a constitutive expression cassette flanked by ePiggyBac terminal repeats SEQ ID NO:69.

Establishment and Analysis of Micropatterned Cell Cultures

For routine culture maintenance, RUES2 cells were grown in HUESM medium that was conditioned by mouse embryonic fibroblasts (MEF-CM) and supplemented with 20 ng/ml bFGF. Cells were tested for mycoplasma prior to beginning experiments and then again at two-month intervals. Cells were grown on tissue culture dishes coated with Matrigel (BD Biosciences 1:40 dilution). Dishes were coated in Matrigel overnight at 4° C. and then incubated at 37° C. for 1 hour immediately prior to seeding the cells on the surface.

For the micropatterned cell culture, micropatterned glass coverslips (CYTOO) were first coated with 50 µg/ml Poly-D-Lysine in $H_2O$ (PDL; Millipore) for 2 hours. The PDL was then removed by serial dilutions without allowing the coverslip to dry (dilution 1:4 in $H_2O$, six times), before performing two complete washes with $H_2O$. Coverslips were then incubated with Matrigel (1:100 dilution in DMEM-F12) overnight at 4° C. Before cell seeding, the Matrigel was removed with serial dilutions in ice-cold PBS (dilution 1:4, six times) before 2 complete washes in ice cold PBS. Cells already resuspended in growth medium were seeded onto the coverslips immediately following the removal of the PBS. Applicants found it was important to maintain the coverslips at 4° C. at all times when in Matrigel solution and to ensure that the coverslips were not allowed to dry at any time after the application of the Matrigel. Both polymerization and drying of the Matrigel lead to inconsistent cell adhesion with cells more likely to detach from the support surface during the experiment.

Alternatively, cells were coated with Laminin521 for 2 hours, and Laminin521 was removed by serial dilutions in PBS, without allowing coverslips to dry.

Cell seeding onto micropatterned coverslips was performed as follows: cells growing in MEF-CM and FGF were pretreated with the Rock-inhibitor Y27632 (Rock-I; 10 uM) for 1 hour, washed once with PBS, and dissociated with Trypsin. Cells were centrifuged and 5×105 cells were resuspended in 2.5 ml growth medium contain Rock-I and the entire solution placed over the coverslip in a 35 mm tissue culture dish. After 2 hours, the medium was replaced with MEF-CM without Rock-I and cells were incubated overnight.

For immunofluorescence analysis of micropatterned cells, coverslips were rinsed once with PBS, fixed with 4% paraformaldehyde, rinsed twice with PBS, then blocked and permiabilized with 3% Donkey Serum, 0.1% Triton X-100 in PBS for 30 minutes. When performing immunofluorescence for pSmad1, cells were pretreated with 1% SDS in PBS for 30 min at 37° C. before blocking. Coverslips were incubated with primary antibodies overnight at 4° C., washed three times in PBS for 30 minutes each wash, incubated with secondary antibodies (Alexa488, Alexa555 or Alex647 conjugated (Molecular probes); dilution 1:500) and DAPI nuclear counterstain for 30 minutes, and then washed twice with PBS. Coverslips were mounted on slides using Fluoromount-G mounting medium (Southern Biotech).

For image analysis of micropatterned cells, all widefield images were acquired on an Olympus IX71 inverted microscope with a 20×, 0.75 Na lens. Tiled image acquisition was used to acquire images of the entire coverslip (approximately 2500 stage positions/coverslip) in four channels corresponding to DAPI and Alexa488, Alexa555, and Alexa647 conjugated antibodies. All confocal images were acquired on a Leica SP8 inverted confocal microscope with a 40×, 1.1 Na water immersion objective. Three-dimensional visualization and rendering was performed using Imaris software.

PCR:

Genomic DNA was extracted from cells using DNeasy Blood and Tissue extraction kit (Qiagen) and PCRs were run using GC-Rich PCR System kit (Roche). Primers used to screen to identify correctly targeted clones are below:

| F1 | CGTGAATTGCTGCCCTCT | (SEQ ID NO: 46) |
| --- | --- | --- |
| R1 | CAGAAACCCCTAGCTTCCAA | (SEQ ID NO: 47) |
| F2 | CCCAGAGCCCCATTCATTG | (SEQ ID NO: 48) |
| R2 | AGGACAAGGGAAGACCCAAG | (SEQ ID NO: 49) |

Western Blot:

Cells were lysed on ice using RIPA Buffer and 3× protease inhibitor cocktail (HALT protease inhibitor, Pierce), samples were spun at 20,000×g for 15 min at 4° C. Protein concentration in cell lysates was determined using the DC protein assay kit (BioRad). Equal amounts of protein were loaded and were probed using α-HTT (Cell signaling #5656; 1:2000), α-vinculin (Millipore #05-386; 1:5000), α-Tubulin (Sigma #T9026; 1:5000). Lysate were separated using the NuPage gel system and transferred to nitrocellulose membrane.

Cell Assays:

hESCs were grown in standard conditions on laminin-521 (Biolamina; 5 µg/ml)-coated Ibidi dishes for all immunofluorescent experiments. All imaging was performed on a Zeiss Axio Observer microscope using the appropriate filters. Exposure time was kept constant across control and experimental conditions for each experiment. Image analysis and quantification was performed using ImageJ software.

The catalase assay was performed according to manufacturer's instructions (Cell Biolabs). Briefly, 70-80% confluent hESC were harvested using PBS/1% EDTA. Cells were homogenized and spun down for 15 min at 4° C. at >10,000×g. Protein concentration was determined using the DC protein assay kit (BioRad). The catalase assay was performed using a BioTEK Synergy NEO machine at the High Throughput and Spectroscopy Center at The Rockefeller University.

Rhodamine123 and MitoTracker Red staining were performed simultaneously on live cell cultures. MitoTracker Red (100 nM) was added to the culture media and the cells were incubated for 30 min at 37° C. Cells were washed once with PBS+/+ and then stained with Rhodamine123 (5 ng/ml) and Hoechst 33342 (Life Technologies, 2 µg/ml) at room temperature for 10 min in media. Cell were washed 3 times with PBS+/+ and then imaged.

Caspase and EdU staining were performed simultaneously according to manufacturer's instructions. Briefly, cells were pulsed with EdU (10 µM) for 6 hours at 37° C. Cells were then fixed using 4% paraformaldehyde at room temperature for 20 min and permeabilized using a 0.5% Triton-X solution for 20 min. EdU incorporation was detected using the Click-iT reaction kit (Life Technologies). Cells were then blocked in 2% normal donkey serum for 1 hour at room temperature and then stained with α-activated Caspase-3 (R&D Systems #AF835; 1:1000) overnight at 4° C. Nuclei were stained with Hoechst 33342 (Life Technologies, 2 µg/ml) at room temperature for 10 min. Cells were washed in PBS 3 times, stained with secondary antibody Alexa555 antirabbit for 1 hour at room temperature, washed again with PBS and mounted using ProLong Gold.

For oxidative stress staining, cells were incubated with CellROX Green (Life Technologies) in media for 30 minutes at 37° C., and then stained with Hoechst 33342 (2 µg/ml) at room temperature for 10 minutes, washed in PBS+/+ and then fixed in 4% paraformaldehyde for 20 minutes at room temperature before mounting with ProLong Gold (Life Technologies).

RNA-seq Analysis:

High throughput sequencing (100 bp, paired-end) was performed at The Rockefeller University Genomics Core Resource Center, using an Illumina HiSeq2000 instrument. Sequencing data were analyzed with the Tuxedo software66. Briefly, the reads in the sequencer output file were aligned to the hg19 reference genome using TopHat2 and transcripts were assembled and quantified using the Cufflinks suite. Gene Ontology analysis was performed using the DAVID suite of resources.

Metabolite Extraction for Metabolomics Analysis:

hESCs were grown under standard conditions in 6-well plates to 70-80% confluency. For analysis of cellular metabolites, cells were quickly washed twice with ice-cold PBS, followed by metabolic quenching and metabolite extraction using −70° C. 80:20 methanol:water (LC-MS grade methanol, Fisher Scientific). Cold-quenched cells were scrape-harvested using a teflon cell scraper and transferred with 80% cold MeOH to 2.0 ml Tissuelyser tubes (Qiagen). The Cell-MeOH mixtures were incubated on dry ice for 10 min then subjected to bead-beating for 45 sec using a Tissuelyser cell disrupter (Qiagen). Extracts were centrifuged for 5 min at 5,000 rpm to pellet insoluble material and supernatants were transferred to clean tubes. This extraction was repeated two additional times and all three supernatants were pooled, dried in a speed-vac (Savant) and stored at −80° C. until analysis. For normalization of sample analyses, post-extracted cell pellets were solubilized in 200 µl 0.2M aqueous NaOH at 95° C. for 20 min and the pellet protein was quantified using the BioRad DC assay. On the day of metabolite analysis, dried cell extracts were reconstituted in 70% acetonitrile with 0.2% ammonium hydroxide at a relative protein concentration of 8 µg/µl and 3 µl of this reconstituted extract was injected for LC/MS-based untargeted metabolite profiling.

Untargeted Metabolite Profiling:

Cell extracts were analyzed by LC/MS essentially as described previously, using a platform comprised of an Agilent Model 1200 liquid chromatography system coupled to an Agilent Model 6230 time-of-flight MS analyzer. Metabolite separation was performed using aqueous neutral phase gradient chromatography on a Diamond Hydride column (Microsolv) and mobile phases as follows: A: 50% isopropanol, containing 0.025% acetic acid, and B: 90% acetonitrile containing 5 mM ammonium acetate. Raw data were analyzed using Agilent MassHunter Qual software, and Mass Profiler Professional software. Briefly, Qual performs untargeted molecular feature extraction to generate compounds/metabolites based on the elution profile at identical mass and retention times within a specified mass accuracy (5 ppm). Aligned molecular features detected in all biological replicates were directly applied for statistical analysis across treatment groups by Mass Profiler Professional. The Bonferroni family-wise-error-rate correction was applied for multiple testing corrections of p-values (corrected for $p < 0.05$).

Methods—for Example 9

Generation of an Isogenic Set of HD-Modeling hESC Lines

In order to establish an optimal platform for understanding the effects of HD mutations, CRISPR/Cas9 technology was used to generate a set of isogenic hESC lines that would differ only in the HTT locus, bearing different lengths of the CAG tract. The already established and registered RUES2 hESC line (NIHhESC-09-0013) was used as the parental line. Genetic analysis of the HTT gene in RUES2 showed that it contained 20 and 22 CAGs.

The homology donors for the CRISPR/Cas9-mediated homologous recombination (HR) were designed to contain ~1 kb homology arms flanking HTT exon1, a piggyback transposable element containing a Puro-TK cassette (for both negative and positive selections), and various versions of the HTT exon1, containing different lengths of the CAG tract (20, 42, 48, 56, 67 CAGs). To construct the homology donors, we first generated a parental plasmid using Gibson assembly, in which we could easily swap the length of the CAG tract. All fragments needed for the assembly were amplified using Q5 high-fidelity polymerase (NEB) using the following primers:

were unsuccessful. However, an optimized strategy that combined two sgRNAs targeting sequences that flanked the CAG tract proved to be much more efficient in generating the desired homologous recombination:

| sgRNA | Protospacer + PAM sequence | SEQ ID NO: |
|---|---|---|
| hHTT_sgRNA25 | GGTAAAAGCAGAACCTGAG CGG | 67 |
| hHTT_sgRNA14 | GCTGCACCGACCGTGAGTTT GGG | 68 |

These two sgRNAs were cloned into a Cas9-nickase expression vector (pX335 from the Zhang lab). Both CRISPR plasmids, together with the appropriate homology donor, were nucleofected into RUES2 cells using a Nucleofector II instrument and Cell Line Nucleofector Kit L (Lonza). Puromycin was added to the cultures 5 days after nucleofection, and kept in for 5 more days, to ensure selection of correctly targeted clones. Puromycinresistant cells were then nucleofected with an excision-only piggybac transposase (Transposagen), and a subsequent ganciclovir treatment selected clones in which the selection cassette had

| Fragment | Fw primer sequence | SEQ ID NO: | Rv primer sequence | SEQ ID NO: | Template |
|---|---|---|---|---|---|
| pUC57-Kan bb | CTCCAGCTTTTGTTCCC TTT | 59 | CCAATTCGCCCTATAG TGAGTC | 60 | pUC57-Kan plasmid |
| Left homology arm | AAAGGGAACAAAAGCT GGAGgggtcacacttggggtcc t | 61 | TCTAGGGTTAAaagcaga acctgagcggc | 62 | gDNA from RUES2 (WT) |
| ePB-PUTK | aggttctgcttTTAACCCTAG AAAGATAGTCTGC | 63 | GGGCCGCAGGTTAACC CTAGAAAGATAATCATA TTG | 64 | ePB-CAG-PUTK-pA plasmid |
| Right homology arm | TTTCTAGGGTTAACCTG CGGCCCAGAGCCC | 65 | GACTCACTATAGGGCG AATTGGCCTCCCCATC AGCAACGTGT | 66 | gDNA from RUES2 (WT) |

This resulting "base" homology donor plasmid contained a 20CAG tract, which could be easily swapped using the flanking XmnI and BbsI sites. To create the homology donor plasmids with expanded CAG lengths, we PCR-amplified the HTT exon1 region from genomic DNAs obtained from iPSCs or fibroblasts derived from HD patients, and cloned them into the "base" plasmid using XmnI and BbsI restriction enzymes. The primers used for the CAG tract amplification were SEQ ID NO:57: polyCAG_Fw CCAAGATGGACGGCCGCTC and SEQ ID NO:58: polyCAG_Rv AGGACAAGGGAAGACCCAAG. The origin of the templates that were used for each CAG length are summarized in the following table:

| CAG length | Origin of genomic DNA template | Obtained from |
|---|---|---|
| 42 | ND38548 iPSC | Coriell Biorepository |
| 48 | GENEA20 hESC | GENEA |
| 56 | QS-001 fibroblasts | Tabrizi's lab |
| 67 | QS-004 fibroblasts | Tabrizi's lab |

For the CRISPR/Cas9-mediated targeting, multiple sgRNAs were designed to recognize sequences near the CAG tract, but gene targeting attempts using one single sgRNA been correctly removed, leaving a minimal footprint (one extra nucleotide in the 5'UTR). Colonies derived from single cells were picked and expanded for screening. PCR amplification and Sanger-sequencing identified correctly targeted clones, with no mutations in the CRISPR/Cas9 target sites or the piggybac excision site. All positive clones were heterozygously targeted, which is a common finding in long genetic insertions via CRISPR/Cas9-mediated HR, and there seemed to be no preference in which allele had been targeted. Three independent clones were selected for each CAG length, that would serve as independent biological replicates for an optimal experimental setup. Normal HTT expression was confirmed through western blot, and all lines were karyotyped to assess their genomic integrity. The pluripotency status and absence of differentiation of the clones were validated through RT-qPCRs and immunofluorescence stainings. Finally, all targeted clones were screened for their ability to generate all three embryonic layers, by culturing them in micropatterns and inducing their differentiation by adding BMP4.

Example 10

The generation of a set of 18 isogenic human embryonic stem cell (hESCs) lines representing different levels of disease severity and onset are described herein. When submitted to neural induction, all lines generated neural rosettes and neural progenitors. However, we find that self-organization in, and among, rosettes are perturbed in the HD-mutant lines. In rosettes, we find: (i) a misregulation of the mitotic spindle orientation; (ii) the appearance of multipolar mitotic figures; (iii) the emergence of multiple centrioles in progenitor cells; and (iv) impaired ciliogenesis. Among rosettes, we show that a previously unnoticed self-organization of their spatial distribution is lost. Finally, examination of post-mitotic telencephalic neocortical human neurons after 45 days of differentiation revealed the presence of multinucleated giant cells, never detected before in HD models. The frequency of these abnormal progenitors, which are caused by a failure in cytokinesis, increased proportionally to the polyQ length. Our results provide for the first time, a highly quantitative, human phenotypic signature of HD, and strongly suggest that HD-mutation causes aberrances during embryonic development of the human brain, with the devastating consequences manifesting symptoms decades later.

In order to precisely model the correlation between the polyQ length and disease severity, we generated a collection of "pristine human HD-isogenic lines", which are genetically identical except for the length of the polyQ expansions. To this end, CRISPR-Cas9 technology was combined with ePiggyBac transposition to edit the genome of RUES2 (an hESC line derived in our laboratory; NIH0013). RUES2 is a female (XX) line with a wild type HTT locus (WT-HTT) that encodes 22Qs on one allele, and 24Qs on the second.

Five different polyQ lengths (45, 50, 58, 67, 74Q) were introduced in one of the two alleles to generate: RUES2-Q45, RUES2-Q50, RUES2-Q58, RUES2-Q67, and RUES2-Q74, and were chosen to model the spectrum observed in most HD patients, including two extreme lengths (67 and 74Q) that cause Juvenile-Onset HD. To make sure that our gene-editing process itself does not influence any readout, we used the exact same approach to reinsert the normal 22Q repeat, thus creating a sixth line by regenerating a new wildtype RUES2 line: RUES2-Q22 (FIG. 13A-C). Three independent clones were picked for each polyQ length and validated for off-targets defects by using the most stringent criteria: whole genome sequencing. No CRISPR-Cas9 off-target mutations or major modifications of the genome were observed in any of our lines. Karyotype, self-renewal, pluripotency, and differentiation ability were unchanged amongst all 18 HD-isogenic lines tested (FIG. 13C). This demonstrates that HD mutations do not affect pluripotency and very early cell fate specifications.

This collection of isogenic HD-hESC lines represents a unique tool that allows, for the first time, the comparison of molecular and cellular differences specifically due to HD mutations, with no background variability, directly in human pluripotent cells, which can differentiate to all human cell types.

Figure 15:
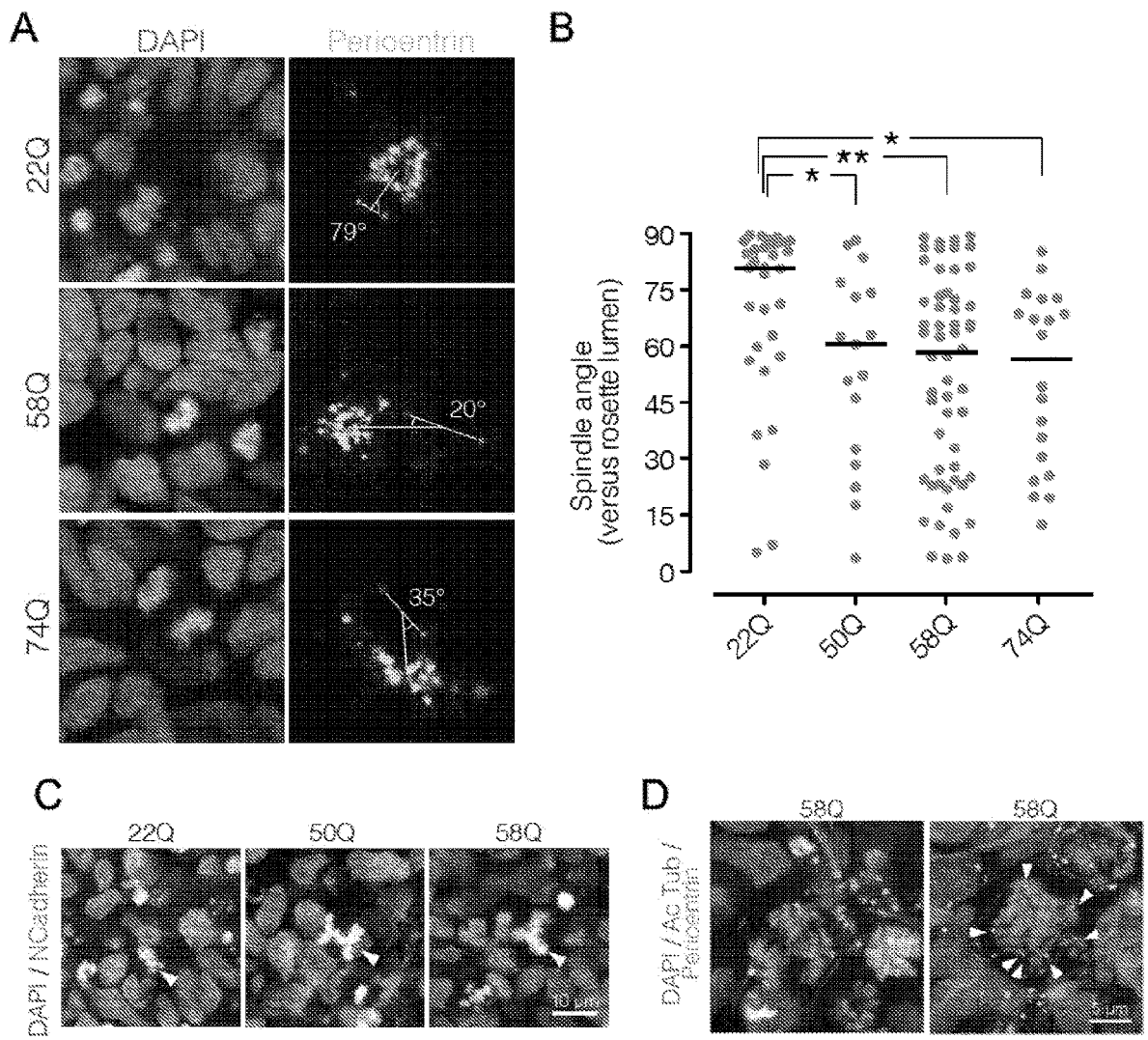

Nuclear localization of mutant HTT protein has been postulated to be critical for HD pathogenesis. There have been, however, no reports of the localization of either WT- or mutant-HTT in mESCs or hESCs. The exact subcellular localization of HTT protein in our isogenic collection was determined. These data illustrate for the first time that human HTT protein is excluded from the nucleus and confined to the cytoplasm in hESCs, and that the expansion of the polyQ tract does not affect its intracellular localization (FIG. 15B). This is significant for at least two reasons. First, it eliminates any possible role of HTT in nuclear functions, including transcription, in hESCs. Second, it demonstrates that mutant-HTT, regardless of polyQ length, does not function by altering the subcellular localization of either the WT-allele or the polyQ-expanded HTT itself. As HD is recognized as a neurodegenerative disease, our comparative phenotypic analysis focused first on the ability of the lines to undergo neural induction and differentiation, the earliest step in embryonic neural development. Neural induction occurs by an evolutionary conserved default mechanism whereby inhibition of both branches of the TGFβ signaling, which can be accomplished by the presentation of two small compounds: SB and LDN, leads to conversion of the pluripotent state to anterior telencephalic fate. At day 19, all isogenic lines generated typical radially symmetrical neural rosettes of similar morphology and cell densities (data not shown).

Examination of markers of pan-neural identity, such as PAX6, SOX1 and NESTIN, showed similar levels of expression across all lines, and uniform FOXG1 expression within and between lines demonstrated uniform telencephalic positional identity. This demonstrates that expansion of polyQ in HTT does not interfere with the initial stages of neural induction and differentiation. HTT protein still localized in the cytoplasm of the neural progenitors at this stage, regardless of the polyQ length (data not shown).

The minute details of self-organization were next analyzed, during neural induction and patterning, for individual rosettes comparatively across our isogenic lines. The experiments were designed to determine whether polarity, especially during cell divisions, was affected across the isogenic lines. Neural progenitors display a very polarized morphology at this stage, with a single cilia sprouting out of their centrosomes in their apical-luminal region. Mimicking the pattern of the developing brain, the nucleus of progenitor neurons migrates toward the lumen of the neural rosette, and cell division occurs proximal to the apical surface with the mitotic plane orthogonal to the rosette lumen (FIG. 15A-B). However, examination of pairs of pericentrin-positive centrosomes during cell divisions showed randomized mitotic angles in the HD lines, suggesting a deregulation of the mitotic spindle orientation (FIG. 15A-B). HD mutant lines also displayed multipolar metaphase figures (FIG. 15C). Additionally, a few individual progenitor cells displayed supernumerary centrosomes (FIG. 15D), although the total number of centrosomes per cell was not globally affected at this stage. Close examination of cilia structure revealed that cilia in HD neural progenitors were significantly shorter than in control lines (data not shown). While mitotic angle defects, and centrosomal and ciliary misregulations have been previously reported in HD mouse models, and in human fibroblasts with long polyQ tracts, the consequences of these on neural self-organization have not been previously noticed in a disease-relevant human cell type.

Figure 16:
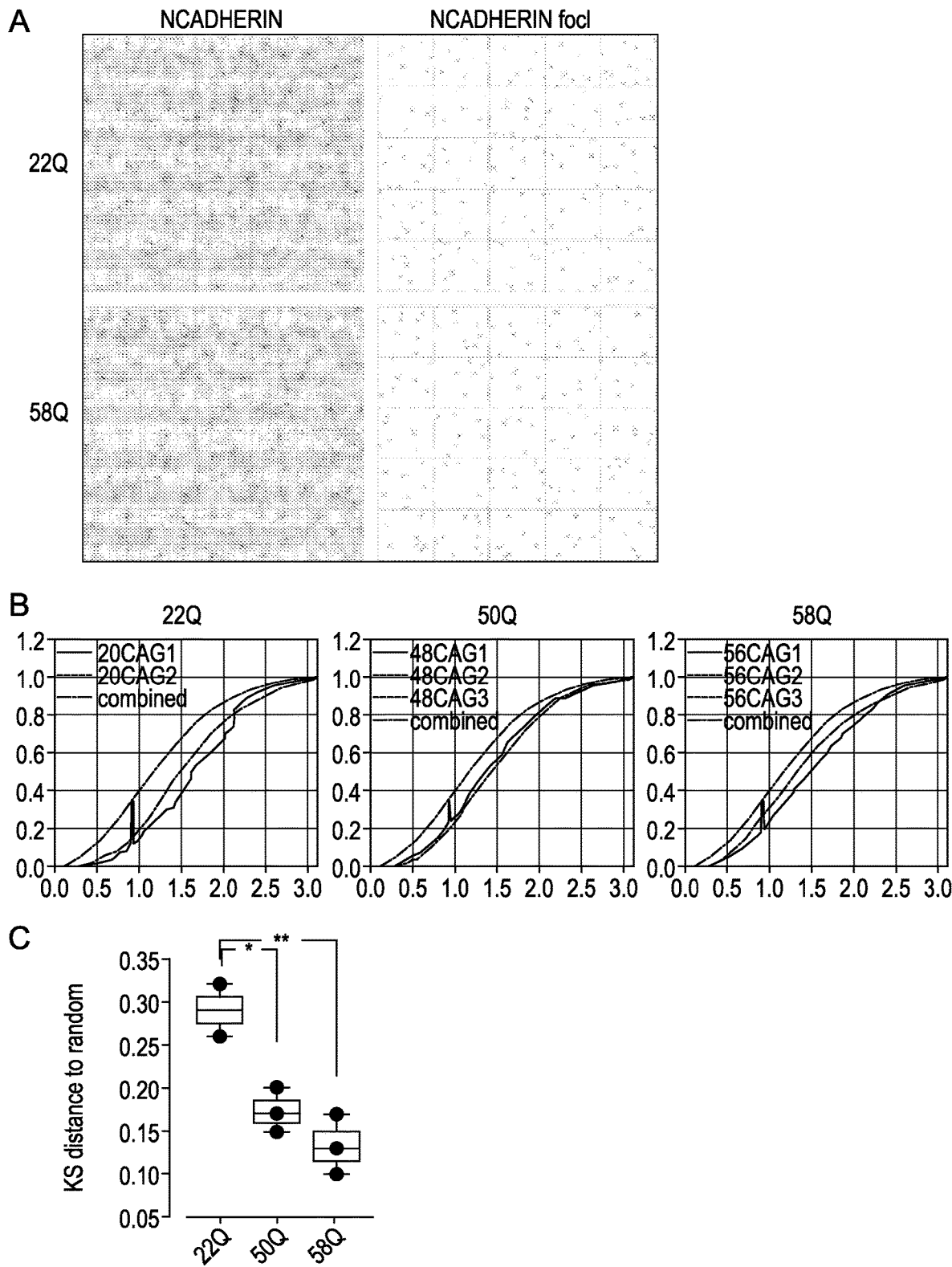

The observed randomization of the mitotic spindle orientation could have an impact in the global spatial organization of the neural rosettes. The distribution of the distances from the center of each neural rosette was analyzed, identified as an N-Cadherin focus, to its nearest neighbor. Interestingly, neural rosettes in control lines formed a very regular structure, in which the distribution of distances differed significantly from a theoretical random distribution (FIG. 16A-C). This observation further demonstrates that cultured neural rosettes have a strong tendency to self-organize symmetrically in space in a very reproducible and quantifiable manner. Surprisingly, neural rosettes from HD mutant lines, on the contrary, did not spatially self-organize with the same efficiency, as the distributions of the nearest neighbor distances between rosette centers were closer to a random distribution (FIG. 16-A), suggesting a loss of their ability to selforganize into regular patterns. For the first time, these data show that HD is affecting global morphogenetic self-organization during human neural induction, indicating that HD alterations already start during neurodevelopmental processes rather than in adulthood, as commonly thought.

Figure 17:
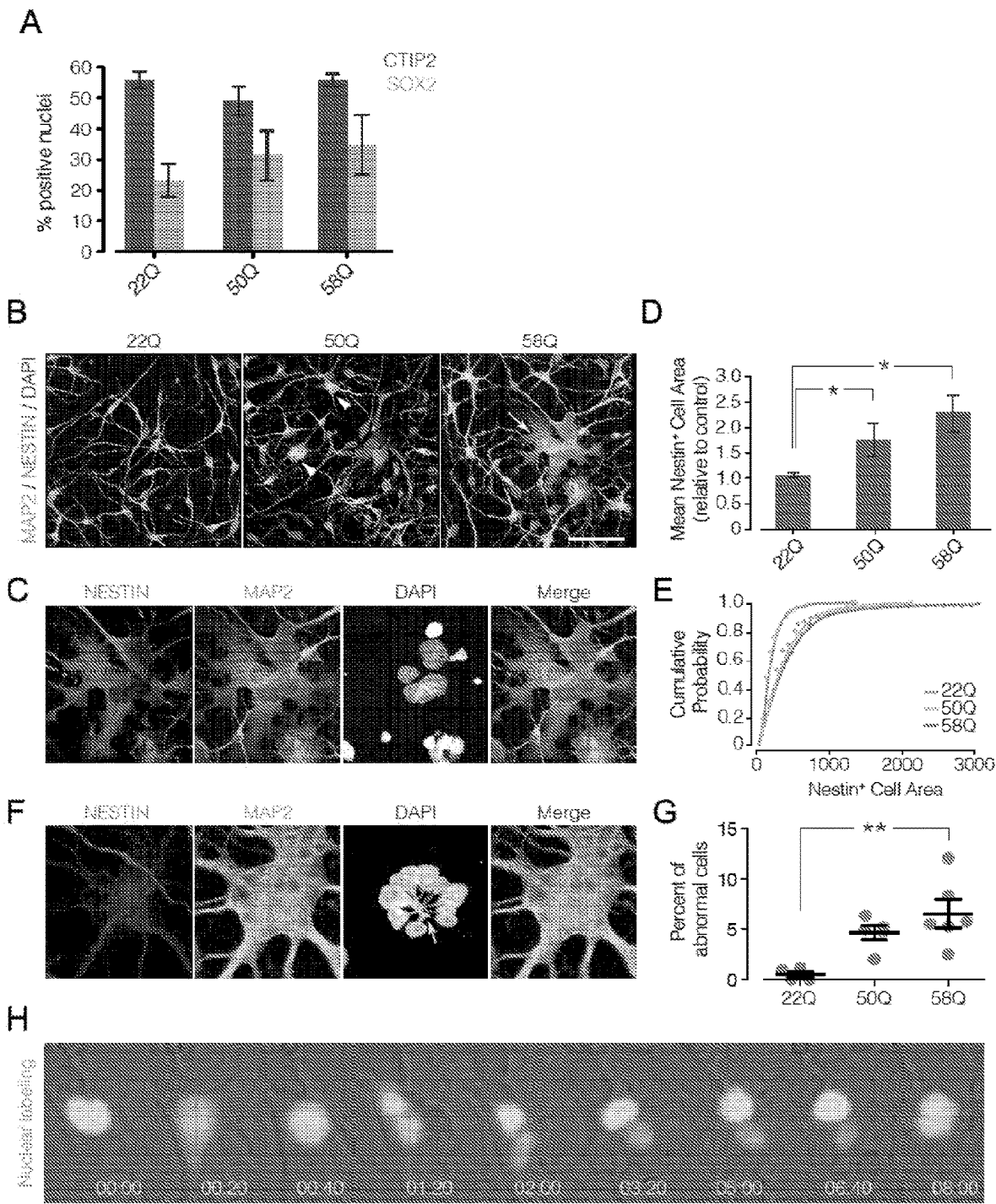

The expanded polyQ length affects were also analyzed at the next stage of neurodevelopment, when neuroepithelial progenitor cells begin to produce post-mitotic lower layer projection neurons. This happens at day 45 of neural induction in vitro, and at this stage cultures of control lines consisted of both neural progenitors (SOX2+, NESTIN+) and post-mitotic neurons (CTIP2+, MAP2+) (FIG. 17A). Expanded polyQ lines generated post-mitotic neurons with similar efficiency to control lines (FIG. 17A). However, both progenitors and post-mitotic neurons from HD mutant clones exhibited dramatic abnormal phenotypes compared to control clones. On one hand, many NESTIN+ progenitor cells displayed enlarged cell soma, with multiple nuclei, disorganized filaments and vacuoles (FIG. 17B-E). Mutant HD lines also produced frequent MAP2+ neurons with multiple nuclei tethered together in bouquet shapes by strands of by DNA (FIG. 17F). Interestingly, the frequency of these abnormal phenotypes increased proportionally to the length of polyQ expansion (FIG. 17G). Since the genetic basis of Huntington's was identified, the remarkable direct linear correlation between CAG-length and disease severity has been a tantalizing clue to the logic of the disease. However, this is believed to be the first CAG-length proportional phenotype identified in a disease-relevant human cell system, suggesting key mechanisms of HD pathophysiology and potentially identifying new upstream therapeutic targets. To determine whether multiply nucleated progenitor and neuronal cells arose from cell fusion or dysregulation of cell division, cell mixing experiments were performed with nuclear labeling under continuous timelapse acquisition. No cell fusion events were detected in any genotype. However, while control clones exhibited normal cell cycle progression, expanded CAG lines consistently displayed failed cytokinesis (FIG. 16H). These unsuccessful divisions usually failed at the final separation of the two daughter cells (abscission). It was concluded that mutant HTT during neural induction and differentiation results in errors in several aspects of neural progenitor cell divisions, including proper control of centrosomal replication, metaphase assembly and cytokinesis.

Interestingly, the failure of cytokinesis, along with rosette nuclear figures, has not been reported in HD mouse models or patients, but it strikingly phenocopies the knockout of citron kinase (CIT), where impairment in the final abscission of the midbody results in both multinucleated neurons with nuclear rosette shapes, and cells with multiple centrosomes 14-16. This phenocopy therefore generates a series of molecular targets including citron-kinase, Src and Ephrin pathways.

One option for how these aberrant cell division phenotypes contribute to HD pathology is that cellular reserve or resilience is diminished in the development of the corticostriatal circuit. This could be the result of unbalanced production of neurons, or the glia cells which progenitor cells give rise to in the third trimester. Because of developmental plasticity and compensation and redundancy, deficits are only revealed with age as progenitor cells or neurons are culled by stress. It is also possible that degenerating progenitors and neurons initiate inflammatory and cytotoxic imbalances in very early development, which are successfully compensated for many years before their burden exceeds homeostatic capacity. Most fundamentally these options collectively argue that the consequences of early defects must be considered when developing therapies for Huntington's disease, even when symptoms only appear decades later.

Example 10 Methods—Generation of an Isogenic Set of HD-Modeling hESC Lines

In order to establish an optimal platform for understanding the effects of HD mutations, CRISPR/Cas9 technology was used to generate a set of isogenic hESC lines that would differ only in the HTT locus, bearing different lengths of the CAG tract. The already established and registered RUES2 hESC line (NIHhESC-09-0013) was used as the parental line. Genetic analysis of the HTT gene in RUES2 showed that it contained 20 and 22 CAGs. The homology donors for the CRISPR/Cas9-mediated homologous recombination (HR) were designed to contain ~1 kb homology arms flanking HTT exon1, a piggyback transposable element containing a Puro-TK cassette (for both negative and positive selections), and various versions of the HTT exon1, containing different lengths of the CAG tract (20, 42, 48, 56, 67 CAGs). To construct the homology donors, we first generated a parental plasmid using Gibson assembly, in which we could easily swap the length of the CAG tract. All fragments needed for the assembly were amplified using Q5 high-fidelity polymerase (NEB) using the following primers:

| Fragment | Fw primer sequence | SEQ ID NO: | Rv primer sequence | SEQ ID NO: | Template |
|---|---|---|---|---|---|
| pUC57-Kan bb | CTCCAGCTTTTGTTCCC TTT | 59 | CCAATTCGCCCTATAG TGAGTC | 60 | pUC57-Kan plasmid |
| Left homology arm | AAAGGGAACAAAAGCT GGAGgggtcacacttggggtcc t | 61 | TCTAGGGTTAAaagcaga acctgagcggc | 62 | gDNA from RUES2 (WT) |
| ePB-PUTK | aggttctgcttTTAACCCTAG AAAGATAGTCTGC | 63 | GGGCCGCAGGTTAACC CTAGAAAGATAATCATA TTG | 64 | ePB-CAG-PUTK-pA plasmid |
| Right homology arm | TTTCTAGGGTTAACCTG CGGCCCAGAGCCC | 65 | GACTCACTATAGGGCG AATTGGCCTCCCCATC AGCAACGTGT | 66 | gDNA from RUES2 (WT) |

This resulting "base" homology donor plasmid contained a 20CAG tract, which could be easily swapped using the flanking XmnI and BbsI sites. To create the homology donor plasmids with expanded CAG lengths, we PCR-amplified the HTT exon1 region from genomic DNAs obtained from iPSCs or fibroblasts derived from HD patients, and cloned them into the "base" plasmid using XmnI and BbsI restriction enzymes. The primers used for the CAG tract amplification were

```
SEQ ID NO: 57: polyCAG_Fw
CCAAGATGGACGGCCGCTC

SEQ ID NO: 58: polyCAG_Rv
AGGACAAGGGAAGACCCAAG.
```

The origin of the templates that were used for each CAG length are summarized in the following table:

| polyQ length | Origin of genomic DNA template | Obtained from |
|---|---|---|
| 44 | ND38548 iPSC | Coriell Biorepository |
| 50 | GENEA20 hESC | GENEA |
| 58 | QS-001 fibroblasts | Tabrizi's lab |
| 69 | QS-004 fibroblasts | Tabrizi's lab |
| 75 | QS-004 fibroblasts | Tabrizi's lab |

For the CRISPR/Cas9-mediated targeting, multiple sgRNAs were designed to recognize sequences near the CAG tract, but gene targeting attempts using one single sgRNA were unsuccessful. However, an optimized strategy that combined two sgRNAs targeting sequences that flanked the CAG tract proved to be much more efficient in generating the desired homologous recombination:

| sgRNA | Protospacer + PAM sequence | SEQ ID NO: |
|---|---|---|
| hHTT_sgRNA25 | GGTAAAAGCAGAACCTGAG CGG | 67 |
| hHTT_sgRNA14 | GCTGCACCGACCGTGAGTTT GGG | 68 |

These two sgRNAs were cloned into a Cas9-nickase expression vector (pX335 from the Zhang lab). Both CRISPR plasmids, together with the appropriate homology donor, were nucleofected into RUES2 cells using a Nucleofector II instrument and Cell Line Nucleofector Kit L (Lonza). Puromycin was added to the cultures 5 days after nucleofection, and kept in for 5 more days, to ensure selection of correctly targeted clones. Puromycinresistant cells were then nucleofected with an excision-only piggybac transposase (Transposagen), and a subsequent ganciclovir treatment selected clones in which the selection cassette had been correctly removed, leaving a minimal footprint (one extra nucleotide in the 5'UTR). Colonies derived from single cells were picked and expanded for screening. PCR amplification and Sanger-sequencing identified correctly targeted clones, with no mutations in the CRISPR/Cas9 target sites or the piggybac excision site. All positive clones were heterozygously targeted, which is a common finding in long genetic insertions via CRISPR/Cas9-mediated HR, and there seemed to be no preference in which allele had been targeted. 3 independent clones were selected for each CAG length, that would serve as independent biological replicates for an optimal experimental setup. Normal HTT expression was confirmed through western blot, and all lines were karyotyped to assess their genomic integrity. The pluripotency status and absence of differentiation of the clones were validated through RT-qPCRs and immunofluorescence stainings. Finally, all targeted clones were screened for their ability to generate all three embryonic layers, by culturing them in micropatterns and inducing their differentiation by adding BMP4.

Neural Differentiation

Isogenic lines were subjected to default neural induction protocol adapted from [doi:10.1038/nprot.2012.116]

In short, cultures seeded in suspension at 0.5-1 Mcells/ml and fed every other day with N2B27 serum free medium with ROCK inhibitor (20 uM) for the first 2 days, TGFB inhibition (SB10 µM/LDN 0.2 µM) for the first 10 days, treated with 5 ng/ml FGF8 from day 12-22 to optimize CTIP2 abundance, dissociated and seeded on adherent substrate (poly-ornithine laminin) at day 14, fixed and analyzed at day 19 or continued in culture with added BDNF and IGF1 (10 ng/ml), cAMP(1 µM), and ascorbic acid, until dissociation and reseeding on subtstrate at day 41, and fixation and analysis at day 45.

Immunostaining and Imaging

Cultures were rinsed once with PBS, fixed with 4% paraformaldehyde, rinsed twice with PBS, and then blocked and permeabilized with 3% donkey serum and 0.1% Triton X-100 in PBS for 30 min. Samples were incubated with primary antibodies overnight at 4° C., washed three times in PBS for 30 min each wash, incubated with secondary antibodies (Alexa 488, Alexa 555 or Alex 647 conjugated (Molecular Probes); dilution 1:500) and DAPI nuclear counterstain for 30 min, and then washed twice with PBS. Z-stack images were acquired on a Leica SP8 inverted confocal microscope at 12 bits in 1024 pixels×1024 pixels using an HCX PL APO CS×20/0.75 numerical aperture air-immersion, an HC PL APO CS2×40/1.10 numerical aperture water-immersion objective or a ×100 oil-immersion objective. Images were then deconvolved with a three-dimensional blind algorithm (ten iterations) using AutoDeblur X software (Autoquant).

Analysis of Neural Rosette Spatial Distribution

Rosettes were identified by training a classifier on N-Cadherin antibody stains using Ilastik (ilasik.org). N-Cadherin positive areas were thresholded in size (15 µm2) to eliminate small N-Cadherin spots that were not fully developed rosettes. The quantification results were not dependent on the specific value chosen for the threshold. The nearest neighbor distributions were obtained using the kd tree implementation in scikit-learn (scikit-learn.org) and were compared to the random distribution by using the one-sample Kolmogorov-Smirnov (KS) distance between them. The cumulative nearest neighbor distribution for a random set of points in two dimensions can easily be calculated as $$F_D(d)=Pr(D \leq d)=0.1-e^{-\lambda \pi d}s$$

where $\lambda$ is the two-dimensional density of foci. We rescaled the data for the individual lines separately according to their foci density $\lambda$.

Time-Lapse Imaging

After single-cell seeding into gridded 35 mm dishes (Ibidi) at day 41 of the neural induction protocol, cells were transduced with CellLight Nucleus-GFP or Nucleus-RFP BacMam 2.0 for 16 h. After 3 days, at which point strong green and red nuclear staining could be observed, cultures were imaged every 30 mins in a Cell Voyager CV1000 spinning disk confocal imaging system for 3 days. Images were analyzed using Cell Voyager software and Fiji/ImageJ.

Example 11

A library of compounds is screened in parallel against the three highly quantitative HD-specific phenotypic platforms described herein: (i) germ layer micropattern assay; (ii) neural rosettes in micropatterns; and (iii) giant neuron phenotypes. The screen results in a list of hit compounds ranked by the number of HD phenotypes that they are able to rescue or improve. The highest ranked candidate compounds are then re-tested from the original solid stocks for the reversal of all three phenotypes as well as for potency and toxicity. These candidate compounds, together with kinetin and minoxidil, are ranked based on their phenotype reversal ability, their therapeutic potency and toxicity. The top candidates from this list are then assessed for their ability to revert HD phenotypes in vivo.

Pharmacokinetics studies are then performed to identify the optimal route of administration and dosing regimen in order to reach a therapeutically effective concentration (determined in in vitro potency studies) in adult brains and embryos in in vivo animal models, for example using a mouse model of HD. That dosing strategy is used to test the reversal/amelioration of two independent HD phenotypes in vivo: (i) the neurodevelopmental alterations observed in brains of newborn HD mice by examination of molecular markers and histopathology; and (ii) the typical behavioral alterations and neurodegeneration observed in adult HD mice. The successful amelioration, or reversal of both developmental and adult in vivo phenotypes by any of the compounds provides a highly validated therapeutic candidate worth of further preclinical studies for HD treatment.

A. Compounds that can Rescue Germ Layer Phenotypic Signature

Data described in earlier examples has shown that when cultured on micropatterned substrate and stimulated with BMP4, each of the 8 isogenic HD-RUES2 lines self-organize to generate CAG-length dependent phenotypic signatures of embryonic germ layers. While the relative positioning of the ectoderm (SOX2) in the center, extra-embryonic tissue (CDX2) at the edge, and mesoderm (BRA) in the middle are maintained, their relative size and cell numbers changes. The software and analysis allows subcellular resolution quantification of the phenotypes and is described in Etoc et al., 2016. As validation of this model, the aberrant HD signatures can be at least partially rescued by two compounds, kinetin and minoxidil, which have been selected from a compound library on the basis of their ability to partially reverse HD phenotype in the germ layer micropattern assay.

Test compounds are screened for their ability to rescue the BMP4-induced HD-germ layer phenotype in a high-throughput manner, using multiwell plates and robotic handling and imaging. To streamline the screening approach the testing can be initiated in 3 of the HD-RUES2 isogenic lines: HD-RUES2-20 (as a control), HD-RUES2-48, and HD-RUES2-56. Test compounds are copresented with BMP4, and after 48 hours all wells are fixed and stained by IF to detect the differentiation patterns of SOX2, BRA, and CDX2. Software analysis is used (as described in Etoc et al., 2016) to quantify cellular response and changes in patterns with single cell resolution in each colony in order to identify positive hits that can revert or improve HD-phenotypic signature.

Positive hits obtained from this approach, along with the two already identified (kinetin and minoxidil), are submitted to dose-response analysis to establish potency and toxicity in the other 5 HD-RUES2 lines.

Hits that rescue only one, or a few, but not all of the HD-RUES2 lines are submitted to the two neuronal assays described herein, to evaluate the range of effect on those alternate platforms.

B. Compounds that can Rescue Two HD-Neural-Specific Phenotypic Signatures

The compound library, as well as kinetin and minoxidil, is initially screened for their ability to rescue two neuronal phenotypes: early HD-neuronal phenotype cultured as micropatterned colonies, and elimination or reduction of giant multinucleated neurons, in HD-RUES2-20, HD-RUES2-48, and HD-RUES2-56. This allows the triage of hits from part A, prioritizing those that can rescue more than one phenotypic platform, and identifying hits that can only rescue neuronal but not embryonic germ-layer phenotypes.

Aspects of experimental design, methods and techniques, data analysis, and logistics are very similar to those described for part A, except that SB+LDN are used instead of BMP4 to induce neural progenitors as described below:

For the early HD-neuronal phenotype, isogenic HD-RUES2-20, HD-RUES2-48, and HD-RUES2-56 cells are cultured on micropatterns in the presence of SB+LDN+/−individual compounds. The rationale for co-presentation of compound with inducers is based on blocking HD-deteriorating effects before, or during, neural induction. At the end of the experiment all wells are fixed and cells are immunostained with PAX6 and N-CAD, to confirm neural induction, and to measure Lumen/colony area ratios, followed by quantification using the automatic bioinformatics tool described in Etoc et al., 2016.

For the giant multinucleated neuronal phenotype, the protocol outlined herein above is generally followed using HD-RUES2-20, HD-RUES2-48, and HD-RUES2-56 isogenic lines, except for miniaturization and automation of the assay. Compounds are presented on Day 1 and maintained during the course of the experiment. Cells are passaged robotically at day 15, fixed at day 30, and stained with DAPI to detect nuclear bouquets. Quantification is achieved using the bioinformatic tool described herein.

Successful execution of these experiments is expected to determine the neuronal rescue activity of kinetin and minoxidil on neural cells and triage positive hits from part A. It is expected that a number of outcomes is attained, including novel hits that failed to rescue the embryonic germ layer phenotype (in part A) but are successful in neuronal ones.

Positive hits from the initial 3 lines are selectively tested for their ability to rescue the other expanded-CAG lines of the isogenic collection. The collection of hits is expected to include those that can rescue only one or two of the three phenotypic screens.

C. In Vivo Validation of Candidate Compounds in an HD Mouse Model

Parts A and B are expected to generate a list of compounds, including the two previously identified leads, ranked based on the number of independent human in vitro HD phenotypes that are able to rescue (all 3, or just 2, etc.), together with their potency and toxicity. Testing their in vivo efficacy in a model organism is the next step towards clinical translation. Whether these compounds can rescue in vivo HD phenotypes in a HD mouse model is tested. The successful reversal of HD phenotypes with any of the candidate compounds is expected to: i) generate a novel in vivo-validated lead compound for further drug development; ii) validate the utility of this screening approach for further screening of compound libraries; and iii) provide new understanding of the developmental underpinnings of HD and its molecular mechanisms.

The human in vitro HD phenotypes (described herein) clearly demonstrate that HD produces strong developmental alterations that should be taken into account when developing HD therapeutics.

The identified candidate compounds are tested for their ability to rescue HD phenotypes in vivo in the HD mouse model both during embryonic development and adulthood. Progressive motor and cognitive/behavioral symptoms are observable as early as 4 months, as well as HTT aggregates and loss of expression of striatal gene markers. In addition to classical adult-onset phenotypes in mice, newer work has identified profound neurodevelopmental changes in regulation of neural progenitor cell biology.

In vivo studies are conducted using the most promising hits identified in A and B.

To test the ability to rescue the neurodevelopmental phenotypes, compounds are administered to HD mice in utero and the embryos subsequently scored for striatal HD phenotypes that closely match those described in part B above: mutant striatal progenitor cells with misshaped nuclei, multinucleated cells, and the impaired progression of MSN differentiation (evidenced by lower numbers of ISL1, CTIP2, FOXP1, DARPP32-positive cells).

To test for the ability to ameliorate adult HD phenotypes, the same compounds administered to young adult mice. Behavioral testing (open-field, tapered balance beam, rotarod) is used to assess progression of the disease phenotype. Animals are eventually sacrificed and disease-affected neuronal tissues are analyzed for indicators of HD, such HTT protein aggregates, neuron loss (NeuN), and medium spiny neuron and cortical projection neuron markers (FOXP1, CTIP2, DARPP32, GABA, ISL1, TBR1, CTIP2). Candidate and unbiased methods (qPCR, RNASeq) are used to further understand the molecular mechanisms through which the positive compounds exert their effects.

These tests are anticipated to provide data and results pointing to the in vivo disease relevance of compounds identified in parts A-B.

General Methods

Standard methods in molecular biology are described Sambrook, Fritsch and Maniatis (1982 & 1989 2$^{nd}$ Edition, 2001 3$^{rd}$ Edition) *Molecular Cloning, A Laboratory Manual*, Cold Spring Harbor Laboratory Press, Cold Spring Harbor, N.Y.; Sambrook and Russell (2001) *Molecular Cloning*, 3$^{rd}$ ed., Cold Spring Harbor Laboratory Press, Cold Spring Harbor, N.Y.; Wu (1993) *Recombinant DNA*, Vol. 217, Academic Press, San Diego, Calif.). Standard methods also appear in Ausbel, et al. (2001) *Current Protocols in Molecular Biology*, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan, et al. (2000) *Current Protocols in Protein Science*, Vol. 1, John Wiley and Sons, Inc., New York). Chemical analysis, chemical modification, post-translational modification, production of fusion proteins, glycosylation of proteins are described (see, e.g., Coligan, et al. (2000) *Current Protocols in Protein Science*, Vol. 2, John Wiley and Sons, Inc., New York; Ausubel, et al. (2001) *Current Protocols in Molecular Biology*, Vol. 3, John Wiley and Sons, Inc., NY, N.Y., pp. 16.0.5-16.22.17; Sigma-Aldrich, Co. (2001) *Products for Life Science Research*, St. Louis, Mo.; pp. 45-89; Amersham Pharmacia Biotech (2001) *BioDirectory*, Piscataway, N.J., pp. 384-391). Production, purification, and fragmentation of polyclonal and monoclonal antibodies are described (Coligan, et al. (2001) *Current Protocols in Immunology*, Vol. 1, John Wiley and Sons, Inc., New York; Harlow and Lane (1999) *Using Antibodies*, Cold Spring Harbor Laboratory Press, Cold Spring Harbor, N.Y.; Harlow and Lane, supra). Standard techniques for characterizing ligand/receptor interactions are available (see, e.g., Coligan, et al. (2001) *Current Protocols in Immunology*, Vol. 4, John Wiley, Inc., New York).

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

SEQUENCES ANNEX

```
CAGCAACAGCAGCAACAGCAGCAGCAACAGCAGCAACAGCAGCAGCAGCA
GCAGCAGCAGCAGCAGCAGCAACAACAGCAGCAGCAGCAGCAACAGCAGC
AGCAACAGCAGCAGCAGCAGCAACAGCAGCAGCAGCAACAGCAGCAGCAG
CAACAGCAGCAGCAGCAGCAACAGCAGCAGCAGCAGCAGCAGCAGCAACA
GCAACAGCAGCAGCAACAGCAGCAGCAGCAGCAACAGCAACAGCAGCAGC
AGCAGCAGCAGCAACAACAGCAGCAGCAGCAGCAGCAGCAACAGCAGCAA
CAGCAGCAACAGCAGCAACAGCAACAGCAGCAGCAGCAGCAGCAGCAACA
GCAGCAGCAACAGCAACAGCAACAGCAACAGCAACAGCAACAGCAACAGC
AGCAGCAGCAGCAGCAGCAGCAGCAGCAGCAGCAACAGCAGCAGCAACA
G. (SEQ ID NO: 1)

TGGTCCTGCAACTTTATCCGCCTCCATCCAGTCTATTAATTGTTGCCGGG
AAGCTAGAGTAAGTAGTTCGCCAGTTAATAGTTTGCGCAACGTTGTTGCC
ATTGCTACAGGCATCGTGGTGTCACGCTCGTCGTTTGGTATGGCTTCATT
CAGCTCCGGTTCCCAACGATCAAGGCGAGTTACATGATCCCCCATGTTGT
GCAAAAAAGCGGTTAGCTCCTTCGGTCCTCCGATCGTTGTCAGAAGTAAG
TTGGCCGCAGTGTTATCACTCATGGTTATGGCAGCACTGCATAATTCTCT
TACTGTCATGCCATCCGTAAGATGCTTTTCTGTGACTGGTGAGTACTCAA
CCAAGTCATTCTGAGAATAGTGTATGCGGCGACCGAGTTGCTCTTGCCCG
GCGTCAATACGGGATAATACCGCGCCACATAGCAGAACTTTAAAAGTGCT
CATCATTGGAAAACGTTCTTCGGGGCGAAAACTCTCAAGGATCTTACCGC
TGTTGAGATCCAGTTCGATGTAACCCACTCGTGCACCCAACTGATCTTCA
GCATCTTTTACTTTCACCAGCGTTTCTGGGTGAGCAAAAACAGGAAGGCA
AAATGCCGCAAAAAAGGGAATAAGGGCGACACGGAAATGTTGAATACTCA
TACTCTTCCTTTTTCAATATTATTGAAGCATTTATCAGGGTTATTGTCTC
ATGAGCGGATACATATTTGAATGTATTTAGAAAAATAAACAAATAGGGGT
TCCGCGCACATTTCCCCGAAAAGTGCCACCTAAATTGTAAGCGTTAATAT
TTTGTTAAAATTCGCGTTAAATTTTTGTTAAATCAGCTCATTTTTTAACC
AATAGGCCGAAATCGGCAAAATCCCTTATAAATCAAAAGAATAGACCGAG
ATAGGGTTGAGTGTTGTTCCAGTTTGGAACAAGAGTCCACTATTAAAGAA
CGTGGACTCCAACGTCAAAGGGCGAAAAACCGTCTATCAGGGCGATGCC
CACTACGTGAACCATCACCCTAATCAAGTTTTTTGGGGTCGAGGTGCCGT
AAAGCACTAAATCGGAACCCTAAAGGGAGCCCCCGATTTAGAGCTTGACG
GGGAAAGCCGGCGAACGTGGCGAGAAAGGAAGGGAAGAAAGCGAAAGGAG
CGGGCGCTAGGGCGCTGGCAAGTGTAGCGGTCACGCTGCGCGTAACCACC
```

SEQUENCES ANNEX

ACACCCGCCGCGCTTAATGCGCCGCTACAGGGCGCGTCCCATTCGCCATT
CAGGCTGCGCAACTGTTGGGAAGGGCGATCGGTGCGGGCCTCTTCGCTAT
TACGCCAGCTGGCGAAAGGGGGATGTGCTGCAAGGCGATTAAGTTGGGTA
ACGCCAGGGTTTTCCCAGTCACGACGTTGTAAAACGACGGCCAGTGAATT
ACCAGCGATGGAACGAGCTCTTTCTCACCTGGCCTCCTTCAGCATTTCTG
TCCCTCAGTCCTTAGCAAGCCCAGGAGCTGTTGAGTTTGGCAGGTGCCGA
GTGCTGTTCCTGCCTGTGTAGCTGTGGCTCAGTCCTGTGGGGGCCCCGCT
GTGGCCCGAGTGCAGTGATTCGAGGCGCTGAGTGTTCCCTGACTCCTTCT
CCAGGAGCTGTGTTCAGACTTTCGCAGCTCTTGGCTTGGAGCTCCTGGAG
GGCTTGGCATTGCCGACCAATGTGGAGGTCGACAGTGAGAGAGGAGGAAT
GCTAGCTTTCTTGACCAGTCCATTAAATAAGTGGGATATTGGCCAGGCAC
GGCGGCTCACGCCTTAATCCCAGCACTTTGGGAGGCTGAGGCGGGTGGAT
CACGAGCTCAGGAGTTCAAGACCAGCCTGGCCAACATGGTGAAACCCCCT
CTATACTAAAAATACAAATATTAGCTGGGCGTGGTGGCAGGCGCCTGTAA
TCCTAGCTACTTGGGAGGCTGAGGCAGGAGAACAGCTTGAAACCGGAAGG
TGGAGTTTGCAGTGAGCCAAGATTGCGCCACTGCACTCCAACCTGGGCAA
CAAGAGCAAAACTCTATCTCAAAAAAAAAAAAAAAGTAGGATATCTGTT
TCTGCTTAGAAAAATCAGAATTTTCTAAATGCCAGGTGTTCTGAATACGT
AAGTATGGGAGACGACTCAGCCTGTTTCATTTTTATGTAAAATCTTCGCG
TAGCCATGTGGCACTGGACCGAGATGAAAGCAAAGACATTTCTCCTTAAC
TTTGTTTCTAGGAATGTTCCGGAGAATCACAGCAGCTGCCACTAGGCTGT
TCCGCAGTGATGGCTGTGGCGGCAGTTTCTACACCCTGGACAGCTTGAAC
TTGCGGGCTCGTTCCATGATCACCACCCACCCGGCCCTGGTGCTGCTCTG
GTGTCAGATACTGCTGCTTGTCAACCACACCGACTACCGCTGGTGGACGG
AAGTGCAGCAGACCCCGAACCTAGGTGACACAGCAAGACGTTGTCTCTGG
GGAAAAAGAAAGAAACGGAACCACGCGGTGTGCAGCCTTCTGAGTCTGG
CCCCTTTCGGTAGGTTCATAATGCCCCACAGCCCAGGGCGCCAGCCCAGA
TAACTTCGTATAGCATACATTATACGAAGTTATTAGGAATTCGTCTGAAG
AGGAGTTTACGTCCAGCCAAGCTTAGGATCTCGACCTCGAAATTCTACCG
GGTAGGGGAGGCGCTTTTCCCAAGGCAGTCTGGAGCATGCGCTTTAGCAG
CCCCGCTGGGCACTTGGCGCTACACAAGTGGCCTCTGGCCTCGCACACAT
TCCACATCCACCGGTAGGCGCCAACCGGCTCCGTTCTTTGGTGGCCCCTT
CGCGCCACCTTCTACTCCTCCCCTAGTCAGGAAGTTCCCCCCGCCCCGC
AGCTCGCGTCGTCAGGACGTGACAAATGGAAGTAGCACGTCTCACTAGT
CTCGTGCAGATGGACAGCACCGCTGAGCAATGGAAGCGGGTAGGCCTTTG
GGGCAGCGGCCAATAGCAGCTTTGCTCCTTCGCTTTCTGGGCTCAGAGGC
TGGGAAGGGGTGGGTCCGGGGGCGGGCTCAGGGGCGGGCTCAGGGGCGGG
GCGGGCGCCCGAAGGTCCTCCGGAGGCCCGGCATTCTGCACGCTTCAAAA
GCGCACGTCTGCCGCGCTGTTCTCCTCTTCCTCATCTCCGGGCCTTTCGA
CCTGCATCCATCTAGATCTCGAGCAGCTGAAGCTTAGCTAGCATGACCGA
GTACAAGCCCACGGTGCGCCTCGCCACCCGCGACGACGTCCCCGGGCCG
TACGCACCCTCGCCGCCGCGTTCGCCGACTACCCCGCCACGCGCCACACC
GTCGACCCGGACCGCCACATCGAGCGGGTCACCGAGCTGCAAGAACTCTT
CCTCACGCGCGTCGGGCTCGACATCGGCAAGGTGTGGGTCGCGGACGACG
AGCGCCGCGGTGGCGGTCTGGACCACGCCGGAGGCGTCGAAGCGGGGCG
GTGTTCGCCGAGATCGGCCCGCGCATGGCCGAGTTGAGCGGTTCCCGGCT
GGCCGCGCAGCAACAGATGGAAGGCCTCCTGGCGCCGCACCGGCCCAAGG
AGCCCGCGTGGTTCCTGGCCACCGTCGGCGTCTCGCCCGACCACCAGGGC
AAGGGTCTGGGCAGCGCCGTCGTGCTCCCCGGAGTGGAGGCGGCCGAGCG
CGCCGGGGTGCCCGCCTTCCTGGAGACCTCCGCCCCGCAACCTCCCCT
TCTACGAGCGGCTCGGCTTCACCGTCACCGCCGACGTCGAGGTGCCCGAA
GGACCGCGCACCTGGTGCATGACCCGCAAGCCCGGTGCCTGAGGATCCTC
TGCAGAAATTGATGATCTATTAAACAATAAAGATGTCCACTAAAATGAAA
GTTTTTCCTGTCATACTTTGTTAAGAAGGGTGAGAACAGAGTACCTACAT
TTTGAATGGAAGGATTGGAGCTACGGGGGTGGGGGTGGGGTGGGATTAGA
TAAATGCCTGCTCTTTACTGAAGGCTCTTTACTATTGCTTTATGATAATG
TTTCATAGTTGGATATCATAATTTAAACAAGCAAAACCAAATTAAGGGCC
AGCTCATTCCTCCCACTCATGATCTATAGATCTATAGATCTCTCGTGGGA
TCATTGTTTTTCTCTTGATTCCCACTTTGTGGTTCTAAGTACTGTGGTTT
CCAAATGTGTCAGTTTCATAGCCTGAAGAACGAGATCAGCAGCCTCTGTT
CCACATACACTTCATTCTCAGTATTGTTTTGCCAAGTTCTAATTCCATCA
GAAGCTGACTCTAGAGGCCTATAACTTCGTATAGCATACATTATACGAAG
TTATCACCCTGTCCTGAGACTCCCAGTAACCTGAGCTTTGGCCACCGTTA
AAGCATTTTCATTTTCATTTTTTGTGAGGGCTTGTGAAATTTCTGCTGC
ATATTAATATTCCTTTCATGGACAGCATATTATTGGGACAAACATGCGGT
CCAGCTAAAGGCATTCAAAATAGCAGTTGCTTTCTAAATGCGATTTTCTT
TGGCAGGTTCTTTGACACCATTGCATCTTGTGGGATATGCTTGTCATGCT
CTGTGGCTCCTACTAAGTTCTAGTCCTTAAATTGGTTCCATAGCCAGACA
TGTTGCAATGTCTTAACCTCATTATAAAGTAAATGTGGTTCTGGTTATCC
TTAGATAATGAAGTAACAGTGTAGCAAATTTCAAAACCTCTTGGAAATGT
TATTTTACCATTCAAAAAGGCTTACTAAGGTTCTCGTTATGGGTGGCCCT
CTTTTTGCAAAAGGTTTTCAGGCTTAAGCTCCATTTCTAGGTGCTCCAAC
ACTCCATTATTTGTATATGTATGGAAATAAAAGCTGTGACCACCCCCAAC
CCTGGCCCCCGCCCAGCTGAATCCTCAGCACAGTATTTCTGGAAGGCTCA
AGATCCCACGCTGGGGAAAAGAAGTTCTGGAGACAAAAGAGGGCAGGTGC
TGCCGTGCCTCTCTGCTCAGTATGGATACTGGACCTTGTGCTGCCAGGGC
TCCCAGTAGGGCCAGTTCATGGCACTCAGCTGGAAAGTCCACTGTTGGGA
GGCATTCTTAACCATCCACTCTGTGCCGTATGTAGTGGGGTCTGGTCATT
CTGTTGGAGGAGACAGACCAGTGACGACATTTGAAATGCTTGGTGGATGT
CTTAGGCCTGTTACGATGACTGAGCACTGTGGGGGCAGGAGACAGAAAGT
CAGTGTCTCCTAGTTCTGTGCTGCTTTAACGTGCATAGAAATCAGCTGCG
GATTCAGCAGATCACTCCTTTTCTGACAGATGGGCCTGCTTACTCTGATG
TTATTTGTGAGCCAGGTACCGTTCCATCAGTCCAGCTTGGCGTAATCATG
GTCATAGCTGTTTCCTGTGTGAAATTGTTATCCGCTCACAATTCCACACA
ACATACGAGCCGGAAGCATAAAGTGTAAAGCCTGGGGTGCCTAATGAGTG
AGCTAACTCACATTAATTGCGTTGCGCTCACTGCCCGCTTTCCAGTCGGG
AAACCTGTCGTGCCAGCTGCATTAATGAATCGGCCAACGCGCGGGAGAG
GCGGTTTGCGTATTGGGCGCTCTTCCGCTTCCTCGCTCACTGACTCGCTG
CGCTCGGTCGTTCGGCTGCGGCGAGCGGTATCAGCTCACTCAAAGGCGGT
AATACGGTTATCCACAGAATCAGGGGATAACGCAGGAAAGAACATGTGAG
CAAAAGGCCAGCAAAAGGCCAGGAACCGTAAAAAGGCCGCGTTGCTGGCG
TTTTTCCATAGGCTCCGCCCCCCTGACGAGCATCACAAAAATCGACGCTC
AAGTCAGAGGTGGCGAAACCCGACAGGACTATAAAGATACCAGGCGTTTC
CCCCTGGAAGCTCCCTCGTGCGCTCTCCTGTTCCGACCCTGCCGCTTACC
GGATACCTGTCCGCCTTTCTCCCTTCGGGAAGCGTGGCGCTTTCTCATAG
CTCACGCTGTAGGTATCTCAGTTCGGTGTAGGTCGTTCGCTCCAAGCTGG
GCTGTGTGCACGAACCCCCCGTTCAGCCCGACCGCTGCGCCTTATCCGGT
AACTATCGTCTTGAGTCCAACCCGGTAAGACACGACTTATCGCCACTGGC
AGCAGCCACTGGTAACAGGATTAGCAGAGCGAGGTATGTAGGCGGTGCTA
CAGAGTTCTTGAAGTGGTGGCCTAACTACGGCTACACTAGAAGGACAGTA
TTTGGTATCTGCGCTCTGCTGAAGCCAGTTACCTTCGGAAAAAGAGTTGG
TAGCTCTTGATCCGGCAAACAAACCACCGCTGGTAGCGGTGGTTTTTTTG
TTTGCAAGCAGCAGATTACGCGCAGAAAAAAAGGATCTCAAGAAGATCCT
TTGATCTTTTCTACGGGGTCTGACGCTCAGTGGAACGAAAACTCACGTTA
AGGGATTTTGGTCATGAGATTATCAAAAAGGATCTTCACCTAGATCCTTT
TAAATTAAAAATGAAGTTTTAAATCAATCTAAAGTATATATGAGTAAACT
TGGTCTGACAGTTACCAATGCTTAATCAGTGAGGCACCTATCTCAGCGAT
CTGTCTATTTCGTTCATCCATAGTTGCCTGACTCCCCGTCGTGTAGATAA
CTACGATACGGGAGGGCTTACCATCTGGCCCCAGTGCTGCAATGATACCG
CGAGACCCACGCTCACCGGCTCCAGATTTATCAGCAATAAACCAGCCAGC
CGGAAGGGCCGAGCGCAGAAG (SEQ ID NO: 45)

REFERENCES

The following references, to the extent that they provide exemplary procedural or other details supplementary to those set forth herein, are specifically incorporated herein by reference.

1. Munoz-Sanjuan, I. & Bates, G. P. The importance of integrating basic and clinical research toward the development of new therapies for Huntington disease. J. Clin. Invest. 121, 476-483 (2011).
2. Ruzo, A. et al. Discovery of novel isoforms of Huntingtin reveals a new hominidspecific exon. PLoS ONE 2015; 10:e0127687
3. Sathasivam, K. et al. Aberrant splicing of HTT generates the pathogenic exon 1 protein in Huntington disease. Proc. Natl. Acad. Sci. 110, 2366-2370 (2013).
4. Greig, L. C., Woodworth, M. B., Galazo, M. J., Padmanabhan, H. & Macklis, J. D. Molecular logic of neocortical projection neuron specification, development and diversity. Nat. Rev. Neurosci. 14, 755-769 (2013).
5. Jinek, M. et al. A Programmable Dual-RNA-Guided DNA Endonuclease in Adaptive Bacterial Immunity. Science 337, 816-821 (2012).
6. Sander, J. D. & Joung, J. K. CRISPR-Cas systems for editing, regulating and targeting genomes. Nat. Biotechnol. 32, 347-355 (2014).
7. An, M. C. et al. Genetic correction of Huntington's disease phenotypes in induced pluripotent stem cells. Cell Stem Cell 11, 253-263 (2012).
8. Puri, M. C. & Nagy, A. Concise review: Embryonic stem cells versus induced pluripotent stem cells: the game is on. Stem Cells Dayt. Ohio 30, 10-14 (2012).
9. Kim, K. et al. Epigenetic memory in induced pluripotent stem cells. Nature 467, 285-290 (2010).

10. Mali, P. et al. RNA-Guided Human Genome Engineering via Cas9. Science 339, 823-826 (2013).
11. Cong, L. et al. Multiplex Genome Engineering Using CRISPR/Cas Systems. Science 339, 819-823 (2013).
12. James, D., Noggle, S. A., Swigut, T. & Brivanlou, A. H. Contribution of human embryonic stem cells to mouse blastocysts. Dev. Biol. 295, 90-102 (2006).
13. Rosa, A., Spagnoli, F. M. & Brivanlou, A. H. The miR-430/427/302 Family Controls Mesendodermal Fate Specification via Species-Specific Target Selection. Dev. Cell 16, 517-527 (2009).
14. Ozair, M. Z., Noggle, S., Warmflash, A., Krzyspiak, J. E. & Brivanlou, A. H. SMAD7 Directly Converts Human Embryonic Stem Cells to Telencephalic Fate by a Default Mechanism. STEM CELLS 31, 35-47 (2013).
15. Hemmati-Brivanlou, A. & Melton, D. A. A truncated activin receptor inhibits mesoderm induction and formation of axial structures in Xenopus embryos. Nature 359, 609-614 (1992).
16. Hemmati-Brivanlou, A. & Melton, D. A. Inhibition of activin receptor signaling promotes neuralization in Xenopus. Cell 77, 273-281 (1994).
17. Muñoz-Sanjuán, I. & Brivanlou, A. H. Neural induction, the default model and embryonic stem cells. Nat. Rev. Neurosci. 3, 271-280 (2002).
18. Landles, C. et al. Proteolysis of mutant huntingtin produces an exon 1 fragment that accumulates as an aggregated protein in neuronal nuclei in Huntington disease. J Biol Chem 285, 8808-8823 (2010).
19. Alfonso-Prieto, M., Biarnés, X., Vidossich, P. & Rovira, C. The Molecular Mechanism of the Catalase Reaction. J. Am. Chem. Soc. 131, 11751-11761 (2009).
20. del Hoyo, P. et al. Oxidative stress in skin fibroblasts cultures of patients with Huntington's disease. Neurochem. Res. 31, 1103-1109 (2006).
21. Aras, S. et al. MNRR1 (formerly CHCHD2) is a bi-organellar regulator of mitochondrial metabolism. Mitochondrion 20, 43-51 (2015).
22. Baughman, J. M. et al. A Computational Screen for Regulators of Oxidative Phosphorylation Implicates SLIRP in Mitochondrial RNA Homeostasis. PLoS Genet. 5, (2009).
23. Feyeux, M. et al. Early transcriptional changes linked to naturally occurring Huntington's disease mutations in neural derivatives of human embryonic stem cells. Hum. Mol. Genet. 21, 3883-3895 (2012).
24. Santamaría, I., Velasco, G., Pendás, A. M., Paz, A. & López-Otín, C. Molecular cloning and structural and functional characterization of human cathepsin F, a new cysteine proteinase of the papain family with a long propeptide domain. J. Biol. Chem. 274, 13800-13809 (1999).
25. Wang, B. et al. Human cathepsin F. Molecular cloning, functional expression, tissue localization, and enzymatic characterization. J. Biol. Chem. 273, 32000-32008 (1998).
26. De Plaen, E., Naerhuyzen, B., De Smet, C., Szikora, J. P. & Boon, T. Alternative promoters of gene MAGE4a. Genomics 40, 305-313 (1997).
27. Zhao, Q., Caballero, O. L., Simpson, A. J. G. & Strausberg, R. L. Differential Evolution of MAGE Genes Based on Expression Pattern and Selection Pressure. PLoS ONE 7, e48240 (2012).
28. Capone, M. C., Gorman, D. M., Ching, E. P. & Zlotnik, A. Identification through bioinformatics of cDNAs encoding human thymic shared Ag-1/stem cell Ag-2. A new member of the human Ly-6 family. J. Immunol. Baltim. Md. 1950 157, 969-973 (1996).
29. Mao, M. et al. RIG-E, a human homolog of the murine Ly-6 family, is induced by retinoic acid during the differentiation of acute promyelocytic leukemia cell. Proc. Natl. Acad. Sci. U.S.A. 93, 5910-5914 (1996).
30. Saitoh, S. et al. Modulation of TCR-mediated signaling pathway by thymic shared antigen-1 (TSA-1)/stem cell antigen-2 (Sca-2). J. Immunol. Baltim. Md. 1950 155, 5574-5581 (1995).
31. Fanjul-Fernández, M. et al. Cell-cell adhesion genes CTNNA2 and CTNNA3 are tumour suppressors frequently mutated in laryngeal carcinomas. Nat. Commun. 4, 2531 (2013).
32. Corre, J., Hébraud, B. & Bourin, P. Concise review: growth differentiation factor 15 in pathology: a clinical role? Stem Cells Transl. Med. 2, 946-952 (2013).
33. Kempf, T. et al. The Transforming Growth Factor-β Superfamily Member Growth-Differentiation Factor-15 Protects the Heart From Ischemia/Reperfusion Injury. Circ. Res. 98, 351-360 (2006).
34. Xu, J. et al. GDF15/MIC-1 Functions As a Protective and Antihypertrophic Factor Released From the Myocardium in Association With SMAD Protein Activation. Circ. Res. 98, 342-350 (2006).
35. McKay, R. R. et al. Cloning and expression of the human transient receptor potential 4 (TRP4) gene: localization and functional expression of human TRP4 and TRP3. Biochem. J. 351 Pt 3, 735-746 (2000).
36. Cioffi, D. L. et al. Activation of the endothelial store-operated ISOC Ca2+ channel requires interaction of protein 4.1 with TRPC4. Circ. Res. 97, 1164-1172 (2005).
37. Graziani, A. et al. Cell-cell contact formation governs Ca2+ signaling by TRPC4 in the vascular endothelium: evidence for a regulatory TRPC4-beta-catenin interaction. J. Biol. Chem. 285, 4213-4223 (2010).
38. Peng, H. et al. Nlrp2, a Maternal Effect Gene Required for Early Embryonic Development in the Mouse. PLoS ONE 7, (2012).
39. de Rivero Vaccari, J. P., Dietrich, W. D. & Keane, R. W. Activation and regulation of cellular inflammasomes: gaps in our knowledge for central nervous system injury. J. Cereb. Blood Flow Metab. Off. J. Int. Soc. Cereb. Blood Flow Metab. 34, 369-375 (2014).
40. Minkiewicz, J., de Rivero Vaccari, J. P. & Keane, R. W. Human astrocytes express a novel NLRP2 inflammasome. Glia 61, 1113-1121 (2013).
41. Shah, A. et al. Thioredoxin-interacting protein mediates high glucose-induced reactive oxygen species generation by mitochondria and the NADPH oxidase, Nox4, in mesangial cells. J. Biol. Chem. 288, 6835-6848 (2013).
42. Zhang, X. et al. Reactive oxygen species-induced TXNIP drives fructose-mediated hepatic inflammation and lipid accumulation through NLRP3 inflammasome activation. Antioxid. Redox Signal. 22, 848-870 (2015).
43. Zhou, R., Tardivel, A., Thorens, B., Choi, I. & Tschopp, J. Thioredoxin-interacting protein links oxidative stress to inflammasome activation. Nat. Immunol. 11, 136-140 (2010).
44. Li, Y., Mair, D. C., Schuller, R. M., Li, L. & Wu, J. Genetic mechanism of human neutrophil antigen 2 deficiency and expression variations. PLoS Genet. 11, e1005255 (2015).
45. Vietinghoff, S. von et al. NB1 mediates surface expression of the ANCA antigen proteinase 3 on human neutrophils. Blood 109, 4487-4493 (2007).

46. Stroncek, D. F. Neutrophil-specific antigen HNA-2a, NB1 glycoprotein, and CD177. Curr. Opin. Hematol. 14, 688-693 (2007).
47. Aruga, J. & Mikoshiba, K. Identification and characterization of Slitrk, a novel neuronal transmembrane protein family controlling neurite outgrowth. Mol. Cell. Neurosci. 24, 117-129 (2003).
48. Aruga, J., Yokota, N. & Mikoshiba, K. Human SLITRK family genes: genomic organization and expression profiling in normal brain and brain tumor tissue. Gene 315, 87-94 (2003).
49. Jimenez-Sanchez, M. et al. siRNA screen identifies QPCT as a druggable target for Huntington's disease. Nat. Chem. Biol. advance online publication, (2015).
50. Liu, K.-Y. et al. Disruption of the nuclear membrane by perinuclear inclusions of mutant huntingtin causes cell-cycle re-entry and striatal cell death in mouse and cell models of Huntington's disease. Hum. Mol. Genet. 24, 1602-1616 (2015).
51. Zhou, W. et al. HIF1α induced switch from bivalent to exclusively glycolytic metabolism during ESC-to-EpiSC/hESC transition: Metabolic switch in ESC-to-EpiSC/hESC transition. EMBO J. 31, 2103-2116 (2012).
52. Varum, S. et al. Energy Metabolism in Human Pluripotent Stem Cells and Their Differentiated Counterparts. PLoS ONE 6, (2011).
53. Zhang, J. et al. UCP2 regulates energy metabolism and differentiation potential of human pluripotent stem cells: UCP2 regulates hPSC metabolism and differentiation. EMBO J. 30, 4860-4873 (2011).
54. Borlongan, C. V. et al. Free radical damage and oxidative stress in Huntington's disease. J. Fla. Med. Assoc. 83, 335-341 (1996).
55. Shukla, V., Mishra, S. K. & Pant, H. C. Oxidative Stress in Neurodegeneration. Adv. Pharmacol. Sci. 2011, e572634 (2011).
56. Ismailoglu, I. et al. Huntingtin protein is essential for mitochondrial metabolism, bioenergetics and structure in murine embryonic stem cells. Dev. Biol. 391, 230-240 (2014).
57. Castiglioni, V., Onorati, M., Rochon, C. & Cattaneo, E. Induced pluripotent stem cell lines from Huntington's disease mice undergo neuronal differentiation while showing alterations in the lysosomal pathway. Neurobiol. Dis. 46, 30-40 (2012).
58. Odefrey, F. et al. Common genetic variants associated with breast cancer and mammographic density measures that predict disease. Cancer Res. 70, 1449-1458 (2010).
59. Grbesa, I. et al. Loss of imprinting of IGF2 and H19, loss of heterozygosity of IGF2R and CTCF, and *Helicobacter pylori* infection in laryngeal squamous cell carcinoma. J. Mol. Med. Berl. Ger. 86, 1057-1066 (2008).
60. Miyasaka, K. Y., Kida, Y. S., Sato, T., Minami, M. & Ogura, T. Csrp1 regulates dynamic cell movements of the mesendoderm and cardiac mesoderm through interactions with Dishevelled and Diversin. Proc. Natl. Acad. Sci. 104, 11274-11279 (2007).
61. HD iPSC Consortium. Induced pluripotent stem cells from patients with Huntington's disease show CAG-repeat-expansion-associated phenotypes. Cell Stem Cell 11, 264-278 (2012).
62. Seong, I. S. et al. HD CAG repeat implicates a dominant property of huntingtin in mitochondrial energy metabolism. Hum. Mol. Genet. 14, 2871-2880 (2005).
63. Jacobsen, J. C. et al. HD CAG-correlated gene expression changes support a simple dominant gain of function. Hum. Mol. Genet. 20, 2846-2860 (2011).
64. Hallen, A., Jamie, J. F. & Cooper, A. J. L. Lysine metabolism in mammalian brain: an update on the importance of recent discoveries. Amino Acids 45, (2013).
65. Schneider, C. A., Rasband, W. S. & Eliceiri, K. W. NIH Image to ImageJ: 25 years of image analysis. Nat. Methods 9, 671-675 (2012).
66. Trapnell, C. et al. Differential gene and transcript expression analysis of RNA-seq experiments with TopHat and Cufflinks. Nat. Protoc. 7, 562-78 (2012).
67. Huang, D. W., Sherman, B. T. & Lempicki, R. A. Systematic and integrative analysis of large gene lists using DAVID bioinformatics resources. Nat. Protoc. 4, 44-57 (2009).
68. Huang, D. W., Sherman, B. T. & Lempicki, R. A. Bioinformatics enrichment tools: paths toward the comprehensive functional analysis of large gene lists. Nucleic Acids Res. 37, 1-13 (2009).
69. Chen, Q. et al. Untargeted plasma metabolite profiling reveals the broad systemic consequences of xanthine oxidoreductase inactivation in mice. PloS One 7, e37149 (2012).
70. Ring K. L., et al and Ellerby, L. M. Genomic Analysis Reveals Disruption of Striatal Neuronal Development and Therapeutic Targets in Human Huntington's Disease Neural Stem CellsStem Cell Reports. 2015 Dec. 8; 5(6):1023-38. doi: 10.1016/j.stemcr.2015.11.005.
71. Etoc F, Metzger J, Ruzo A, Kirst C, Yoney A, Ozair M Z, et al.: A Balance between Secreted Inhibitors and Edge Sensing Controls Gastruloid Self-Organization. Dev Cell 2016 Nov. 7; 39:302-315.
72. Deglincerti A, Etoc F, Guerra M C, Martyn I, Metzger J, Ruzo A, et al.: Self-organization of human embryonic stem cells on micropatterns. Nat Protoc 2016 November; 11:2223-2232.
73. Deglincerti A, Etoc F, Ozair M Z, Brivanlou A H: Self-Organization of Spatial Patterning in Human Embryonic Stem Cells. Curr Top Dev Biol 2016; 116:99-113.

All references cited herein are incorporated by reference to the same extent as if each individual publication, database entry (e.g. Genbank sequences or GeneID entries), patent application, or patent, was specifically and individually indicated to be incorporated by reference. This statement of incorporation by reference is intended by Applicants, pursuant to 37 C.F.R. § 1.57(b)(1), to relate to each and every individual publication, database entry (e.g. Genbank sequences or GeneID entries), patent application, or patent, each of which is clearly identified in compliance with 37 C.F.R. § 1.57(b)(2), even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

The foregoing written specification is considered to be sufficient to enable one skilled in the art to practice the invention. Various modifications of the invention in addition to those shown and described herein will become apparent to those skilled in the art from the foregoing description and fall within the scope of the appended claims.

The invention claimed is:

1. A method for identifying therapeutic candidates for treatment of Huntington's Disease (HD) comprising:
   (a) contacting a test substance with each of:
      (i) a first clonal population of human embryonic stem cells comprising a wild type Huntingtin (HTT) gene, and
      (ii) a second clonal population of human embryonic stem cells isogenic to the first population, wherein the cells in the second population are genetically modified to comprise at the endogenous HTT gene locus a nucleotide segment, wherein the nucleotide segment, upon expression, results in a polyQ repeat peptide segment comprising at least 36 or at least 40 glutamine residues in the N-terminal region of the HTT protein,
   wherein the first clonal population of human embryonic stem cells and the second clonal population of embryonic stems cells are each cultured on a micropatterned confined surface pretreated with an adherent substrate; and (b) determining whether the test substance:
   (i) wholly or partially reverses a perturbed organization of the cells of the second clonal population or cells differentiated therefrom; and
   (ii) reverts a change in three-dimensional cellular geometry associated with a micropattern signature in the second clonal population or cells differentiated therefrom.

2. A method for identifying a therapeutic candidate for Huntington's disease comprising:
   (a) contacting a clonal population of human embryonic stem cells or human neural progenitor cells or human neurons differentiated therefrom, wherein the clonal population is genetically modified at the endogenous Huntingtin (HTT) gene locus to expresses a mutant Huntingtin (HTT) gene which encodes an HTT protein comprising a polyQ repeat peptide segment of least 40 glutamine residues with a test compound;
   (b) culturing said clonal population on a micropatterned confined surface pretreated with an adherent substrate; and
   (c) detecting whether a perturbed organization of the clonal population, or cells differentiated therefrom, partially or fully reverts to the wild-type organization; and
   (d) determining whether the test compound reverts a change in three-dimensional cellular geometry associated with a micropattern signature in the clonal population or cells differentiated therefrom,
   wherein a test compound that causes a partial or complete reversion to the wild-type organization and reverts a change in three-dimensional cellular geometry is a therapeutic candidate for Huntington's disease.

3. The method of claim 2, wherein the clonal population is a differentiating clonal population of human neural progenitor cells or human neurons, and wherein the method step (b) further comprises concurrently:
   (i) inducing neural differentiation in a clonal population of human embryonic stem cells that expresses a mutant Huntingtin (HTT) gene which encodes an HTT protein comprising a polyQ repeat peptide segment of least 40 glutamine residues; and
   (ii) culturing said clonal population of human embryonic stem cells on a micropatterned confined surface pretreated with an adherent substrate, under conditions in which neural differentiation occurs to produce the differentiating clonal population.

4. A method of screening for a therapeutic candidate for Huntington's Disease, comprising:
   (a) culturing
      (i) on a micropatterned confined surface pretreated with an adherent substrate, a first clonal population comprising human embryonic stem cells or human neuronal cell progenitors or human neurons differentiated therefrom, said cells in the first clonal population comprising a wild-type Huntingtin gene (HTT); and
      (ii) on a micropatterned confined surface pretreated with an adherent substrate, a second clonal population of human embryonic stem cells, human neuronal cell progenitors or human neurons, said cells in the second clonal population isogenic to the first population but comprising an HTT genetically modified at the endogenous HTT gene locus to comprise a nucleotide segment, wherein the nucleotide segment, upon expression, results in a polyQ repeat peptide segment comprising at least 40 glutamine residues in the N-terminal region of the HTT protein;
   in the presence of a differentiating agent and a therapeutic candidate; and
   (b) determining whether the therapeutic candidate reverts a change in the three-dimensional cellular geometry associated with a micropattern signature in the second clonal cell population, or cells differentiated therefrom.

5. The method of claim 4, wherein the first clonal population and second clonal population are cultured in the presence of the test substance under differentiating conditions.

6. The method of claim 1, wherein the polyQ repeat peptide segment comprises 42-150 glutamine residues in the N-terminal region of the HTT protein.

7. The method of claim 2, wherein the polyQ repeat peptide segment comprises 42-150 glutamine residues in the N-terminal region of the HTT protein.

8. The method of claim 3, wherein the polyQ repeat peptide segment comprises 42-150 glutamine residues in the N-terminal region of the HTT protein.

9. The method of claim 4, wherein the polyQ repeat peptide segment comprises 42-150 glutamine residues in the N-terminal region of the HTT protein.

10. The method of claim 1, wherein the micropatterned confined surface is a micropatterned glass coverslip.

11. The method of claim 1, wherein the micropattern of the micropatterned confined surface is a circular micropattern.

12. The method of claim 2, wherein the micropatterned confined surface is a micropatterned glass coverslip.

13. The method of claim 2, wherein the micropattern of the micropatterned confined surface is a circular micropattern.

14. The method of claim 3, wherein the micropatterned confined surface is a micropatterned glass coverslip.

15. The method of claim 3, wherein the micropattern of the micropatterned confined surface is a circular micropattern.

16. The method of claim 4, wherein the micropatterned confined surface is a micropatterned glass coverslip.

17. The method of claim 4, wherein the micropattern of the micropatterned confined surface is a circular micropattern.

* * * * *